United States Patent
De Sauvage et al.

(10) Patent No.: US 10,330,683 B2
(45) Date of Patent: Jun. 25, 2019

(54) MUTANT SMOOTHENED AND METHODS OF USING THE SAME

(71) Applicants: Genentech, Inc., South San Francisco, CA (US); Curis, Inc., Lexington, MA (US); Assistance Publique-Hopitaux de Paris, Paris (FR); Universite Paris Diderot—Paris 7, Paris (FR)

(72) Inventors: Frederic J. De Sauvage, Foster City, CA (US); Robert L. Yauch, Redwood City, CA (US); Gerrit J. P. Dijkgraaf, South San Francisco, CA (US); Hayley Sharpe, San Francisco, CA (US); Nicole Basset-Seguin, Paris (FR)

(73) Assignees: Genentech, Inc., South San Francisco, CA (US); Curis, Inc., Lexington, MA (US); Assistance Publique-Hopitaux de Paris, Paris (FR); Universite Paris Diderot—Paris 7, Paris (FR)

( * ) Notice: Subject to any disclaimer, the term of this patent is extended or adjusted under 35 U.S.C. 154(b) by 0 days.

(21) Appl. No.: 15/548,591

(22) PCT Filed: Feb. 4, 2016

(86) PCT No.: PCT/US2016/016614
§ 371 (c)(1),
(2) Date: Aug. 3, 2017

(87) PCT Pub. No.: WO2016/126972
PCT Pub. Date: Aug. 11, 2016

(65) Prior Publication Data
US 2018/0045729 A1 Feb. 15, 2018

Related U.S. Application Data

(60) Provisional application No. 62/112,074, filed on Feb. 4, 2015.

(51) Int. Cl.
| | | |
|---|---|---|
| *C07K 14/47* | (2006.01) |
| *C12N 15/12* | (2006.01) |
| *C12N 15/63* | (2006.01) |
| *G01N 33/68* | (2006.01) |
| *C07H 21/04* | (2006.01) |
| *G01N 33/574* | (2006.01) |
| *G01N 33/50* | (2006.01) |
| *C07K 14/705* | (2006.01) |
| *C12Q 1/6886* | (2018.01) |
| *A61K 47/68* | (2017.01) |
| *A61K 31/551* | (2006.01) |
| *C07K 14/71* | (2006.01) |
| *C07K 16/28* | (2006.01) |

(52) U.S. Cl.
CPC ..... *G01N 33/57492* (2013.01); *A61K 31/551* (2013.01); *A61K 47/6849* (2017.08); *C07H 21/04* (2013.01); *C07K 14/47* (2013.01); *C07K 14/705* (2013.01); *C07K 14/71* (2013.01); *C07K 16/2863* (2013.01); *C12N 15/63* (2013.01); *C12Q 1/6886* (2013.01); *G01N 33/502* (2013.01); *G01N 33/5011* (2013.01); *G01N 33/5041* (2013.01); *G01N 33/6872* (2013.01); *C07K 2317/24* (2013.01); *C07K 2317/569* (2013.01); *C07K 2317/76* (2013.01); *C12Q 2600/106* (2013.01); *C12Q 2600/156* (2013.01); *G01N 2333/4704* (2013.01); *G01N 2333/71* (2013.01); *G01N 2500/04* (2013.01); *G01N 2500/10* (2013.01)

(58) Field of Classification Search
None
See application file for complete search history.

(56) References Cited

U.S. PATENT DOCUMENTS 8,623,997 B2   1/2014  Bosanac

FOREIGN PATENT DOCUMENTS

| CN | 102112612 A | 6/2011 |
|---|---|---|
| WO | 2011028950 A1 | 3/2011 |
| WO | 2012047968 A2 | 4/2012 |
| WO | 2014107655 A1 | 7/2014 |

OTHER PUBLICATIONS

Dijkgraaf et al Cancer Research. Jan. 2011. 71(2): 435-444.*
Lam et al Oncogene. 1999. 18: 833-836.*
International Search Report dated Jul. 25, 2016 issued in corresponding PCT/US2016/016614 application (6 pages).
S.X. Atwood et al., "Smoothened Variants Explain the Majority of Drug Resistance in Basal Cell Carcinoma", Cancer Cell, vol. 27, No. 3 (2015) pp. 342-353.
T. Ishii et al., "Inhibition Mechanism Exploration of Investigational Drug TAK-441 as Inhibitor Against Vismodegib-Resistant Smoothened Mutant", European Journal of Pharmacology, vol. 723 (2014) pp. 305-313.
H. Tao et al., "Small Molecule Antagonists in Distinct Binding Modes Inhibit Drug-Resistant Mutant of Smoothened", Chemistry & Biology, vol. 18, No. 4 (2011) pp. 432-437.
(Continued)

*Primary Examiner* — Zachary C Howard
(74) *Attorney, Agent, or Firm* — Millen, White, Zelano & Branigan, PC

(57) ABSTRACT

The emergence of mutations in tyrosine kinases following treatment of cancer patients with molecular-targeted therapy represents a major mechanism of acquired drug resistance. Here, mutations in the serpentine receptor, Smoothened (SMO) are described, which result in resistance to a Hedgehog (Hh) pathway inhibitor, such as in medulloblastoma. Amino acid substitutions in conserved residues of SMO maintain Hh signaling, but result in the inability of the Hh pathway inhibitor, GDC-0449, to bind SMO and suppress the pathway. In some embodiments, the disclosure provides for novel mutant SMO proteins and nucleic acids and for screening methods to detect SMO mutations and methods to screen for drugs that specifically modulate mutant SMO exhibiting drug resistance.

56 Claims, 46 Drawing Sheets
Specification includes a Sequence Listing.

(56) References Cited

OTHER PUBLICATIONS

S. Nachtergaele et al., "Structure and Function of the Smoothened Extracellular Domain in Vertebrate Hedgehog Signaling", Elife, vol. 127 (2013) pp. 1-32.

J. Kim et al., "Itraconazole and Arsenic Trioxide Inhibit Hedgehog Pathway Activation and Tumor Growth Associated with Acquired Resistance to Smoothened Antagonists", Cancer Cell, vol. 23, No. 1 (2013) pp. 23-34.

S. Pricl et al., "Smoothened (SMO) Receptor Mutations Dictate Resistance to Vismodegib in Basal Cell Carcinoma", Molecular Oncology, vol. 9, No. 2 (2015) pp. 389-397.

T. Brinkhuizen et al., "Acquired Resistance to the Hedgehog Pathway Inhibitor Vismodegib Due to Smoothened Mutations in Treatment of Locally Advanced Basal Cell Carcinoma", Journal of the American Academy of Dermatology, vol. 71, No. 5 (2014) pp. 1005-1008.

Office Action dated Jul. 12, 2018 issued in corresponding SIPO application 2016800192598(9 pages).

Wang, Xi-De; PLoS One. 2013; 8(1): e54415. Published online Jan. 18, 2013. doi: 10.1371/journal.pone.0054415 (8 pages).

Stone, D; EMBL-EBI database; Q99835 dated May 1, 1997 (14 pages).

International Preliminary Report on Patentability dated Aug. 8, 2017 issued in corresponding PCT/US2016/016614 application (8 pages).

Second Office Action issued by the State Intellectual Property Office of the P.R.C. (SIPO) in Chinese Patent Application No. 201680019259.8 dated Jan. 29, 2019 (pp. 1-2).

* cited by examiner

FIG. 1A

SEQ ID NO: 1 (WT SMO)

Met Ala Ala Ala Arg Pro Ala Arg Gly Pro Glu Leu Pro Leu Leu
Gly Leu Leu Leu Leu Leu Leu Leu Gly Asp Pro Gly Arg Gly Ala
Ala Ser Ser Gly Asn Ala Thr Gly Pro Gly Pro Arg Ser Ala Gly
Gly Ser Ala Arg Arg Ser Ala Ala Val Thr Gly Pro Pro Pro Pro
Leu Ser His Cys Gly Arg Ala Ala Pro Cys Glu Pro Leu Arg Tyr
Asn Val Cys Leu Gly Ser Val Leu Pro Tyr Gly Ala Thr Ser Thr
Leu Leu Ala Gly Asp Ser Asp Ser Gln Glu Glu Ala His Gly Lys
Leu Val Leu Trp Ser Gly Leu Arg Asn Ala Pro Arg Cys Trp Ala
Val Ile Gln Pro Leu Leu Cys Ala Val Tyr Met Pro Lys Cys Glu
Asn Asp Arg Val Glu Leu Pro Ser Arg Thr Leu Cys Gln Ala Thr
Arg Gly Pro Cys Ala Ile Val Glu Arg Glu Arg Gly Trp Pro Asp
Phe Leu Arg Cys Thr Pro Asp Arg Phe Pro Glu Gly Cys Thr Asn
Glu Val Gln Asn Ile Lys Phe Asn Ser Ser Gly Gln Cys Glu Val
Pro Leu Val Arg Thr Asp Asn Pro Lys Ser Trp Tyr Glu Asp Val
Glu Gly Cys Gly Ile Gln Cys Gln Asn Pro Leu Phe Thr Glu Ala
Gln His Gln Asp Met His Ser Tyr Ile Ala Ala Phe Gly Ala Val
Thr Gly Leu Cys Thr Leu Phe Thr Leu Ala Thr Phe Val Ala Asp
Trp Arg Asn Ser Asn Arg Tyr Pro Ala Val Ile Leu Phe Tyr Val
Asn Ala Cys Phe Phe Val Gly Ser Ile Gly Trp Leu Ala Gln Phe
Met Asp Gly Ala Arg Arg Glu Ile Val Cys Arg Ala Asp Gly Thr
Met Arg Leu Gly Glu Pro Thr Ser Asn Glu Thr Leu Ser Cys Val
Ile Ile Phe Val Ile Val Tyr Tyr Ala Leu Met Ala Gly Val Val
Trp Phe Val Val Leu Thr Tyr Ala Trp His Thr Ser Phe Lys Ala
Leu Gly Thr Thr Tyr Gln Pro Leu Ser Gly Lys Thr Ser Tyr Phe
His Leu Leu Thr Trp Ser Leu Pro Phe Val Leu Thr Val Ala Ile
Leu Ala Val Ala Gln Val Asp Gly Asp Ser Val Ser Gly Ile Cys
Phe Val Gly Tyr Lys Asn Tyr Arg Tyr Arg Ala Gly Phe Val Leu
Ala Pro Ile Gly Leu Val Leu Ile Val Gly Gly Tyr Phe Leu Ile
Arg Gly Val Met Thr Leu Phe Ser Ile Lys Ser Asn His Pro Gly
Leu Leu Ser Glu Lys Ala Ala Ser Lys Ile Asn Glu Thr Met Leu
Arg Leu Gly Ile Phe Gly Phe Leu Ala Phe Gly Phe Val Leu Ile
Thr Phe Ser Cys His Phe Tyr Asp Phe Phe Asn Gln Ala Glu Trp
Glu Arg Ser Phe Arg Asp Tyr Val Leu Cys Gln Ala Asn Val Thr
Ile Gly Leu Pro Thr Lys Gln Pro Ile Pro Asp Cys Glu Ile Lys
Asn Arg Pro Ser Leu Leu Val Glu Lys Ile Asn Leu Phe Ala Met
Phe Gly Thr Gly Ile Ala Met Ser Thr Trp Val Trp Thr Lys Ala
Thr Leu Leu Ile Trp Arg Arg Thr Trp Cys Arg Leu Thr Gly Gln
Ser Asp Asp Glu Pro Lys Arg Ile Lys Lys Ser Lys Met Ile Ala
Lys Ala Phe Ser Lys Arg His Glu Leu Leu Gln Asn Pro Gly Gln
Glu Leu Ser Phe Ser Met His Thr Val Ser His Asp Gly Pro Val
Ala Gly Leu Ala Phe Asp Leu Asn Glu Pro Ser Ala Asp Val Ser
Ser Ala Trp Ala Gln His Val Thr Lys Met Val Ala Arg Arg Gly
Ala Ile Leu Pro Gln Asp Ile Ser Val Thr Pro Val Ala Thr Pro
Val Pro Pro Glu Glu Gln Ala Asn Leu Trp Leu Val Glu Ala Glu
Ile Ser Pro Glu Leu Gln Lys Arg Leu Gly Arg Lys Lys Lys Arg
Arg Lys Arg Lys Lys Glu Val Cys Pro Leu Ala Pro Pro Pro Glu
Leu His Pro Pro Ala Pro Ala Pro Ser Thr Ile Pro Arg Leu Pro
Gln Leu Pro Arg Gln Lys Cys Leu Val Ala Ala Gly Ala Trp Gly
Ala Gly Asp Ser Cys Arg Gln Gly Ala Trp Thr Leu Val Ser Asn
Pro Phe Cys Pro Glu Pro Ser Pro Pro Gln Asp Pro Phe Leu Pro
Ser Ala Pro Ala Pro Val Ala Trp Ala His Gly Arg Arg Gln Gly
Leu Gly Pro Ile His Ser Arg Thr Asn Leu Met Asp Thr Glu Leu
Met Asp Ala Asp Ser Asp Phe

FIG. 1B

SEQ ID NO: 2 (mutation at aa position 281 of SMO)

Met Ala Ala Ala Arg Pro Ala Arg Gly Pro Gln Leu Pro Leu Leu
Gly Leu Leu Leu Leu Leu Leu Leu Gly Asp Pro Gly Arg Gly Ala
Ala Ser Ser Gly Asn Ala Thr Gly Pro Gly Pro Arg Ser Ala Gly
Gly Ser Ala Arg Arg Ser Ala Ala Val Thr Gly Pro Pro Pro Pro
Leu Ser His Cys Gly Arg Ala Ala Pro Cys Glu Pro Leu Arg Tyr
Asn Val Cys Leu Gly Ser Val Leu Pro Tyr Gly Ala Thr Ser Thr
Leu Leu Ala Gly Asp Ser Asp Ser Gln Glu Glu Ala His Gly Lys
Leu Val Leu Trp Ser Gly Leu Arg Asn Ala Pro Arg Cys Trp Ala
Val Ile Gln Pro Leu Leu Cys Ala Val Tyr Met Pro Lys Cys Glu
Asn Asp Arg Val Glu Leu Pro Ser Arg Thr Leu Cys Gln Ala Thr
Arg Gly Pro Cys Ala Ile Val Glu Arg Glu Arg Gly Trp Pro Asp
Phe Leu Arg Cys Thr Pro Asp Arg Phe Pro Glu Gly Cys Thr Asn
Glu Val Gln Asn Ile Lys Phe Asn Ser Ser Gly Gln Cys Glu Val
Pro Leu Val Arg Thr Asp Asn Pro Lys Ser Trp Tyr Glu Asp Val
Glu Gly Cys Gly Ile Gln Cys Gln Asn Pro Leu Phe Thr Glu Ala
Glu His Gln Asp Met His Ser Tyr Ile Ala Ala Phe Gly Ala Val
Thr Gly Leu Cys Thr Leu Phe Thr Leu Ala Thr Phe Val Ala Asp
Trp Arg Asn Ser Asn Arg Tyr Pro Ala Val Ile Leu Phe Tyr Val
Asn Ala Cys Phe Phe Val Gly Ser Ile Gly Xaa Leu Ala Gln Phe
Met Asp Gly Ala Arg Arg Glu Ile Val Cys Arg Ala Asp Gly Thr
Met Arg Leu Gly Glu Pro Thr Ser Asn Glu Thr Leu Ser Cys Val
Ile Ile Phe Val Ile Val Tyr Tyr Ala Leu Met Ala Gly Val Val
Trp Phe Val Val Leu Thr Tyr Ala Trp His Thr Ser Phe Lys Ala
Leu Gly Thr Thr Tyr Gln Pro Leu Ser Gly Lys Thr Ser Tyr Phe
His Leu Leu Thr Trp Ser Leu Pro Phe Val Leu Thr Val Ala Ile
Leu Ala Val Ala Gln Val Asp Gly Asp Ser Val Ser Gly Ile Cys
Phe Val Gly Tyr Lys Asn Tyr Arg Tyr Arg Ala Gly Phe Val Leu
Ala Pro Ile Gly Leu Val Leu Ile Val Gly Gly Tyr Phe Leu Ile
Arg Gly Val Met Thr Leu Phe Ser Ile Lys Ser Asn His Pro Gly
Leu Leu Ser Glu Lys Ala Ala Ser Lys Ile Asn Glu Thr Met Leu
Arg Leu Gly Ile Phe Gly Phe Leu Ala Phe Gly Phe Val Leu Ile
Thr Phe Ser Cys His Phe Tyr Asp Phe Phe Asn Gln Ala Glu Trp
Glu Arg Ser Phe Arg Asp Tyr Val Leu Cys Gln Ala Asn Val Thr
Ile Gly Leu Pro Thr Lys Gln Pro Ile Pro Asp Cys Glu Ile Lys
Asn Arg Pro Ser Leu Leu Val Glu Lys Ile Asn Leu Phe Ala Met
Phe Gly Thr Gly Ile Ala Met Ser Thr Trp Val Trp Thr Lys Ala
Thr Leu Leu Ile Trp Arg Arg Thr Trp Cys Arg Leu Thr Gly Gln
Ser Asp Asp Glu Pro Lys Arg Ile Lys Lys Ser Lys Met Ile Ala
Lys Ala Phe Ser Lys Arg His Glu Leu Leu Gln Asn Pro Gly Gln
Glu Leu Ser Phe Ser Met His Thr Val Ser His Asp Gly Pro Val
Ala Gly Leu Ala Phe Asp Leu Asn Glu Pro Ser Ala Asp Val Ser
Ser Ala Trp Ala Gln His Val Thr Lys Met Val Ala Arg Arg Gly
Ala Ile Leu Pro Gln Asp Ile Ser Val Thr Pro Val Ala Thr Pro
Val Pro Pro Glu Glu Gln Ala Asn Leu Trp Leu Val Glu Ala Glu
Ile Ser Pro Glu Leu Gln Lys Arg Leu Gly Arg Lys Lys Lys Arg
Arg Lys Arg Lys Lys Glu Val Cys Pro Leu Ala Pro Pro Pro Glu
Leu His Pro Pro Ala Pro Ala Pro Ser Thr Ile Pro Arg Leu Pro
Gln Leu Pro Arg Gln Lys Cys Leu Val Ala Ala Gly Ala Trp Gly
Ala Gly Asp Ser Cys Arg Gln Gly Ala Trp Thr Leu Val Ser Asn
Pro Phe Cys Pro Glu Pro Ser Pro Pro Gln Asp Pro Phe Leu Pro
Ser Ala Pro Ala Pro Val Ala Trp Ala His Gly Arg Arg Gln Gly
Leu Gly Pro Ile His Ser Arg Thr Asn Leu Met Asp Thr Glu Leu
Met Asp Ala Asp Ser Asp Phe

FIG. 1C

SEQ ID NO: 3 (mutation at aa position 459 of SMO)

Met Ala Ala Ala Arg Pro Ala Arg Gly Pro Glu Leu Pro Leu Leu
Gly Leu Leu Leu Leu Leu Leu Leu Gly Asp Pro Gly Arg Gly Ala
Ala Ser Ser Gly Asn Ala Thr Gly Pro Gly Pro Arg Ser Ala Gly
Gly Ser Ala Arg Arg Ser Ala Ala Val Thr Gly Pro Pro Pro Pro
Leu Ser His Cys Gly Arg Ala Ala Pro Cys Glu Pro Leu Arg Tyr
Asn Val Cys Leu Gly Ser Val Leu Pro Tyr Gly Ala Thr Ser Thr
Leu Leu Ala Gly Asp Ser Asp Ser Gln Glu Gln Ala His Gly Lys
Leu Val Leu Trp Ser Gly Leu Arg Asn Ala Pro Arg Cys Trp Ala
Val Ile Gln Pro Leu Leu Cys Ala Val Tyr Met Pro Lys Cys Glu
Asn Asp Arg Val Glu Leu Pro Ser Arg Thr Leu Cys Gln Ala Thr
Arg Gly Pro Cys Ala Ile Val Glu Arg Glu Arg Gly Trp Pro Asp
Phe Leu Arg Cys Thr Pro Asp Arg Phe Pro Glu Gly Cys Thr Asn
Glu Val Gln Asn Ile Lys Phe Asn Ser Ser Gly Gln Cys Glu Val
Pro Leu Val Arg Thr Asp Asn Pro Lys Ser Trp Tyr Glu Asp Val
Glu Gly Cys Gly Ile Gln Cys Gln Asn Pro Leu Phe Thr Glu Ala
Gln His Gln Asp Met His Ser Tyr Ile Ala Ala Phe Gly Ala Val
Thr Gly Leu Cys Thr Leu Phe Thr Leu Ala Thr Phe Val Ala Asp
Trp Arg Asn Ser Asn Arg Tyr Pro Ala Val Ile Leu Phe Tyr Val
Asn Ala Cys Phe Phe Val Gly Ser Ile Gly Trp Leu Ala Gln Phe
Met Asp Gly Ala Arg Arg Glu Ile Val Cys Arg Ala Asp Gly Thr
Met Arg Leu Gly Glu Pro Thr Ser Asn Glu Thr Leu Ser Cys Val
Ile Ile Phe Val Ile Val Tyr Tyr Ala Leu Met Ala Gly Val Val
Trp Phe Val Val Leu Thr Tyr Ala Trp His Thr Ser Phe Lys Ala
Leu Gly Thr Thr Tyr Gln Pro Leu Ser Gly Lys Thr Ser Tyr Phe
His Leu Leu Thr Trp Ser Leu Pro Phe Val Leu Thr Val Ala Ile
Leu Ala Val Ala Gln Val Asp Gly Asp Ser Val Ser Gly Ile Cys
Phe Val Gly Tyr Lys Asn Tyr Arg Tyr Arg Ala Gly Phe Val Leu
Ala Pro Ile Gly Leu Val Leu Ile Val Gly Gly Tyr Phe Leu Ile
Arg Gly Val Met Thr Leu Phe Ser Ile Lys Ser Asn His Pro Gly
Leu Leu Ser Glu Lys Ala Ala Ser Lys Ile Asn Glu Thr Met Leu
Arg Leu Gly Ile Phe Gly Phe Leu Xaa Phe Gly Phe Val Leu Ile
Thr Phe Ser Cys His Phe Tyr Asp Phe Phe Asn Gln Ala Glu Trp
Glu Arg Ser Phe Arg Asp Tyr Val Leu Cys Gln Ala Asn Val Thr
Ile Gly Leu Pro Thr Lys Gln Pro Ile Pro Asp Cys Glu Ile Lys
Asn Arg Pro Ser Leu Leu Val Glu Lys Ile Asn Leu Phe Ala Met
Phe Gly Thr Gly Ile Ala Met Ser Thr Trp Val Trp Thr Lys Ala
Thr Leu Leu Ile Trp Arg Arg Thr Trp Cys Arg Leu Thr Gly Gln
Ser Asp Asp Glu Pro Lys Arg Ile Lys Lys Ser Lys Met Ile Ala
Lys Ala Phe Ser Lys Arg His Glu Leu Leu Gln Asn Pro Gly Gln
Glu Leu Ser Phe Ser Met His Thr Val Ser His Asp Gly Pro Val
Ala Gly Leu Ala Phe Asp Leu Asn Glu Pro Ser Ala Asp Val Ser
Ser Ala Trp Ala Gln His Val Thr Lys Met Val Ala Arg Arg Gly
Ala Ile Leu Pro Gln Asp Ile Ser Val Thr Pro Val Ala Thr Pro
Val Pro Pro Glu Glu Gln Ala Asn Leu Trp Leu Val Glu Ala Glu
Ile Ser Pro Glu Leu Gln Lys Arg Leu Gly Arg Lys Lys Lys Arg
Arg Lys Arg Lys Lys Glu Val Cys Pro Leu Ala Pro Pro Pro Glu
Leu His Pro Pro Ala Pro Ala Pro Ser Thr Ile Pro Arg Leu Pro
Gln Leu Pro Arg Gln Lys Cys Leu Val Ala Ala Gly Ala Trp Gly
Ala Gly Asp Ser Cys Arg Gln Gly Ala Trp Thr Leu Val Ser Asn
Pro Phe Cys Pro Glu Pro Ser Pro Pro Gln Asp Pro Phe Leu Pro
Ser Ala Pro Ala Pro Val Ala Trp Ala His Gly Arg Arg Gln Gly
Leu Gly Pro Ile His Ser Arg Thr Asn Leu Met Asp Thr Glu Leu
Met Asp Ala Asp Ser Asp Phe

FIG. 1D

SEQ ID NO: 4 (mutation at aa position 535)

Met Ala Ala Ala Arg Pro Ala Arg Gly Pro Glu Leu Pro Leu Leu
Gly Leu Leu Leu Leu Leu Leu Leu Gly Asp Pro Gly Arg Gly Ala
Ala Ser Ser Gly Asn Ala Thr Gly Pro Gly Pro Arg Ser Ala Gly
Gly Ser Ala Arg Arg Ser Ala Ala Val Thr Gly Pro Pro Pro Pro
Leu Ser His Cys Gly Arg Ala Ala Pro Cys Glu Pro Leu Arg Tyr
Asn Val Cys Leu Gly Ser Val Leu Pro Tyr Gly Ala Thr Ser Thr
Leu Leu Ala Gly Asp Ser Asp Ser Gln Glu Glu Ala His Gly Lys
Leu Val Leu Trp Ser Gly Leu Arg Asn Ala Pro Arg Cys Trp Ala
Val Ile Gln Pro Leu Leu Cys Ala Val Tyr Met Pro Lys Cys Glu
Asn Asp Arg Val Glu Leu Pro Ser Arg Thr Leu Cys Gln Ala Thr
Arg Gly Pro Cys Ala Ile Val Glu Arg Glu Arg Gly Trp Pro Asp
Phe Leu Arg Cys Thr Pro Asp Arg Phe Pro Glu Gly Cys Thr Asn
Glu Val Gln Asn Ile Lys Phe Asn Ser Ser Gly Gln Cys Glu Val
Pro Leu Val Arg Thr Asp Asn Pro Lys Ser Trp Tyr Glu Asp Val
Glu Gly Cys Gly Ile Gln Cys Glu Asn Pro Leu Phe Thr Glu Ala
Glu His Gln Asp Met His Ser Tyr Ile Ala Ala Phe Gly Ala Val
Thr Gly Leu Cys Thr Leu Phe Thr Leu Ala Thr Phe Val Ala Asp
Trp Arg Asn Ser Asn Arg Tyr Pro Ala Val Ile Leu Phe Tyr Val
Asn Ala Cys Phe Phe Val Gly Ser Ile Gly Trp Leu Ala Gln Phe
Met Asp Gly Ala Arg Arg Glu Ile Val Cys Arg Ala Asp Gly Thr
Met Arg Leu Gly Glu Pro Thr Ser Asn Glu Thr Leu Ser Cys Val
Ile Ile Phe Val Ile Val Tyr Tyr Ala Leu Met Ala Gly Val Val
Trp Phe Val Val Leu Thr Tyr Ala Trp His Thr Ser Phe Lys Ala
Leu Gly Thr Thr Tyr Gln Pro Leu Ser Gly Lys Thr Ser Tyr Phe
His Leu Leu Thr Trp Ser Leu Pro Phe Val Leu Thr Val Ala Ile
Leu Ala Val Ala Gln Val Asp Gly Asp Ser Val Ser Gly Ile Cys
Phe Val Gly Tyr Lys Asn Tyr Arg Tyr Arg Ala Gly Phe Val Leu
Ala Pro Ile Gly Leu Val Leu Ile Val Gly Gly Tyr Phe Leu Ile
Arg Gly Val Met Thr Leu Phe Ser Ile Lys Ser Asn His Pro Gly
Leu Leu Ser Glu Lys Ala Ala Ser Lys Ile Asn Glu Thr Met Leu
Arg Leu Gly Ile Phe Gly Phe Leu Ala Phe Gly Phe Val Leu Ile
Thr Phe Ser Cys His Phe Tyr Asp Phe Phe Asn Gln Ala Glu Trp
Glu Arg Ser Phe Arg Asp Tyr Val Leu Cys Gln Ala Asn Val Thr
Ile Gly Leu Pro Thr Lys Gln Pro Ile Pro Asp Cys Glu Ile Lys
Asn Arg Pro Ser Leu Leu Val Glu Lys Ile Asn Leu Phe Ala Met
Phe Gly Thr Gly Ile Ala Met Ser Thr Xaa Val Trp Thr Lys Ala
Thr Leu Leu Ile Trp Arg Arg Thr Trp Cys Arg Leu Thr Gly Gln
Ser Asp Asp Glu Pro Lys Arg Ile Lys Lys Ser Lys Met Ile Ala
Lys Ala Phe Ser Lys Arg His Glu Leu Leu Gln Asn Pro Gly Gln
Glu Leu Ser Phe Ser Met His Thr Val Ser His Asp Gly Pro Val
Ala Gly Leu Ala Phe Asp Leu Asn Glu Pro Ser Ala Asp Val Ser
Ser Ala Trp Ala Gln His Val Thr Lys Met Val Ala Arg Arg Gly
Ala Ile Leu Pro Gln Asp Ile Ser Val Thr Pro Val Ala Thr Pro
Val Pro Pro Glu Glu Gln Ala Asn Leu Trp Leu Val Glu Ala Glu
Ile Ser Pro Glu Leu Gln Lys Arg Leu Gly Arg Lys Lys Lys Arg
Arg Lys Arg Lys Lys Glu Val Cys Pro Leu Ala Pro Pro Pro Glu
Leu His Pro Pro Ala Pro Ala Pro Ser Thr Ile Pro Arg Leu Pro
Gln Leu Pro Arg Gln Lys Cys Leu Val Ala Ala Gly Ala Trp Gly
Ala Gly Asp Ser Cys Arg Gln Gly Ala Trp Thr Leu Val Ser Asn
Pro Phe Cys Pro Glu Pro Ser Pro Pro Gln Asp Pro Phe Leu Pro
Ser Ala Pro Ala Pro Val Ala Trp Ala His Gly Arg Arg Gln Gly
Leu Gly Pro Ile His Ser Arg Thr Asn Leu Met Asp Thr Glu Leu
Met Asp Ala Asp Ser Asp Phe

FIG. 1E

SEQ ID NO: 5 (WT SMO)

```
atggccgctg cccgcccagc gcggggccg gagctcccgc tcctggggct    50
gctgctgctg ctgctgctgg gggacccggg ccggggggcg gcctcgagcg   100
ggaacgcgac cggcctgggc cctggagcg cggggcggag cgcgaggagg   150
agcgggcgg tgactggccc tccgccgcg ctgagccact gcggccggc    200
tgccccctgc gagccgctgc gctacaacgt gtgcctgggc tggtgctgc    250
cctacgggc cacctccaca ctgctggccg gagactcgga ctcccaggag   300
gaagcgacg ggaagctgt gctctggtcg ggcctccgga atgccccg     350
ctgctgggca gtgatccagc ccctgctgtg tgccgtatac atgcccaagt   400
gtgagaatga ccgggtggag ctgccagcc gtacccctctg ccaggccacc   450
cgaggccct gtgccatcgt ggagagggag cgggtggc ctgacttcct    500
gcgctgcact cctgaccgct tcctgaagg ctgcacgaat gaggtgcaga   550
acatcaagtt caacagttca ggccagtgcg aagtgccctt ggttcggaca   600
gacaacccca agagctggta cgaggacgtg gagggtgcg catccagtg    650
ccagaaccc ctcttcacag aggtgagcca ccaggacatg cacagctaca   700
tgcgggcctt cgggccgtc agggcctct gcacgctct caccctggcc    750
acattcgtgg ctgactggcg gaactgaat cgctaccctg ctgttattct   800
cttctacgtc aatgctgct tcttgtggg cagcattggc tggctgygcc    850
agttcatgga tggtgccgc cgagagatcg tctgccgtgc agatggcacc    900
atgaggcttg gggagcccac ctccaatgag actctgtcct gcgtcatcat    950
ctttgtcatc gtgtactacg ccctgatggc tggtgtggtt tggtttgtgg  1000
tcctcaccta tgctggcac acttcttca aagccctggg caccacctac   1050
cagcctctct cgggcaagac ctcctacttc caactgctca cctggccact   1100
cccctttgtc ctcactgtgg caatccttgc tgtggcgcag gtggatgggg  1150
actctgtgag tggcatttgt ttgtgggct acaagaacta ccgataccgt   1200
ggggcttcg tgctggcccc aatcgggctg gtgctcatcg tgggaggcta   1250
cttcctcatc cgaggagtca tgactctgtt ctccatcaag agcaaccacc   1300
ccggctgct gagtgagaag gctgccagca agatcaacga gaccatgctg   1350
cgcctgggca ttttttggct cctggcctt ggctttgtgc tcattacctt   1400
cagctgccac ttctacgact tcttcaacca ggctgagtgg gagagcagct   1450
tcgggacta tgtgctatgt caggccaatg tgaccatcgg gctgccacc   1500
aagcagccca tccctgactg tgagatcaag aatcgcccga gccttctggt   1550
ggagaagatc aacctgtttg ccatgtttgg aactggcatc gccatgagca   1600
cctggtctg gaccaaggcc acgtgctca tctggagcg tacctggtgc   1650
aggttgactg ggcagagtga cgatgagcca aagggatca agaagagcaa   1700
gatgattgcc aaggccttct ctaagcggca cgagctctg cagaacccag   1750
gccaggagct gtccttcagc atgcagactg tgtcccacga cgggccggtg   1800
gggctgg cctttgacct caatgagccc tcagtgatg tctcctctgc   1850
ctgggccag cagtcacca agatggtggc tcggagagga gcataccgc    1900
ccaggatat ttctgtcacc cctgtggcaa ctccagtgcc cccagaggaa   1950
caagccaacc tgggctggt tgaggcagag atctccccag agctgcagaa   2000
gcgcctgggc cggaagaaga agaggaggaa gaggaagaag gaggtgtgcc   2050
cgctggcc gccccctgag cttcaccccc ctgcccctgc cccagtacc   2100
attcctgcac tgcctcagct gcccggcag aaatgctgg tgctgcagg    2150
tgcctgggga gctgggact cttgccgaca gggagcgtgg acctggtct    2200
ccaacccatt ctgccagag cccagtcccc ctcaggatcc attctgtgcc   2250
agtgcacgg ccccgtggc atggctcat ggccgcgac agggctgyg    2300
gcctattcac tcccgcacca acctgatgga cacagaactc atggatgcag   2350
actcggactt ctga                                         2364
```

FIG. 1F

SEQ ID NO: 6 – Mutation at aa position 241 of SMO
Met Ala Ala Ala Arg Pro Ala Arg Gly Pro Glu Leu Pro Leu Leu Gly Leu Leu Leu Leu
Leu Leu Leu Gly Asp Pro Gly Arg Gly Ala Ala Ser Ser Gly Asn Ala Thr Gly Pro Gly
Pro Arg Ser Ala Gly Gly Ser Ala Arg Arg Ser Ala Ala Val Thr Gly Pro Pro Pro Leu
Ser His Cys Gly Arg Ala Ala Pro Cys Glu Pro Leu Arg Tyr Asn Val Cys Leu Gly Ser
Val Leu Pro Tyr Gly Ala Thr Ser Thr Leu Leu Ala Gly Asp Ser Asp Ser Gln Glu Glu Ala
His Gly Lys Leu Val Leu Trp Ser Gly Leu Arg Asn Ala Pro Arg Cys Trp Ala Val Ile Gln
Pro Leu Leu Cys Ala Val Tyr Met Pro Lys Cys Glu Asn Asp Arg Val Glu Leu Pro Ser
Arg Thr Leu Cys Gln Ala Thr Arg Gly Pro Cys Ala Ile Val Glu Arg Glu Arg Gly Trp Pro
Asp Phe Leu Arg Cys Thr Pro Asp Arg Phe Pro Glu Gly Cys Thr Asn Glu Val Gln Asn
Ile Lys Phe Asn Ser Ser Gly Gln Cys Glu Val Pro Leu Val Arg Thr Asp Asn Pro Lys Ser
Trp Tyr Glu Asp Val Glu Gly Cys Gly Ile Gln Cys Gln Asn Pro Leu Phe Thr Glu Ala
Glu His Gln Asp Met His Ser Tyr Ile Ala Ala Phe Gly Ala Val Xaa Gly Leu Cys Thr Leu
Phe Thr Leu Ala Thr Phe Val Ala Asp Trp Arg Asn Ser Asn Arg Tyr Pro Ala Val Ile Leu
Phe Tyr Val Asn Ala Cys Phe Phe Val Gly Ser Ile Gly Trp Leu Ala Gln Phe Met Asp Gly
Ala Arg Arg Glu Ile Val Cys Arg Ala Asp Gly Thr Met Arg Leu Gly Glu Pro Thr Ser
Asn Glu Thr Leu Ser Cys Val Ile Ile Phe Val Ile Val Tyr Tyr Ala Leu Met Ala Gly Val
Val Trp Phe Val Val Leu Thr Tyr Ala Trp His Thr Ser Phe Lys Ala Leu Gly Thr Thr Tyr
Gln Pro Leu Ser Gly Lys Thr Ser Tyr Phe His Leu Leu Thr Trp Ser Leu Pro Phe Val Leu
Thr Val Ala Ile Leu Ala Val Ala Gln Val Asp Gly Asp Ser Val Ser Gly Ile Cys Phe Val
Gly Tyr Lys Asn Tyr Arg Tyr Arg Ala Gly Phe Val Leu Ala Pro Ile Gly Leu Val Leu Ile
Val Gly Gly Tyr Phe Leu Ile Arg Gly Val Met Thr Leu Phe Ser Ile Lys Ser Asn His Pro
Gly Leu Leu Ser Glu Lys Ala Ala Ser Lys Ile Asn Glu Thr Met Leu Arg Leu Gly Ile Phe
Gly Phe Leu Ala Phe Gly Phe Val Leu Ile Thr Phe Ser Cys His Phe Tyr Asp Phe Phe Asn
Gln Ala Glu Trp Glu Arg Ser Phe Arg Asp Tyr Val Leu Cys Gln Ala Asn Val Thr Ile Gly
Leu Pro Thr Lys Gln Pro Ile Pro Asp Cys Glu Ile Lys Asn Arg Pro Ser Leu Leu Val Glu
Lys Ile Asn Leu Phe Ala Met Phe Gly Thr Gly Ile Ala Met Ser Thr Trp Val Trp Thr Lys
Ala Thr Leu Leu Ile Trp Arg Arg Thr Trp Cys Arg Leu Thr Gly Gln Ser Asp Asp Glu
Pro Lys Arg Ile Lys Lys Ser Lys Met Ile Ala Lys Ala Phe Ser Lys Arg His Glu Leu Leu
Gln Asn Pro Gly Gln Glu Leu Ser Phe Ser Met His Thr Val Ser His Asp Gly Pro Val Ala
Gly Leu Ala Phe Asp Leu Asn Glu Pro Ser Ala Asp Val Ser Ser Ala Trp Ala Gln His Val
Thr Lys Met Val Ala Arg Arg Gly Ala Ile Leu Pro Gln Asp Ile Ser Val Thr Pro Val Ala
Thr Pro Val Pro Pro Glu Glu Gln Ala Asn Leu Trp Leu Val Glu Ala Glu Ile Ser Pro Glu
Leu Gln Lys Arg Leu Gly Arg Lys Lys Lys Arg Arg Lys Arg Lys Lys Glu Val Cys Pro
Leu Ala Pro Pro Pro Glu Leu His Pro Pro Ala Pro Ala Pro Ser Thr Ile Pro Arg Leu Pro
Gln Leu Pro Arg Gln Lys Cys Leu Val Ala Ala Gly Ala Trp Gly Ala Gly Asp Ser Cys
Arg Gln Gly Ala Trp Thr Leu Val Ser Asn Pro Phe Cys Pro Glu Pro Ser Pro Gln Asp
Pro Phe Leu Pro Ser Ala Pro Ala Pro Val Ala Trp Ala His Gly Arg Arg Gln Gly Leu Gly
Pro Ile His Ser Arg Thr Asn Leu Met Asp Thr Glu Leu Met Asp Ala Asp Ser Asp Phe

FIG. 1G

SEQ ID NO: 7 – (mutation at aa position 408 of SMO)
Met Ala Ala Ala Arg Pro Ala Arg Gly Pro Glu Leu Pro Leu Leu Gly Leu Leu Leu Leu
Leu Leu Leu Gly Asp Pro Gly Arg Gly Ala Ala Ser Ser Gly Asn Ala Thr Gly Pro Gly
Pro Arg Ser Ala Gly Gly Ser Ala Arg Arg Ser Ala Ala Val Thr Gly Pro Pro Pro Pro Leu
Ser His Cys Gly Arg Ala Ala Pro Cys Glu Pro Leu Arg Tyr Asn Val Cys Leu Gly Ser
Val Leu Pro Tyr Gly Ala Thr Ser Thr Leu Leu Ala Gly Asp Ser Asp Ser Gln Glu Glu Ala
His Gly Lys Leu Val Leu Trp Ser Gly Leu Arg Asn Ala Pro Arg Cys Trp Ala Val Ile Gln
Pro Leu Leu Cys Ala Val Tyr Met Pro Lys Cys Glu Asn Asp Arg Val Glu Leu Pro Ser
Arg Thr Leu Cys Gln Ala Thr Arg Gly Pro Cys Ala Ile Val Glu Arg Glu Arg Gly Trp Pro
Asp Phe Leu Arg Cys Thr Pro Asp Arg Phe Pro Glu Gly Cys Thr Asn Glu Val Gln Asn
Ile Lys Phe Asn Ser Ser Gly Gln Cys Glu Val Pro Leu Val Arg Thr Asp Asn Pro Lys Ser
Trp Tyr Glu Asp Val Glu Gly Cys Gly Ile Gln Cys Gln Asn Pro Leu Phe Thr Glu Ala
Gln His Gln Asp Met His Ser Tyr Ile Ala Ala Phe Gly Ala Val Thr Gly Leu Cys Thr Leu
Phe Thr Leu Ala Thr Phe Val Ala Asp Trp Arg Asn Ser Asn Arg Tyr Pro Ala Val Ile Leu
Phe Tyr Val Asn Ala Cys Phe Phe Val Gly Ser Ile Gly Trp Leu Ala Gln Phe Met Asp Gly
Ala Arg Arg Glu Ile Val Cys Arg Ala Asp Gly Thr Met Arg Leu Gly Glu Pro Thr Ser
Asn Glu Thr Leu Ser Cys Val Ile Ile Phe Val Ile Val Tyr Tyr Ala Leu Met Ala Gly Val
Val Trp Phe Val Val Leu Thr Tyr Ala Trp His Thr Ser Phe Lys Ala Leu Gly Thr Thr Tyr
Gln Pro Leu Ser Gly Lys Thr Ser Tyr Phe His Leu Leu Thr Trp Ser Leu Pro Phe Val Leu
Thr Val Ala Ile Leu Ala Val Ala Gln Val Asp Gly Asp Ser Val Ser Gly Ile Cys Phe Val
Gly Tyr Lys Asn Tyr Arg Tyr Arg Ala Gly Phe Val Leu Ala Pro Xaa Gly Leu Val Leu
Ile Val Gly Gly Tyr Phe Leu Ile Arg Gly Val Met Thr Leu Phe Ser Ile Lys Ser Asn His
Pro Gly Leu Leu Ser Glu Lys Ala Ala Ser Lys Ile Asn Glu Thr Met Leu Arg Leu Gly Ile
Phe Gly Phe Leu Ala Phe Gly Phe Val Leu Ile Thr Phe Ser Cys His Phe Tyr Asp Phe Phe
Asn Gln Ala Glu Trp Glu Arg Ser Phe Arg Asp Tyr Val Leu Cys Gln Ala Asn Val Thr
Ile Gly Leu Pro Thr Lys Gln Pro Ile Pro Asp Cys Glu Ile Lys Asn Arg Pro Ser Leu Leu
Val Glu Lys Ile Asn Leu Phe Ala Met Phe Gly Thr Gly Ile Ala Met Ser Thr Trp Val Trp
Thr Lys Ala Thr Leu Leu Ile Trp Arg Arg Thr Trp Cys Arg Leu Thr Gly Gln Ser Asp
Asp Glu Pro Lys Arg Ile Lys Lys Ser Lys Met Ile Ala Lys Ala Phe Ser Lys Arg His Glu
Leu Leu Gln Asn Pro Gly Gln Glu Leu Ser Phe Ser Met His Thr Val Ser His Asp Gly Pro
Val Ala Gly Leu Ala Phe Asp Leu Asn Glu Pro Ser Ala Asp Val Ser Ser Ala Trp Ala Gln
His Val Thr Lys Met Val Ala Arg Arg Gly Ala Ile Leu Pro Gln Asp Ile Ser Val Thr Pro
Val Ala Thr Pro Val Pro Pro Glu Glu Gln Ala Asn Leu Trp Leu Val Glu Ala Glu Ile Ser
Pro Glu Leu Gln Lys Arg Leu Gly Arg Lys Lys Lys Arg Arg Lys Arg Lys Lys Glu Val
Cys Pro Leu Ala Pro Pro Pro Glu Leu His Pro Pro Ala Pro Ala Pro Ser Thr Ile Pro Arg
Leu Pro Gln Leu Pro Arg Gln Lys Cys Leu Val Ala Ala Gly Ala Trp Gly Ala Gly Asp
Ser Cys Arg Gln Gly Ala Trp Thr Leu Val Ser Asn Pro Phe Cys Pro Glu Pro Ser Pro Pro
Gln Asp Pro Phe Leu Pro Ser Ala Pro Ala Pro Val Ala Trp Ala His Gly Arg Arg Gln Gly
Leu Gly Pro Ile His Ser Arg Thr Asn Leu Met Asp Thr Glu Leu Met Asp Ala Asp Ser
Asp Phe

FIG. 1H

SEQ ID NO: 8 – (mutation at aa position 469 of SMO)
Met Ala Ala Ala Arg Pro Ala Arg Gly Pro Glu Leu Pro Leu Leu Gly Leu Leu Leu Leu
Leu Leu Leu Gly Asp Pro Gly Arg Gly Ala Ala Ser Ser Gly Asn Ala Thr Gly Pro Gly
Pro Arg Ser Ala Gly Gly Ser Ala Arg Arg Ser Ala Ala Val Thr Gly Pro Pro Pro Pro Leu
Ser His Cys Gly Arg Ala Ala Pro Cys Glu Pro Leu Arg Tyr Asn Val Cys Leu Gly Ser
Val Leu Pro Tyr Gly Ala Thr Ser Thr Leu Leu Ala Gly Asp Ser Asp Ser Gln Glu Glu Ala
His Gly Lys Leu Val Leu Trp Ser Gly Leu Arg Asn Ala Pro Arg Cys Trp Ala Val Ile Gln
Pro Leu Leu Cys Ala Val Tyr Met Pro Lys Cys Glu Asn Asp Arg Val Glu Leu Pro Ser
Arg Thr Leu Cys Gln Ala Thr Arg Gly Pro Cys Ala Ile Val Glu Arg Glu Arg Gly Trp Pro
Asp Phe Leu Arg Cys Thr Pro Asp Arg Phe Pro Glu Gly Cys Thr Asn Glu Val Gln Asn
Ile Lys Phe Asn Ser Ser Gly Gln Cys Glu Val Pro Leu Val Arg Thr Asp Asn Pro Lys Ser
Trp Tyr Glu Asp Val Glu Gly Cys Gly Ile Gln Cys Gln Asn Pro Leu Phe Thr Glu Ala
Glu His Gln Asp Met His Ser Tyr Ile Ala Ala Phe Gly Ala Val Thr Gly Leu Cys Thr Leu
Phe Thr Leu Ala Thr Phe Val Ala Asp Trp Arg Asn Ser Asn Arg Tyr Pro Ala Val Ile Leu
Phe Tyr Val Asn Ala Cys Phe Phe Val Gly Ser Ile Gly Trp Leu Ala Gln Phe Met Asp Gly
Ala Arg Arg Glu Ile Val Cys Arg Ala Asp Gly Thr Met Arg Leu Gly Glu Pro Thr Ser
Asn Glu Thr Leu Ser Cys Val Ile Ile Phe Val Ile Val Tyr Tyr Ala Leu Met Ala Gly Val
Val Trp Phe Val Val Leu Thr Tyr Ala Trp His Thr Ser Phe Lys Ala Leu Gly Thr Thr Tyr
Gln Pro Leu Ser Gly Lys Thr Ser Tyr Phe His Leu Leu Thr Trp Ser Leu Pro Phe Val Leu
Thr Val Ala Ile Leu Ala Val Ala Gln Val Asp Gly Asp Ser Val Ser Gly Ile Cys Phe Val
Gly Tyr Lys Asn Tyr Arg Tyr Arg Ala Gly Phe Val Leu Ala Pro Ile Gly Leu Val Leu Ile
Val Gly Gly Tyr Phe Leu Ile Arg Gly Val Met Thr Leu Phe Ser Ile Lys Ser Asn His Pro
Gly Leu Leu Ser Glu Lys Ala Ala Ser Lys Ile Asn Glu Thr Met Leu Arg Leu Gly Ile Phe
Gly Phe Leu Ala Phe Gly Phe Val Leu Ile Thr Phe Ser Xaa His Phe Tyr Asp Phe Phe Asn
Gln Ala Glu Trp Glu Arg Ser Phe Arg Asp Tyr Val Leu Cys Gln Ala Asn Val Thr Ile Gly
Leu Pro Thr Lys Gln Pro Ile Pro Asp Cys Glu Ile Lys Asn Arg Pro Ser Leu Leu Val Glu
Lys Ile Asn Leu Phe Ala Met Phe Gly Thr Gly Ile Ala Met Ser Thr Trp Val Trp Thr Lys
Ala Thr Leu Leu Ile Trp Arg Arg Thr Trp Cys Arg Leu Thr Gly Gln Ser Asp Asp Glu
Pro Lys Arg Ile Lys Lys Ser Lys Met Ile Ala Lys Ala Phe Ser Lys Arg His Glu Leu Leu
Gln Asn Pro Gly Gln Glu Leu Ser Phe Ser Met His Thr Val Ser His Asp Gly Pro Val Ala
Gly Leu Ala Phe Asp Leu Asn Glu Pro Ser Ala Asp Val Ser Ser Ala Trp Ala Gln His Val
Thr Lys Met Val Ala Arg Arg Gly Ala Ile Leu Pro Gln Asp Ile Ser Val Thr Pro Val Ala
Thr Pro Val Pro Pro Glu Glu Gln Ala Asn Leu Trp Leu Val Glu Ala Glu Ile Ser Pro Glu
Leu Gln Lys Arg Leu Gly Arg Lys Lys Lys Arg Arg Lys Arg Lys Lys Glu Val Cys Pro
Leu Ala Pro Pro Pro Glu Leu His Pro Pro Ala Pro Ala Pro Ser Thr Ile Pro Arg Leu Pro
Gln Leu Pro Arg Gln Lys Cys Leu Val Ala Ala Gly Ala Trp Gly Ala Gly Asp Ser Cys
Arg Gln Gly Ala Trp Thr Leu Val Ser Asn Pro Phe Cys Pro Glu Pro Ser Pro Pro Gln Asp
Pro Phe Leu Pro Ser Ala Pro Ala Pro Val Ala Trp Ala His Gly Arg Arg Gln Gly Leu Gly
Pro Ile His Ser Arg Thr Asn Leu Met Asp Thr Glu Leu Met Asp Ala Asp Ser Asp Phe

FIG. 1I

SEQ ID NO: 9 – (mutation at aa position 533 of SMO)
Met Ala Ala Ala Arg Pro Ala Arg Gly Pro Glu Leu Pro Leu Leu Gly Leu Leu Leu Leu
Leu Leu Leu Gly Asp Pro Gly Arg Gly Ala Ala Ser Ser Gly Asn Ala Thr Gly Pro Gly
Pro Arg Ser Ala Gly Gly Ser Ala Arg Arg Ser Ala Ala Val Thr Gly Pro Pro Pro Pro Leu
Ser His Cys Gly Arg Ala Ala Pro Cys Glu Pro Leu Arg Tyr Asn Val Cys Leu Gly Ser
Val Leu Pro Tyr Gly Ala Thr Ser Thr Leu Leu Ala Gly Asp Ser Asp Ser Gln Glu Glu Ala
His Gly Lys Leu Val Leu Trp Ser Gly Leu Arg Asn Ala Pro Arg Cys Trp Ala Val Ile Gln
Pro Leu Leu Cys Ala Val Tyr Met Pro Lys Cys Glu Asn Asp Arg Val Glu Leu Pro Ser
Arg Thr Leu Cys Gln Ala Thr Arg Gly Pro Cys Ala Ile Val Glu Arg Glu Arg Gly Trp Pro
Asp Phe Leu Arg Cys Thr Pro Asp Arg Phe Pro Glu Gly Cys Thr Asn Glu Val Gln Asn
Ile Lys Phe Asn Ser Ser Gly Gln Cys Glu Val Pro Leu Val Arg Thr Asp Asn Pro Lys Ser
Trp Tyr Glu Asp Val Glu Gly Cys Gly Ile Gln Cys Gln Asn Pro Leu Phe Thr Glu Ala
Glu His Gln Asp Met His Ser Tyr Ile Ala Ala Phe Gly Ala Val Thr Gly Leu Cys Thr Leu
Phe Thr Leu Ala Thr Phe Val Ala Asp Trp Arg Asn Ser Asn Arg Tyr Pro Ala Val Ile Leu
Phe Tyr Val Asn Ala Cys Phe Phe Val Gly Ser Ile Gly Trp Leu Ala Gln Phe Met Asp Gly
Ala Arg Arg Glu Ile Val Cys Arg Ala Asp Gly Thr Met Arg Leu Gly Glu Pro Thr Ser
Asn Glu Thr Leu Ser Cys Val Ile Ile Phe Val Ile Val Tyr Ala Leu Met Ala Gly Val
Val Trp Phe Val Val Leu Thr Tyr Ala Trp His Thr Ser Phe Lys Ala Leu Gly Thr Thr Tyr
Gln Pro Leu Ser Gly Lys Thr Ser Tyr Phe His Leu Leu Thr Trp Ser Leu Pro Phe Val Leu
Thr Val Ala Ile Leu Ala Val Ala Gln Val Asp Gly Asp Ser Val Ser Gly Ile Cys Phe Val
Gly Tyr Lys Asn Tyr Arg Tyr Arg Ala Gly Phe Val Leu Ala Pro Ile Gly Leu Val Leu Ile
Val Gly Gly Tyr Phe Leu Ile Arg Gly Val Met Thr Leu Phe Ser Ile Lys Ser Asn His Pro
Gly Leu Leu Ser Glu Lys Ala Ala Ser Lys Ile Asn Glu Thr Met Leu Arg Leu Gly Ile Phe
Gly Phe Leu Ala Phe Gly Phe Val Leu Ile Thr Phe Ser Cys His Phe Tyr Asp Phe Phe Asn
Gln Ala Glu Trp Glu Arg Ser Phe Arg Asp Tyr Val Leu Cys Gln Ala Asn Val Thr Ile Gly
Leu Pro Thr Lys Gln Pro Ile Pro Asp Cys Glu Ile Lys Asn Arg Pro Ser Leu Leu Val Glu
Lys Ile Asn Leu Phe Ala Met Phe Gly Thr Gly Ile Ala Met Xaa Thr Trp Val Trp Thr Lys
Ala Thr Leu Leu Ile Trp Arg Arg Thr Trp Cys Arg Leu Thr Gly Gln Ser Asp Asp Glu
Pro Lys Arg Ile Lys Lys Ser Lys Met Ile Ala Lys Ala Phe Ser Lys Arg His Glu Leu Leu
Gln Asn Pro Gly Gln Glu Leu Ser Phe Ser Met His Thr Val Ser His Asp Gly Pro Val Ala
Gly Leu Ala Phe Asp Leu Asn Glu Pro Ser Ala Asp Val Ser Ser Ala Trp Ala Gln His Val
Thr Lys Met Val Ala Arg Arg Gly Ala Ile Leu Pro Gln Asp Ile Ser Val Thr Pro Val Ala
Thr Pro Val Pro Pro Glu Glu Gln Ala Asn Leu Trp Leu Val Glu Ala Glu Ile Ser Pro Glu
Leu Gln Lys Arg Leu Gly Arg Lys Lys Lys Arg Arg Lys Arg Lys Lys Glu Val Cys Pro
Leu Ala Pro Pro Pro Glu Leu His Pro Pro Ala Pro Ala Pro Ser Thr Ile Pro Arg Leu Pro
Gln Leu Pro Arg Gln Lys Cys Leu Val Ala Ala Gly Ala Trp Gly Ala Gly Asp Ser Cys
Arg Gln Gly Ala Trp Thr Leu Val Ser Asn Pro Phe Cys Pro Glu Pro Ser Pro Pro Gln Asp
Pro Phe Leu Pro Ser Ala Pro Ala Pro Val Ala Trp Ala His Gly Arg Arg Gln Gly Leu Gly
Pro Ile His Ser Arg Thr Asn Leu Met Asp Thr Glu Leu Met Asp Ala Asp Ser Asp Phe

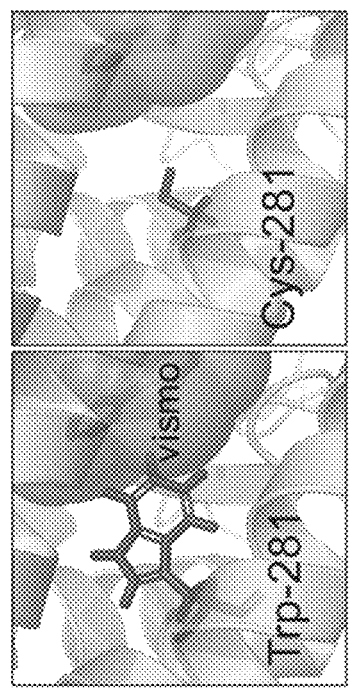
FIG. 4

| | % HEK293 cells with cell surface expression |
|---|---|
| Empty vector | 0.321 |
| SMO-WT | 58.8 |
| SMO-W281C | 52.8 |
| SMO-I408V | 46.3 |

| | % HEK293 cells with cell surface expression |
|---|---|
| Empty vector | 0.321 |
| SMO-WT | 58.8 |
| SMO-A459V | 60.8 |
| SMO-S533N | 61.7 |
| SMO-W535L | 54.1 |

MUTANT SMOOTHENED AND METHODS OF USING THE SAME

RELATED APPLICATION

This application claims the benefit of priority to U.S. provisional application Ser. No. 62/112,074, filed Feb. 4, 2015. The disclosure of the foregoing application is hereby incorporated by reference in its entirety.

SEQUENCE LISTING

The instant application contains a Sequence Listing which has been filed electronically in ASCII format and is hereby incorporated by reference in its entirety. Said ASCII copy, created on Aug. 8, 2018, is named CURGEN-0226_SL.txt and is 68,800 bytes in size.

BACKGROUND OF THE INVENTION

Molecular-targeted cancer therapeutics have shown impressive activity in the clinic. Some of the best noted examples include the tyrosine kinase inhibitors imatinib in Philadelphia chromosome-positive chronic myelogenous leukemia (CML) or KIT/PDGFR-mutant gastrointestinal stromal tumors (GISTs) and erlotinib in EGFR-mutant non-small cell lung cancer (NSCLC) (Krause, D. S. and R. A. Van Etten (2005) *N. Engl. J. Med.* 353(2):172-187). Treatment with these agents has led to dramatic anti-tumor responses in patient populations harboring these molecular abnormalities. However, despite the impressive initial clinical responses, most patients eventually progress due to the acquisition of drug resistance (Engelman, J. A. and J. Settleman (2008) *Curr. Opin. Genet. Dev.* 18(1):73-79). Identification of mechanisms of resistance have consequently opened the door to more rational drug combinations and the development of "second-generation" inhibitors that can potentially overcome or avoid the emergence of resistance.

Medulloblastoma is a primitive neuroectodermal tumor of the cerebellum that represents the most common brain malignancy in children (Polkinghorn, W. R. and N. J. Tarbell (2007) *Nat. Clin. Pract. Oncol.* 4(5):295-304). One form of treatment for medulloblastoma is adjuvant radiation therapy. Despite improvements in survival rates, adjuvant radiation is associated with debilitating side effects, thus supporting the need for new molecular targeted therapies.

The Hedgehog (Hh) signaling pathway has been directly implicated in the pathogenesis of medulloblastoma. Constitutive Hh signaling, most often due to underlying loss of function mutations in the inhibitory receptor PTCH1, has been demonstrated in approximately 30% of sporadic cases (Zurawel, R. H. et al. (2000) *Genes Chromosomes Cancer* 27(1):44-51; Kool, M. et al. (2008) *PLoS ONE* 3(8):e3088; Dellovade, T. et al. (2006) *Annu. Rev. Neurosci.* 29:539; Rubin, L. L. and F. J. de Sauvage (2006) *Nat. Rev. Drug Discov.* 5:1026). Mice heterozygous for Ptch1 (Ptch1$^{+/-}$) can spontaneously develop medulloblastoma and treatment with Hh pathway inhibitors results in tumor elimination and prolonged survival (Goodrich, L. V. et al. (1997) *Science* 277(5329):1109-1113; Romer, J. T. et al. (2004) *Cancer Cell* 6(3):229-240). However, it has recently been observed that a patient treated with the novel Hh pathway inhibitor, GDC-0449 initially showed a dramatic response to treatment (Charles M. Rudin et al. (2009) *N. Engl. J. Med.* (submitted)), only to fail to have a durable response to treatment and a relapse of the tumor.

BCC is the most common human cancer and is predominantly driven by hyperactivation of the Hh pathway (Oro et al., 1997; Xie et al., 1998). The association between Hh signaling and cancer was first discovered in patients with Gorlin or basal cell nevus syndrome (BCNS), who are highly susceptible to medulloblastoma (MB) and BCC. These patients generally possess heterozygous germline mutations in Patched 1 (PTCH1), which encodes a receptor for Hh ligands (Hahn et al., 1996; Johnson et al., 1996). Hh ligand binding relieves PTCH1 suppression of the serpentine transmembrane (TM) signal transducer Smoothened (SMO). The vast majority of sporadic BCCs are driven by inactivating mutations and loss of heterozygosity (LOH) in PTCH1, with most of the remainder harboring activating mutations in SMO (Reifenberger et al., 2005). SMO promotes the activation and nuclear localization of GLI transcription factors by inhibition of Suppressor of fused (SUFU) and Protein kinase A (PKA). SUFU negatively regulates the Hh pathway by binding and sequestering GLI transcription factors in the cytoplasm (Stone et al., 1999). Loss-of-function mutations in SUFU are also associated with Gorlin Syndrome (Pastorino et al., 2009; Smith et al., 2014; Taylor et al., 2002). Approximately 50% of sporadic BCCs also have TP53 mutations (Jayaraman et al., 2014).

Several Hh pathway inhibitors (HPIs) are currently under clinical investigation for both BCC and MB (Amakye et al., 2013). Vismodegib, previously known as GDC-0449, is a SMO inhibitor approved for the treatment of metastatic and locally advanced BCC (Sekulic et al., 2012). The majority of BCC patients treated with vismodegib experience a clinical benefit, including both complete and partial responses (Sekulic et al., 2012).

However, a preliminary estimate suggests that up to 20% of advanced BCC patients develop resistance to vismodegib within the first year of treatment (Chang and Oro, 2012). To date, the only functionally characterized mechanism of acquired resistance to vismodegib in the clinic came from a patient with metastatic MB. A SMO-D473H mutation was detected in a biopsy from a relapsed metastatic tumor and was shown to abrogate drug binding in vitro (Yauch et al., 2009). Four other clinical SMO mutations were recently reported in vismodegib-resistant BCC, but were not examined functionally (Brinkhuizen et al., 2014; Pricl et al., 2014). Several resistance mechanisms to SMO inhibitors have been delineated from preclinical models, including additional SMO mutations, amplification of downstream Hh pathway components such as GLI2, and activation of bypass signaling pathways including phosphatidylinositol 3-kinase (PI3K) kinase and atypical protein kinase C ι/λ (aPKC-ι/λ) (Atwood et al., 2013; Buonamici et al., 2010; Dijkgraaf et al., 2011). However, it remains unclear which mechanisms drive resistance in patients.

There is an urgent need in the art to identify additional GDC-0449-resistant mutant SMO proteins and to find compounds that modulate SMO activity in such mutant SMO proteins to overcome drug resistance upon treatment with GDC-0449. There is further a need to a method to diagnose patients who may be resistant to treatment either through natural variation of their SMO genotype or through acquired mutation and resistance.

SUMMARY OF THE DISCLOSURE

The present disclosure relates, in certain embodiments, to isolated mutant SMO nucleic acids and proteins, such as those related to chemotherapeutic resistance of tumors and methods of screening for compounds that bind to SMO mutants, or modulate SMO activity, and to cancer diagnostics and therapies and in particular to the detection of mutations that are diagnostic and/or prognostic and treatment of drug-resistant tumors.

In some embodiments, the disclosure provides for a method of screening for compounds that inhibit signaling of a mutant SMO protein that incorporates a mutation at amino acid 241 comprising contacting said mutant SMO with a test compound and detecting binding of said compound to said mutant SMO whereby binding of said test compound to mutant SMO indicates that said test compound is an inhibitor of mutant SMO.

In some embodiments, the disclosure provides for a method of screening for compounds that inhibit signaling of a mutant SMO protein that incorporates a mutation at amino acid 241 comprising contacting a cell that expresses said mutant SMO with a test compound and detecting activity of Gli in said cell whereby the presence of Gli activity indicates that said test compound is not an inhibitor of mutant SMO.

In some embodiments, the disclosure provides for a method of screening for compounds that inhibit signaling of a mutant SMO protein that incorporates a mutation at amino acid 469 comprising contacting said mutant SMO with a test compound and detecting binding of said compound to said mutant SMO whereby binding of said test compound to mutant SMO indicates that said test compound is an inhibitor of mutant SMO.

In some embodiments, the disclosure provides for a method of screening for compounds that inhibit signaling of a mutant SMO protein that incorporates a mutation at amino acid 469 comprising contacting a cell that expresses said mutant SMO with a test compound and detecting activity of Gli in said cell whereby the presence of Gli activity indicates that said test compound is not an inhibitor of mutant SMO.

In some embodiments, the disclosure provides for an isolated mutant SMO protein comprising an amino acid sequence that is at least 95% identical to SEQ ID NO: 6 wherein said amino acid sequence comprises an amino acid other than threonine at amino acid 241. In some embodiments, the isolated mutant SMO protein comprises the amino acid sequence of SEQ ID NO: 6 wherein said amino acid sequence comprises an amino acid other than threonine at amino acid 241. In some embodiments, the amino acid sequence comprises methionine (M) at amino acid 241.

In some embodiments, the disclosure provides for an isolated mutant SMO protein comprising an amino acid sequence that is at least 95% identical to SEQ ID NO: 8 wherein said amino acid sequence comprises an amino acid other than cysteine (C) at amino acid 469. In some embodiments, the mutant SMO protein comprises the amino acid sequence of SEQ ID NO: 8 wherein said amino acid sequence comprises an amino acid other than cysteine (C) at amino acid 469. In some embodiments, the amino acid sequence comprises tyrosine (Y) at amino acid 469.

In some embodiments, the disclosure provides for a method of identifying a hedgehog pathway inhibitor, wherein the method comprises: contacting a cell with an amount of a test agent, wherein the cell is responsive to hedgehog protein or has increased hedgehog signaling and/or activation of the hedgehog signaling pathway, and wherein the cell expresses any of the mutant SMO proteins disclosed herein, and b) determining, as compared to a control, whether the test agent inhibits hedgehog signaling in the cell, wherein if the test agent inhibits hedgehog signaling in the cell relative to the control, then the test agent is identified as a hedgehog pathway inhibitor. In some embodiments, the ability of the test agent to inhibit hedgehog signaling in the cell is determined using a Gli1 expression assay.

In some embodiments, the disclosure provides for a method of identifying a hedgehog pathway inhibitor, wherein the method comprises: contacting a cell with an amount of a test agent, wherein the cell is responsive to hedgehog protein or has increased hedgehog signaling and/or activation of the hedgehog signaling pathway, and wherein the cell expresses any of the mutant SMO proteins disclosed herein, and b) determining, as compared to a control, whether the test agent inhibits growth and/or proliferation of the cell, wherein if the test agent inhibits growth and/or proliferation of the cell relative to the control, then the test agent is identified as a hedgehog pathway inhibitor. In some embodiments, the control is a cell expressing a wildtype SMO protein. In some embodiments, the control is a cell expressing the same mutant SMO proteins as the cell contacted with the test agent, wherein the control is treated with a control agent to which the mutant SMO protein is partially or completely resistant. In some embodiments, the control agent is vismodegib, LY2940680, LDE225 and/or compound 5. In some embodiments, the test agent binds to mutant SMO protein but not wildtype SMO protein. In some embodiments, the test agent binds to both the mutant SMO protein and wildtype SMO protein. In some embodiments, the test agent is more effective in inhibiting the hedgehog signaling pathway in a cell expressing mutant SMO protein than in a cell expressing wildtype SMO protein. In some embodiments, the test agent is more effective in inhibiting growth and/or proliferation of a cell expressing mutant SMO protein than of a cell expressing wildtype SMO protein.

In some embodiments, the disclosure provides for an isolated nucleic acid molecule encoding a mutant SMO protein comprising an amino acid sequence that is at least 95% identical to SEQ ID NO: 1 wherein said amino acid sequence comprises an amino acid other than threonine at amino acid 241. In some embodiments, the mutant SMO protein comprises the amino acid sequence of SEQ ID NO: 6 wherein said amino acid sequence comprises a methionine (M) at amino acid 241. In some embodiments, the nucleic acid comprises a parental nucleic acid sequence of SEQ ID NO: 5, wherein said sequence contains a mutation that alters the sequence encoding amino acid 241 to encode a different amino acid.

In some embodiments, the disclosure provides for an isolated nucleic acid molecule encoding a mutant SMO protein comprising an amino acid sequence that is at least 95% identical to SEQ ID NO: 1 wherein said amino acid sequence comprises an amino acid other than cysteine (C) at amino acid 469. In some embodiments, the mutant SMO protein comprises the amino acid sequence of SEQ ID NO: 8 wherein said amino acid sequence comprises a tyrosine (Y) at amino acid 469. In some embodiments, the isolated nucleic acid molecule comprises a parental nucleic acid sequence of SEQ ID NO: 5, wherein said sequence contains a mutation that alters the sequence encoding amino acid 469 to encode a different amino acid.

In some embodiments, the disclosure provides for a vector comprising any of the nucleic acids disclosed herein.

In some embodiments, the disclosure provides for a host cell comprising any of the vectors disclosed herein.

In some embodiments, the disclosure provides for a host cell comprising and capable of expressing any of the vectors disclosed herein.

In some embodiments, the disclosure provides for a method of identifying a hedgehog pathway inhibitor, wherein the method comprises: contacting a cell with an amount of a test agent, wherein the cell is responsive to hedgehog protein or has increased hedgehog signaling and/or activation of the hedgehog signaling pathway, and wherein the cell expresses any of the vectors disclosed herein, and b) determining, as compared to a control, whether the test agent inhibits hedgehog signaling in the cell, wherein if the test agent inhibits hedgehog signaling in the cell relative to the control, then the test agent is identified as a hedgehog pathway inhibitor.

In some embodiments, the ability of the test agent to inhibit hedgehog signaling in the cell is determined using a Gli1 expression assay.

In some embodiments, the disclosure provides for a method of identifying a hedgehog pathway inhibitor, wherein the method comprises: contacting a cell with an amount of a test agent, wherein the cell is responsive to hedgehog protein or has increased hedgehog signaling and/or activation of the hedgehog signaling pathway, and wherein the cell expresses any of the vectors disclosed herein, and b) determining, as compared to a control, whether the test agent inhibits growth and/or proliferation of the cell, wherein if the test agent inhibits growth and/or proliferation of the cell relative to the control, then the test agent is identified as a hedgehog pathway inhibitor.

In some embodiments, the disclosure provides for a method of detecting a mutated SMO gene in a sample comprising amplifying from said sample nucleic acid corresponding to the carboxy-terminus of the first extracellular loop of SMO, or a fragment thereof suspected of containing a mutation, and comparing the electrophoretic mobility of the amplified nucleic acid to the electrophoretic mobility of corresponding wild-type SMO gene or fragment thereof. In some embodiments, the electrophoretic mobility is determined on polyacrylamide gel.

In some embodiments, the disclosure provides for a method of detecting a mutated SMO gene in a sample comprising amplifying from said sample nucleic acid corresponding to the carboxy-terminus of transmembrane domain 6 of SMO, or a fragment thereof suspected of containing a mutation, and comparing the electrophoretic mobility of the amplified nucleic acid to the electrophoretic mobility of corresponding wild-type SMO gene or fragment thereof. In some embodiments, the electrophoretic mobility is determined on polyacrylamide gel.

In some embodiments, the disclosure provides for a method of identifying at least one SMO mutation in a sample comprising contacting nucleic acid from said sample with a nucleic acid probe that is capable of specifically hybridizing to nucleic acid encoding a mutated SMO protein, or fragment thereof incorporating a mutation that alters the sequence encoding amino acid 241 to an amino acid other than threonine, and detecting said hybridization. In some embodiments, the probe is detectably labeled. In some embodiments, the probe is an antisense oligomer. In some embodiments, the SMO gene or a fragment thereof in said nucleic acid said sample is amplified and contacted with said probe.

In some embodiments, the disclosure provides for a method of identifying at least one SMO mutation in a sample comprising contacting nucleic acid from said sample with a nucleic acid probe that is capable of specifically hybridizing to nucleic acid encoding a mutated SMO protein, or fragment thereof incorporating a mutation that alters the sequence encoding amino acid 469 to an amino acid other than cysteine, and detecting said hybridization. In some embodiments, the probe is detectably labeled. In some embodiments, the probe is an antisense oligomer. In some embodiments, the SMO gene or a fragment thereof in said nucleic acid said sample is amplified and contacted with said probe.

In some embodiments, the disclosure provides for a method for identifying a tumor in a human subject that is resistant to treatment with GDC-0449 comprising determining the presence of a mutated SMO gene or mutated SMO protein in a sample of said tumor, wherein said mutated SMO gene encodes a SMO protein comprising a mutation at amino acid 241, and wherein said SMO protein comprises a mutation at amino acid 241, whereby the presence of said mutated SMO gene or mutated SMO protein indicates that said tumor is resistant to treatment with a GDC-0449. In some embodiments, the method further comprises treating said subject having a tumor that is not or is no longer susceptible to treatment with GDC-0449 with a compound that binds said mutated SMO. In some embodiments, the presence or absence of said mutation is determined by examining a nucleic acid sample. In some embodiments, the presence or absence of said mutation is determined by examining a protein sample.

In some embodiments, the disclosure provides for a method for identifying a tumor in a human subject that is resistant to treatment with GDC-0449 comprising determining the presence of a mutated SMO gene or mutated SMO protein in a sample of said tumor, wherein said mutated SMO gene encodes a SMO protein comprising a mutation at amino acid 469, and wherein said SMO protein comprises a mutation at amino acid 469, whereby the presence of said mutated SMO gene or mutated SMO protein indicates that said tumor is resistant to treatment with a GDC-0449. In some embodiments, the method further comprises treating said subject having a tumor that is not or is no longer susceptible to treatment with GDC-0449 with a compound that binds said mutated SMO. In some embodiments, the presence or absence of said mutation is determined by examining a nucleic acid sample. In some embodiments, the presence or absence of said mutation is determined by examining a protein sample.

In some embodiments, the disclosure provides for a method of inhibiting proliferation or growth of a cell having aberrant hedgehog signaling, comprising administering to said cell a bromodomain inhibitor, wherein said cell expresses a smoothened protein having a mutation at any one or more of the amino acid positions corresponding to amino acid positions 241 or 469 of SEQ ID NO: 1. In some embodiments, the cell is in a subject. In some embodiments, the cell is a cancer cell. In some embodiments, the cell further comprises a SUFU mutation. In some embodiments, the cell is a human cell, and wherein said cell comprises a 10q deletion mutation that results in the loss of a copy of the SUFU gene. In some embodiments, the 10q deletion further results in the loss of a copy of the PTEN gene. In some embodiments, the bromodomain inhibitor is I-BET762, JQ1 or JQ2.

In some embodiments, the disclosure provides for a nucleic acid probe capable of specifically hybridizing to nucleic acid encoding a mutated SMO protein or fragment thereof incorporating a mutation in the sequence encoding amino acid 241. In some embodiments, the probe is complementary to said nucleic acid encoding the mutated SMO or said fragment thereof. In some embodiments, the probe has a length of about 10 to about 50 nucleotides. In some embodiments, the probe further comprises a detectable label.

In some embodiments, the disclosure provides for a nucleic acid probe capable of specifically hybridizing to nucleic acid encoding a mutated SMO protein or fragment thereof incorporating a mutation in the sequence encoding amino acid 469. In some embodiments, the probe is complementary to said nucleic acid encoding the mutated SMO or said fragment thereof. In some embodiments, the probe has a length of about 10 to about 50 nucleotides. In some embodiments, the probe further comprises a detectable label.

In some embodiments, the disclosure provides for an antibody that specifically binds to any of the mutant SMO proteins disclosed herein, wherein said antibody does not bind wild-type SMO having an threonine at amino acid 241. In some embodiments, the antibody is a monoclonal antibody, a chimeric antibody, a humanized antibody, a single chain antibody or an antigen-binding fragment thereof. In some embodiments, the antibody is conjugated to a cytotoxic agent. In some embodiments, the antibody is conjugated to a detectable label. In some embodiments, the antibody inhibits SMO activity.

In some embodiments, the disclosure provides for an antibody that specifically binds to any of the mutant SMO proteins disclosed herein, wherein the epitope of said antibody does not bind wild-type SMO having a cysteine at amino acid 469. In some embodiments, the antibody is a monoclonal antibody, a chimeric antibody, a humanized antibody, a single chain antibody or an antigen-binding fragment thereof. In some embodiments, the antibody is conjugated to a cytotoxic agent. In some embodiments, the antibody is conjugated to a detectable label. In some embodiments, the antibody inhibits SMO activity.

BRIEF DESCRIPTION OF THE DRAWINGS

FIGS. 1A-1I show the amino acid sequences for wildtype human SMO (1A) and for several human mutant SMOs (1B-1I). FIG. 1A shows SEQ ID NO: 1. FIG. 1B shows SEQ ID NO:2. FIG. 1C shows SEQ ID NO: 3. FIG. 1D shows SEQ ID NO: 4. FIG. 1E shows SEQ ID NO: 5. FIG. 1F shows SEQ ID NO: 6. FIG. 1G shows SEQ ID NO: 7. FIG. 1H shows SEQ ID NO: 8. FIG. 1I shows SEQ ID NO: 9.

FIG. 4 shows the vismodegib binding pocket of a SMO mutant having a W281 mutation.

FIG. 10B, middle shows the C281 mutant from PT02 likely disrupts the interaction with vismodegib. FIG. 10B, right shows the M321 mutant from PT09 is expected to impact the conformation of W281.

DETAILED DESCRIPTION

Figure 2:
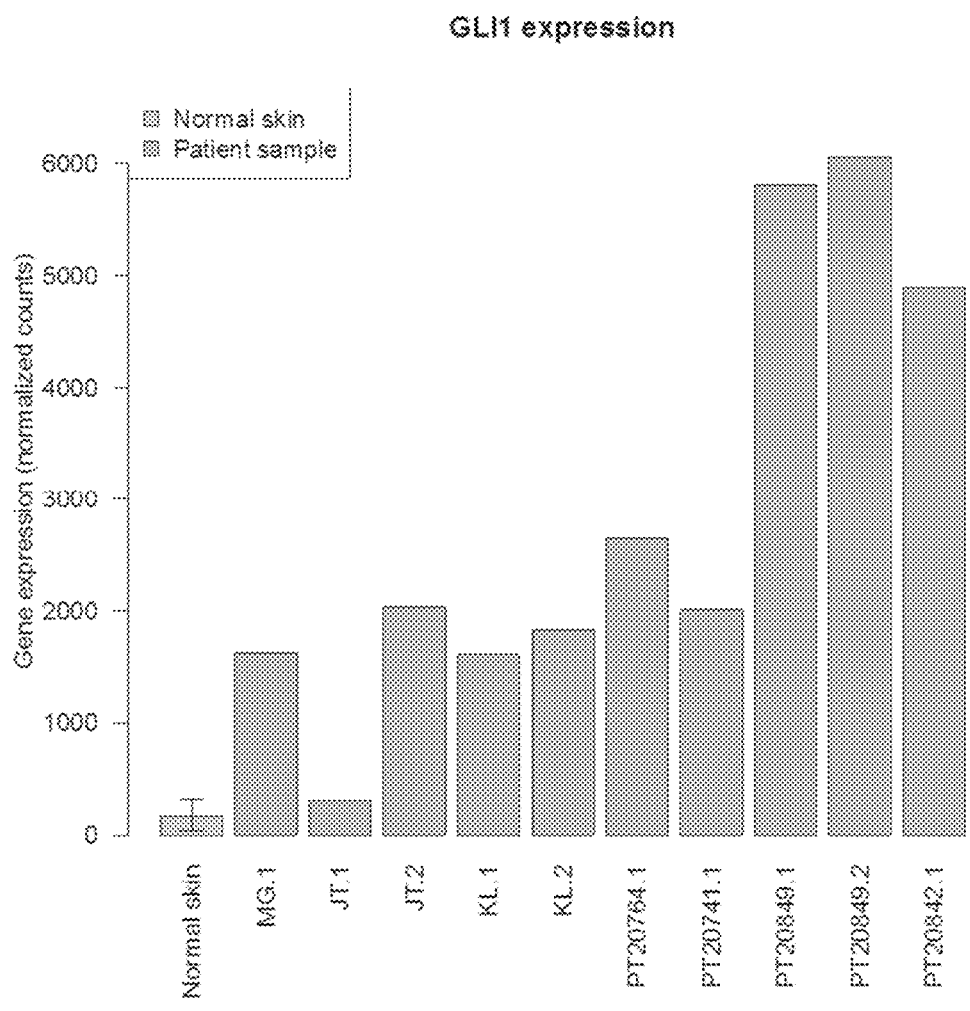
FIG. 2 shows the results of experiments performed to determine hedgehog pathway signaling levels in vismodegib-resistant BCCs.

It is a discovery of the present disclosure that mutational events associated with resistance to chemotherapy for hedgehog-dependent tumors occur in Smoothened (SMO) which impart resistance of the tumors to treatment with compounds that inhibit hedgehog signaling such as cyclopamine and GDC-0449. The present disclosure provides compositions and methods that are useful as prognostics, diagnostics and therapeutics for cancer that is dependent on Hedgehog signaling.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3rd. edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): PCR 2: A Practical Approach (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993). Cited references are incorporated by reference in their entirety.

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. As used herein, the term "polypeptide," "peptide" and "protein" encompass, at least, any of the mutant SMO proteins, variants or fragments thereof described herein.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, and in some embodiments, comprise the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthiin, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this disclosure. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler and Milstein, *Nature*, 256: 495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34):12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and U.S. Pat. No. 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | C | Contact |
|------|---|---------|
| L1 | LLL | L30-L36 |
| L2 | LLL | L46-L55 |
| L3 | LLL | L89-L96 |
| H1 |  | H31-H35B H26-H35B H H30 (Kabat Numbering) |
| H1 | HHH | H30 (Chothia Numbering) |
| H2 | HHH | H47-H58 |
| H3 |  | H95-H102 H95-H102 H9 H93-H101 |

HVRs may comprise "extended HVRs" as follows: 24-36 or 24-34 (L), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced using certain procedures known in the art. For example, Marks et al. *Bio/Technology* 10:779-783 (1992) describes affinity maturation by VH and VL domain shuffling. Random mutagenesis of HVR and/or framework residues is described by, for example, Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody," as used herein, is an antibody which partially or fully mimics at least one of the functional activities of a polypeptide of int "Growth inhibitory" antibodies are those that prevent or reduce proliferation of a cell expressing an antigen to which the antibody binds. For example, the antibody may prevent or reduce proliferation of cancer cells that express Smo or mutant in vitro and/or in vivo.

Antibodies that "induce apoptosis" are those that induce programmed cell death as determined by standard apoptosis assays, such as binding of annexin V, fragmentation of DNA, cell shrinkage, dilation of endoplasmic reticulum, cell fragmentation, and/or formation of membrane vesicles (called apoptotic bodies).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, and, in some embodiments, one or more amino acid substitution(s). In some embodiments, the variant Fc region has at least one amino acid substitution compared to a native sequence Fc region or to the Fc region of a parent polypeptide, e.g. from about one to about ten amino acid substitutions, and, in some embodiments, from about one to about five amino acid substitutions in a native sequence Fc region or in the Fc region of the parent polypeptide. The variant Fc region herein will in some embodiments possess at least about 80% homology with a native sequence Fc region and/or with an Fc region of a parent polypeptide, and in some embodiments at least about 90% homology therewith, and in some embodiments at least about 95% homology therewith.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. J. Biol. Chem. 9(2):6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. PNAS (USA) 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., J. Immunol. Methods 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. J. Immunol. 164: 4178-4184 (2000).

The term "Fc region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this disclosure can comprise an antibody with K447, with all K447 removed, or a mixture of antibodies with and without the K447 residue.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative and exemplary embodiments for measuring binding affinity are described in the following.

In one embodiment, the "Kd" or "Kd value" according to this disclosure is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, the Kd or Kd value is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN-20™ surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

An "on-rate," "rate of association," "association rate," or "$k_{on}$" according to this disclosure can also be determined as described above using a BIACORE®-2000 or a BIACORE®-3000 system (BIAcore, Inc., Piscataway, N.J.).

The term "substantially similar" or "substantially the same," as used herein, denotes a sufficiently high degree of similarity between two numeric values (for example, one associated with an antibody of the disclosure and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Purified" means that a molecule is present in a sample at a concentration of at least 95% by weight, or at least 98% by weight of the sample in which it is contained.

An "isolated" nucleic acid molecule is a nucleic acid molecule that is separated from at least one other nucleic acid molecule with which it is ordinarily associated, for example, in its natural environment. An isolated nucleic acid molecule further includes a nucleic acid molecule contained in cells that ordinarily express the nucleic acid molecule, but the nucleic acid molecule is present extrachromosomally or at a chromosomal location that is different from its natural chromosomal location.

An "isolated" protein is a protein that is separated from at least one other cellular component with which it is ordinarily associated, for example, in its natural environment. In some embodiments, an "isolated" protein is a protein expressed in a cell in which the protein is not normally expressed. In some embodiments, the isolated protein is a recombinant protein.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. In some embodiments, the nucleic acid is a cDNA molecule, or fragment thereof. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "Smo," or "SMO" or "smoothened" as used interchangeably herein, refers to any native smoothened protein or nucleic acid from any vertebrate source, including mammals such as primates (e.g. humans) and rodents (e.g., mice and rats), unless otherwise indicated. The term encompasses "full-length," unprocessed SMO as well as any form of SMO that results from processing in the cell. The term also encompasses naturally occurring variants of SMO, e.g., splice variants or allelic variants. In some embodiments, "mutant SMO" or "mutant SMO polypeptide" or "mutant SMO protein" as used herein, refers to SMO having a mutation in the first transmembrane of SMO at position 241 of human SMO, to SMO having a mutation in the second transmembrane of SMO at position 281 of human SMO, to SMO having a mutation in the fifth transmembrane domain of SMO at position 408 of human SMO, to SMO having a mutation in transmembrane domain 6 of SMO at position 459 or 469 of human SMO, and/or to SMO having a mutation in the carboxy-terminal portion of transmembrane domain 7 of SMO at position 533 or 535 of human SMO. In some embodiments, "mutant SMO" or "mutant SMO polypeptide" or "mutant SMO protein" as used herein, refers to a smoothened polypeptide comprising a mutation at one or more amino acids corresponding to positions 241, 281, 408, 412, 459, 469, 533 and/or 535 of SEQ ID NO: 1. In some embodiments, the mutation at one or more amino acids corresponding to positions 241, 281, 408, 412, 459, 469, 533 and/or 535 of SEQ ID NO: 1 comprises T241M, W281C, I408V, A459V, C469Y, S533N and/or W535L. Similarly, a mutant SMO protein is described as having variation at any one or more of the foregoing position of wildtype human SMO. The disclosure contemplates that any of the mutant polypeptides or nucleic acids described herein can be described relative to a sequence identifier or described relative to wildtype human SMO. Moreover, mutants can be described relative to SEQ ID NO: 1 or described relative to any of the other sequence identifiers.

In some embodiments, as used herein, "treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the disclosure are used to delay development of a disease or disorder or to slow the progression of a disease or disorder. In some embodiments, as used herein, "treating" or "treatment" or "alleviation" refers to improving, alleviating, and/or decreasing the severity of one or more symptoms of a condition being treated. By way of example, treating cancer refers to improving (improving the patient's condition), alleviating, delaying or slowing progression or onset, decreasing the severity of one or more symptoms of cancer. For example, treating cancer includes any one or more of: decreasing tumor size, decreasing rate of tumor size increase, halting increase in size, decreasing the number of metastases, decreasing pain, increasing survival, and increasing progression free survival.

"Treating" or "treatment" or "alleviation" refers to improving, alleviating, and/or decreasing the severity of one or more symptoms of a condition being treated. By way of example, treating cancer refers to improving (improving the patient's condition), alleviating, delaying or slowing progression or onset, decreasing the severity of one or more symptoms of cancer. For example, treating cancer includes any one or more of: decreasing tumor size, decreasing rate of tumor size increase, halting increase in size, decreasing the number of metastases, decreasing pain, increasing survival, and increasing progression free survival. "Diagnosing" refers to the process of identifying or determining the distinguishing characteristics of a disease or tumor. In the case of cancer, the process of diagnosing is sometimes also expressed as staging or tumor classification based on severity or disease progression.

"Diagnosing" refers to the process of identifying or determining the distinguishing characteristics of a disease or tumor. In the case of cancer, the process of diagnosing is sometimes also expressed as staging or tumor classification based on severity or disease progression.

An "individual," "subject," or "patient" is a vertebrate, such as a human. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

The term "pharmaceutical formulation" refers to a preparation which is in such form as to permit the biological activity of the active ingredient to be effective, and which contains no additional components which are unacceptably toxic to a subject to which the formulation would be administered. Such formulations may be sterile. In certain embodiments, the pharmaceutical formulation is pyrogen free.

A "sterile" formulation is aseptic or free from all living microorganisms and their spores. An "effective amount" refers to an amount effective, at dosages and for periods of time necessary, to achieve the desired therapeutic or prophylactic result.

A "therapeutically effective amount" of a substance/molecule of the disclosure may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents a cellular function and/or causes cell death or destruction. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, g Lys Lys Glu Val Cys Pro Leu Ala Pro Pro Pro Glu Leu His Pro Pro Ala Pro Ala Pro bacterial, fungal, plant or animal origin, including fragments and/or variants thereof, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omega1I (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), pegylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

A "growth inhibitory agent" when used herein refers to a compound or composition which inhibits growth of a cell (such as a cell expressing SMO) either in vitro or in vivo. Thus, the growth inhibitory agent may be one which significantly reduces the percentage of cells (such as a cell expressing SMO) in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

A "mutant Smo antagonist" is a compound that inhibits the biological activity of a SMO having an amino acid substitution at position 241, 281, 408, 459, 469, 533, or 535 of human SMO that changes the wild-type amino acid at this position to any other amino acid. In some embodiments, the biological activity of SMO is the ability to transduce a signal upon stimulation with hedgehog to activation of Gli transcription factor.

The term "hedgehog pathway inhibitor," as used herein, is intended to refer to an agent that is capable of inhibiting hedgehog signaling in a cell. In particular embodiments, the hedgehog antagonist is capable of inhibiting hedgehog signaling in a cell that expresses any of the mutant SMO proteins described herein. In some embodiments, the hedgehog pathway inhibitor is capable of inhibiting hedgehog signaling in a cell that expresses a smoothened polypeptide comprising a mutation at one or more amino acids corresponding to 241, 281, 408, 459, 469, 533 or 535 of SEQ ID NO: 1 (e.g., to the corresponding position in wildtype human SMO). In some embodiments, the hedgehog pathway inhibitor is capable of inhibiting hedgehog signaling in a cell that expresses a smoothened polypeptide comprising any of the following mutations: T241M, W281C, I408V, A459V, C469Y, S533N and/or W535L.

I. Nucleic Acids

The nucleic acids of the disclosure include isolated mutant SMO-encoding sequences. In some embodiments, the nucleic acids encode a mutant SMO protein that is partially or fully resistant to vismodegib. In some embodiments, the nucleic acid encodes a mutant SMO protein that is partially or fully resistant to vismodegib in a cell having an additional mutation in a gene encoding a protein in the hedgehog signaling pathway. In some embodiments, the additional mutation is any of the patched and/or SUFU mutations described herein.

In some embodiments, the disclosure provides for an isolated nucleic acid molecule encoding a mutant SMO protein wherein said amino acid sequence comprises an amino acid other than alanine at the amino acid position corresponding to position 239 of the wildtype SMO amino acid sequence. In some embodiments nucleic acids comprise a sequence that is at least 80%, 85%, 86%, 87%, 88%, 89%, 90%, 91%, 92%, 93%, 94%, 95%, 96%, 97%, 98%, 99% or 100% identical to the nucleic acid sequence of SEQ ID NO:5, and which contain at least one mutation such that the nucleic acid encodes a SMO polypeptide comprising an amino acid other than alanine (A) at the amino acid position corresponding to position 239 of SEQ ID NO: 1. In some embodiments, such a nucleic acid encodes valine (V) at the amino acid position corresponding to position 239 of SEQ ID NO: 1. In some embodiments, the nucleic acid has at least one mutation from the parental wild-type SMO at a nucleotide position corresponding to position 715, 716, and/or 717 of SEQ ID NO: 5. In some embodiments, the percent identity is 85%, 86%, 87%, 88%, 89%, 90%, 91%, 92%, 93%, 94%, 95%, 96%, 97%, 98%, 99% or 100% with SEQ ID NO: 5 providing that there is at least one mutation at a nucleotide position corresponding to positions 715, 716, and/or 717 of SEQ ID NO: 5. In some embodiments, the disclosure provides for an isolated nucleic acid molecule encoding a mutant SMO protein wherein said amino acid sequence comprises an amino acid other than threonine at the amino acid position corresponding to position 241 of the wildtype SMO amino acid sequence. In some embodiments nucleic acids comprise a sequence that is at least 80%, 85%, 86%, 87%, 88%, 89%, 90%, 91%, 92%, 93%, 94%, 95%, 96%, 97%, 98%, 99% or 100% identical to the nucleic acid sequence of SEQ ID NO:5, and which contain at least one mutation such that the nucleic acid encodes a SMO polypeptide comprising an amino acid other than threonine (T) at the amino acid position corresponding to position 241 of SEQ ID NO: 1. In some embodiments, such a nucleic acid encodes methionine (M) at the amino acid position corresponding to position 241 of SEQ ID NO: 1. In some embodiments, the nucleic acid has at least one mutation from the parental wild-type SMO at a nucleotide position corresponding to position 721, 722, and/or 723 of SEQ ID NO: 5. In some embodiments, the percent identity is 85%, 86%, 87%, 88%, 89%, 90%, 91%, 92%, 93%, 94%, 95%, 96%, 97%, 98%, 99% or 100% with SEQ ID NO: 5 providing that there is at least one mutation at a nucleotide position corresponding to positions 721, 722, and/or 723 of SEQ ID NO: 5. In some embodiments, the disclosure provides for an isolated nucleic acid molecule encoding a mutant SMO protein wherein said amino acid sequence comprises an amino acid other than tryptophan at the amino acid position corresponding to position 281 of the wildtype SMO amino acid sequence. In some embodiments nucleic acids comprise a sequence that is at least 80%, 85%, 86%, 87%, 88%, 89%, 90%, 91%, 92%, 93%, 94%, 95%, 96%, 97%, 98%, 99% or 100% identical to the nucleic acid sequence of SEQ ID NO:5 and which contain at least one mutation such that the nucleic acid encodes a SMO polypeptide comprising an amino acid other than tryptophan (W) at the nucleotide position corresponding to nucleotide position 281 of SEQ ID NO: 1. In some embodiments, the nucleic acid encodes cysteine (C) at the amino acid position corresponding to position 281 of SEQ ID NO: 1. In some embodiments, the nucleic acid has at least one mutation from the parental wild-type SMO at a nucleotide position corresponding to nucleotide position 841, 842, and/or 843 of SEQ ID NO: 5. In some embodiments, the percent identity is 85%, 86%, 87%, 88%, 89%, 90%, 91%, 92%, 93%, 94%, 95%, 96%, 97%, 98%, 99% or 100% with SEQ ID NO:5 providing that there is at least one mutation at a nucleotide position corresponding to positions 841, 842, and/or 843 of SEQ ID NO: 5. In some embodiments, the disclosure provides for an isolated nucleic acid molecule encoding a mutant SMO protein wherein said amino acid sequence comprises an amino acid other than isoleucine at the amino acid position corresponding to position 408 of the wildtype SMO amino acid sequence. In some embodiments nucleic acids comprise a sequence that is at least 80%, 85%, 86%, 87%, 88%, 89%, 90%, 91%, 92%, 93%, 94%, 95%, 96%, 97%, 98%, 99% or 100% identical to the nucleic acid sequence of SEQ ID NO: 5, and which contain at least one mutation such that the nucleic acid encodes a SMO polypeptide comprising an amino acid other than isoleucine (I) at the amino acid position corresponding to position 408 of SEQ ID NO: 1. In some embodiments, the nucleic acid encodes valine (V) at the amino acid position corresponding to position 408 of SEQ ID NO: 1. In some embodiments, the nucleic acid has at least one mutation from the parental wild-type SMO at a nucleotide position corresponding to position 1222, 1223 and/or 1224 of SEQ ID NO: 5. In some embodiments, the percent identity is 85%, 86%, 87%, 88%, 89%, 90%, 91%, 92%, 93%, 94%, 95%, 96%, 97%, 98%, 99% or 100% with SEQ ID NO: 5 providing that there is at least one mutation at a nucleotide position corresponding to positions 1222, 1223 and/or 1224 of SEQ ID NO: 5. In some embodiments, the disclosure provides for an isolated nucleic acid molecule encoding a mutant SMO protein wherein said amino acid sequence comprises an amino acid other than alanine at the amino acid position corresponding to position 459 of the wildtype SMO amino acid sequence. In some embodiments nucleic acids comprise a sequence that is at least 80%, 85%, 86%, 87%, 88%, 89%, 90%, 91%, 92%, 93%, 94%, 95%, 96%, 97%, 98%, 99% or 100% identical to the nucleic acid sequence of SEQ ID NO:5 and which contain at least one mutation such that the nucleic acid encodes a SMO polypeptide comprising an amino acid other than alanine (A) at the amino acid position corresponding to position 459 of SEQ ID NO: 1. In some embodiments, the nucleic acid encodes valine (V) at the amino acid position corresponding to position 459 of SEQ ID NO: 1. In some embodiments, the nucleic acid has at least one mutation from the parental wild-type SMO at a nucleotide position corresponding to position 1375, 1376, and/or 1377 of SEQ ID NO: 5. In some embodiments, the percent identity is 85%, 86%, 87%, 88%, 89%, 90%, 91%, 92%, 93%, 94%, 95%, 96%, 97%, 98%, 99% or 100% with SEQ ID NO: 5 providing that there is at least one mutation at a nucleotide position corresponding to positions 1375, 1376, and/or 1377 of SEQ ID NO: 5. In some embodiments, the disclosure provides for an isolated nucleic acid molecule encoding a mutant SMO protein wherein said amino acid sequence comprises an amino acid other than cysteine at the amino acid position corresponding to position 469 of the wildtype SMO amino acid sequence. In some embodiments nucleic acids comprise a sequence that is at least 80%, 85%, 86%, 87%, 88%, 89%, 90%, 91%, 92%, 93%, 94%, 95%, 96%, 97%, 98%, 99% or 100% identical to the nucleic acid sequence of SEQ ID NO: 5, and which contain at least one mutation such that the nucleic acid encodes a SMO polypeptide comprising an amino acid other than cysteine (C) at the amino acid position corresponding to position 469 of SEQ ID NO: 1. In some embodiments, the nucleic acid encodes tyrosine (Y) at the amino acid position corresponding to position 469 of SEQ ID NO: 1. In some embodiments, the nucleic acid has at least one mutation from the parental wild-type SMO at a nucleotide position corresponding to position 1405, 1406 and/or 1407 of SEQ ID NO: 5. In some embodiments, the percent identity is 85%, 86%, 87%, 88%, 89%, 90%, 91%, 92%, 93%, 94%, 95%, 96%, 97%, 98%, 99% or 100% with SEQ ID NO:5 providing that there is at least one mutation at a nucleotide position corresponding to positions 1405, 1406 and/or 1407 of SEQ ID NO: 5. In some embodiments, the disclosure provides for an isolated nucleic acid molecule encoding a mutant SMO protein wherein said amino acid sequence comprises an amino acid other than serine at the amino acid position corresponding to position 533 of the wildtype SMO amino acid sequence. In some embodiments nucleic acids comprise a sequence that is at least 80%, 85%, 86%, 87%, 88%, 89%, 90%, 91%, 92%, 93%, 94%, 95%, 96%, 97%, 98%, 99% or 100% identical to the nucleic acid sequence of SEQ ID NO:5, and which contain at least one mutation such that the nucleic acid encodes a SMO polypeptide comprising an amino acid other than serine (S) at the amino acid position corresponding to position 533 of SEQ ID NO: 1. In some embodiments, the nucleic acid encodes asparagine (N) at the amino acid position corresponding to position 533 of SEQ ID NO: 1. In some embodiments, the nucleic acid has at least one mutation from the parental wild-type SMO at a nucleotide position corresponding to position 1597, 1598 and/or 1599 of SEQ ID NO: 5. In some embodiments, the percent identity is 85%, 86%, 87%, 88%, 89%, 90%, 91%, 92%, 93%, 94%, 95%, 96%, 97%, 98%, 99% or 100% with SEQ ID NO:5 providing that there is at least one mutation at a nucleotide position corresponding to positions 1597, 1598 and/or 1599 of SEQ ID NO: 5. In some embodiments, the disclosure provides for an isolated nucleic acid molecule encoding a mutant SMO protein wherein said amino acid sequence comprises an amino acid other than tryptophan at the amino acid position corresponding to position 535 of the wildtype SMO amino acid sequence. In some embodiments nucleic acids comprise a sequence that is at least 80%, 85%, 86%, 87%, 88%, 89%, 90%, 91%, 92%, 93%, 94%, 95%, 96%, 97%, 98%, 99% or 100% identical to the nucleic acid sequence of SEQ ID NO:5 and which contain at least one mutation such that the nucleic acid encodes a SMO polypeptide comprising an amino acid other than tryptophan (W) at an amino acid position corresponding to position 535 of SEQ ID NO: 1. In some embodiments, the nucleic acid encodes leucine (L) at a nucleotide position corresponding to amino acid position 535 of SEQ ID NO: 1. In some embodiments, the nucleic acid has at least one mutation from the parental wild-type SMO at a nucleotide position corresponding to position 1603, 1604, and/or 1605 of SEQ ID NO: 5. In some embodiments, the percent identity is 85%, 86%, 87%, 88%, 89%, 90%, 91%, 92%, 93%, 94%, 95%, 96%, 97%, 98%, 99% or 100% with SEQ ID NO: 5 providing that there is at least one mutation at a nucleotide position corresponding to nucleotide position 1603, 1604, and/or 1605 of SEQ ID NO: 5. In some embodiments nucleic acids comprise a sequence that is at least 80%, 85%, 86%, 87%, 88%, 89%, 90%, 91%, 92%, 93%, 94%, 95%, 96%, 97%, 98%, 99% or 100% identical to the nucleic acid sequence of SEQ ID NO:5, and which contain at least one mutation such that the nucleic acid encodes a SMO polypeptide comprising any one or more of the amino acid alterations indicated in Table 4 (See, Example 6).

The disclosure also contemplates fragments of such nucleic acids that span the region of the mutations described above in fragments that are at least 20 nucleotides in length. In some embodiments, the nucleotide fragments are 25, 30, 35, 40, 45, 50, 55, 60, 65, 70, 75, 80, 85, 90, 95, or 100 nucleotides in length. The fragments may be any length that spans the region of the mutations described above up to the full length mutant SMO-encoding nucleic acid molecule. Isolated mutant SMO and fragments thereof may be used, for example, for hybridization, to generate primers and probes for the prognostic and diagnostic assays of the disclosure, and for expression in recombinant systems (such as to generate mutant SMO protein or portions thereof for use as immunogens and for use in assays of the disclosure as described herein).

The disclosure provides nucleic acid probes which may be used to identify the mutant SMO nucleic acid molecule in the methods of the disclosure. Nucleic acid samples derived from tissue suspected of having a mutant SMO or from tissue wherein the status of SMO is unknown may be screened using a specific probe for mutant SMO using standard procedures, such as described in Sambrook et al., MOLECULAR CLONING: A LABORATORY MANUAL, Cold Spring Harbor Laboratory Press, NY, 1989). Alternatively, the nucleic acid encoding SMO may be amplified from the tissue and probed with a specific probe of the disclosure to determine the presence of absence of mutant SMO. PCR methodology is well known in the art (Sambrook et al., supra; Dieffenbach et al., PCR PRIMER: A LABORATORY MANUAL, Cold Spring Harbor Laboratory Press, NY, 1995).

Nucleotide sequences (or their complement) encoding mutant SMO have various applications in the art of molecular biology, including uses as hybridization probes, and in the generation of anti-sense RNA and DNA probes. Mutant SMO-encoding nucleic acid will also be useful for the preparation of mutant SMO polypeptides by the recombinant techniques described herein, wherein those mutant SMO polypeptides may find use, for example, in the preparation of anti-mutant SMO antibodies as described herein.

The full-length mutant SMO nucleic acids, or portions thereof, may be used as hybridization probes for identifying mutant SMO.

Optionally, the length of the probes will be about 20 to about 50 bases. The hybridization probes may be derived from at least the mutant region of the full length mutant SMO nucleotide sequence.

By way of example, a screening method will comprise isolating the coding region of mutant SMO using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the mutant SMO gene of the present disclosure can be used to screen libraries of human cDNA, genomic DNA or mRNA to determine which members of such libraries the probe hybridizes to. Hybridization products may be resolved on polyacrylamide gels. In addition, the SMO mutations may be determined using the method described in the Examples. Hybridization conditions, including moderate stringency and high stringency, are provided in Sambrook et al., supra.

Sequences identified in such library screening methods can be compared and aligned to the known sequences for SMO and mutant SMO. Sequence identity at the first, second, fifth, sixth or seventh transmembrane domain, at the carboxy-terminal region of transmembrane domain 6, or the carboxy-terminal region of transmembrane domain 7 can be determined using methods known in the art.

Other useful fragments of the SMO-encoding nucleic acids include antisense or sense oligonucleotides comprising a single-stranded nucleic acid sequence (either RNA or DNA) capable of binding to target mutant SMO mRNA (sense) or mutant SMO DNA (antisense) sequences. Antisense or sense oligonucleotides, according to the present disclosure, comprise a fragment of the coding region of mutant SMO DNA containing the mutation region. Such a fragment generally comprises at least about 14 nucleotides, and, in some embodiments, from about 14 to 30 nucleotides. The ability to derive an antisense or a sense oligonucleotide, based upon a cDNA sequence encoding a given protein is described in, for example, Stein and Cohen (1988) *Cancer Res.* 48:2659 and van der Krol et al. (1988) *BioTechniques* 6:958.

In some embodiments, the disclosure provides for nucleic acids capable of inhibiting expression of any of the mutant SMO nucleic acids described herein. Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present disclosure. The antisense oligonucleotides thus may be used to block expression of mutant SMO proteins, wherein those mutant SMO proteins may play a role in the resistance of cancer in mammals to chemotherapeutics such as GDC-0449. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Specific examples of antisense compounds useful for inhibiting expression of mutant SMO proteins include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. In some embodiment, modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. In some embodiments, oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In some embodiments, the nucleic acid comprises modified nucleotides or modified oligonucleotide backbones. In some embodiments, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH.sub.2 component parts. Representative United States patents that teach the preparation of such oligonucleosides include, but are not limited to: U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312;

5,633,360; 5,677,437; 5,792,608; 5,646,269 and 5,677,439, each of which is herein incorporated by reference.

In some embodiments of antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al. (1991) *Science* 254:1497-1500.

In some embodiments, antisense oligonucleotides incorporate phosphorothioate backbones and/or heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester backbone is represented as —O—P—O—$CH_2$—) described in the above referenced U.S. Pat. No. 5,489,677, and the amide backbones of the above referenced U.S. Pat. No. 5,602,240. In some embodiments, antisense oligonucleotides have morpholino backbone structures of the above-referenced U.S. Pat. No. 5,034,506.

Modified oligonucleotides may also contain one or more substituted sugar moieties. In some embodiments, oligonucleotides comprise one of the following at the 2' position: OH; F; O-alkyl, S-alkyl, or N-alkyl; O-alkenyl, S-alkeynyl, or N-alkenyl; O-alkynyl, S-alkynyl or N-alkynyl; or O-alkyl-O-alkyl, wherein the alkyl, alkenyl and alkynyl may be substituted or unsubstituted C1 to C10 alkyl or C2 to C10 alkenyl and alkynyl. In some embodiments, the oligonucleotides are O[($CH_2$)$_n$O]$_m$$CH_3$, O($CH_2$)$_n$O$CH_3$, O($CH_2$)$_n$NH$_2$, O(CH2)$_n$$CH_3$, O($CH_2$)$_n$ONH$_2$, and O($CH_2$)$_n$ON[($CH_2$)$_n$$CH_3$)]$_2$, where n and m are from 1 to about 10. In some embodiments, antisense oligonucleotides comprise one of the following at the 2' position: C1 to C10 lower alkyl, substituted lower alkyl, alkenyl, alkynyl, alkaryl, aralkyl, O-alkaryl or O-aralkyl, SH, S$CH_3$, OCN, Cl, Br, CN, $CF_3$, O$CF_3$, SO$CH_3$, SO$_2$ $CH_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In some embodiments, a modification includes 2'-methoxyethoxy (2'-O—$CH_2$CH2O$CH_3$, also known as 2'-O-(2-methoxyethyl) or 2'-MOE) (Martin et al. (1995) *Helv. Chim. Acta* 78:486-504) i.e., an alkoxyalkoxy group. In some embodiments, a modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$.

In some embodiments, a modification includes Locked Nucleic Acids (LNAs) in which the 2'-hydroxyl group is linked to the 3' or 4' carbon atom of the sugar ring thereby forming a bicyclic sugar moiety. The linkage is, in some embodiments, a methelyne (—$CH_2$—)$_n$ group bridging the 2' oxygen atom and the 4' carbon atom wherein n is 1 or 2. LNAs and preparation thereof are described in WO 98/39352 and WO 99/14226.

In some embodiments, modifications include 2'-methoxy (2'-O—$CH_3$), 2'-aminopropoxy (2'-O$CH_2$$CH_2$$CH_2$NH$_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. In some embodiments, a 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

In some embodiments, oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$ or —$CH_2$—C≡CH) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in THE CONCISE ENCYCLOPEDIA OF POLYMER SCIENCE AND ENGINEERING, Kroschwitz, J. I., ed., John Wiley & Sons, 1990, pp. 858-859, and those disclosed by Englisch et al., ANGEWANDTE CHEMIE, INTERNATIONAL EDITION, Wiley-VCH, Germany, 1991, 30:613. Certain of these nucleobases are particularly useful for increasing the binding affinity of the oligomeric compounds of the disclosure. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al. ANTISENSE RESEARCH AND APPLICATIONS, CRC Press, Boca Raton, 1993, pp. 276-278) and are possible base substitutions, even more particularly when combined with 2'-O-methoxyethyl sugar modifications. Representative U.S. patents that teach the preparation of modified nucleobases include, but are not limited to: U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,681,941 and 5,750,692, each of which is herein incorporated by reference.

Another modification of antisense oligonucleotides involves chemically linking to the oligonucleotide one or more moieties or conjugates which enhance the activity, cellular distribution or cellular uptake of the oligonucleotide. The compounds of the disclosure can include conjugate groups covalently bound to functional groups such as primary or secondary hydroxyl groups. Conjugate groups of the disclosure include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this disclosure, include groups that improve oligomer uptake, enhance oligomer resistance to degradation, and/or strengthen sequence-specific hybridization with RNA. Groups that enhance the pharmacokinetic properties, in the context of this disclosure, include groups that improve oligomer uptake, distribution, metabolism or excretion. Conjugate moieties include but are not limited to lipid moieties such as a cholesterol moiety (Letsinger et al. (1989) Proc. Natl. Acad. Sci. USA 86:6553-6556), cholic acid (Manoharan et al. (1994) Bioorg. Med. Chem. Lett. 4:1053-1060), a thioether, e.g., hexyl-S-tritylthiol (Manoharan et al. (1992) Ann. N.Y. Acad. Sci. 660: 306-309; Manoharan et al. (1993) Bioorg. Med. Chem. Lett. 3:2765-2770), a thiocholesterol (Oberhauser et al. (1992) Nucl. Acids Res. 20:533-538), an aliphatic chain, e.g., dodecandiol or undecyl residues (Saison-Behmoaras et al. (1991) EMBO J. 10:1111-1118; Kabanov et al. (1990) FEBS Lett. 259:327-330; Svinarchuk et al. (1993) Biochimie 75:49-54, a phospholipid, e.g., di-hexadecyl-rac-glycerol or triethylammonium 1,2-di-O-hexadecyl-rac-glycero-3-H-phosphonate (Manoharan et al. (1995) Tetrahedron Lett. 36:3651-3654; Shea et al. (1990) Nucl. Acids Res. 18:3777-3783), a polyamine or a polyethylene glycol chain (Manoharan et al. (1995) Nucleosides & Nucleotides 14:969-973), or adamantane acetic acid (Manoharan et al. (1995) Tetrahedron Lett. 36:3651-3654), a palmityl moiety (Mishra et al. (1995) Biochim. Biophys. Acta 1264:229-237), or an octadecylamine or hexylamino-carbonyl-oxycholesterol moiety. Oligonucleotides of the disclosure may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941 and 6,656,730, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present disclosure also includes antisense compounds which are chimeric compounds. "Chimeric" antisense compounds or "chimeras," in the context of this disclosure, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the disclosure may be formed as composite structures of two or more oligonucleotides, modified oligonucleotides, oligonucleosides and/or oligonucleotide mimetics as described above. In some embodiments, chimeric antisense oligonucleotides incorporate at least one 2' modified sugar (e.g., 2'-O—$(CH_2)_2$—O—$CH_3$) at the 3' terminal to confer nuclease resistance and a region with at least 4 contiguous 2'-H sugars to confer RNase H activity. Such compounds have also been referred to in the art as hybrids or gapmers. In some embodiments, gapmers have a region of 2' modified sugars (e.g., 2'-O—$(CH_2)_2$—O—$CH_3$) at the 3'-terminal and at the 5' terminal separated by at least one region having at least 4 contiguous 2'-H sugars and, in some embodiments, incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this disclosure may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the disclosure may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416, 016; 5,459,127; 5,521,291; 5,543,158; 5,547,932; 5,583, 020; 5,591,721; 4,426,330; 4,534,899; 5,013,556; 5,108, 921; 5,213,804; 5,227,170; 5,264,221; 5,356,633; 5,395, 619; 5,416,016; 5,417,978; 5,462,854; 5,469,854; 5,512, 295; 5,527,528; 5,534,259; 5,543,152; 5,556,948; 5,580, 575; and 5,595,756, each of which is herein incorporated by reference.

Other examples of sense or antisense oligonucleotides include those oligonucleotides which are covalently linked to organic moieties, such as those described in WO 90/10048, and other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In one embodiment, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. In some embodiments, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is, in some embodiments, dissociated within the cell by an endogenous lipase.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

Nucleotide sequences encoding a mutant SMO can also be used to construct hybridization probes for mapping the gene which encodes that SMO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

A potential mutant SMO antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example nucleic acids encoding mutant SMO herein, are used to design an antisense RNA oligonucleotide of from about 10 to 40 base pairs in length. A DNA oligonucleotide is designed to be complementary to a region of the gene involved in transcription (triple helix—see Lee et al. (1979) *Nucl. Acids Res.* 6:3073; Cooney et al. (1988) *Science* 241:456; Dervan et al. (1991) *Science* 251: 1360), thereby preventing transcription and the production of mutant SMO. The antisense RNA oligonucleotide hybridizes to the mRNA in vivo and blocks translation of the mRNA molecule into the mutant SMO (Okano (1991) *Neurochem.* 56:560); OLIGODEOXYNUCLEOTIDES AS ANTISENSE INHIBITORS OF GENE EXPRESSION, CRC Press, Boca Raton, Fla., 1988). The oligonucleotides described above can also be delivered to cells such that the antisense RNA or DNA may be expressed in vivo to inhibit production of the mutant SMO. When antisense DNA is used, oligodeoxyribonucleotides derived from the translation-initiation site, e.g., between about −10 and +10 positions of the target gene nucleotide sequence, may be used in some embodiments.

Any of the nucleic acids are suitable for use in expressing mutant SMO proteins and identifying natural targets or binding partners for the expressed mutant smoothened proteins (e.g., a smoothened protein having a T241M, W281C, I408V, A459V, C469Y, S533N and/or W535L mutation relative to wildtype SMO, such as wildtype human SMO). The nucleic acids may also be used to study mutant smoothened bioactivity, to purify mutant smoothened and its binding partners from various cells and tissues, and to identify additional components of the hedgehog signaling pathway.

II. Small Molecules

Potential antagonists of mutant SMO include small molecules that bind to the site occupied in wild-type SMO by GDC-0449, thereby blocking the biological activity of mutant SMO. Examples of small molecules include, but are not limited to, small peptides or peptide-like molecules, e.g., soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi (1994) *Current Biology*, 4:469-471, and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

III. Proteins

The disclosure provides isolated mutant SMO proteins. Wild-type human SMO is shown in SEQ ID NO: 1. In some embodiments, the mutant SMO proteins are partially or fully resistant to vismodegib. In some embodiments, the mutant SMO proteins are partially or fully resistant to vismodegib in a cell having an additional mutation in a gene encoding a protein in the hedgehog signaling pathway. In some embodiments, the additional mutation is any of the patched and/or SUFU mutations described herein.

In some embodiments, the disclosure provides for an isolated mutant SMO protein comprising an amino acid sequence, wherein the amino acid sequence comprises an amino acid other than alanine at the amino acid position corresponding to position 239 of the wildtype SMO amino acid sequence. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that there is a substitution at amino acid position 239. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the amino acid sequence comprises an amino acid other than alanine (A) at the amino acid position corresponding to position 239 of SEQ ID NO: 1. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the SMO protein comprises a valine (V) at the amino acid position corresponding to position 239 of SEQ ID NO: 1.

In some embodiments, the disclosure provides for an isolated mutant SMO protein comprising an amino acid sequence, wherein the amino acid sequence comprises an amino acid other than threonine at the amino acid position corresponding to position 241 of the wildtype SMO amino acid sequence. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that there is a substitution at amino acid position 241. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the amino acid sequence comprises an amino acid other than threonine (T) at the amino acid position corresponding to position 241 of SEQ ID NO: 1. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the SMO protein comprises a methionine (M) at the amino acid position corresponding to position 241 of SEQ ID NO: 1.

In some embodiments, the disclosure provides for an isolated mutant SMO protein comprising an amino acid sequence, wherein the amino acid sequence comprises an amino acid other than tryptophan at the amino acid position corresponding to position 281 of the wildtype SMO amino acid sequence. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that there is a substitution at amino acid position 281. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the amino acid sequence comprises an amino acid other than tryptophan (W) at the amino acid position corresponding to position 281 of SEQ ID NO: 1. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the SMO protein comprises a cysteine (C) at the amino acid position corresponding to position 281 of SEQ ID NO: 1.

In some embodiments, the disclosure provides for an isolated mutant SMO protein comprising an amino acid sequence, wherein the amino acid sequence comprises an amino acid other than isoleucine at the amino acid position corresponding to position 408 of the wildtype SMO amino acid sequence. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that there is a mutation at amino acid position 408. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the amino acid sequence comprises an amino acid other than isoleucine (I) at the amino acid position corresponding to position 408 of SEQ ID NO: 1. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the SMO protein comprises a valine (V) at the amino acid position corresponding to position 408 of SEQ ID NO: 1.

In some embodiments, the disclosure provides for an isolated mutant SMO protein comprising an amino acid sequence, wherein the amino acid sequence comprises an amino acid other than alanine at the amino acid position corresponding to position 459 of the wildtype SMO amino acid sequence. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that there is a mutation at amino acid position 459. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the amino acid sequence comprises an amino acid other than alanine (A) at the amino acid position corresponding to position 459 of SEQ ID NO: 1. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the SMO protein comprises a valine (V) at the amino acid position corresponding to position 459 of SEQ ID NO: 1.

In some embodiments, the disclosure provides for an isolated mutant SMO protein comprising an amino acid sequence, wherein the amino acid sequence comprises an amino acid other than cysteine at the amino acid position corresponding to position 469 of the wildtype SMO amino acid sequence. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that there is a mutation at amino acid position 469. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the amino acid sequence comprises an amino acid other than cysteine (C) at the amino acid position corresponding to position 469 of SEQ ID NO: 1. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the SMO protein comprises a tyrosine (Y) at the amino acid position corresponding to position 469 of SEQ ID NO: 1.

In some embodiments, the disclosure provides for an isolated mutant SMO protein comprising an amino acid sequence, wherein the amino acid sequence comprises an amino acid other than serine at the amino acid position corresponding to position 533 of the wildtype SMO amino acid sequence. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that there is a mutation at amino acid position 533. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the amino acid sequence comprises an amino acid other than serine (S) at the amino acid position corresponding to position 533 of SEQ ID NO: 1. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the SMO protein comprises a asparagine (N) at the amino acid position corresponding to position 533 of SEQ ID NO: 1.

In some embodiments, the disclosure provides for an isolated mutant SMO protein comprising an amino acid sequence, wherein the amino acid sequence comprises an amino acid other than trytophan at the amino acid position corresponding to position 535 of the wildtype SMO amino acid sequence. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that there is a mutation at amino acid position 535.

In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the amino acid sequence comprises an amino acid other than tryptophan (W) at the amino acid position corresponding to position 535 of SEQ ID NO: 1. In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the SMO protein comprises a leucine (L) at the amino acid position corresponding to position 535 of SEQ ID NO: 1.

In some embodiments, the SMO protein comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that the SMO protein comprises at least one of the amino acid mutations indicated in Table 4 (See, Example 6).

In some embodiments, the mutant human SMO is shown in SEQ ID NO: 6 wherein amino acid 241 is shown as "Xaa" which, with respect to this application stands for any amino acid other than threonine (T). In some embodiments, the Xaa is methionine (M).

In some embodiments, the mutant human SMO is shown in SEQ ID NO:2 wherein amino acid 281 is shown as "Xaa" which, with respect to this application stands for any amino acid other than tryptophan (W). In some embodiments, the Xaa is cysteine (C).

In some embodiments, the mutant human SMO is shown in SEQ ID NO: 7 wherein amino acid 408 is shown as "Xaa" which, with respect to this application stands for any amino acid other than isoleucine (I). In some embodiments, the Xaa is valine (V).

In some embodiments, the mutant human SMO is shown in SEQ ID NO:3 wherein amino acid 459 is shown as "Xaa" which, with respect to this application stands for any amino acid other than alanine (A). In some embodiments, the Xaa is valine (V).

In some embodiments, the mutant human SMO is shown in SEQ ID NO: 8 wherein amino acid 469 is shown as "Xaa" which, with respect to this application stands for any amino acid other than cysteine (C). In some embodiments, the Xaa is tyrosine (Y).

In some embodiments, the mutant human SMO is shown in SEQ ID NO: 9 wherein amino acid 533 is shown as "Xaa" which, with respect to this application stands for any amino acid other than serine (S). In some embodiments, the Xaa is asparagine (N).

In some embodiments, the Xaa is valine (V). In some embodiments, the mutant human SMO is shown in SEQ ID NO: 4 wherein amino acid 535 is shown as "Xaa" which, with respect to this application stands for any amino acid other than tryptophan (W). In some embodiments, the Xaa is leucine (L).

In some embodiments, any of the mutant SMO proteins lack the N-terminal methionine corresponding to position 1 of any of SEQ ID NOs; 1-9.

Mutant SMO and fragments thereof may be produced in recombinant systems as is well known in the art using the mutant SMO nucleic acids described herein. Such nucleic acids may be incorporated into expression vectors as are well-known in that art and transfected into host cells, which may be prokaryotic or eukaryotic cells depending on the proposed use of the protein. Full length or fragments of mutant SMO (in which the fragments contain at least a first transmembrane of SMO and position 241 of human SMO, a second transmembrane domain of SMO and position 281 of human SMO, a fifth transmembrane domain of SMO and position 408 of human SMO, a sixth transmembrane domain of SMO and position 459 or 469 of human SMO, and/or the seventh transmembrane of SMO and position 533 or 535 of human SMO.) may be used as immunogens to produce antibodies of the disclosure, or to purify antibodies of the disclosure, for example.

In some embodiments, the SMO protein or fragment thereof has at least one of the same biological activities of a wildtype SMO polypeptide (e.g., a SMO protein having the amino acid sequence of SEQ ID NO: 1). In some embodiments, a mutant SMO protein (e.g., a SMO protein having a mutation at amino acid positions corresponding to amino acids 241 or 459 of SEQ ID NO: 1) has increased basal biological activity as compared to wildtype SMO protein (e.g., a SMO protein having the amino acid sequence of SEQ ID NO: 1). By the terms "biological activity", "bioactivity" or "functional" is meant the ability of the SMO protein or fragment thereof to carry out at least one of the functions associated with wildtype SMO proteins, for example, transducing the hedgehog signaling pathway and/or inducing Gli1 expression. In certain embodiments, the SMO protein binds kinesin motor protein Costal-2. The terms "biological activity", "bioactivity", and "functional" are used interchangeably herein.

In some embodiments, any of the SMO proteins (e.g., any of the mutant SMO proteins described herein) is capable of transducing hedgehog signaling. By the terms "has the ability" or "is capable of" is meant the recited protein will carry out the stated bioactivity under suitable conditions (e.g., physiological conditions or standard laboratory conditions). In certain embodiments, the term "can" may be used to describe this ability (e.g., "can bind" or "binds" to a given sequence). For example, if a SMO protein (e.g., any of the mutant SMO proteins described herein) has the ability or is capable of facilitating hedgehog signaling, the SMO protein is capable of facilitating hedgehog signaling in a cell under normal physiological conditions. One of ordinary skill in the art would understand what conditions would be needed to test whether a polypeptide has the ability or is capable of carrying out a recited bioactivity.

In some embodiments, the SMO and mutant SMO proteins described herein comprise a smoothened gain-of-function mutation. In some embodiments, the gain-of-function smoothened mutation results in a constitutively active smoothened protein. In certain embodiments, the mutation in Smoothened comprises a mutation at any of the specific positions, such as position corresponding to a particular position in SEQ ID NO: 1, as set forth above with respect to the screening assay. See, e.g., WO 2011/028950 and WO2012047968, each of which is incorporated by reference. In some embodiments, the smoothened mutation is a mutation at a position corresponding to position 535 of SEQ ID NO: 1. In certain embodiments, the mutation is a mutation at a position corresponding to position 562 of SEQ ID NO: 1. In certain embodiments, the mutation is W535L at position 535 or at that corresponding position in SEQ ID NO: 1. In some embodiments, the smoothened mutation is a mutation corresponding to position R562Q of SEQ ID NO: 1 (a R562Q mutation at position 562 or at a position corresponding to position 562 of SEQ ID NO: 1. In some embodiments, the smoothened mutation is a mutation at a position corresponding to position 412 of SEQ ID NO: 1, such as a L412F at such a position of SEQ ID NO: 1. In some embodiments, the smoothened mutation has a mutation that renders it resistant to certain smoothened inhibitors. In some embodiments, the smoothened protein comprises an alternative amino acid alteration at amino acid position 518 of SEQ ID NO: 1 or at a position corresponding to position 518 of SEQ ID NO: 1. In some embodiments, the amino acid alteration is E518K or E518A substitution at the amino acid position corresponding to amino acid position 518 of SEQ ID NO: 1. In some embodiments, the smoothened protein comprises an amino acid alteration at amino acid position 473 of SEQ ID NO: 1 or at a position corresponding to position 473 of SEQ ID NO: 1.

In some embodiments, any of the SMO proteins described herein (e.g., any of the mutant SMO proteins described herein) is fused to another agent. In some embodiments, the SMO protein is fused to another polypeptide.

Any of the mutant SMO proteins described herein are suitable for use in identifying natural targets or binding partners for mutant smoothened proteins (e.g., a smoothened protein having a T241M, W281C, I408V, A459V, C469Y, S533N and/or W535L mutation). The mutant SMO proteins may also be used to study mutant smoothened bioactivity, to purify mutant smoothened and its binding partners from various cells and tissues, and to identify additional components of the hedgehog signaling pathway.

IV. Antibodies

A. Anti-Mutant SMO Antibodies

In one aspect, the disclosure provides antibodies that bind to SMO, particularly mutant SMO. In some embodiments, any of the antibodies disclosed herein specifically bind any of the mutant SMO polypeptides described herein. For example, a mutant SMO polypeptide comprises an epitope specifically bound by antibodies of the disclosure. In some embodiments, the antibodies specifically bind SMO protein that comprises an amino acid sequence that is at least 85%, 86%, 87%, 88%, 89%, 90%, 91%, 92%, 93%, 94%, 95%, 96%, 97%, 98%, 99% or 100% identical to SEQ ID NO: 1, provided that there is a mutation at an amino acid position corresponding to positions 241, 281, 408, 459, 469, 533 and/or 535 of SEQ ID NO: 1. In some embodiments, the antibodies do not specifically bind a SMO protein having the amino acid sequence of SEQ ID NO: 1 or preferentially bind a mutant SMO protein in comparison to a SMO protein having the amino acid sequence of SEQ ID NO: 1 (e.g., binding is selective for a mutant SMO protein). In some embodiments, the antibodies do not bind a SMO protein that lacks a mutation at any one of the amino acid positions corresponding to positions 241, 281, 408, 459, 469, 533 and/or 535 of SEQ ID NO: 1.

In one embodiment, an anti-SMO antibody is a monoclonal antibody. In one embodiment, an anti-SMO antibody is an antibody fragment, e.g., a Fab, Fab'-SH, Fv, scFv, or (Fab')$_2$ fragment. In one embodiment, an anti-mutant SMO antibody is a chimeric, humanized, or human antibody. In one embodiment, an anti-SMO antibody is purified. In certain embodiments, a composition is a pharmaceutical formulation for the treatment of cancer.

1. Antibody Fragments

The present disclosure encompasses antibody fragments. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

2. Humanized Antibodies

The disclosure encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies. See, e.g., Carter et al. (1992) *Proc. Natl. Acad. Sci. USA*, 89:4285; Presta et al. (1993) *J. Immunol.*, 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

3. Human Antibodies

Human antibodies of the disclosure can be constructed by combining Fv clone variable domain sequence(s) selected from human-derived phage display libraries with known human constant domain sequence(s) as described above. Alternatively, human monoclonal antibodies of the disclosure can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci USA*, 90: 2551 (1993); Jakobovits et al., *Nature*, 362: 255 (1993); Bruggermann et al., *Year in Immunol.*, 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

4. Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for SMO and the other is for any other antigen. In certain embodiments, bispecific antibodies may bind to two different epitopes of SMO. Bispecific antibodies may also be used to localize cytotoxic agents to cells which express SMO. These antibodies possess a SMO-binding arm and an arm which binds a cytotoxic agent, such as, e.g., saporin, anti-interferon-α, vinca alkaloid, ricin A chain, methotrexate or radioactive isotope hapten. Bispecific antibodies can be prepared as full length antibodies or antibody fragments (e.g. F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature,* 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.,* 10: 3655 (1991).

According to a different approach, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach, the interface between a pair of antibody molecules can be engineered to maximize the percentage of heterodimers which are recovered from recombinant cell culture. The interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking method. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.,* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

5. Multivalent Antibodies

A multivalent antibody may be internalized (and/or catabolized) faster than a bivalent antibody by a cell expressing an antigen to which the antibodies bind. The antibodies of the present disclosure can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

6. Single-Domain Antibodies

In some embodiments, an antibody of the disclosure is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

7. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are possible locations for mutagenesis is called "alanine scanning mutagenesis" as described by Cunningham and Wells (1989) *Science,* 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody of the disclosure is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. (1997) *TIBTECH* 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the disclosure may be made in order to create antibody variants with certain improved properties.

For example, antibody variants are provided having a carbohydrate structure that lacks fucose attached (directly or indirectly) to an Fc region. Such variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, an antibody variant comprises an Fc region with one or more amino acid substitutions which further improve ADCC, for example, substitutions at positions 298, 333, and/or 334 of the Fc region (Eu numbering of residues). Such substitutions may occur in combination with any of the variations described above.

In certain embodiments, the disclosure contemplates an antibody variant that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-92 (1991). Non-limiting examples of in vitro assays to assess ADCC activity of a molecule of interest is described in U.S. Pat. No. 5,500,362 (see, e.g. Hellstrom, I., et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, for example, Petkova, S. B. et al., *Int'l. Immunol.* 18(12):1759-1769 (2006)).

Other antibody variants having one or more amino acid substitutions are provided. Sites of interest for substitutional mutagenesis include the hypervariable regions, but FR alterations are also contemplated. Conservative substitutions are shown in Table 1 under the heading of "preferred substitutions." More substantial changes, denominated "exemplary substitutions" are provided in Table 1, or as further described below in reference to amino acid classes. Amino acid substitutions may be introduced into an antibody of interest and the products screened, e.g., for a desired activity, such as improved antigen binding, decreased immunogenicity, improved ADCC or CDC, etc.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |

TABLE 1-continued

| Original Residue | Exemplary Substitutions | Preferred Substitutions |
|---|---|---|
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. An exemplary substitutional variant is an affinity matured antibody, which may be conveniently generated using phage display-based affinity maturation techniques. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and variants with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the disclosure, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the disclosure may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter, Nature 322:738-40 (1988); U.S. Pat. Nos. 5,648,260; 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. J. Immunol. 164: 4178-4184 (2000).

In another aspect, the disclosure provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In yet another aspect, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc r 8. Antibody Derivatives The antibodies of the present disclosure can be further modified to contain additional nonproteinaceous moieties that are known in the art and readily available. In some embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Certain Methods of Making Antibodies

1. Certain Hybridoma-Based Methods

Monoclonal antibodies of the disclosure can be made using the hybridoma method first described by Kohler et al., *Nature*, 256:495 (1975), and further described, e.g., in Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, Xiandai Mianyixue, 26(4): 265-268 (2006) regarding human-human hybridomas.

Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

For various other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide comprising mutant SMO or a fragment thereof, and an adjuvant, such as monophosphoryl lipid A (MPL)/trehalose dicrynomycolate (TDM) (Ribi Immunochem. Research, Inc., Hamilton, Mont.). A polypeptide comprising mutant SMO or a fragment thereof may be prepared using methods well known in the art, such as recombinant methods, some of which are further described herein. Serum from immunized animals is assayed for anti-mutant SMO antibodies, and booster immunizations are optionally administered. Lymphocytes from animals producing anti-mutant SMO antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, *Monoclonal Antibodies: Principles and Practice*, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. In some embodiments, serum-free hybridoma cell culture methods are used to reduce use of animal-derived serum such as fetal bovine serum, as described, for example, in Even et al., *Trends in Biotechnology*, 24(3), 105-108 (2006).

Oligopeptides as tools for improving productivity of hybridoma cell cultures are described in Franek, *Trends in Monoclonal Antibody Research*, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to mutant SMO. The binding specificity of monoclonal antibodies produced by hybridoma cells may be determined by immunoprecipitation or by an in vitro binding assay, such as radioimmunoassay (RIA) or enzyme-linked immunoadsorbent assay (ELISA). The binding affinity of the monoclonal antibody can be determined, for example, by Scatchard analysis. See, e.g., Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No. 6,919,436. The method includes using minimal salts, such as lyotropic salts, in the binding process and, in some embodiments, also using small amounts of organic solvents in the elution process.

2. Certain Library Screening Methods

Antibodies of the disclosure can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in *Methods in Molecular Biology* 178:1-37 (O'Brien et al., ed., Human Press, Totowa, N.J., 2001). For example, one method of generating antibodies of interest is through the use of a phage antibody library as described in Lee et al., J. Mol. Biol. (2004), 340(5):1073-93.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the disclosure can be obtained by designing a suitable antigen screening procedure to select for the phage clone of interest followed by construction of a full length antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-mutant SMO clones is desired, the subject is immunized with mutant SMO to generate an antibody response, and spleen cells and/or circulating B cells other peripheral blood lymphocytes (PBLs) are recovered for library construction. In one embodiment, a human antibody gene fragment library biased in favor of anti-mutant SMO clones is obtained by generating an anti-mutant SMO antibody response in transgenic mice carrying a functional human immunoglobulin gene array (and lacking a functional endogenous antibody production system) such that mutant SMO immunization gives rise to B cells producing human antibodies against mutant SMO. The generation of human antibody-producing transgenic mice is described below.

Additional enrichment for anti-mutant SMO reactive cell populations can be obtained by using a suitable screening procedure to isolate B cells expressing mutant SMO-specific membrane bound antibody, e.g., by cell separation using mutant SMO affinity chromatography or adsorption of cells to fluorochrome-labeled mutant SMO followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which mutant SMO is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci.* (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature,* 341: 544-546 (1989). However, for amplifying from cDNA, back primers can also be based in the leader exon as described in Jones et al., *Biotechnol.,* 9: 88-89 (1991), and forward primers within the constant region as described in Sastry et al., *Proc. Natl. Acad. Sci.* (USA), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., *J. Mol. Biol.,* 222: 581-597 (1991) or as described in the method of Orum et al., *Nucleic Acids Res.,* 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature,* 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.,* 227: 776-798 (1992)), and mapped (reported in Matsuda et al., *Nature Genet.,* 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.,* 227: 381-388 (1992). VH repertoires can also be made with all the sequence diversity focused in a long H3 loop of a single length as described in Barbas et al., *Proc. Natl. Acad. Sci. USA,* 89: 4457-4461 (1992). Human Vκ and Vλ segments have been cloned and sequenced (reported in Williams and Winter, *Eur. J. Immunol.,* 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.,* 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene,* 128: 119-126 (1993), or in vivo by combinatorial infection, e.g., the loxP system described in Waterhouse et al., *Nucl. Acids Res.,* 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., *Proc. Natl. Acad. Sci. USA,* 88: 7978-7982 (1991), or assembled together by PCR and then cloned, e.g. as described in Clackson et al., *Nature,* 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.,* 20: 3831-3837 (1992).

The antibodies produced by naive libraries (either natural or synthetic) can be of moderate affinity ($K_d^{-1}$ of about $10^6$ to $10^7$ M$^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique,* 1: 11-15 (1989)) in the method of Hawkins et al., *J. Mol. Biol.,* 226: 889-896 (1992) or in the method of Gram et al., *Proc. Natl. Acad. Sci USA,* 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.,* 10: 779-783 (1992). This technique allows the production of antibodies and antibody fragments with affinities of about $10^{-9}$ M or less.

Screening of the libraries can be accomplished by various techniques known in the art. For example, mutant SMO can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized mutant SMO under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci USA,* 88: 7978-7982 (1991), or by alkali, e.g. as described in Marks et al., *J. Mol. Biol.,* 222: 581-597 (1991), or by mutant SMO antigen competition, e.g. in a procedure similar to the antigen competition method of Clackson et al., *Nature*, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for mutant SMO. However, random mutation of a selected antibody (e.g. as performed in some affinity maturation techniques) is likely to give rise to many mutants, most binding to antigen, and a few with higher affinity. With limiting mutant SMO, rare high affinity phage could be competed out. To retain all higher affinity mutants, phages can be incubated with excess biotinylated mutant SMO, but with the biotinylated mutant SMO at a concentration of lower molarity than the target molar affinity constant for mutant SMO. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-mutant SMO clones may be selected based on activity. In certain embodiments, the disclosure provides anti-mutant SMO antibodies that bind to living cells that naturally express mutant SMO, such as GDC-0449-resistant tumor cells. In one embodiment, the disclosure provides anti-mutant SMO antibodies that bind to the same region as that bound by GDC-0449 in wild type SMO. Fv clones corresponding to such anti-mutant SMO antibodies can be selected by (1) isolating anti-mutant SMO clones from a phage library as described above, and optionally amplifying the isolated population of phage clones by growing up the population in a suitable bacterial host; (2) selecting mutant SMO and a second protein against which blocking and non-blocking activity, respectively, is desired; (3) adsorbing the anti-mutant SMO phage clones to immobilized mutant SMO; (4) using an excess of the second protein to elute any undesired clones that recognize mutant SMO-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the disclosure is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs*, 130: 151 (1992).

DNA encoding the Fv clones of the disclosure can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-mutant SMO antibody derived from a hybridoma of the disclosure can also be modified, for example, by substituting the coding sequence for human heavy- and light-chain constant domains in place of homologous murine sequences derived from the hybridoma clone (e.g. as in the method of Morrison et al., *Proc. Natl. Acad. Sci. USA*, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the disclosure.

3. Vectors, Host Cells, and Recombinant Methods

Antibodies may also be produced using recombinant methods. For recombinant production of an anti-mutant SMO antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

a) Signal Sequence Component

An antibody of the disclosure may be produced recombinantly not only directly, but also as a fusion polypeptide with a heterologous polypeptide, which is, in some embodiments, a signal sequence or other polypeptide having a specific cleavage site at the N-terminus of the mature protein or polypeptide. The heterologous signal sequence selected, in some embodiments, is one that is recognized and processed (i.e., cleaved by a signal peptidase) by the host cell.

For prokaryotic host cells that do not recognize and process a native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including Saccharomyces and Kluyveromyces Xa-factor leaders), or acid phosphatase leader, the C. albicans glucoamylase leader, or the signal described in WO 90/13646. In mammalian cell expression, mammalian signal sequences as well as viral secretory leaders, for example, the herpes simplex gD signal, are available.

b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2p plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, e.g., primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 µm circular plasmid pKD1 can be used for transformation of Kluyveromyces yeasts. Alternatively, an expression system for large-scale production of recombinant calf chymosin was reported for K. lactis. Van den Berg, Bio/Technology, 8:135 (1990). Stable multi-copy expression vectors for secretion of mature recombinant human serum albumin by industrial strains of Kluyveromyces have also been disclosed. Fleer et al., Bio/Technology, 9:968-975 (1991).

d) Promoter Component

Expression and cloning vectors generally contain a promoter that is recognized by the host organism and is operably linked to nucleic acid encoding an antibody. Promoters suitable for use with prokaryotic hosts include the phoA promoter, 3-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human 3-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding an antibody of this disclosure by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody-encoding sequence, but is, in some embodiments, located at a site 5' from the promoter.

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One possible *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, *Methods in Molecular Biology*, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*. For a review discussing the use of yeasts and filamentous fungi for the production of therapeutic proteins, see, e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, *petunia*, tomato, duckweed (Lemnaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

h) Culturing the Host Cells

The host cells used to produce an antibody of this disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

i) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al. (1986) *EMBO J.* 5:1567-1575). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, in some embodiments, performed at low salt concentrations (e.g., from about 0-0.25M salt).

In general, various methodologies for preparing antibodies for use in research, testing, and clinical are well-established in the art, consistent with the above-described methodologies and/or as deemed appropriate by one skilled in the art for a particular antibody of interest.

C. Immunoconjugates

The disclosure also provides immunoconjugates (interchangeably referred to as "antibody-drug conjugates," or "ADCs") comprising an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005) *Curr. Opinion in Pharmacology* 5:543-549; Wu et al (2005) *Nature Biotechnology* 23(9):1137-1146; Payne, G. (2003) i 3:207-212; Syrigos and Epenetos (1999) *Anticancer Research* 19:605-614; Niculescu-Duvaz and Springer (1997) Adv. Drug Deliv. Rev. 26:151-172; U.S. Pat. No. 4,975,278). Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al., Lancet (Mar. 15, 1986) pp. 603-05; Thorpe (1985) "Antibody Carriers Of Cytotoxic Agents In Cancer Therapy: A Review," in Monoclonal Antibodies '84: Biological And Clinical Applications (A. Pinchera et al., eds) pp. 475-506. Both polyclonal antibodies and monoclonal antibodies have been reported as useful in these strategies (Rowland et al., (1986) Cancer Immunol. Immunother. 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may exert their cytotoxic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLO-TARG™ (gemtuzumab ozogamicin, Wyeth Pharmaceuticals), an antibody-drug conjugate composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody-drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and other cancers. MLN-2704 (Millennium Pharm., BZL Biologics, Immunogen Inc.), an antibody-drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnol. 21(7):778-784) and are under therapeutic development.

In certain embodiments, an immunoconjugate comprises an antibody and a chemotherapeutic agent or other toxin. Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolacca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

1. Maytansine and Maytansinoids

In some embodiments, the immunoconjugate comprises an antibody (full length or fragments) conjugated to one or more maytansinoid molecules.

Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA. 1 that binds the HER-2/neu oncogene. The cytotoxicity of the TA.1-maytansinoid conjugate was tested in vitro on the human breast cancer cell line SK-BR-3, which expresses 3×105 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. In some embodiments, maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., *Cancer Research* 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups may be used in some embodiments. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In one embodiment, the linkage is formed at the C-3 position of maytansinol or a maytansinol analogue.

2. Auristatins and Dolastatins

In some embodiments, the immunoconjugate comprises an antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schrider and K. Lübke, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

3. Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714, 586, 5,739,116, 5,767,285, 5,770,701, 5,770,710, 5,773,001, 5,877,296 (all to American Cyanamid Company). Structural analogues of calicheamicin which may be used include, but are not limited to, $\gamma 1I$, $\alpha 2I$, $\alpha 3I$, N-acetyl-$\gamma 1I$, PSAG and $\theta I1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

4. Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present disclosure further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99}m$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208, 020) may be used.

The compounds expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.). See pages 467-498, 2003-2004 Applications Handbook and Catalog.

5. Preparation of Antibody Drug Conjugates

In the antibody drug conjugates (ADC), an antibody (Ab) is conjugated to one or more drug moieties (D), e.g. about 1 to about 20 drug moieties per antibody (p=1 to about 20), through a linker (L). The ADC of the formula shown below may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

Ab-(L-D)$_p$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC'), and N-Succinimidyl (4-iodo-acetyl) aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide). A variety of radionuclides are available for the production of radioconjugated antibodies. Examples include $^{212}$Bi, $^{131}$I, $^{131}$In, $^{90}$Y, and $^{186}$Re.

V. Methods

A. Diagnostic Methods and Methods of Detection of Mutant SMO with Antibodies

In one aspect, antibodies of the disclosure are useful for detecting the presence of mutant SMO in a biological sample. The term "detecting" as used herein encompasses quantitative or qualitative detection. In certain embodiments, a biological sample comprises a cell or tissue, such as tumor tissue.

In one aspect, the disclosure provides a method of detecting the presence of mutant SMO in a biological sample. In certain embodiments, the method comprises contacting the biological sample with an anti-mutant SMO antibody under conditions permissive for binding of the anti-mutant SMO antibody to mutant SMO, and detecting whether a complex is formed between the anti-mutant SMO antibody and mutant SMO.

In one aspect, the disclosure provides a method of diagnosing a disorder associated with expression of mutant SMO or a condition, such as drug resistance, associated with expression of mutant SMO. In certain embodiments, the method comprises contacting a test cell with an anti-mutant SMO antibody; determining the level of expression (either quantitatively or qualitatively) of mutant SMO by the test cell by detecting binding of the anti-mutant SMO antibody to mutant SMO; and comparing the level of expression of mutant SMO by the test cell with the level of expression of mutant SMO by a control cell (e.g., a normal cell of the same tissue origin as the test cell or a cell that expresses wild-type SMO at levels comparable to such a normal cell), wherein a higher level of expression of mutant SMO by the test cell as compared to the control cell indicates the presence of a disorder associated with increased expression of mutant SMO. In certain embodiments, the test cell is obtained from an individual suspected of having a disorder associated with increased expression of mutant SMO. In certain embodiments, the disorder is a cell proliferative disorder, such as a cancer or a tumor. It is appreciated that in, for example, a tumor sample, there may be heterogeneity in SMO expression. Thus, it is appreciated that in a sample only a subset of cells in the sample may express the mutant SMO, and such expression is sufficient to, for example, be associated with drug resistance. Accordingly, evaluating expression includes evaluating expression in a sample and detecting mutant SMO protein in a subset of cells in a sample.

Exemplary disorders that may be diagnosed or in which drug resistance can be evaluated using an antibody of the disclosure include, but are not limited to medulloblastoma, pancreatic cancer basal cell carcinoma.

Certain other methods can be used to detect binding of antibodies to mutant SMO. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, antibodies are immobilized on an insoluble matrix. Immobilization may entail separating an anti-mutant SMO antibody from any mutant SMO that remains free in solution. This conventionally is accomplished by either insolubilizing the anti-mutant SMO antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-mutant SMO antibody after formation of a complex between the anti-mutant SMO antibody and mutant SMO, e.g., by immunoprecipitation.

It is understood that any of the above embodiments of diagnosis or detection may be carried out using an immunoconjugate of the disclosure in place of or in addition to an anti-mutant SMO antibody.

B. Methods of Detecting Mutant SMO with Nucleic Acid Probes

In one aspect, nucleic acid probes as described herein are useful for detecting the presence of mutant SMO nucleic acid in a biological sample. The term "detecting" as used herein encompasses quantitative or qualitative detection. In certain embodiments, a biological sample comprises a cell or tissue, such as tumor tissue.

In one aspect, the disclosure provides a method of detecting the presence of mutant SMO-encoding nucleic acid in a biological sample. In certain embodiments, the method comprises contacting nucleic acid from the biological sample with a probe as described herein and hybridizing the probe to the nucleic acid under conditions permissive for hybridization under stringent conditions, and detecting whether a complex is formed between the probe and the nucleic acid sample.

The mutant SMO-encoding nucleic acid may be detected using any methodology known in the art including, but not limited to the use of probes as described herein, or by PCR amplification, rtPCR sequencing, single strand conformational polymorphism (SSCP), differential restriction digestion of DNA, hybridization, or any other method known in the art.

In these methods, detection of a mutant SMO as described herein in a cell indicates the presence of a disorder associated with increased expression of mutant SMO (i.e., resistance to treatment with a Smo inhibitor such as GDC-0449). In certain embodiments, the test cell is obtained from an individual suspected of having a resistant tumor associated with expression of mutant SMO. As detailed above, it is appreciated that mutations may be in a subset of cells from a sample, such as a subset of cells from a tumor sample.

Exemplary disorders that may be diagnosed using an antibody of the disclosure include, but are not limited to medulloblastoma, pancreatic cancer basal cell carcinoma.

C. Methods of Detecting Mutant SMO in Cell Based Assays

Mutant SMO may be detected in cell based assays as known in the art including, but not limited to binding of a mutant SMO-detecting antibody to the surface of a cell sample, such as a tumor sample in vitro Immunohistochemical staining of histological preparations of tumor samples or tissue suspected of containing mutant SMO. Functional assays in which a tissue sample is contacted with GDC-0449 and hedgehog to determine whether Hh signaling occurs (e.g., by measuring activation of pathway components, expression of Gli, and the like). Any functional assay using the Hh signaling pathway that can be disrupted using GDC-0449 may be used in the method of the disclosure to determine the presence and activity of a mutant SMO.

D. Methods of Screening for Compounds that Bind to Mutant SMO

In some embodiments, the disclosure provides for a method of screening for a hedgehog pathway inhibitor that is capable of inhibiting hedgehog signaling in a cell that expresses any of the mutant SMO proteins disclosed herein. In some embodiments the screen is of single agents or a discrete number of agents. In some embodiments, the screen is of pools of agents. In some embodiments, the screen is high-throughput screening. In some embodiments, the screen is of a library or libraries of compounds (e.g., libraries of small molecules, libraries of antisense oligonucleotides, or libraries of antibodies or peptides). In some embodiments, screening may involve a primary assay alone or a primary assay and one or more secondary assays. In some embodiments, the agents can be assessed in an assay (e.g., a hedgehog signaling assay (e.g., by using any of the Gli1 expression assays described herein or known in the art to examine Gli1 nucleic acid or protein expression in response to an agent), a mutant SMO protein binding assay (e.g., by using any of the mutant SMO binding assays described herein), a cell proliferation assay (e.g., by using any of the cell proliferation assays described herein or known in the art). Use in screening assays is an exemplary use for the mutant SMO proteins and nucleic acids of the disclosure (e.g., a mutant SMO protein can be used in a cell free or cell based assay; a mutant SMO nucleic acid can be provided in a vector and used to express a mutant SMO protein in host cells or a host organism suitable for a screening assay.

The disclosure provides a method for screening for compounds that bind to mutant SMO. Without being held to any particular mode of operation, it is expected that much in the way that GDC-0449 binds wild-type SMO and doesn't bind mutant SMO, a compound which acts as an inhibitor of mutant SMO would bind mutant SMO. Thus, one may express the mutant SMO protein or a fragment thereof, such as a fragment comprising all or a portion of transmembrane domain 6 (TM6), and run binding assays using a library of compounds by any means known in the art. Also one may use a smaller library of compounds represented by variations of GDC-0449 using a modeling approach based on potential contact points of GDC-0449 and then modeling similar contact points for mutant SMO and variations of GDC-0449. Such modeling programs and algorithms may be any that are known in the art. Compounds that bind mutant SMO and wild-type SMO may be identified that are inhibitors of both wild-type and mutant SMO. Alternatively, compounds may be discovered that bind to mutant SMO, but which do not bind to wild-type SMO and therefore are inhibitors only for mutant SMO. In certain embodiments, binding and/or some other readout (e.g., hedgehog signaling) are assessed and compare to that for wildtype SMO or a suitable control (e.g., empty vector).

In one embodiment, the compounds to be screened are small molecule compounds such as variants of GDC-0449.

In other embodiments, the compounds that bind mutant SMO are antibodies that specifically recognize an epitope that is in the same region as the binding site of GDC-0449 to wild-type SMO. In one embodiment the antibody binds to a region in the carboxy-terminal portion of TM6 of mutant SMO and inhibits mutant SMO activity.

Compounds may alternatively, or additionally be screened for their ability to inhibit mutant SMO activity. In these embodiments, one may assess the ability of these compounds to inhibit hedgehog signaling in cells expressing mutant SMO.

These assays may be performed in cells that have a hedgehog signaling pathway intact but which express a recombinant SMO bearing the mutation in place of, or in addition to wild-type SMO. In these assays one determines the ability of the cell to have active hedgehog signaling when incubated with hedgehog in the presence or absence of the candidate inhibitor. If hedgehog signaling is inhibited in the presence of the candidate compound, such compound is a hedgehog inhibitor. In some embodiments the cells express both wild-type and mutant SMO and are incubated with GDC-0449 and a candidate inhibitor. In other embodiments, the cells express only mutant SMO and may be incubated with Hh and the candidate inhibitor alone (i.e., in the absence of GDC-0449). The compound is an inhibitor of mutant SMO if Hh signaling is reduced or inhibited in such cells.

In some embodiments, the disclosure provides for a method of identifying a hedgehog pathway inhibitor, wherein the method comprises: contacting a cell with an amount of a test agent, wherein the cell is responsive to hedgehog protein or has increased hedgehog signaling and/or activation of the hedgehog signaling pathway, and wherein the cell expresses any of the mutant SMO proteins described herein, and b) determining, as compared to a control, whether the test agent inhibits hedgehog signaling in the cell, wherein if the test agent inhibits hedgehog signaling in the cell relative to the control, then the test agent is identified as a hedgehog pathway inhibitor. In some embodiments, the control (or basis for comparison) is a cell expressing a wildtype SMO protein (e.g, a SMO protein having the amino acid sequence of SEQ ID NO: 1). In some embodiments, the control is a cell expressing the same mutant SMO proteins as the cell contacted with the test agent, wherein the control is untreated or treated with a control agent to which the mutant SMO protein is partially or completely resistant. In some embodiments, the control agent is vismodegib, LY2940680, LDE225 and/or compound 5. In some embodiments, the test agent binds to mutant SMO protein but not wildtype SMO protein. In some embodiments, the test agent binds to both the mutant SMO protein and wildtype SMO protein. In some embodiments, the test agent is more effective in inhibiting hedgehog signaling in a cell expressing mutant SMO protein than in a cell expressing wildtype SMO protein.

In some embodiments, the disclosure provides for a method of identifying a hedgehog pathway inhibitor, wherein the method comprises: contacting a cell with an amount of an agent, wherein the cell is responsive to hedgehog protein or has increased hedgehog signaling and/or activation of the hedgehog signaling pathway, and wherein the cell expresses any of the mutant SMO proteins described herein, and b) determining, as compared to a control, whether the agent inhibits growth and/or proliferation of the cell, wherein if the agent inhibits growth and/or proliferation of the cell relative to the control, then the agent is identified as a hedgehog pathway inhibitor. In some embodiments, the control is a cell expressing a wildtype SMO protein (e.g, a SMO protein having the amino acid sequence of SEQ ID NO: 1). In some embodiments, the control is a cell expressing the same mutant SMO proteins as the cell contacted with the test agent, wherein the control is untreated or treated with a control agent to which the mutant SMO protein is partially or completely resistant. In some embodiments, the control agent is vismodegib, LY2940680, LDE225 and/or compound 5. In some embodiments, the test agent binds to mutant SMO protein but not wildtype SMO protein. In some embodiments, the test agent binds to both the mutant SMO protein and wildtype SMO protein. In some embodiments, the test agent is more effective in inhibiting growth and/or proliferation of a cell expressing mutant SMO protein than of a cell expressing wildtype SMO pr In some embodiments, the cell used in the screening methods described herein is in culture. In some embodiments, the agent contacted with the cells in the culture is sufficient to inhibit, partially or entirely, hedgehog signaling in at least 10%, 15%, 20%, 25%, 30%, 40%, 50%, 60%, 70%, 80%, 90%, or 100% of cells in a cell culture. In some embodiments, the agent contacted with the cells in the culture is sufficient to reduce the rate of proliferation of a cell and/or rate of survival of at least 10%, 15%, 20%, 25%, 30%, 40%, 50%, 60%, 70%, 80%, 90%, or 100% of cells in a cell culture, wherein the cells are expressing or overexpressing hedgehog or have active hedgehog signaling.

In other embodiments, the cell is in an animal. In some embodiments, the animal is a mammal or other vertebrate. In some embodiments, the animal is post-natal. In some embodiments, the animal is pediatric. In some embodiments, the animal is adult. When referring to cells in vitro, the cells may be of any vertebrate species, such as a mammal, such as rodent, hamster, or human. In vitro or in vivo, a cell may be a cancer cell, such as a primary cancer cell, a metastatis cancer cell, or a cancer cell line. In some embodiments, the cell is a medullablastoma cell. In some embodiments, the cell is a basal cell carcinoma cell. In some embodiments, the cell is a nevoid basal cell carcinoma cell. In some embodiments, the cell is a Gorlin's Syndrome cell.

In some embodiments, the cell comprises one or more mutations in a hedgehog signaling pathway gene. In some embodiments, the one or more mutations are in patched. In some embodiments, the patched mutation is loss-of-function mutation. In some embodiments, the one or more mutations are in smoothened. In some embodiments, the smoothened mutation is a smoothened gain-of-function mutation. In some embodiments, the gain-of-function smoothened mutation results in a constitutively active smoothened protein. In some embodiments, the one or more mutations are in suppressor-of-fused, and the cell has suppressor-of-fused (SuFu) loss-of-function. In some embodiments, the SuFu mutation results in a partial loss-of-function of SuFu activity. In some embodiments, the SuFu mutation results in a full loss-of-function in SuFu activity. In some embodiments, the SuFu mutation confers resistance to vismodegib.

In some embodiments, the agent tested in any of the screening methods described herein is a small molecule. In other embodiments, the agent is a polypeptide. In other embodiments, the agent is an siRNA antagonist.

In some embodiments of any of the screening methods described herein, the mutant SMO DNA is exogenously expressed in a cell. In some embodiments, the mutant SMO DNA is stably expressed in the cell. In some embodiments, the mutant SMO DNA is transiently expressed in the cell.

The growth inhibitory effects of the various hedgehog pathway inhibitors useable in the disclosure may be assessed by methods known in the art, e.g., using cells which express a mutant SMO polypeptide either endogenously or following transfection with the respective mutant SMO gene. For example, appropriate tumor cell lines and cells transfected with mutant SMO-encoding DNA may be treated with the hedgehog pathway inhibitors of the disclosure at various concentrations for a few days (e.g., 2-7 days) and stained with crystal violet, MTT or analyzed by some other colorimetric or luciferase-based (eg CellTiterGlo) assay. Another method of measuring proliferation would be by comparing $^3$H-thymidine uptake by the cells treated in the presence or absence of such hedgehog pathway inhibitors. After treatment, the cells are harvested and the amount of radioactivity incorporated into the DNA quantitated in a scintillation counter. Appropriate positive controls include treatment of a selected cell line with a growth inhibitory antibody or small molecule known to inhibit growth of that cell line. Growth inhibition of tumor cells in vivo can be determined in various ways known in the art. In some embodiments, the tumor cell is one that has one or more mutations in a hedgehog pathway signaling gene. In some embodiments, such hedgehog pathway inhibitors will inhibit cell proliferation of a hedgehog-expressing tumor cell in vitro or in vivo by about 10-25%, by about 25-100%, by about 30-100%, by about 50-100%, or by about or 70-100% compared to the untreated tumor cell. Growth inhibition can be measured at a hedgehog pathway inhibitor concentration of about 0.5 to 30 µg/ml, about 0.5 nM to 200 nM, about 200 nM to 1 µM, about 1 µM to 5 µM, or about 5 µM to 10 µM, in cell culture, where the growth inhibition is determined 1-10 days after exposure of the tumor cells to the antagonist. The antagonist is growth inhibitory in vivo if administration of antagonist and/or agonist at about 1 µg/kg to about 100 mg/kg body weight results in reduction in tumor size or reduction of tumor cell proliferation within about 5 days to 3 months from the first administration of the antibody or small molecule antagonist, in some embodiments, within about 5 to 30 days.

In some embodiments, to select for hedgehog pathway inhibitors which induce cell death, loss of membrane integrity as indicated by, e.g., propidium iodide (PI), trypan blue or 7AAD uptake may be assessed relative to control. A PI uptake assay can be performed in the absence of complement and immune effector cells. In some embodiments, mutant SMO protein-expressing expressing tumor cells are incubated with medium alone or medium containing the appropriate hedgehog pathway inhibitor. The cells are incubated for a 3 day time period. Following each treatment, cells are washed and aliquoted a into 35 mm strainer-capped 12×75 tubes (1 ml per tube, 3 tubes per treatment group) for removal of cell clumps. Tubes then receive PI (10 g/ml). Samples may be analyzed using a FACSCAN® flow cytometer and FACSCONVERT® CellQuest software (Becton Dickinson), or any other device used by the skilled worker for analyses. Those hedgehog pathway inhibitors that induce statistically significant levels of cell death as determined by PI uptake may then be selected.

In some embodiments, to screen for hedgehog pathway inhibitors which bind to an epitope on a mutant SMO polypeptide, a routine cross-blocking assay such as that described in Antibodies: A Laboratory Manual, Cold Spring Harbor Laboratory, Ed Harlow and David Lane (1988), can be performed. This assay can be used to determine if a test antibody, polypeptide, oligopeptide or other organic molecule binds the same site or epitope as a known hedgehog pathway inhibitor. Alternatively, or additionally, epitope mapping can be performed by methods known in the art. For example, the mutant SMO protein sequence can be mutagenized such as by alanine scanning or by making chimerae with immunologically distinct GPCR proteins, to identify contact residues. The mutant antigen is initially tested for binding with polyclonal antibody to ensure proper folding. In a different method, peptides corresponding to different regions of a mutant SMO protein can be used in competition assays with the test antibodies or with a test antibody and an antibody with a characterized or known epitope.

In some embodiments, the mutant SMO protein or the candidate hedgehog pathway inhibitor agent is immobilized on a solid phase, e.g., on a microliter plate, by covalent or non-covalent attachments. Non-covalent attachment generally is accomplished by coating the solid surface with a solution of the mutant SMO protein or candidate hedgehog signaling agent and drying. Alternatively, an immobilized antibody, e.g., a monoclonal antibody, specific for the target portion of mutant SMO to be immobilized can be used to anchor it to a solid surface. The assay may be performed by adding the non-immobilized component, which may be labeled by a detectable label, to the immobilized component, e.g., the coated surface containing the anchored component. When the reaction is complete, the non-reacted components may be removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate hedgehog pathway inhibitor interacts with but does not bind directly to a hedgehog signaling polypeptide identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London). 340:245-246 (1989); Chien et al, Proc. Natl. Acad. Sci. USA, 88:9578-9582 (1991)) as disclosed by Chevray and Nathans, Proc. Natl. Acad. Sci. USA. 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-LacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

The assays can be performed in a variety of formats, including protein-protein binding assays, biochemical screening assays, immunoassays, and cell-based assays, which are well characterized in the art.

Agents that interfere with the interaction of hedgehog signaling polypeptide and other intra- or extracellular components (e.g., Costal-2) can be tested by means well-known by the skilled worker. In some embodiments, a reaction mixture is prepared containing the mutant SMO polypeptide and an intra- or extracellular component under conditions and for a time allowing for the interaction and binding of the two products. In some embodiments, to test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test agent indicates that the test agent interferes with the interaction of the test compound and its reaction partner.

The disclosure contemplates methods for identifying hedgehog pathway inhibitors using any one or combination of the foregoing assay steps. In other words various screening assays can be combined to identify antagonists having, for example, a particular activity or to confirm that an agent that antagonizes mutant SMO in one assay also inhibits hedgehog signaling in an independent assay. For any assay or method of identification, results may be compared to one or more appropriate controls, including positive and/or negative controls.

For any of the foregoing assay methods for screening and/or identifying hedgehog pathway inhibitors, agents may be screened singly or in pools. Agents may be screened from a library of agents or a set of candidate agents. Suitable agents that may be screened include, but are not limited to, antibodies, antibody fragments, peptides, antisense oligonucleotides, RNAi and small molecules (e.g., a bromodomain inhibitor).

In some embodiments, the cell used in any of the screening methods disclosed herein comprises one or more mutations in a gene that results in an activation or increase hedgehog signaling. In some embodiments, the one or more mutations are in the patched gene resulting in a patched loss of function. In some embodiments, the one or more mutations in the patched gene result in a mutant gene that encodes a patched protein having one or more of the following mutations: S616G, fs251, E380*, Q853*, W926*, P1387S, sp2667, Q501H, fs1017, fs108, or A1380V.

In some embodiments, the one or more mutations in a gene that results in an activation or increase hedgehog signaling are in smoothened, and the cell has a smoothened mutation. In some embodiments, the smoothened mutation is a smoothened gain-of-function mutation. In some embodiments, the gain-of-function smoothened mutation results in a constitutively active smoothened protein. See, e.g., WO 2011/028950 and WO2012047968, each of which is incorporated by reference. In some embodiments, the smoothened mutation is a mutation at a position corresponding to position 535 of SEQ ID NO: 1. In certain embodiments, the mutation is a mutation at a position corresponding to position 562 of SEQ ID NO: 1. In certain embodiments, the mutation is W535L at position 535 or at that corresponding position in SEQ ID NO: 1. In some embodiments, the smoothened mutation is a mutation corresponding to position R562Q of SEQ ID NO: 1 (a R562Q mutation at position 562 or at a position corresponding to position 562 of SEQ ID NO: 1. In some embodiments, the smoothened mutation is a mutation at a position corresponding to position 412 of SEQ ID NO: 1, such as a L412F at such a position of SEQ ID NO: 1. In some embodiments, the smoothened mutation has an alternative mutation that renders it resistant to certain smoothened inhibitors. In some embodiments, the smoothened protein comprises an amino acid alteration at amino acid position 518 of SEQ ID NO: 1 or at a position corresponding to position 518 of SEQ ID NO: 1. In some embodiments, the amino acid alteration is E518K or E518A substitution at the amino acid position corresponding to amino acid position 518 of SEQ ID NO: 1. In some embodiments, the smoothened protein comprises an amino acid alteration at amino acid position 473 of SEQ ID NO: 1 or at a position corresponding to position 473 of SEQ ID NO: 1.

In some embodiments, the one or more mutations are in a hedgehog gene and result in overexpression of a hedgehog protein. In some embodiments, the overexpressed hedgehog protein is Sonic hedgehog protein. In some embodiments, the overexpressed hedgehog protein is Indian hedgehog protein. In some embodiments, the overexpressed hedgehog protein is Desert hedgehog protein.

In some embodiments, the one or more mutations are in suppressor-of-fused, and the cell has suppressor-of-fused (SuFu or SUFU) loss-of-function. In some embodiments, the results in a loss-of-function in SuFu activity. In some embodiments, the SuFu mutation is in a medulloblastoma, meningioma, adenoid cystic carcinoma, basal cell carcinoma and rhabdomyosarcoma cancer cell. In some embodiments, the SuFu mutation is any of the mutations described in Brugieres et al., 2012, JCO, 30(17):2087-2093, which is incorporated herein in its entirety. In some embodiments, the SuFu mutation is any of the mutations described in Tables 2A or 2B or any of the mutations described in Brugieres et al., 2012, JCO, 30(17):2087-2093, which is incorporated herein in its entirety.

TABLE 2A

| Germline SUFU Mutations | | | | |
|---|---|---|---|---|
| Age at Diagnosis of MB | Histologic Subtype | Associated Symptoms | Inheritance of Mutation | Mutation |
| 4 years | Desmoplastic | Developmental delay | NA | Loss of contiguous genes at 10q |
| | | Frontal bossing, hypertelorism | | IVS1-1A →T |
| NA | Desmoplastic | None | NA | 143insA |
| NA | Desmoplastic | Meningioma in radiation field | NA | |

TABLE 2A-continued

Germline SUFU Mutations

| Age at Diagnosis of MB | Histologic Subtype | Associated Symptoms | Inheritance of Mutation | Mutation |
|---|---|---|---|---|
| 8 months | MBEN | Macrocrania, palmar and plantar pits | Inherited | c.1022 + 1G > A |
| <1 month | MBEN | None | Inherited | c.72delC |
| <3 months | MBEN | None | Inherited | c.72delC |
| <1 months | MBEN | None | Inherited | c.72insC |
| 6-12 months | Desmoplastic/nodular | None | Inherited | c.72insC |
| <6 months | Desmoplastic/nodular | None | Inherited | c.72insC |
| 12-24 months | MB NOS | None | Inherited | c.72insC |
| 22 months | Desmoplastic/nodular | None | NA | c.846insC |
| 23 months | Desmoplastic/nodular | None | NA | c.1022 + 1G > A |

Abbreviations: MB, medulloblastoma; MBEN, MB with extensive nodularity; NA, not available; NOS, not otherwise specified.

TABLE 2B

Germline Pathogenic SUFU Mutations

| Exon/Intron | Type of Mutation | Nucleotide Change (In SEQ ID NO: 11) | Consequence (In SEQ ID NO: 10) | Tumor Analysis |
|---|---|---|---|---|
| Intron 1 | Splice → frameshift | c.182 + 3A > T | p.Thr55fs | Not available |
| Exon 2 | Frameshift | c.294_295dupCT | p.Tyr99fs | Not available |
| Intron 2 | Splice → frameshift | c.318-10delT | p.Phe107fs | Loss of wild-type allele |
| Exon 3 | Large duplication | c.318-?_454 + ?dup | p.Glu106-?_Glu152 + ?dup | UV (c.1022 + 5G > A) |
| Exon 3 | Missense | c.422T > G | p.Met141Arg | Not available |
| Exon 9 | Nonsense | c.1123C > T | p.Gln375X | Not available |
| Exon 9 | Frameshift | c.1149_1150dupCT | p.Cys384fs | Loss of wild-type allele |
| Intron 10 | Splice → frameshift | c.1297-1G > C | p.? | Not available |

Abbreviation: UV, unknown variant.

In some embodiments, the SuFu mutation comprises a mutation at a position corresponding to any of the following amino acid positions in SEQ ID NO: 10: position 15, 184, 123, 295, 187. In certain embodiments, the SuFu mutation comprises any one or more of: P15L, Q184X, R123C, L295fs, or P187L, where the mutation is at that position or at the position corresponding to the stated position in SEQ ID NO: 10. In some embodiments, the SuFU mutation is any of the mutations corresponding to c.1022+1G>A (IVS8-1G>T), c.72delC, c.72insC, 143insA, c.846insC, or IVS1-1A→T of SEQ ID NO: 11. In some embodiments, the SuFu mutation is any of the mutations described in Taylor et al (2002) Nat Genet 31:306-310 (e.g., IVS8-1G>T (=c.1022+1G>A), 1129del, P15L and Ng's two (all +LOH)); Slade et al (2011) Fam Cancer 10:337-342, 2011 (e.g., c.1022+1G>A; c.848insC); Pastorino et al (2009) Am J Med Genet A 149A:1539-1543 (e.g., c.1022+1G>A); Ng et al (2005) Am J Med Genet A 134:399-403 (e.g., 143insA; IVS1-1A>T); Kijima et al (2012) Fam Cancer 11: 565-70 (e.g., c.550C>T (Q184X)); Aavikko et al (2012) Am J Hum Genet 91: 520-526 (e.g., c.367C>T (R123C)); Stephens et al (2013) J Clin Invest 123: 2965-2968 (e.g., x881_882insG (L295fs)); or Reifenberger et al (2005) Brit J Dermatology 152: 43-51 (e.g., c560C>T (P187L)).

In some embodiments, the cell is a human cell and has a chromosome 10 duplication and/or a deletion of a portion of 10q, wherein said portion contains SUFU and PTEN. In some embodiments, the cell comprises a Fs1017 SUFU mutation.

In some embodiments, the cell used in any of the screening methods described herein is a cell in which the hedgehog signaling pathway is active. In some embodiments, the cell is a cell in which the hedgehog signaling pathway is constitutively active. In some embodiments, the cell is a cell that has been stimulated with hedgehog protein or hedgehog agonist. In some embodiments, the activity of the hedgehog pathway in a cell is determined by monitoring Gli1 levels or activity in a Gli-luciferase reporter assay.

In some embodiments, the cell used in any of the screening methods described herein is a cell in culture. In some embodiments, the disclosure provides for a method comprising contacting a culture comprising a plurality of cells. In some embodiments, the cell is in a vertebrate. In some embodiments, the cell is in a mammal, and contacting the cell comprises administering the hedgehog signaling inhibitor to the mammal. In some embodiments, the mammal is a human subject. In some embodiments, the cell is a cancer cell and/or the mammal is a mammal diagnosed with cancer. In some embodiments, the cancer cell is a cancer cell selected from the group consisting of: a colon, lung, prostate, skin, blood, liver, kidney, breast, bladder, bone, brain, medulloblastoma, sarcoma, basal cell carcinoma, gastric, ovarian, esophageal, pancreatic, or testicular cancer cell. In some embodiments, the cancer cell is a medulloblastoma cell, a basal cell carcinoma cell, or a nevoid basal cell carcinoma cell (Gorlin syndrome cell).

In certain embodiments, once an agent is identified as a hedgehog pathway inhibitor, the agent can then be formulated and further evaluated in a cell or animal-based assay. For example, the agent can be tested in a cell or animal-based cancer model to evaluate efficacy as an anti-cancer agent.

VI. Methods of Treatment

In some embodiments, the present disclosure relates to methods of modulating a differentiation state, survival, and/or proliferation of a cell expressing a smoothened protein having any of the smoothened mutations described herein. In some embodiments, the cell is in a subject (e.g., a human patient). In some embodiments, the cell is in culture, and the method comprises an in vitro method. In certain embodiments, the cell is a cancer cell. In certain embodiments, the cell is characterized by unwanted or abnormal cell proliferation. In some embodiments, the cell comprises or has been predetermined to express a smoothened protein comprising any of the smoothened mutations described herein. In certain embodiments, the cell has been predetermined to express a smoothened polypeptide comprising a mutation, relative to wild type human SMO, at an amino acid corresponding to any one or more of 241, 281, 408, 459, 469, 533 and/or 535 of SEQ ID NO: 1. In some embodiments, the cell expresses a smoothened polypeptide comprising any of the following substitutions at an amino acid corresponding to T241M, W281C, I408V, A459V, C469Y, S533N and/or W535L of SEQ ID NO: 1.

In some embodiments, the disclosure provides for a method of reducing hedgehog signaling in a cell, wherein the cell expresses a smoothened protein having any of the smoothened mutations described herein, wherein the cell is responsive to hedgehog protein or comprises one or more mutations in a hedgehog signaling pathway gene (e.g., a component of the hedgehog signaling pathway), wherein the one or more mutations results in increased hedgehog signaling and/or activation of the hedgehog signaling pathway in the absence of ligand, wherein the method comprises the step of contacting the cell with an effective amount of an agent, wherein the agent is a hedgehog pathway inhibitor. In some embodiments, the agent is a compound that selectively binds and inhibits the mutant smoothened protein. In some embodiments, the agent inhibits a component of the hedgehog signaling pathway that acts downstream of the mutant smoothened protein in the cell. In other embodiments, the agent is a bromodomain inhibitor.

In some embodiments, the disclosure provides for a method of treating a subject having a cancer with an anti-cancer therapeutic agent, wherein said subject comprises and/or has been determined to express a mutant SMO protein, wherein said mutant SMO protein has an amino acid other than alanine at position corresponding to position 239 of SEQ ID NO: 1. In some embodiments, the disclosure provides for a method of inhibiting hedgehog signaling in a cell, wherein the cell expresses a mutant SMO protein having an amino acid other than alanine at the position corresponding to position 239 of SEQ ID NO: 1. In some embodiments, the disclosure provides for a method of diagnosing a subject having a cancer, comprising the steps of: a) obtaining a sample from the subject, b) testing said sample for the presence of a nucleic acid encoding a mutant SMO protein having an amino acid other than alanine at the position corresponding to position 239 of SEQ ID NO: 1, wherein if said sample comprises said mutant SMO protein, said subject has cancer. In some embodiments, the cancer is a basal cell carcinoma. In some embodiments, the mutant SMO protein has a valine at the amino acid position corresponding to amino acid position 239 of SEQ ID NO: 1.

In some embodiments, the disclosure provides for a method of inhibiting unwanted growth, proliferation or survival of a cell, wherein the cell expresses a smoothened protein having any of the smoothened mutations described herein, wherein the cell is responsive to hedgehog protein or comprises one or more mutations in a hedgehog signaling pathway gene, wherein the one or more mutations results in increased hedgehog signaling and/or activation of the hedgehog signaling pathway in the absence of ligand, wherein the method comprises the step of contacting the cell with an effective amount of an agent, wherein the agent is a hedgehog pathway inhibitor. In some embodiments, the agent is an agent that selectively binds and inhibits the mutant smoothened protein. In some embodiments, the agent inhibits a component of the hedgehog signaling pathway that acts downstream of the mutant smoothened protein in the cell. In some embodiments, the agent is a bromodomain inhibitor.

In some embodiments, the disclosure provides for a method of inhibiting growth, proliferation or survival of a tumor cell, wherein the tumor cell expresses a smoothened protein having any of the smoothened mutations described herein, wherein the cell is responsive to hedgehog protein or comprises one or more mutations in a hedgehog signaling pathway gene, wherein the one or more mutations results in increased hedgehog signaling and/or activation of the hedgehog signaling pathway in the absence of ligand, wherein the method comprises the step of contacting the cell with an effective amount of an agent, wherein the agent is a hedgehog pathway inhibitor. In some embodiments, the agent is an agent that selectively binds and inhibits the mutant smoothened protein. In some embodiments, the agent inhibits a component of the hedgehog signaling pathway that acts downstream of the mutant smoothened protein in the cell. In other embodiments, the agent is a bromodomain inhibitor. In some embodiments, the method comprises administering an agent to a patient in need thereof.

In some embodiments, the cell treated with any of the methods disclosed herein comprises one or more mutations in a gene that results in an activation or increase hedgehog signaling, wherein said mutations are as described above. In some embodiments, the hedgehog pathway inhibitor used in any of the methods disclosed herein is a polynucleotide molecule that inhibits the expression of any of the mutant smoothened proteins described herein. In some embodiments, the polynucleotide molecule is an antisense oligonucleotide that specifically hybridizes to a nucleic acid encoding any of the mutant smoothened proteins disclosed herein. In some embodiments, the antisense molecule does not hybridize to a nucleic acid that encodes a wildtype smoothened protein (e.g., a nucleic acid that encodes a protein having the sequence of SEQ ID NO: 1). In some embodiments, the hedgehog pathway inhibitor is a RNAi antagonist that targets the mRNA transcript encoding any of the mutant smoothened polypeptides disclosed h In some embodiments, the RNAi antagonist is an siRNA. In some embodiments, the siRNA is 19-23 nucleotides in length. In some embodiments, the siRNA is double stranded, and includes short overhang(s) at one or both ends. In some embodiments, the siRNA targets an mRNA transcript encoding any of the mutant smoothened polypeptides disclosed herein. In some embodiments, the RNAi or siRNA does not target an mRNA transcript that encodes a wildtype smoothened protein (e.g., a nucleic acid that encodes a protein having the sequence of SEQ ID NO: 1). In some embodiments, the RNAi comprises an shRNA.

In some embodiments, the hedgehog pathway inhibitor used in any of the methods disclosed herein is a small molecule that specifically binds to any of the mutant smoothened polypeptides described herein. In some embodiments, the small molecule binds to a polypeptide that acts downstream of smoothened in the hedgehog signaling pathway. In some embodiments, the small molecule binds to a polypeptide in a pathway distinct from the hedgehog signaling pathway. In some embodiments, the small molecule is a bromodomain inhibitor. In some embodiments, the bromodomain inhibitor is a BRD4 inhibitor. In some embodiments, the bromodomain inhibitor is any of the bromodomain inhibitors described in Ciceri et al., 2014, Nature Chemical Biology, 10:305-312; Muller et al., 2014, Med Chem Commun, 5:288-296; Gamier et al., 2014, 24(2): 185-199, which are each incorporated herein in their entirety. In some embodiments, the bromodomain inhibitor is I-BET762, JQ1, JQ2, BRD4 by BI-2536 and TG-101348.

In some embodiments, the hedgehog pathway inhibitor used in any of the methods disclosed herein is an antibody that specifically binds to any of the mutant smoothened polypeptides described herein. In some embodiments, the antibody binds to a polypeptide that acts downstream of smoothened in the hedgehog signaling pathway. In some embodiments, the antibody is a monoclonal antibody.

In some embodiments, the cell contacted with an agent according to any of the methods described herein is also contacted with an additional inhibitor of the hedgehog signaling pathway (e.g., a HPI). In some embodiments, the additional inhibitor of the hedgehog signaling pathway is a veratrum-type steroidal alkaloid. In some embodiments, the veratrum-type steroidal alkaloid is cyclopamine, or KAAD-cyclopamine or any functional derivatives thereof (e.g., IPI-269609 or IPI-926). In some embodiments, the veratrum-type steroidal alkaloid is jervine, or any functional derivatives thereof. In some embodiments, the additional inhibitor is vismodegib, sonidegib, BMS-833923, PF-04449913, or LY2940680, or any functional derivatives thereof. In some embodiments the additional inhibitor is a smoothened inhibitor chemically unrelated to veratrum alkaloids or vismodegib, including but not limited to: sonidegib, BMS-833923, PF-04449913, LY2940680, Erivedge, BMS-833923 (XL319), LDE225 (Erismodegib), PF-04449913, NVP-LDE225, NVP-LEQ506, TAK-441, XL-319, LY-2940680, SEN450, Itraconazole, MRT-10, MRT-83, or PF-04449913.). In some embodiments, the additional inhibitor is any of the compounds disclosed in Amakye, et al., Nature Medicine, 19(11):1410-1422 (which is incorporated herein in its entirety). In some embodiments, the additional inhibitor of the hedgehog signaling pathway is an antibody. In some embodiments, the antibody is an antibody that binds, such as specifically binds, hedgehog proteins. In some embodiments, the additional inhibitor of the hedgehog signaling pathway is an RNAi antagonist.

Subjects in need of treatment or diagnosis include those already with aberrant hedgehog signaling as well as those prone to having or those in whom aberrant hedgehog signaling is to be prevented. For example, a subject or mammal is successfully "treated" for aberrant hedgehog signaling if, according to the method of the present disclosure, after receiving a hedgehog pathway inhibitor, the patient shows observable and/or measurable reduction in or absence of one or more of the following: reduction in the number of tumor cells or absence of such cells; reduction in the tumor size; inhibition (i.e., slow to some extent and, in some embodiments, stop) of tumor cell infiltration into peripheral organs including the spread of cancer into soft tissue and bone; inhibition (i.e., slow to some extent and, in some embodiments, stop) of tumor metastasis; inhibition, to some extent, of tumor growth; and/or relief to some extent, of one or more of the symptoms associated with the specific cancer; reduced morbidity and mortality, and improvement in quality of life issues. To the extent such hedgehog pathway inhibitors may prevent growth and/or kill existing cancer cells, it may be cytostatic and/or cytotoxic. Reduction of these signs or symptoms may also be felt by the patient. Additionally, successful exposure to the hedgehog pathway inhibitor (particularly in cases where no tumor response is measurable) can be monitored by Gli1 expression either in skin punch biopsies or hair follicles (as done for vismodegib).

In certain embodiments, the subject treated with any of the hedgehog pathway inhibitors disclosed herein expresses a mutant smoothened protein that is resistant to vismodegib. In some embodiments, the subject expresses a smoothened protein comprising any of the smoothened mutations described herein. In certain embodiments the subject expresses a smoothened polypeptide comprising a mutation at an amino acid corresponding to any one or more of 241, 281, 408, 459, 469, 533 and/or 535 of SEQ ID NO: 1. In some embodiments the subject expresses a smoothened polypeptide comprising a mutation at an amino acid corresponding to T241M, W281C, I408V, A459V, C469Y, S533N and/or W535L of SEQ ID NO: 1. In some embodiments, prior to being treated with any of the treatment methods described herein, the subject has been determined to express a smoothened protein comprising any of the smoothened mutations described herein. In certain embodiments, prior to being treated with any of the treatment methods described herein, the subject has been determined to express a smoothened polypeptide comprising a mutation at an amino acid corresponding to any one or more of 241, 281, 408, 459, 469, 533 and/or 535 of SEQ ID NO: 1. In some embodiments, prior to being treated with any of the treatment methods described herein, the subject has been determined to express a smoothened polypeptide comprising a mutation at an amino acid corresponding to T241M, W281C, I408V, A459V, C469Y, S533N and/or W535L of SEQ ID NO: 1.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and tests for calcium level and other enzymes to determine the extent of metastasis. CT scans can also be done to look for spread to regions outside of the tumor or cancer. The disclosure described herein relating to the process of prognosing, diagnosing and/or treating involves the determination and evaluation of, for example, Gli1 expression.

"Mammal" for purposes of the treatment of, alleviating the symptoms of or diagnosis of a disease (e.g., cancer) refers to any animal classified as a mammal, including humans, domestic and farm animals, and zoo, sports, or pet animals, such as dogs, cats, cattle, horses, sheep, pigs, goats, rabbits, ferrets, etc. In some embodiments, the mammal is human. In some embodiments, the mammal is post-natal. In some embodiments, the mammal is pediatric. In some embodiments, the mammal is adult.

Administration "in combination with" one or more further therapeutic agents includes simultaneous (concurrent) and consecutive administration in any order.

In certain embodiments, a hedgehog pathway inhibitor is used in the treatment of a cancer selected from any of the cancers described herein or a cancer in which one or more cells of a tumor comprises a mutation in a hedgehog pathway component, such as any of the mutations described herein. It should be generally appreciated and is specifically noted herein that tumors comprise cells that may have a level of heterogeneity. Accordingly, not all cells in a tumor necessarily comprise a particular deleterious mutation. Accordingly, the disclosure contemplates methods in which a cancer or tumor being treated comprises cells having a mutation in a component of the hedgehog pathway, such as any of the mutations described herein, even if such a mutation is not present in every cell of the tumor.

It is further contemplated that use of hedgehog pathway inhibitors may be specifically targeted to disorders where the affected tissue and/or cells exhibit high hedgehog pathway activation. Expression of Gli genes activated by the hedgehog signaling pathway, including Gli1 and Gli2, most consistently correlate with hedgehog signaling across a wide range or tissues and disorders, while Gli3 is somewhat less so. The Gli genes encode transcription factors that activate expression of many genes needed to elicit the full effects of hedgehog signaling. However, the Gli3 transcription factors can also act as a repressor of hedgehog effector genes, and therefore, expression of Gli3 can cause a decreased effect of the hedgehog signaling pathway. Whether Gli3 acts as a transcriptional activator or repressor depends on post-translational events, and therefore it is expected that methods for detecting the activating form (versus the repressing form) of Gli3 protein (such as western blotting) would also be a reliable measure of hedgehog pathway activation. The Gli1 gene is strongly expressed in a wide array of cancers, hyperplasias and immature lungs, and serves as a marker for the relative activation of the hedgehog pathway. In addition, tissues such as immature lung, that have high Gli gene expression, are strongly affected by hedgehog inhibitors. Accordingly, it is contemplated that the detection of Gli gene expression may be used as a powerful predictive tool to identity tissues and disorders that will particularly benefit from treatment with a hedgehog antagonist. In some embodiments, Gli1 expression levels are detected, either by direct detection of the transcript or by detection of protein levels or activity. Transcripts may be detected using any of a wide range of techniques that depend primarily on hybridization or probes to the Gli1 transcripts or to cDNAs synthesized therefrom. Well known techniques include Northern blotting, reverse-transcriptase PCR and microarray analysis of transcript levels. Methods for detecting Gli protein levels include Western blotting, immunoprecipitation, two-dimensional polyacrylamide gel electrophoresis (2D SDS-PAGE—in some embodiments compared against a standard wherein the position of the Gli proteins has been determined), and mass spectroscopy. Mass spectroscopy may be coupled with a series of purification steps to allow high-throughput identification of many different protein levels in a particular sample. Mass spectroscopy and 2D SDS-PAGE can also be used to identify post-transcriptional modifications to proteins including proteolytic events, ubiq-uitination, phosphorylation, lipid modification, etc. Gli activity may also be assessed by analyzing binding to substrate DNA or in vitro transcriptional activation of target promoters. Gel shift assay, DNA footprinting assays and DNA-protein crosslinking assays are all methods that may be used to assess the presence of a protein capable of binding to GU binding sites on DNA. J Mol. Med 77(6):459-68 (1999); Cell 100(4): 423-34 (2000); Development 127(19): 4923-4301 (2000).

Because Gli1 is so ubiquitously expressed during hedgehog activation, any degree of Gli1 overexpression should be useful in determining that a hedgehog pathway inhibitor will be an effective therapeutic. In some embodiments, Gli1 should be expressed at a level at least twice as high as in a normal control cell/tissue/subject. In some embodiments, Gli1 expression is four, six, eight or ten times as high as in a normal cell/tissue/subject.

In certain embodiments, Gli1 transcript levels are measured, and diseased or disordered tissues showing abnormally high Gli1 levels are treated with a hedgehog pathway inhibitor. In other embodiments, the condition being treated is known to have a significant correlation with aberrant activation of the hedgehog pathway, even though a measurement of Gli1 expression levels is not made in the tissue being treated. Premature lung tissue, lung cancers (e.g., adeno carcinomas, bronco-alveolar adenocarcinoma, small cell carcinomas), breast cancers (e.g., inferior ductal carcinomas, inferior lobular carcinomas, tubular carcinomas), prostate cancers (e.g., adenocarcinomas), and benign prostatic hyperplasias all show strongly elevated Gli1 expression levels in certain cases. Accordingly, Gli1 expression levels are a powerful diagnostic device to determine which of these tissues should be treated with a Hedgehog pathway inhibitor. In addition, there is substantial correlative evidence that cancers of the urothelial cells (e.g., bladder cancer, other urogenital cancers) will also have elevated gli-1 levels in certain cases. For example, it is known that loss of heterozygosity on chromosome 9q22 is common in bladder cancers. The Ptch1 gene is located at this position and Ptch1 loss of function is probably a partial cause of hyperproliferation, as in many other cancer types. Accordingly, such cancers would also show high Gli1 expression and would be particularly amenable to treatment with a hedgehog antagonist.

In certain embodiments, any of the hedgehog pathway inhibitors described herein are used for treating a subject having a tumor having a ptch-1 and/or ptch-2 mutation, e.g., a patched-1 or patched-2 loss of function mutation. Expression of ptch-1 and ptch-2 is also activated by the hedgehog signaling pathway, but not typically to the same extent as gli genes, and as a result are inferior to the gli genes as markers of hedgehog pathway activation. In certain tissues, only one of ptch-1 or ptch-2 is expressed although the hedgehog pathway is highly active. For example, in testicular development, desert hedgehog plays an important role and the hedgehog pathway is activated, but only ptc-2 is expressed. Accordingly, these genes may be individually unreliable as markers for hedgehog pathway activation, although simultaneous measurement of both genes is contemplated as a more useful indicator for tissues to be treated with a hedgehog antagonist.

In light of the broad involvement of hedgehog signaling in the formation of ordered spatial arrangements of differentiated tissues in vertebrates, the hedgehog pathway inhibitors of the present disclosure could be used in a process for generating and/or maintaining an array of different vertebrate tissue both in vitro and in vivo. The Hedgehog pathway inhibitor, can be, as appropriate, any of the preparations described above.

In some embodiments, the hedgehog pathway inhibitors can be used as part of a treatment regimen for malignant medulloblastoma and other primary CNS malignant neuroectodermal tumors. Medulloblastoma, a primary brain tumor, is the most common brain tumor in children. A medulloblastoma is a primitive neuroectodermal (PNET) tumor arising in the posterior fossa. They account for approximately 25% of all pediatric brain tumors. Histologically, they are small round cell tumors commonly arranged in a true rosette, but may display some differentiation to astrocytes, ependymal cells or neurons. PNETs may arise in other areas of the brain including the pineal gland (pineoblastoma) and cerebrum. Those arising in the supratentorial region generally have a worsened prognosis.

Medulloblastom/PNETs are known to recur anywhere in the CNS after resection, and can even metastasize to bone. Pretreatment evaluation should therefore include and examination of the spinal cord to exclude the possibility of "dropped metastases". Gadolinium-enhanced MRI has largely replaced myelography for this purpose, and CSF cytology is obtained postoperatively as a routine procedure.

In some embodiments, the hedgehog pathway inhibitors are used as part of a treatment program for ependymomas. Ependymomoas account for approximately 10% of the pediatric brain tumors in children. Grossly, they are tumors that arise from the ependymal lining of the ventricles and microscopically form rosettes, canals, and perivascular rosettes. In the CHOP series of 51 children reported with epenymomas, ¾ were histologically benign, approximately ⅔ arose from the region of the $4^{th}$ ventricule, and one third presented in the supratentorial region. Age at presentation peaks between birth and 4 years. The median age is about 5 years. Because so many children with this disease are babies, they often require multimodal therapy.

In some embodiments, the hedgehog pathway inhibitors of the present disclosure, based on the involvement of hedgehog signaling in various tumors, or expression of hedgehog or its receptors in such tissues during development, can be used to inhibit growth of a tumor having dysregulated hedgehog activity. Such tumors include, but are not limited to: tumors related to Gorlin's syndrome (e.g., medulloblastoma, meningioma, etc.), tumors associated with a ptch mutation (e.g., hemangiona, rhabdomyosarcoma, etc.), tumors resulting from Gli1 amplification (e.g., glioblastoma, sarcoma, etc.), tumors resulting from Smo dysfunction (e.g., basal cell carcinoma, etc.), tumors connected with TRC8, a ptc homolog (e.g., renal carcinoma, thyroid carcinoma, etc.), Ext-1 related tumors (e.g., bone cancer, etc.), Sft/x-induced tumors (e.g., lung cancer, chondrosarcomas, etc.), tumors overexpressing a hedgehog protein, and other tumors (e.g., breast cancer, urogenital cancer (e.g., kidney, bladder, ureter, prostate, etc.), adrenal cancer, gastrointestinal cancer (e.g., stomach, intestine, etc.).

In some embodiments, the hedgehog pathway inhibitors of the present disclosure may also be used to treat several forms of cancer. These cancers include, but are not limited to: prostate cancer, bladder cancer, lung cancer (including small cell and non-small cell), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional cancer types include cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. Further exemplary forms of cancer which can be treated with the hedgehog antagonists of the present disclosure include cancers comprising hedgehog expressing cells. Still further exemplary forms of cancer which can be treated with the hedgehog antagonists of the present disclosure include cancers comprising Gli expressing cells. In one embodiment, the cancer is not characterized by a mutation in patched-1. In some embodiments, the cancer is characterized by a smoothened and/or SuFu mutation.

In certain embodiments, the hedgehog pathway inhibitors may be used to treat a subject having basal cell carcinoma. In particular embodiments, the basal cell carcinoma is nevoid basal cell carcinoma. In particular embodiments, the subject has Gorlin's Syndrome.

The foregoing are merely exemplary of in vitro and in vivo uses for hedgehog pathway inhibitors of the disclosure. Hedgehog pathway inhibitors are also suitable for use in identifying natural targets or binding partners for mutant smoothened proteins (e.g., a smoothened protein having a T241M, W281C, I408V, A459V, C469Y, S533N and/or W535L mutation), to study mutant smoothened bioactivity, to purify mutant smoothened and its binding partners from various cells and tissues, and to identify additional components of the hedgehog signaling pathway.

In certain embodiments, the hedgehog pathway inhibitor is any of the antibodies disclosed. An antibody of the disclosure may be used in, for example, in vitro, ex vivo, and in vivo therapeutic methods. In one aspect, the disclosure provides methods for treating cancer, inhibiting unwanted cellular proliferation, inhibiting metastasis of cancer and inducing apoptosis of tumor cells either in vivo or in vitro, the method comprising exposing a cell to an antibody of the disclosure under conditions permissive for binding of the antibody to mutant SMO. In certain embodiments, the cell is a myelogenous leukemia cell, a lung cancer cell, a gastric cancer cell, a breast cancer cell, a prostate cancer cell, a renal cell cancer cell, and a glioblastoma cell. In one embodiment, an antibody of the disclosure can be used for inhibiting an activity of mutant SMO, the method comprising exposing mutant SMO to an antibody of the disclosure such that the activity of mutant SMO is inhibited.

In one aspect, the disclosure provides methods for treating cancer comprising administering to an individual an effective amount of an antibody of the disclosure. In certain embodiments, a method for treating cancer comprises administering to an individual an effective amount of a pharmaceutical formulation comprising an antibody of the disclosure and, optionally, at least one additional therapeutic agent, such as those provided below.

Antibodies of the disclosure can be used either alone or in combination with other compositions in a therapy. For instance, an antibody of the disclosure may be co-administered with at least one additional therapeutic agent and/or adjuvant. In certain embodiments, an additional therapeutic agent is an anti-VEGF antibody.

Such combination therapies noted above encompass combined administration (where two or more therapeutic agents are included in the same or separate formulations), and separate administration, in which case, administration of the antibody of the disclosure can occur prior to, simultaneously, and/or following, administration of the additional therapeutic agent and/or adjuvant. Antibodies of the disclosure can also be used in combination with radiation therapy.

In one embodiment, an antibody of the disclosure is used in a method for binding mutant SMO in an individual suffering from a disorder associated with increased mutant SMO expression and/or activity, the method comprising administering to the individual the antibody such that mutant SMO in the individual is bound. In one embodiment, the mutant SMO is human mutant SMO, and the individual is human.

An antibody of the disclosure (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

The location of the binding target of an antibody of the disclosure may be taken into consideration in preparation and administration of the antibody. When the binding target is an intracellular molecule, certain embodiments of the disclosure provide for the antibody or antigen-binding fragment thereof to be introduced into the cell where the binding target is located. In one embodiment, an antibody of the disclosure can be expressed intracellularly as an intrabody. The term "intrabody," as used herein, refers to an antibody or antigen-binding portion thereof that is expressed intracellularly and that is capable of selectively binding to a target molecule, as described, e.g., in Marasco, Gene Therapy 4: 11-15 (1997); Kontermann, Methods 34: 163-170 (2004); U.S. Pat. Nos. 6,004,940 and 6,329,173; U.S. Patent Application Publication No. 2003/0104402, and PCT Publication No. WO2003/077945. See also, for example, WO96/07321 published Mar. 14, 1996, concerning the use of gene therapy to generate intracellular antibodies.

Intracellular expression of an intrabody may be effected by introducing a nucleic acid encoding the desired antibody or antigen-binding portion thereof (lacking the wild-type leader sequence and secretory signals normally associated with the gene encoding that antibody or antigen-binding fragment) into a target cell. One or more nucleic acids encoding all or a portion of an antibody of the disclosure can be delivered to a target cell, such that one or more intrabodies are expressed which are capable of binding to an intracellular target polypeptide and modulating the activity of the target polypeptide. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of int In certain embodiments, nucleic acid (optionally contained in a vector) may be introduced into a patient's cells by in vivo and ex vivo methods. In one example of in vivo delivery, nucleic acid is injected directly into the patient, e.g., at the site where therapeutic intervention is required. In a further example of in vivo delivery, nucleic acid is introduced into a cell using transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of certain gene marking and gene therapy protocols, see Anderson et al., Science 256:808-813 (1992), and WO 93/25673 and the references cited therein. In an example of ex vivo treatment, a patient's cells are removed, nucleic acid is introduced into those isolated cells, and the modified cells are administered to the patient either directly or, for example, encapsulated within porous membranes which are implanted into the patient (see, e.g., U.S. Pat. Nos. 4,892,538 and 5,283,187). A commonly used vector for ex vivo delivery of a nucleic acid is a retroviral vector.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the target protein may be advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889-7893 (1993).

Entry of antibodies into target cells can be enhanced by other methods known in the art. For example, certain sequences, such as those derived from HIV Tat or the Antennapedia homeodomain protein are able to direct efficient uptake of heterologous proteins across cell membranes. See, e.g., Chen et al., Proc. Natl. Acad. Sci. USA (1999), 96:4325-4329.

When the binding target of an antibody is located in the brain, certain embodiments of the disclosure provide for the antibody to traverse the blood-brain barrier. Several art-known approaches exist for transporting molecules across the blood-brain barrier, including, but not limited to, physical methods, lipid-based methods, stem cell-based methods, and receptor and channel-based methods.

Physical methods of transporting an antibody across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)), interstitial infusion/convection-enhanced delivery (see, e.g., Bobo et al., Proc. Natl. Acad. Sci. USA 91: 2076-2080 (1994)), and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989)), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody (see, e.g., U.S. Patent Publication No. 2003/0083299).

Lipid-based methods of transporting an antibody across the blood-brain barrier include, but are not limited to, encapsulating the antibody in liposomes that are coupled to antibody binding fragments that bind to receptors on the vascular endothelium of the blood-brain barrier (see, e.g., U.S. Patent Application Publication No. 20020025313), and coating the antibody in low-density lipoprotein particles (see, e.g., U.S. Patent Application Publication No.

20040204354) or apolipoprotein E (see, e.g., U.S. Patent Application Publication No. 20040131692).

Stem-cell based methods of transporting an antibody across the blood-brain barrier entail genetically engineering neural progenitor cells (NPCs) to express the antibody of interest and then implanting the stem cells into the brain of the individual to be treated. See Behrstock et al. (2005) *Gene Ther.* 15 Dec. 2005 advanced online publication (reporting that NPCs genetically engineered to express the neurotrophic factor GDNF reduced symptoms of Parkinson disease when implanted into the brains of rodent and primate models).

Receptor and channel-based methods of transporting an antibody across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Antibodies of the disclosure would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the disclosure (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 mg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 mg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

It is understood that any of the above therapeutic methods may be carried out using an immunoconjugate of the disclosure in place of or in addition to an anti-mutant SMO antibody.

VII. Pharmaceutical Formulations

In some embodiments, any of the hedgehog pathway inhibitors described herein or hedgehog pathway inhibitors in accordance with the disclosure may be formulated in a pharmaceutical composition.

Pharmaceutical compositions of the hedgehog pathway inhibitors used in accordance with the present disclosure may be prepared for storage by mixing the agent(s) having the desired degree of purity with optional pharmaceutically acceptable carriers, excipients or stabilizers (Remington: The Science of Practice of Pharmacy. 20th edition, Gennaro, A. et al., Ed., Philadelphia College of Pharmacy and Science (2000)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG).

In some embodiments, any of the formulations of hedgehog pathway inhibitors in accordance with the present disclosure and/or described herein may also contain more than one active compound as necessary for the particular indication being treated, in some embodiments, those with complementary activities that do not adversely affect each other. It should be recognized that, in certain embodiments, a hedgehog pathway inhibitor and a second active agent are formulated together (e.g., a formulation or composition contains both agents). In other embodiments, the two (or more) active agents are formulated separately such that the separate formulations can be marketed, sold, stored, and used together or separately. When formulated separately, the disclosure contemplates that they can be administered at the same or differing times and, in certain embodiments, may be combined and administered simultaneously.

For example, in addition to the preceding therapeutic agent(s), it may be desirable to include in the formulation, an additional antibody, e.g., a second such therapeutic agent, or an antibody to some other target (e.g., a growth factor that affects the growth of a tumor). In some embodiments, it may be desirable to include in the formulation a hedgehog inhibitor (e.g., robotkinin). Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended. In some embodiments, the additional active compound is a steroidal alkaloid. In some embodiments, the steroidal alkaloid is cyclopamine, or KAAD-cyclopamine or jervine or any functional derivative thereof (e.g., IPI-269609 or IPI-926). In some embodiments, the additional active compound is vismodegib, sonidegib, BMS-833923, PF-04449913, or LY2940680 or any derivative thereof. In some embodiments, the additional active compound is any of the compounds disclosed in Amakye, et al., Nature Medicine, 19(11):1410-1422 (which is incorporated herein in its entirety). In some embodiments the additional active compound is another smoothened inhibitor chemically unrelated to veratrum alkaloids or vismodegib, including but not limited to: Erivedge, BMS-833923 (XL319), LDE225 (Erismodegib), PF-04449913, NVP-LDE225, NVP-LEQ506, TAK-441, XL-319, LY-2940680, SEN450, Itraconazole, MRT-10, MRT-83, or PF-04449913). As noted above, the disclosure contemplates formulations in which a second active agent is formulated together with a hedgehog pathway inhibitor (e.g., as a single formulation comprising two active agents), as well as embodiments in which the two active agents are present in two separate formulations or compositions.

In some embodiments, any of the hedgehog pathway inhibitors of the disclosure, such as those described herein, may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy, supra.

In some embodiments, any of the hedgehog pathway inhibitors of the disclosure are formulated in sustained-release preparations. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D(−)-3-hydroxybutyric acid.

The amount of the compositions of the disclosure for use in the methods of the present disclosure can be determined by standard clinical techniques and may vary depending on the particular indication or use. Effective doses may be extrapolated from dose-response curves derived from in vitro or animal model test systems.

In certain embodiments, compositions of the disclosure, including pharmaceutical preparations, are non-pyrogenic. In other words, in certain embodiments, the compositions are substantially pyrogen free. In one embodiment the formulations of the disclosure are pyrogen-free formulations that are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in relatively large dosages and/or over an extended period of time (e.g., such as for the patient's entire life), even small amounts of harmful and dangerous endotoxin could be dangerous. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

In some embodiments, the hedgehog pathway inhibitors are formulated in sterile formulations. This is readily accomplished by filtration through sterile filtration membranes.

IX. Articles of Manufacture and Kits

In some embodiments, the hedgehog pathway inhibitors of the present disclosure, such as the hedgehog pathway inhibitors disclosed herein are prepared in an article of manufacture. Similarly, polypeptides and nucleic acids of the disclosure, such as mutant SMO polypeptides, may be prepared as an article of manufacture. In some embodiments, the article of manufacture comprises a container and a label or package insert on or associated with the container indicating a use for the inhibition in whole or in part of hedgehog signaling, or alternatively for the treatment of a disorder or condition resulting from activation of the hedgehog signaling pathway. In other embodiments, the article of manufacture comprises a container and a label or package insert on or associated with the container indicating a use in a screening assay. Suitable containers include, for example, bottles, vials, syringes, etc. The containers may be formed from a variety of materials such as glass or plastic. In some embodiments, the container holds a composition which is effective for treating the cancer condition and may have a sterile access port (for example the container may be an intravenous solution bag or a vial having a stopper pierceable by a hypodermic injection needle). At least one active agent in the composition is a hedgehog pathway inhibitor. The label or package insert will further comprise instructions for administering the hedgehog pathway inhibitor or for use the SMO polypeptide or nucleic acid or vector or host cell. Additionally, the article of manufacture may further comprise a second container comprising a pharmaceutically-acceptable buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

In some embodiments, kits are provided that are useful for various other purposes, e.g., for mutant SMO protein-expressing cell killing assays, for purification or immunoprecipitation of hedgehog signaling polypeptide from cells. For isolation and purification of mutant SMO protein, the kit can contain the respective mutant SMO protein-binding reagent coupled to beads (e.g., sepharose beads). Kits can be provided which contain such molecules for detection and quantitation of mutant SMO protein in vitro, e.g., in an ELISA or a Western blot. In some embodiments, as with the article of manufacture, the kit comprises a container and a label or package insert on or associated with the container. In some embodiments, the container holds a composition comprising at least one such hedgehog pathway inhibitor reagent useable with the disclosure. In some embodiments, additional containers may be included that contain, e.g., diluents and buffers, control antibodies. In some embodiments, the label or package insert may provide a description of the composition as well as instructions for the intended in vitro or diagnostic use.

EXAMPLES

The disclosure now being generally described, it will be more readily understood by reference to the following examples, which are included merely for purposes of illustration of certain aspects and embodiments of the present disclosure, and are not intended to limit the disclosure.

Example 1: Genetic Analysis of Vismodegib-Resistant Basal Cell Carcinomas

Clinical responses to targeted therapies (e.g., cancer therapies) can be short-lived due to the acquisition of genetic alterations that confer drug resistance. Identification of resistance mechanisms will guide novel therapeutic strategies. Inappropriate Hh signaling is linked to several cancers, including basal cell carcinoma (BCC). Loss-of-function mutations in PTCH (~90%) and activating mutations in SMO (~10%) are the primary drivers in BCC. Clinical mechanisms of resistance to vismodegib (GDC-0449) were identified using exome, RNA and copy number analysis of relapsed basal cell carcinomas.

As shown in FIG. 2, vismodegib resistance was associated with elevated hedgehog pathway signaling in patients with vismodegib-resistant BCCs. The results of exome sequencing and copy number analysis* of vismodegib-resistant BCCs are shown below in Table 3.

TABLE 3

| Patient | Oncogenic driver | Possible resistance mechanism |
|---|---|---|
| MG | PTCH1.spc1504 (germline) | SMO.W535L |
| JT | SMO.W535L (somatic) | Unknown |
| KL | PTCH1.P1387S, PTCH1. Q853* | Unknown |
| *PT 20764 | PTCH1.Fs1017 (Frameshift (germline) and LOH) | SMO.W281C (G > T) |
| *PT 20741 | PTCH1.A1380V | SUFU. Fs241 |
| *PT 20849 | PTCH1.S616G (splicing and LOH) | Het. SUFU deletion, Het. PTEN deletion |
| *PT 20840 | PTCH1.Q501H (splicing and LOH) | SMO.A459V (C > T) |
| *PT 20842 | PTCH1.Fs108 (Frameshift and LOH) | SMO.A459V (C > T) |

Figure 3:
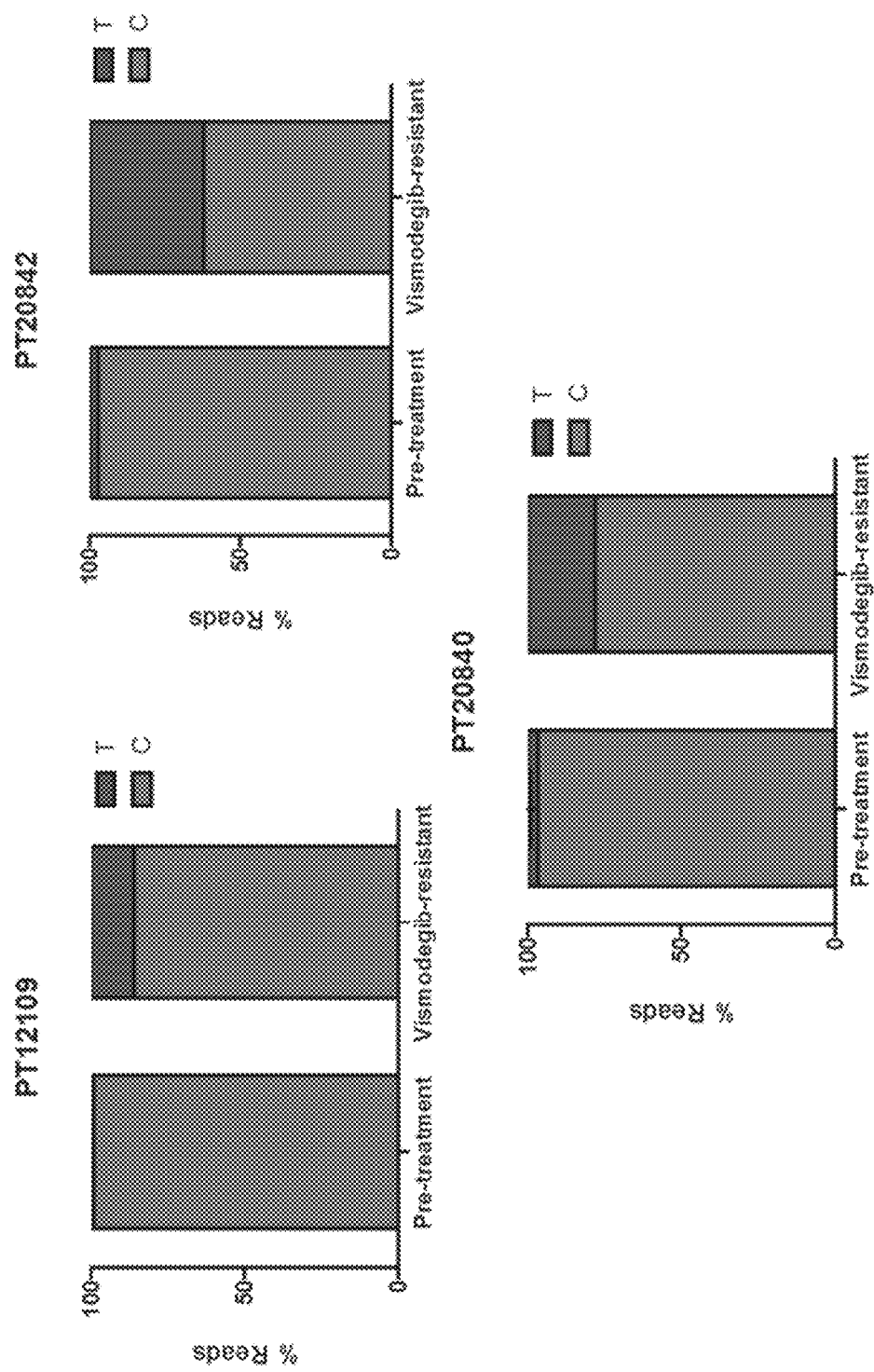
FIG. 3 show the results of experiments performed to determine the frequency of a SMO-A459V mutation in pre-treatment and post-treatment biopsies.

Genotyping revealed a third instance of a SMO-A459V mutation in an additional vismodegib-resistant tumor. SMO-A459V is a recurrent mutation found in post-treatment biopsies in three out of nine resistant patients analyzed. The SMO-A459V mutation was present only after treatment, and absent from 42 independent treatment-naïve BCC samples. (See FIG. 3.) The SMO-A459V mutation was capable of activating SMO.

A SMO-W281C mutation was also detected in relapsed BCCs. As shown in FIG. 4, SMO-W281C is in the vismodegib binding pocket.

Figure 5:
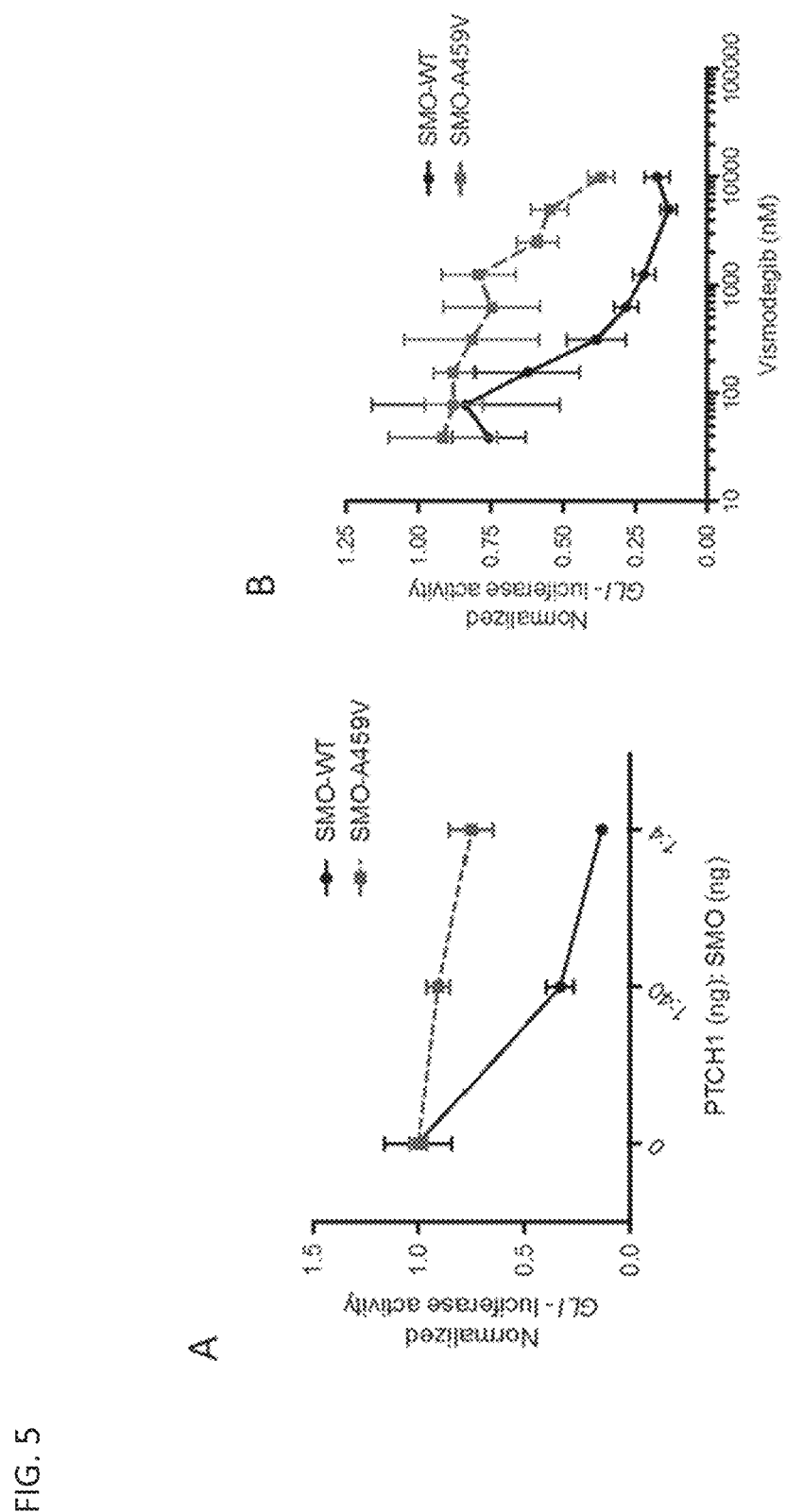
FIG. 5A shows the results of experiments performed to determine whether the SMO-A459V mutant is sensitive to PTCH.
FIG. 5B shows the results of experiments performed to determine whether the SMO-A459V mutant is sensitive to vismodegib.
FIG. 5C shows the results of experiments performed to determine whether the SMO-A459V, SMO-W281C, and SMO-W535L mutants are activating mutations.
FIG. 5D shows the results of experiments performed to determine whether the SMO-W281C mutant is sensitive to PTCH.
FIG. 5E shows the results of experiments performed to determine whether the SMO-W281C mutant is sensitive to vismodegib.
FIG. 5F shows the results of experiments performed to determine whether SMO-A459V and SMO-W281C have impaired binding to vismodegib.
Figure 5:
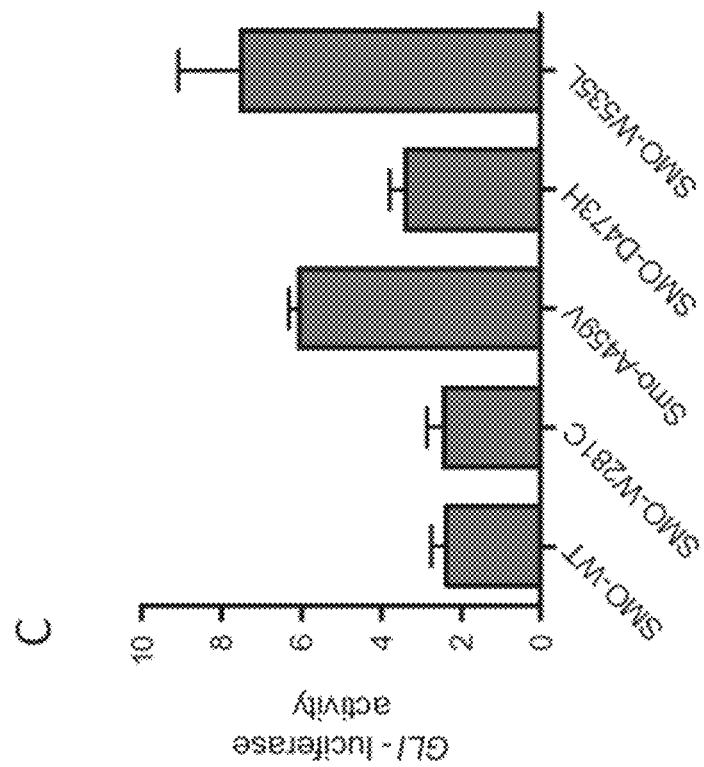
Figure 5:
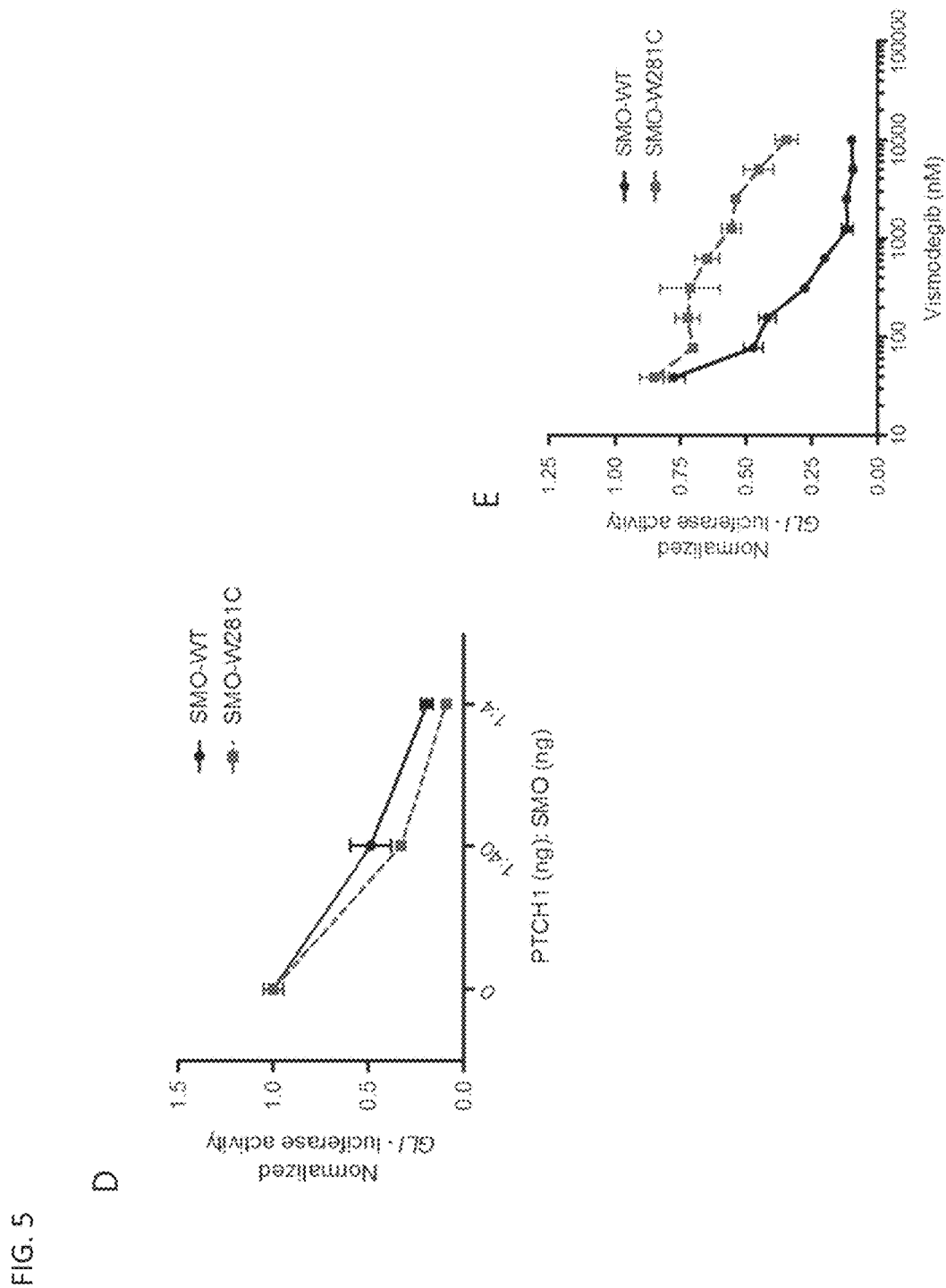
Figure 5:
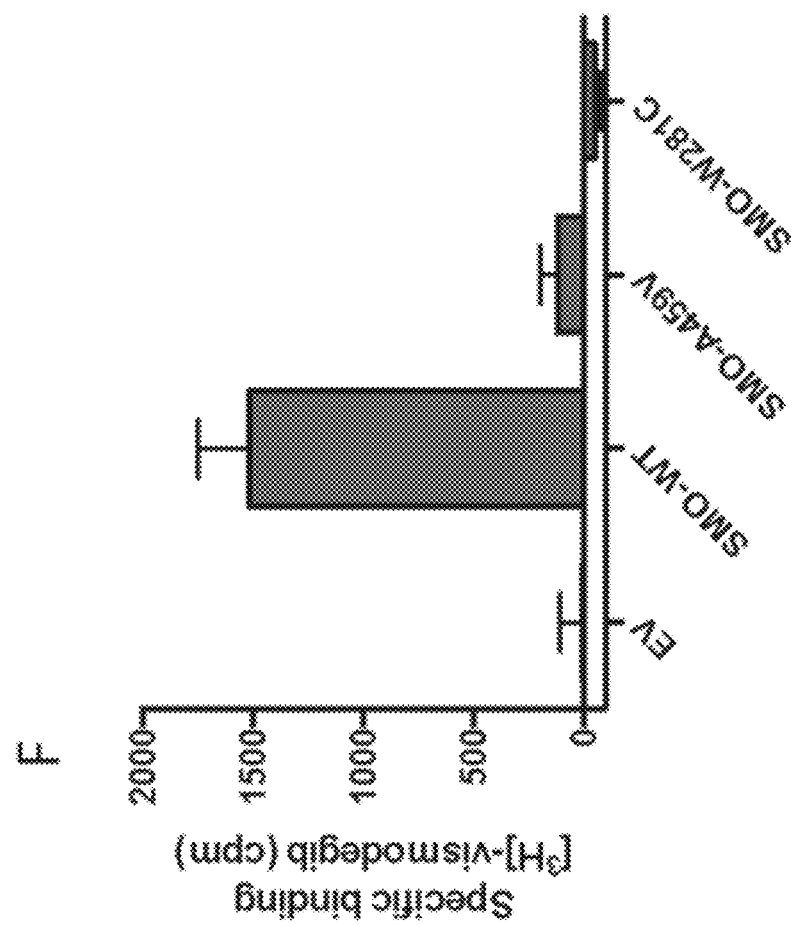

WT-SMO, SMO-W281C, SMO-A459V, PTCH or empty vector (EV) were co-transfected in C3H10T½ cells with a GLI1 luciferase reporter. SMO-A459V was shown to be an activating mutation that has decreased sensitivity to PTCH1 and vismodegib. (FIGS. 5A-5C. Errors bars represent standard deviation.) SMO-W281C is as sensitive to PTCH inhibition as SMO-WT. (FIGS. 5D-5E. Errors bars represent standard deviation.) 293 cells, transfected with indicated constructs, were incubated with 5 nM [$^3$H]-vismodegib with or without 50 μM cold vismodegib. Specific binding=Total−non-specific binding. (FIG. 5E. Errors bars represent standard deviation.) There appear to be two sub-groups of clinical SMO mutations. 1) Activating, with reduced drug sensitivity (including A459V and W535L) and 2) Mutations that maintain Ptch sensitivity, yet disrupt the conformation of the vismodegib binding pocket (including D473H and W281C).

Example 2: Genomic Analysis of Vismodegib-Resistant and Untreated BCCs

To identify mutations associated with vismodegib resistance, whole exome sequencing (WES) was performed of BCCs from Gorlin syndrome (n=5) and sporadic (n=6) patients, and targeted SMO sequencing of a formalin-fixed paraffin-embedded (FFPE) sample from a further Gorlin patient. All patients initially experienced a clinical benefit on vismodegib but subsequently progressed while undergoing treatment.

Figure 6:
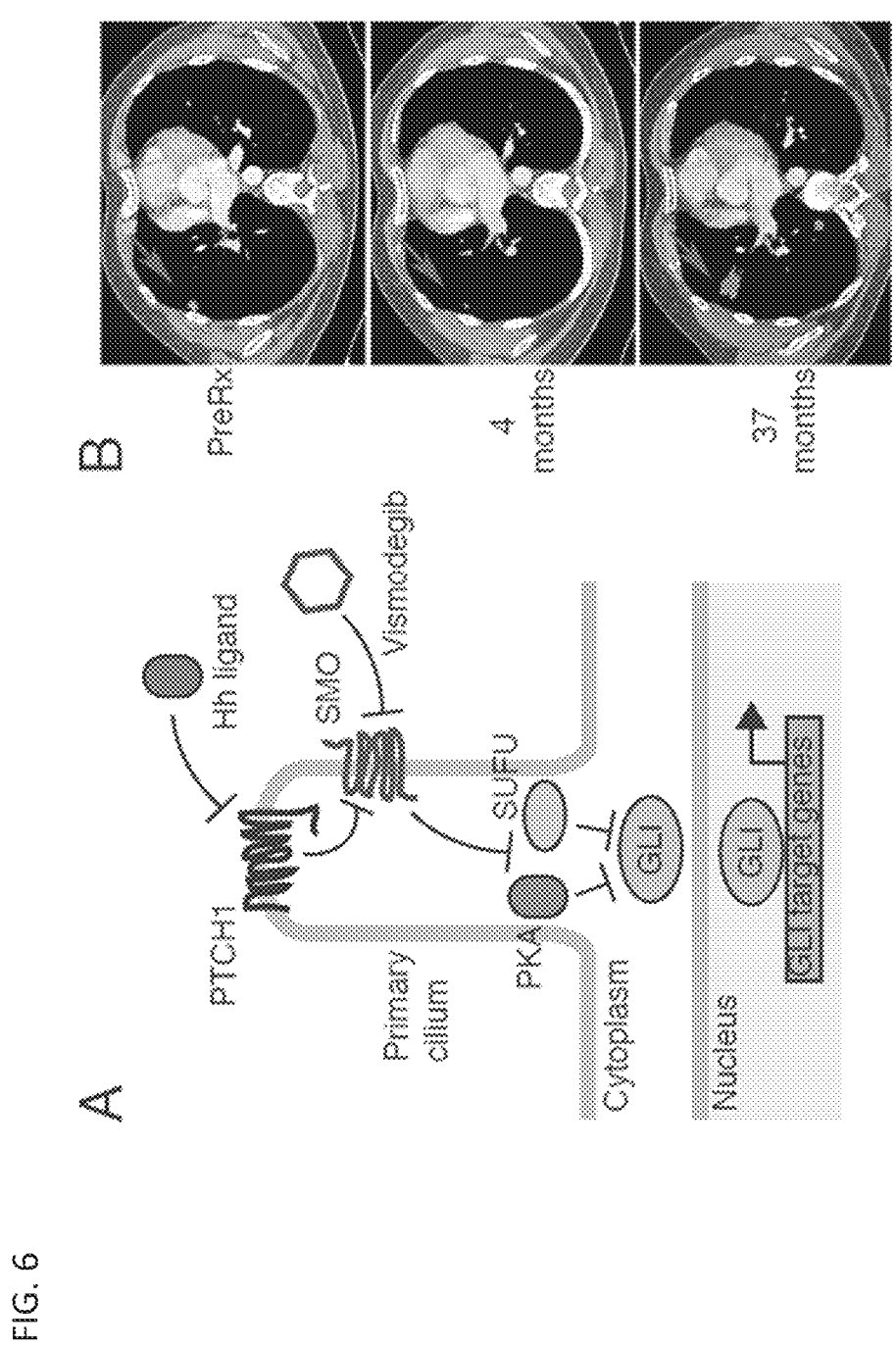
FIG. 6A shows a schematic of the Hh pathway.
FIG. 6B shows scan photographs showing the initial response and disease progression of a sporadic BCC from patient 12 (PT12) that metastasized to lung. A red arrow indicates the target lesion in computerized tomography (CT) scans of the chest before treatment (PreRx) and after 4 (showing a decrease in lesion size) and 37 (revealing disease progression) months of vismodegib treatment.
FIG. 6C shows photographs of two locally advanced BCCs from a Gorlin syndrome patient (PT10) that initially responded to vismodegib but subsequently relapsed (black arrow) after the indicated length of treatment.
FIG. 6D shows Hematoxylin and Eosin (H&E) stained sections of a locally advanced sporadic BCC from patient 9.1 (PT09.1) before and after 11 months of vismodegib treatment. Note that the relapsed lesion maintains the histology of the untreated tumor. The scale bar represents 50 µm.
FIG. 6E is a graph showing GLI1 and MKI67 expression levels in vismodegib-resistant and normal skin biopsies. Pearson's correlation coefficient (R)=0.96. Normalized read counts are shown.
FIG. 6F is a tabular overview of genetic alterations in Hh pathway genes and TP53 identified in 12 relapsed BCC patients. Germline PTCH1 variants are reported for Gorlin BCCs, whereas only somatic mutations are shown for sporadic BCCs. Two regionally distinct biopsies were obtained upon regrowth of the same initial tumor for PT06, PT08 and PT09. Two separate BCCs developed resistance in patient PT10. LOH was determined by minor allele frequencies from SNP arrays. Green boxes highlight LOH events followed by copy number gain of the mutant allele. Allele-specific expression was determined by RNAseq.
Figure 6:
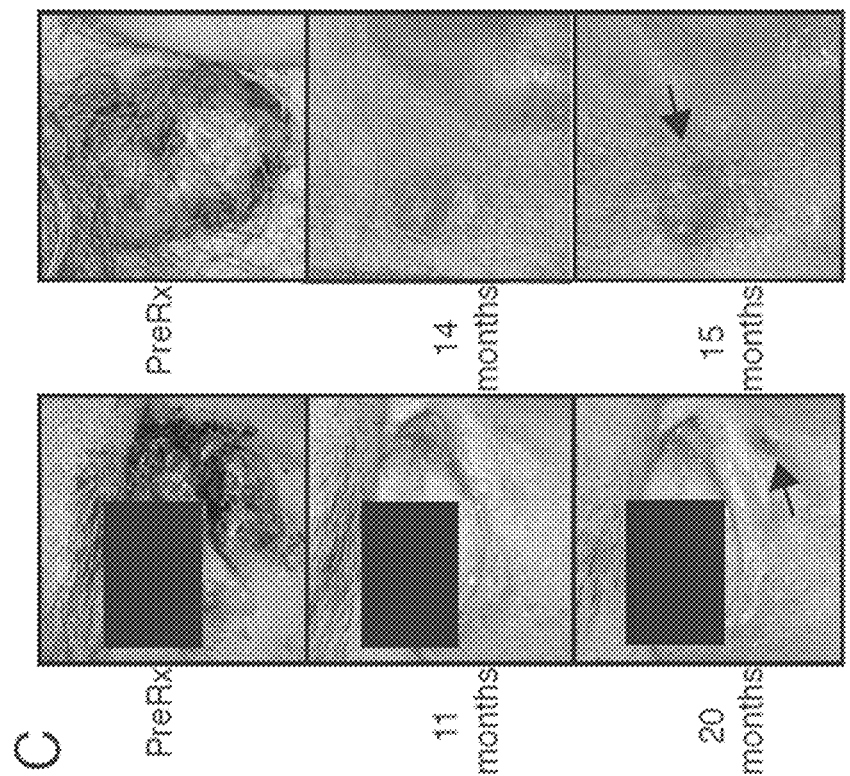
Figure 6:
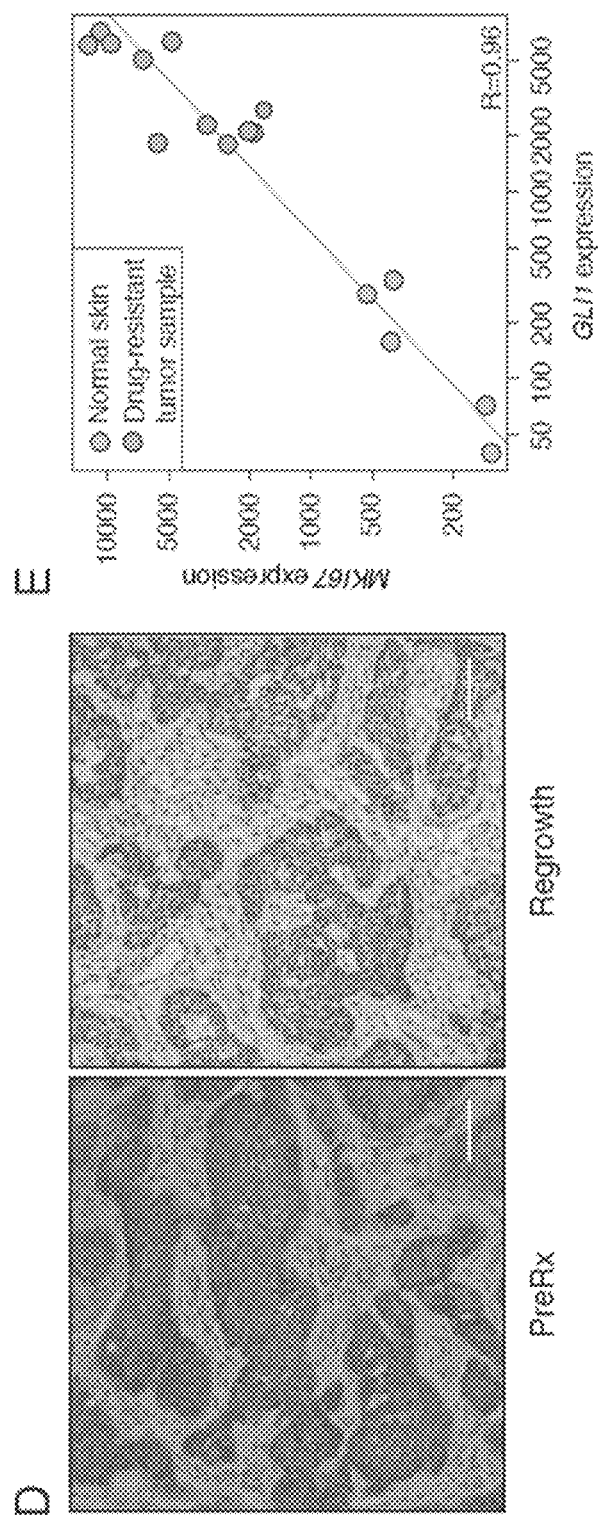
Figure 6F:
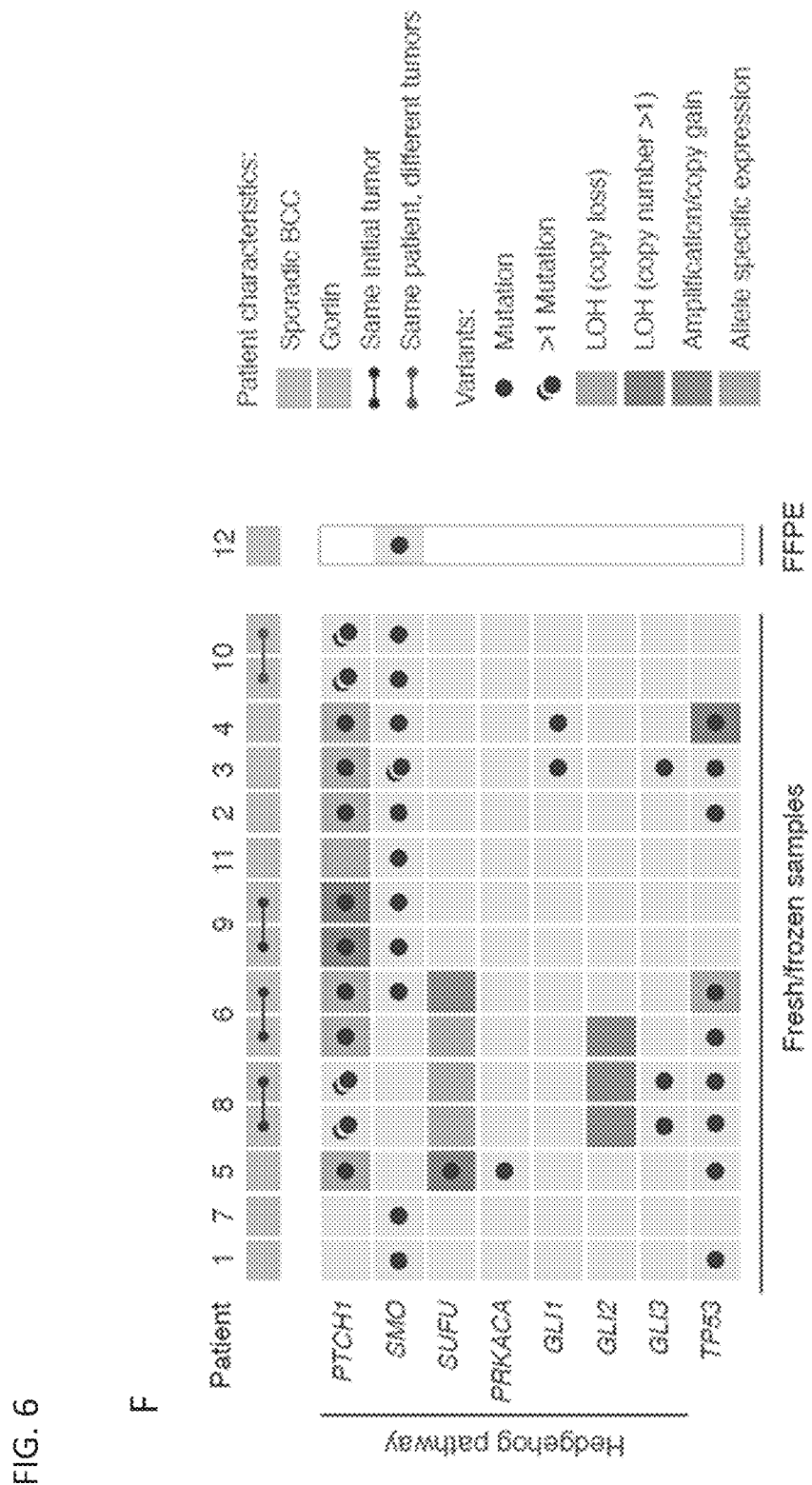

Two distinct biopsies from four of the patients were collected such that a total of sixteen biopsies from vismodegib-resistant BCCs were analyzed. Patients were initially diagnosed with metastatic (FIG. 6B) or locally advanced BCC (FIG. 6C) and it was confirmed histologically that the drug-resistant lesions were BCCs (FIG. 6D). For comparison, tumors from untreated Gorlin syndrome (n=16) and sporadic (n=27) BCC patients were subjected to WES. Two distinct biopsies were obtained from five of the Gorlin patients giving 48 untreated BCC biopsies in total. The mean somatic mutation rate of untreated BCC samples from Gorlin patients was 33.5/megabase (Mb), varying from 6.2-68.9/Mb, and for sporadic patients was 50.5/Mb with a range of 2.4-162.2/Mb. These rates are high in comparison to other cancers, including melanoma (Lawrence et al., 2013). Global analysis of the somatic mutation spectrum revealed a predominance of cytosine to thymine (C>T) transition mutations in both cohorts, indicative of ultraviolet light-induced mutagenesis (Miller, 1985).

Transcriptional analysis of relapsed BCC biopsies (n=11) using RNA-seq, revealed that the Hh target gene GLI1 was expressed 10-fold higher (DESeq2, p<0.003) than in a collection of normal skin samples (FIG. 6E). Additionally, GLI1 expression levels were highly correlated (R=0.96) with expression levels of the proliferation marker MK167, consistent with reactivation of Hh signaling driving BCC regrowth. Therefore, analysis was focused on identifying genetic mechanisms that reactivate Hh signaling to bypass SMO inhibition by vismodegib. To this end, mutations in selected cancer genes (Kandoth et al., 2013) and canonical Hh pathway components were identified. Next, genome-wide copy number alterations and LOH in vismodegib-resistant BCCs were determined using single nucleotide polymorphism (SNP; n=11) and comparative genomic hybridization (CGH; n=4) arrays.

Example 3: PTCH1 and SMO Mutations in BCC Initiation

Consistent with previous reports on BCC genetics (Jayaraman et al., 2014; Reifenberger et al., 2005), all of the relapsed Gorlin (100%) and the majority of sporadic (75%) BCCs displayed mutations in the tumor suppressor PTCH1, which occur throughout the length of the gene and are probably deleterious: seven are truncating, four are likely to affect exon splicing and two are predicted to be deleterious by the Condel algorithm (Gonzalez-Perez and Lopez-Bigas, 2011). The Gorlin patient BCC (PT12) was also likely to have initiated by alterations in PTCH1. The relapsed sporadic tumors without PTCH1 alterations (n=2) harbored the known oncogenic mutation SMO-W535L (Xie et al., 1998). These PTCH1 and SMO variants are likely to be the initiating events in the BCCs that first responded and subsequently displayed vismodegib resistance.

Figure 7:
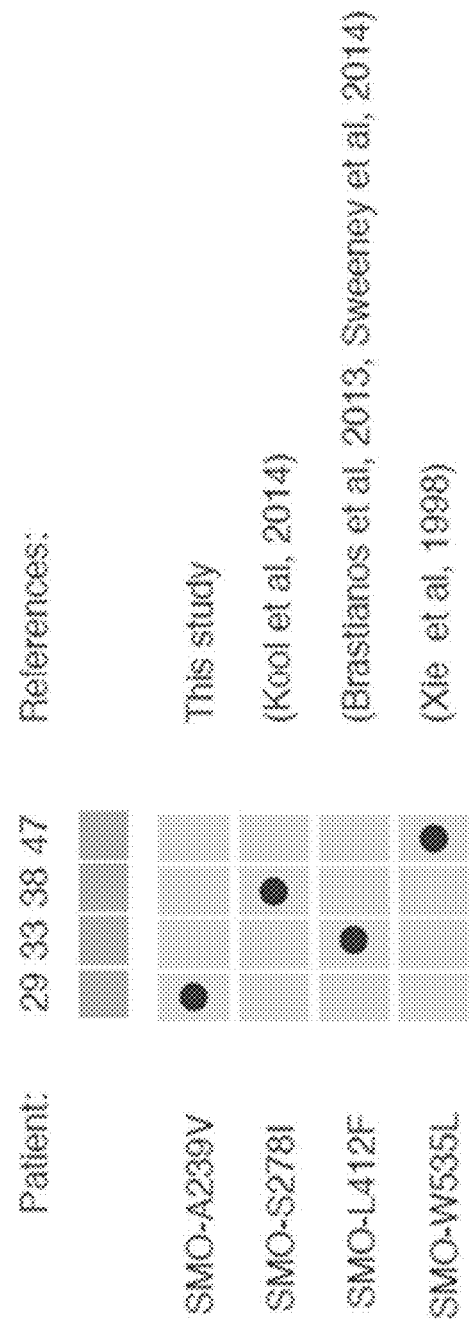
FIG. 7 is a table showing SMO variants identified in treatment-naïve sporadic BCCs. SMO-A239V has not previously been reported (COSMIC/dbSNP), whereas all others are previously reported oncogenic mutations. Note: targeted variant calling identified SMO-A239V, however, due to a different read cut-off and reduced sensitivity, the somatic variant caller VariantTools did not.

A similar trend for the frequency of PTCH1 variants was observed in the untreated Gorlin (90%) and sporadic (78%) BCCs, and identified known oncogenic SMO mutations in three sporadic cases (FIG. 7). Relapsed BCCs showed a similar frequency of TP53 variants between Gorlin (50%) and sporadic (57%) cases, whereas in the untreated cohort TP53 variants were observed more frequently in sporadic BCCs (59%) than Gorlin BCCs (24%), which could reflect the higher mutation rates observed in the untreated sporadic BCCs.

Example 4: Vismodegib-Dependent Selection of SMO Variants

Surprisingly, the majority of relapsed tumor biopsies harbored mutations in the drug target SMO (11/16; 69%) and most co-occurred with PTCH1 variants. By comparison, SMO variants were completely absent from untreated Gorlin BCCs and present in only 4/27 (15%) untreated sporadic BCCs. The SMO mutations identified in relapsed BCCs are outlined in FIG. 8A. SMO-L412F, SMO-W535L and SMO-S533N mutations were previously reported as oncogenic drivers (Reifenberger et al., 1998; Sweeney et al., 2014; Xie et al., 1998), while SMO-W281C and SMO-V321M were recently identified in vismodegib-resistant BCCs (Brinkhuizen et al., 2014). Four SMO mutations were discovered including, SMO-T241M, SMO-I408V, SMO-A459V and SMO-C469Y that were not observed in the untreated BCC cohort or in previous genomic analyses of Hh-driven cancers (Brastianos et al., 2013; Clark et al., 2013; Jayaraman et al., 2014; Kool et al., 2014; Reifenberger et al., 1998), strongly implicating them in vismodegib resistance. All SMO mutations from this study are situated within the TM region (FIGS. 8B and 9A) and confer amino acid substitutions in residues that are highly conserved among SMO proteins from several species, likely reflecting their importance in SMO function.

Figure 8:
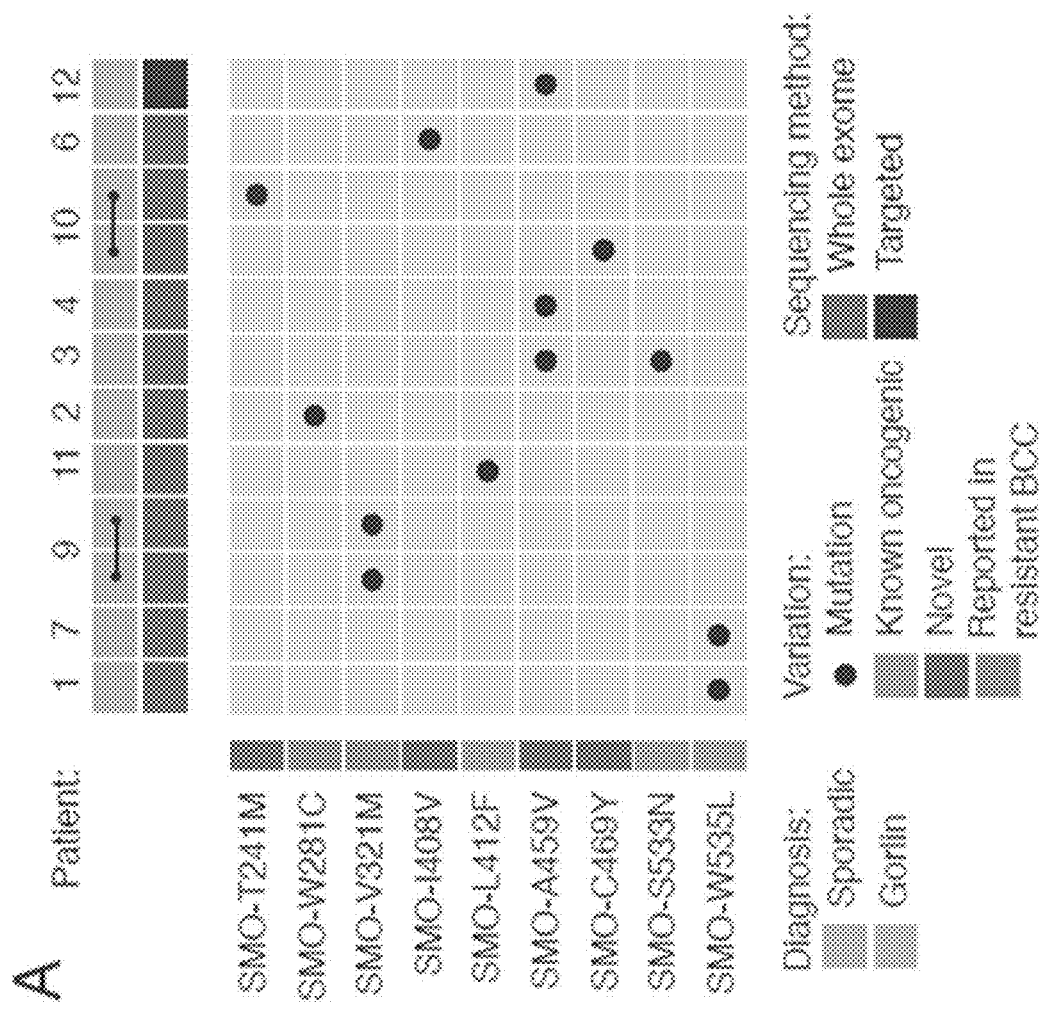
FIG. 8A shows a tabular overview of SMO mutations identified in this study. All mutations were somatic in nature, as they were not detected in either blood or other tissue from the same patient.
FIG. 8B shows a computational model of vismodegib (yellow) docked onto the crystal structure of the SMO TM region (grey helices; Wang et al., 2013). Previously uncharacterized mutant residues are highlighted in green.
FIGS. 8C-F are bar graphs showing the prevalence of SMO mutations in pre- and post-treatment biopsies. Bar graphs show the incorporation frequency of either wild-type (blue) or mutant (red) nucleotides at positions corresponding to SMO-A459V for PT03, PT04, PT12 (8C), SMO-V321M for PT09 (8D), SMO-C469Y and SMO-T241M for PT10 (8E) and SMO-L412F for PT11 (8F) as determined by pyrosequencing. Note that SMO mutations are expected to be heterozygous and that SMO copy number determines the maximum Y-axis value, which is 50% for PT03, PT04, PT12, PT10 and PT11 (SMO copy number is 2) and 25% for PT09 (SMO copy number is 4). Incorporation of mutant nucleotides was considered to be within the background levels (<5%) of the pyrosequencing assay in all pre-treatment samples. Data from quadruplicate assays is plotted relative to the blood control. Error bars represent the range of the data.
FIG. 8G shows photographs of a locally advanced BCC (white arrow) from PT11 that initially responded to vismodegib, but subsequently relapsed after the indicated length of time.
Figure 8:
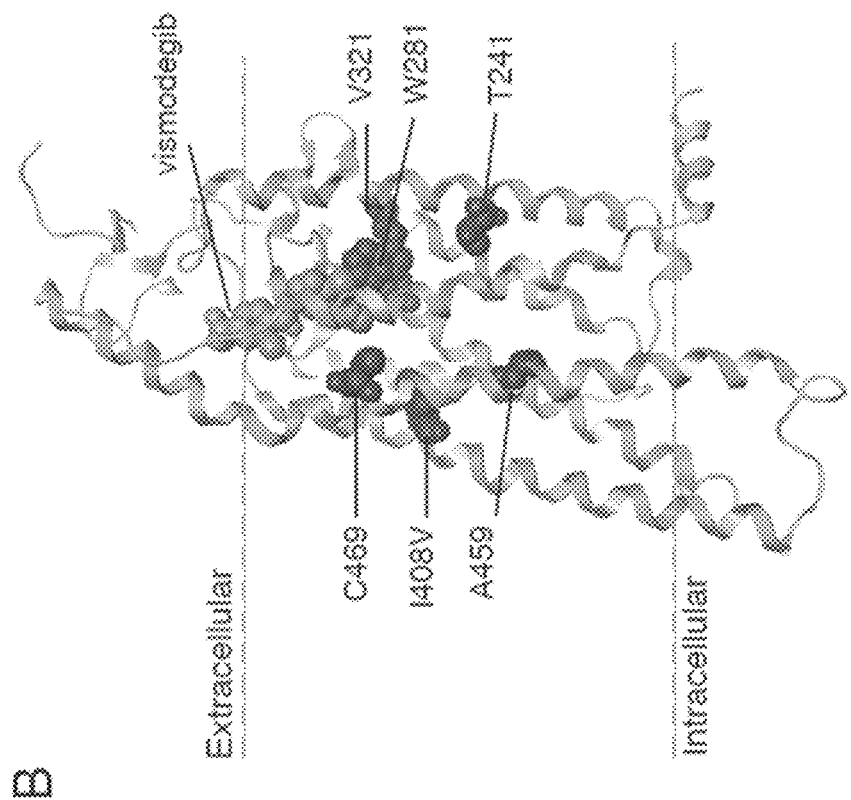
Figure 8:
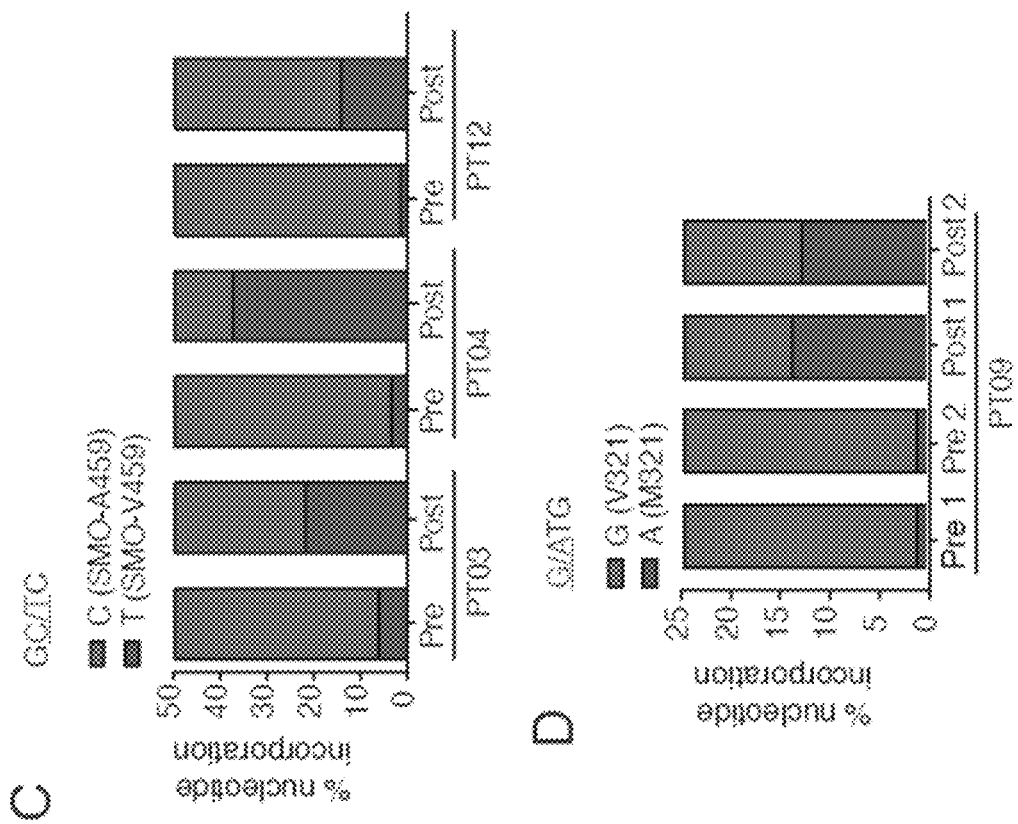
Figure 8:
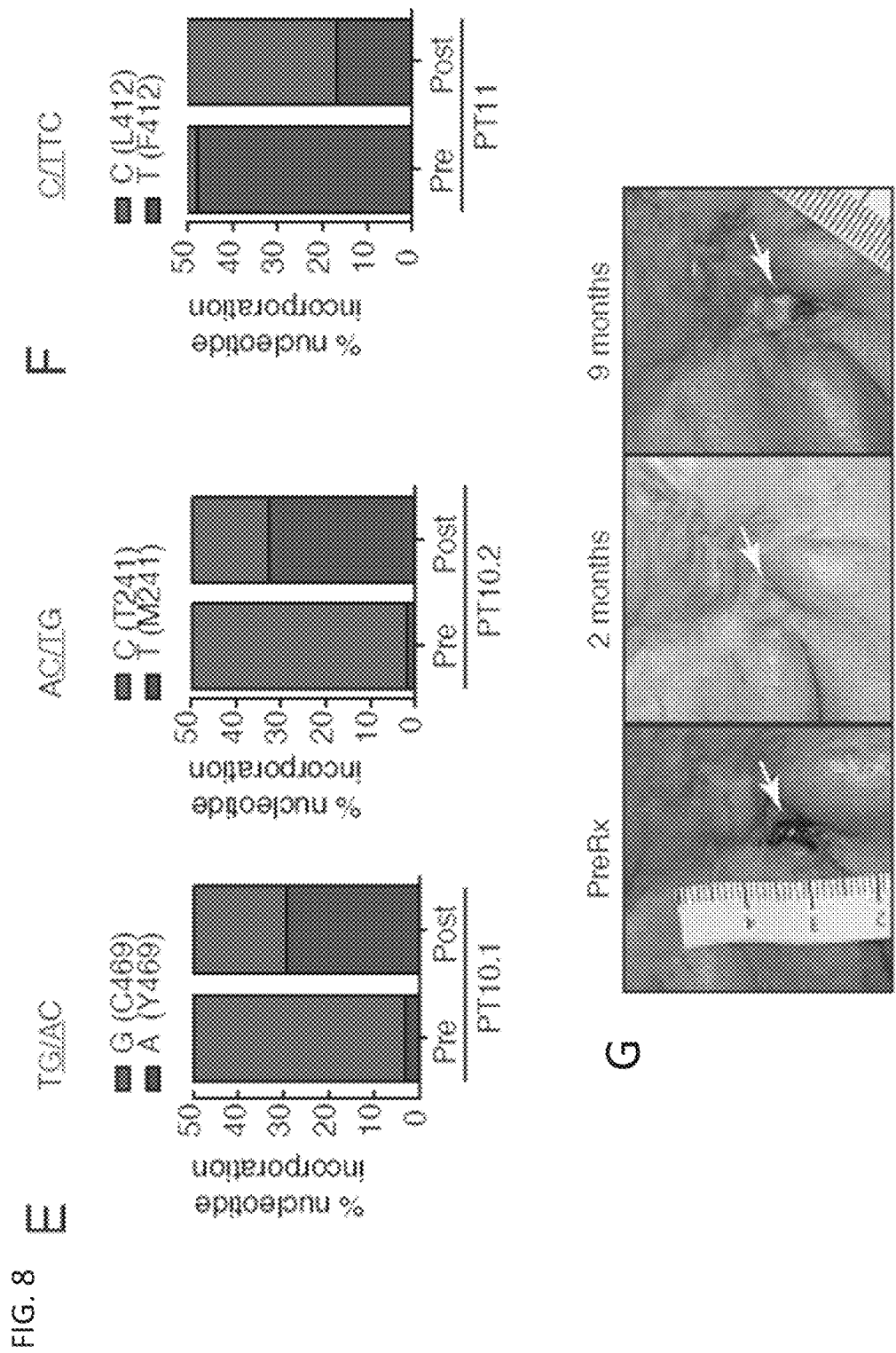
Figure 9:
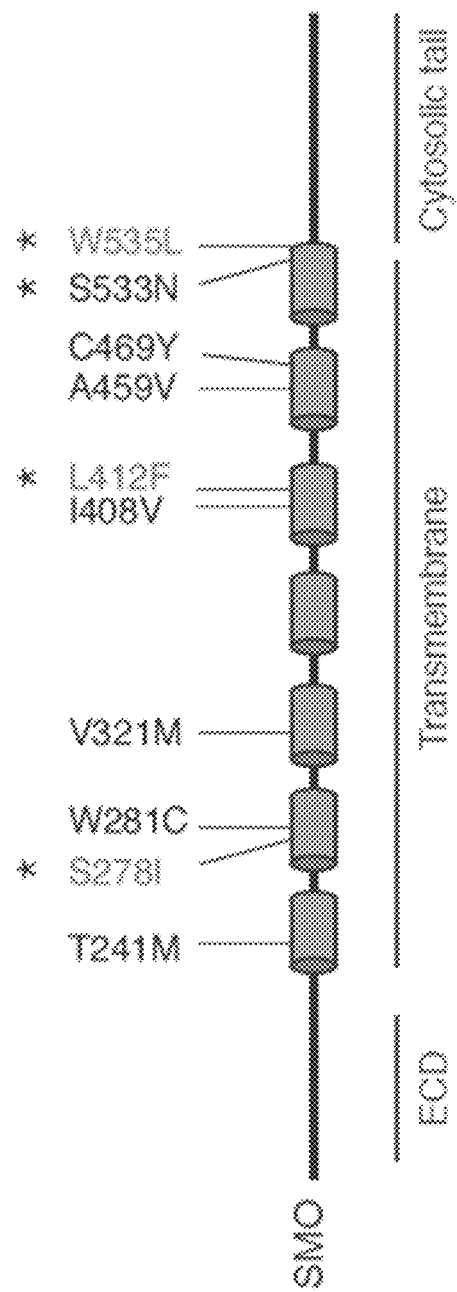
FIG. 9 is a schematic showing the location of mutations identified in treatment-naïve BCCs (light gray—S278I), resistant BCCs (black) or both (light gray-L412F, W535L) within the protein domains of SMO. Asterisks highlight previously reported oncogenic mutations. TM helices are represented by blue cylinders.

Resistance mechanisms can be acquired de novo or more likely by selection of minor subclones present in the pre-treatment tumor. In both scenarios, it was expected that enrichment of alterations responsible for drug-resistance with treatment would be observed. To assess drug dependent selection of SMO mutants, detection of mutations in pre-treatment tumors and the proportion of tumor cells harbored SMO mutations after treatment was examined. To this end, pre-treatment FFPE tumor samples that were available from six patients were sequenced and analyzed for post-treatment tumor clonality. SMO-A459V was detected in post-treatment biopsies from three patients, but was not detectable above background levels in corresponding pre-treatment biopsies (FIG. 8C). Similarly, the nucleotide changes corresponding to SMO-V321M, SMO-T241M and SMO-C469Y were only detectable above background levels in post-treatment samples, consistent with drug-induced selection of SMO mutant cells that arose de novo or were initially present at levels below the detection limit of the assay (FIGS. 8D and 8E). Interestingly, the previously reported SMO-L412F mutation was readily detected in both pre- and posttreatment samples from patient PT11, suggesting that this variant was likely to be the oncogenic driver for this tumor (FIG. 8F). Note that the frequency of mutant nucleotides appears to decrease upon treatment; this is due to a higher level of contaminating normal tissue in the post-treatment sample. Copy number and SNP array analysis revealed that this tumor was initially diploid for PTCH1 and acquired PTCH1 copy number loss after treatment. Without wishing to be bound by theory, the fact that this patient initially responded to vismodegib (FIG. 8H) raises the possibility that reduced PTCH1 levels (through copy loss), in the context of this oncogenic mutation, might promote tumor regrowth while on drug.

To address whether SMO mutations were present in dominant clones in the relapsed BCCs, the tumor cell fractions of PTCH1 and SMO variants were calculated using allele frequencies from WES, as well as copy number and tumor content information derived from SNP arrays (Greenman et al., 2010; Nik-Zainal et al., 2012; Stjernqvist et al., 2011). Heterozygous germline PTCH1 mutations were accounted for in contaminating normal skin in biopsies from Gorlin patients and, where observed, subsequent LOH in tumor cells. Except for PT09, SMO was diploid in relapsed BCCs, therefore, the expected allele frequencies of fully clonal heterozygous SMO variants was 50% of the tumor content, which were then compared with the observed allele frequency. PTCH1 mutations were present in >80% of tumor cells, consistent with deleterious events in PTCH1 being the oncogenic drivers in these tumors. Based on normal contamination and observed allele frequencies, all SMO mutations were estimated to be present in >60% of tumor cells in these vismodegib-resistant BCCs, consistent with their selection upon drug treatment.

Figure 10:
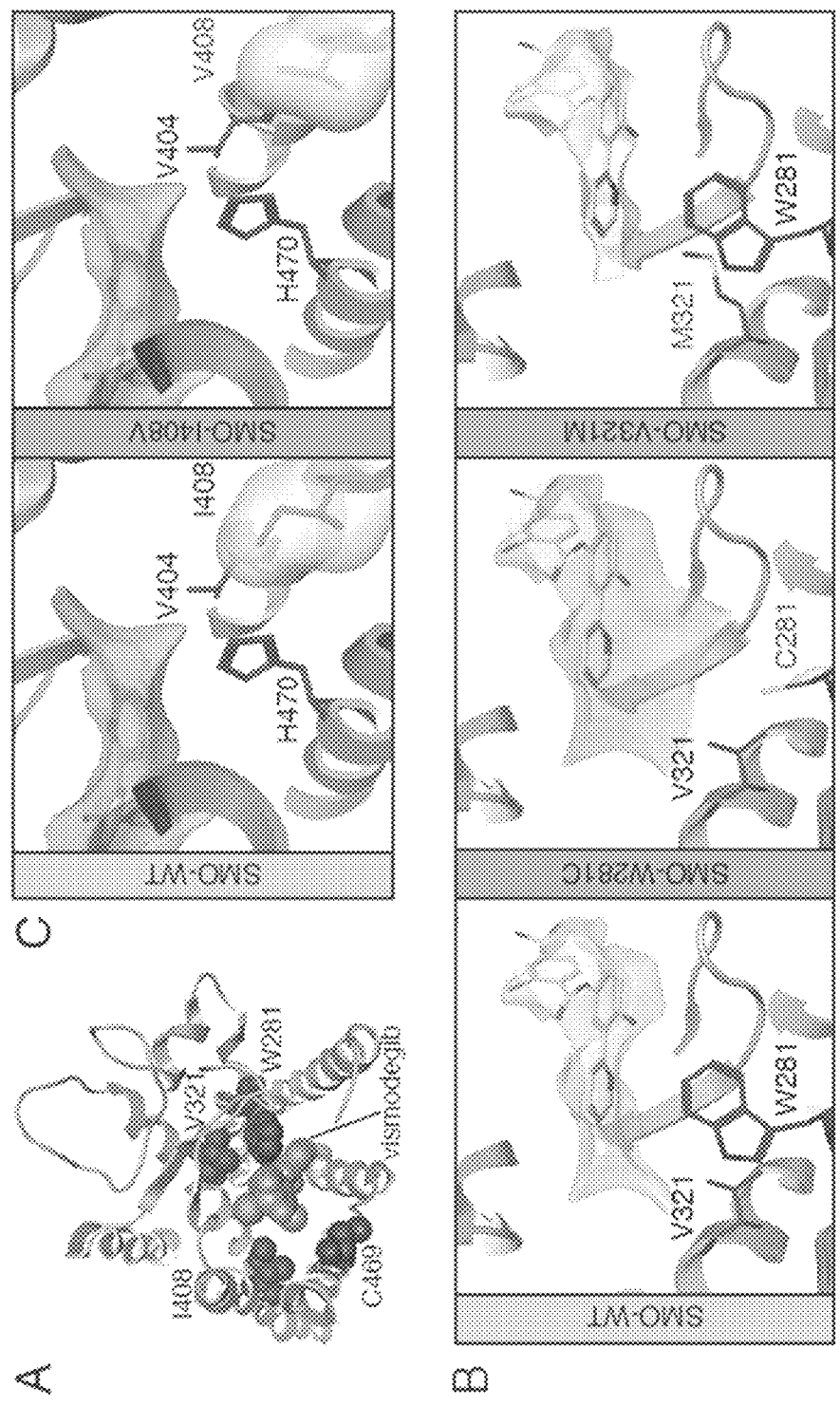
FIG. 10A shows a computational docking model showing a top down view of vismodegib (yellow) binding to SMO (grey) and revealing the proximity of W281, V321, 1408 and C469 (all green) to the drug-binding pocket.
FIG. 10B, left shows the position of V321 and W281 (both green) relative to vismodegib (yellow).
FIG. 10C shows that the mutation of 1408 (left) to valine (right) is predicted to affect the packing of H470 and V404, both of which interact with vismodegib. This mutation may cause even greater changes in the overall protein backbone structure and hence affect drug binding via a second-shell effect. In all panels mutant residues are highlighted in red text.

Example 5: Mutations in the Drug-Binding Pocket of SMO Confer Resistance to Vismodegib To gain insight into the properties of the SMO mutations discovered in this study, the recently solved crystal structure of the SMO TM region was utilized (Wang et al., 2013). Computational docking of vismodegib onto the SMO structure revealed that SMO-W281, SMO-V321, SMO-I408 and SMO-C469 are located in proximity of the drug-binding pocket (DBP; FIG. 10A). The aromatic indole of SMO-W281 forms an edge-to-face pi-stacking interaction with the pyridine ring of vismodegib and helps to form a narrow and hydrophobic pocket, which is disrupted by substitution for the less bulky sulfur of the SMO-W281C mutant (FIG. 10B, middle panel). Furthermore, mutation of valine 321 to methionine is likely to interfere with the positioning of W281, exerting a secondary effect on drug binding (FIG.

10B, right panel). Unlike W281, residue 1408 does not directly contact the drug in the tested computational model; instead it packs against the binding pocket residues H470 and V404 with its delta methyl group, which when lost is expected to affect binding by changing the conformations of these residues (FIG. 10C). It was predicted that substitution of C469 to a bulky tyrosine would elicit steric effects on the binding pocket, disrupting its conformation.

Figure 11:
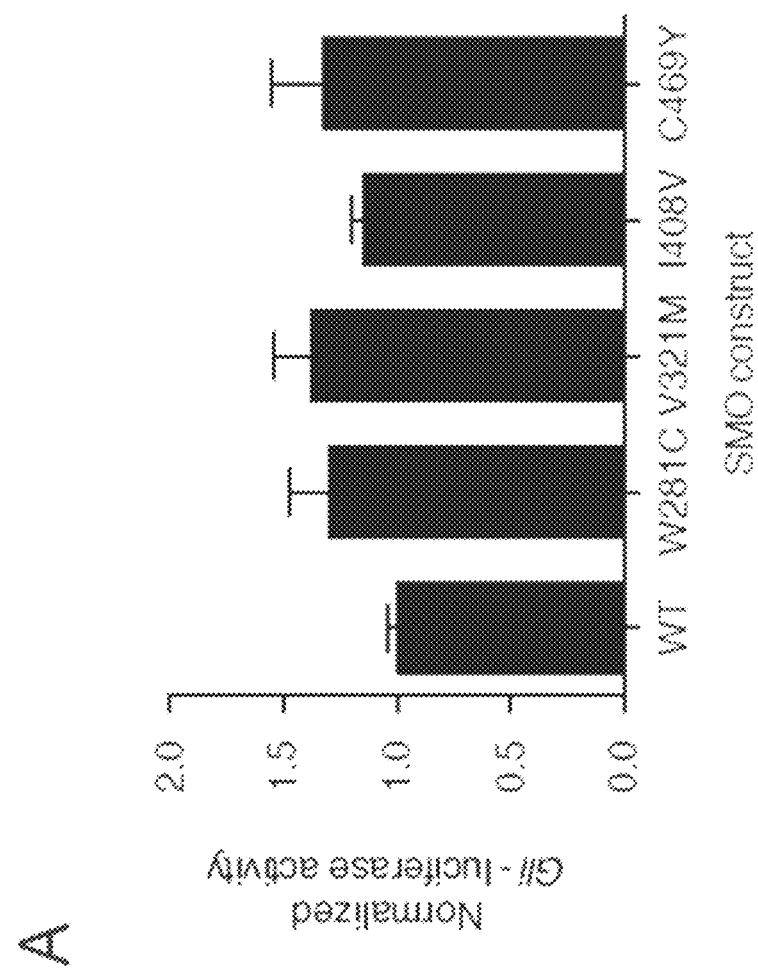
FIG. 11A is a graph showing Gli-luciferase reporter activity in C3H10T½ cells transfected with the indicated SMO constructs. Values were normalized to SMO-WT activity and data plotted are mean+/−SD of triplicates.
FIG. 11B is a graph showing the results from Gli-luciferase reporter assay in C3H10T½ cells transfected with indicated ratios of PTCH1 to SMO expression constructs. Values were normalized to activity without PTCH1 co-transfection and data plotted are mean+/−SD of triplicates.
FIG. 11C is a table showing cell surface expression of SMO drug-binding pocket mutants in HEK-293 cells. Values shown are the percentage of viable cells with cell surface expression of SMO, as determined by FACS for 10,000 cell events and gating on empty vector transfected cells and propidium iodide (PI).
FIG. 11D is a graph showing results from methyl-[3H]-thymidine incorporation of either untransduced (No virus), Control virus (tRFP only) or Cre virus (tRFP-IRES-eGFPcre) infected patient cerebellar granule neuron precursor cells cultured with or without SHH. Methyl-[3H]-thymidine incorporation is expressed in counts per min (CPM) and data plotted are mean+/−SD of triplicates.
FIG. 11E is a bar graph showing the percentage of Ptch1loxp/loxp Tp53loxp/loxp Rosa26LSL-tdTomato (PPT) cerebellar granule neuron precursor cells (CGNPs) positive for tdTomato expression after infection with the indicated viral constructs, as determined by FACS for 10,000 cell events and gating on untransduced cells.
FIG. 11F is a bar graph showing quantification of human SMO mRNA levels in PPT CGNPs from panel E by quantitative RT-PCR. Data are 2-ΔCt values relative to the murine housekeeping gene Rpl19 and are plotted as mean+/−SD of triplicates.
Figure 11B:
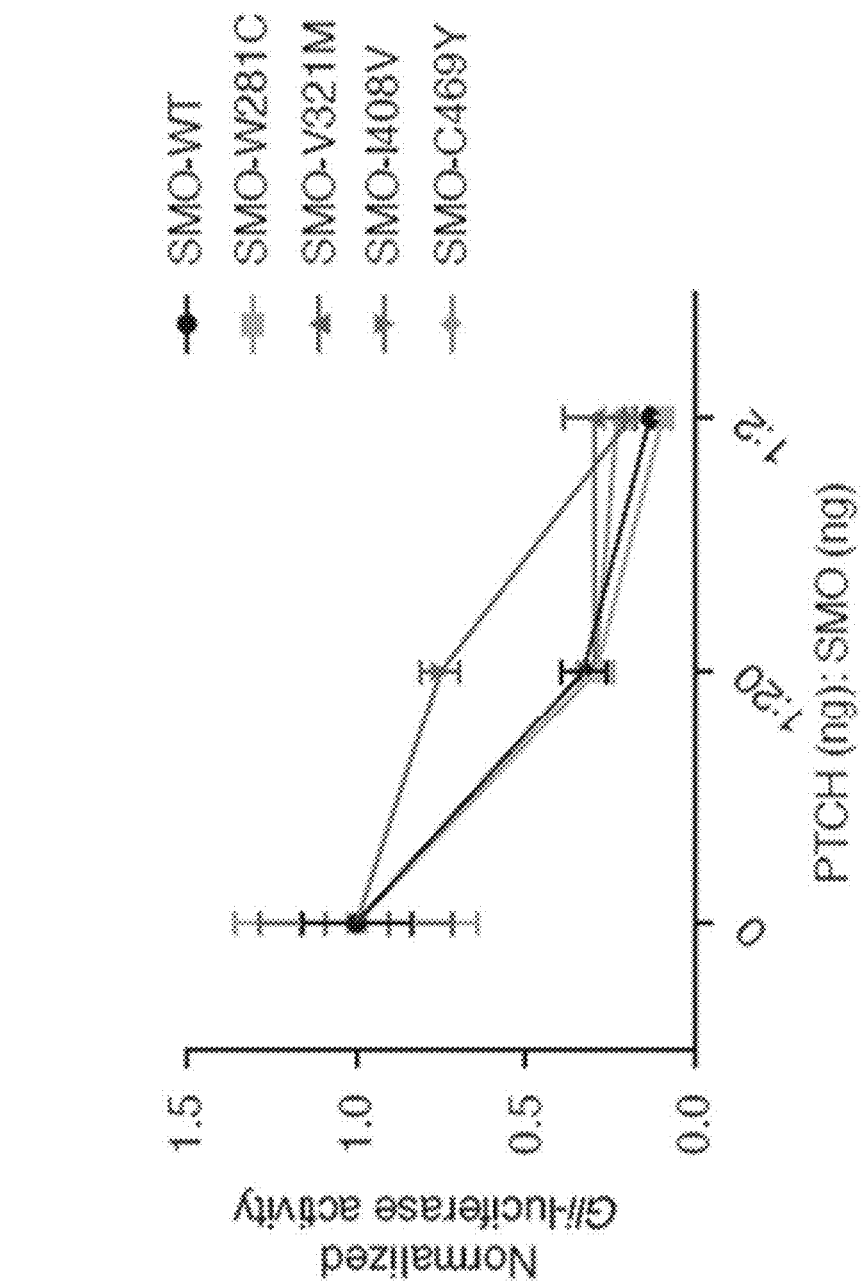
Figure 11:
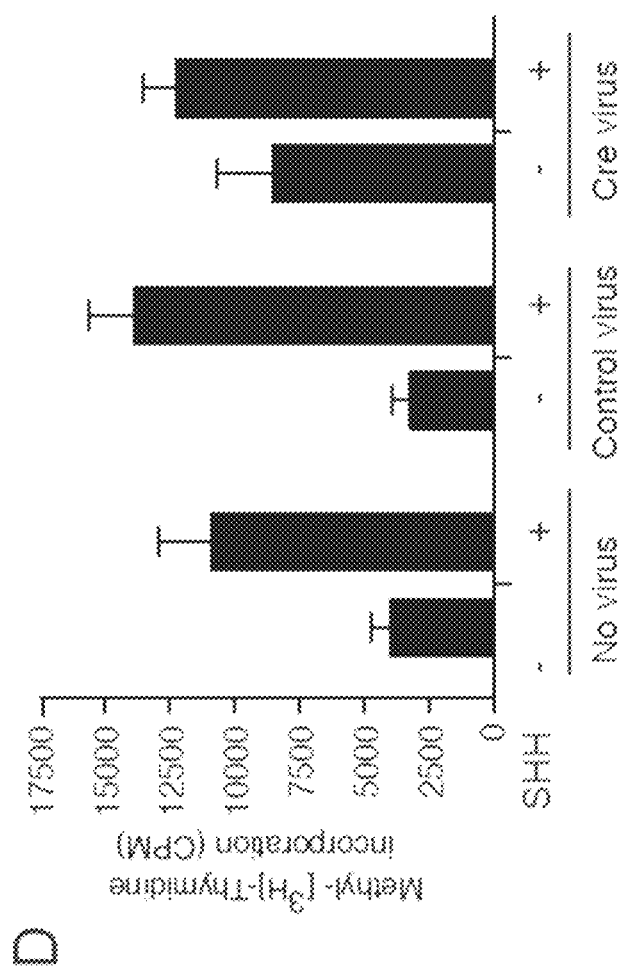
Figure 11:
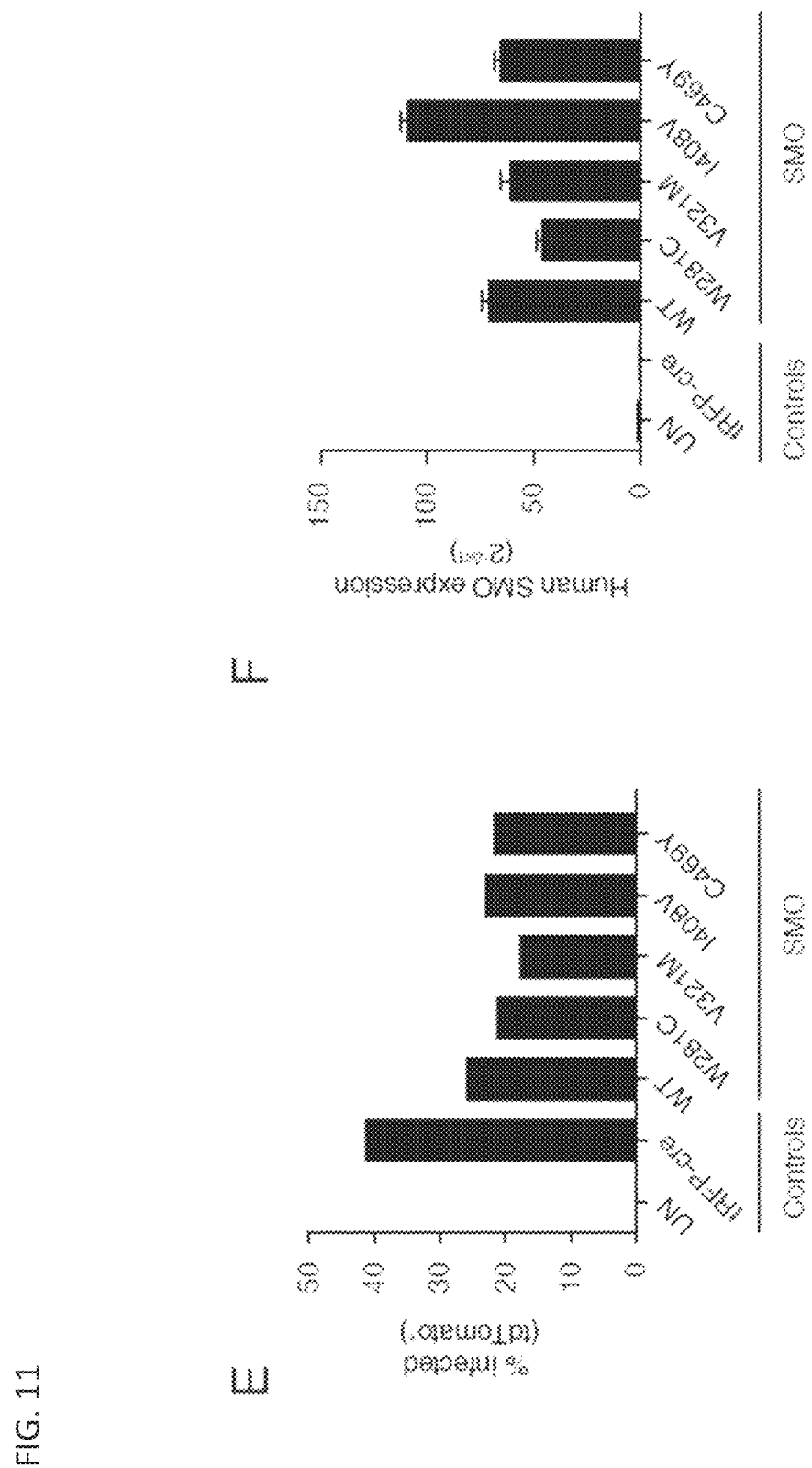
Figure 12:
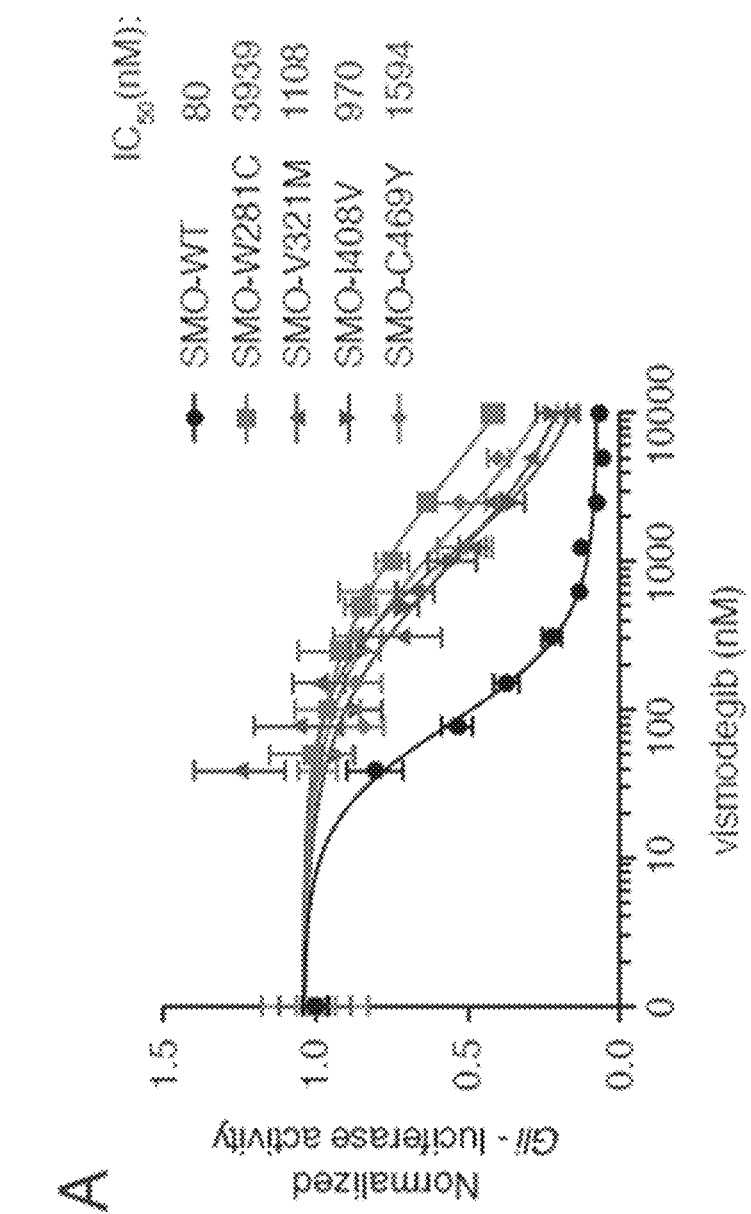
FIG. 12A is a graph showing normalized Gli-luciferase reporter activity in C3H10T½ cells transfected with indicated SMO constructs, following a dose response with vismodegib. Values were normalized to untreated activity and data plotted are mean+/−standard deviation (SD) of triplicates. IC50 values were calculated after non-linear regression fitting.
FIG. 12B is a bar graph showing binding of [3H]-vismodegib to HEK-293 cells transfected with indicated SMO constructs. EV stands for empty vector and drug binding was measured in counts per minute (cpm). Specific binding was calculated after competition with an excess of unlabeled vismodegib by subtracting non-specific binding from total binding. Data shown are the mean+/−SD.
FIG. 12C is a diagram of the viral transduction scheme of primary CGNPs. Only transduced CGNPs proliferate in the absence of SHH, allowing us to specifically test the ability of the SMO variants to promote proliferation in the presence of vismodegib.
FIG. 12D are a series of graphs showing normalized methyl-[3H]-thymidine incorporation of PPT CGNPs transduced with indicated viruses, following a dose response with vismodegib after removal of SHH ligand. Each graph shows the same control data. Data plotted are mean+/−SD of triplicates.
Figure 12:
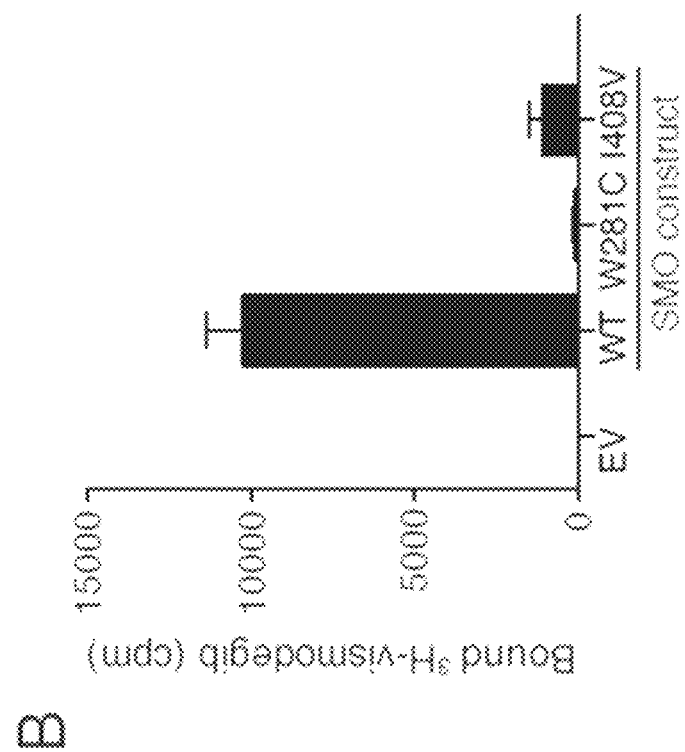
Figure 12:
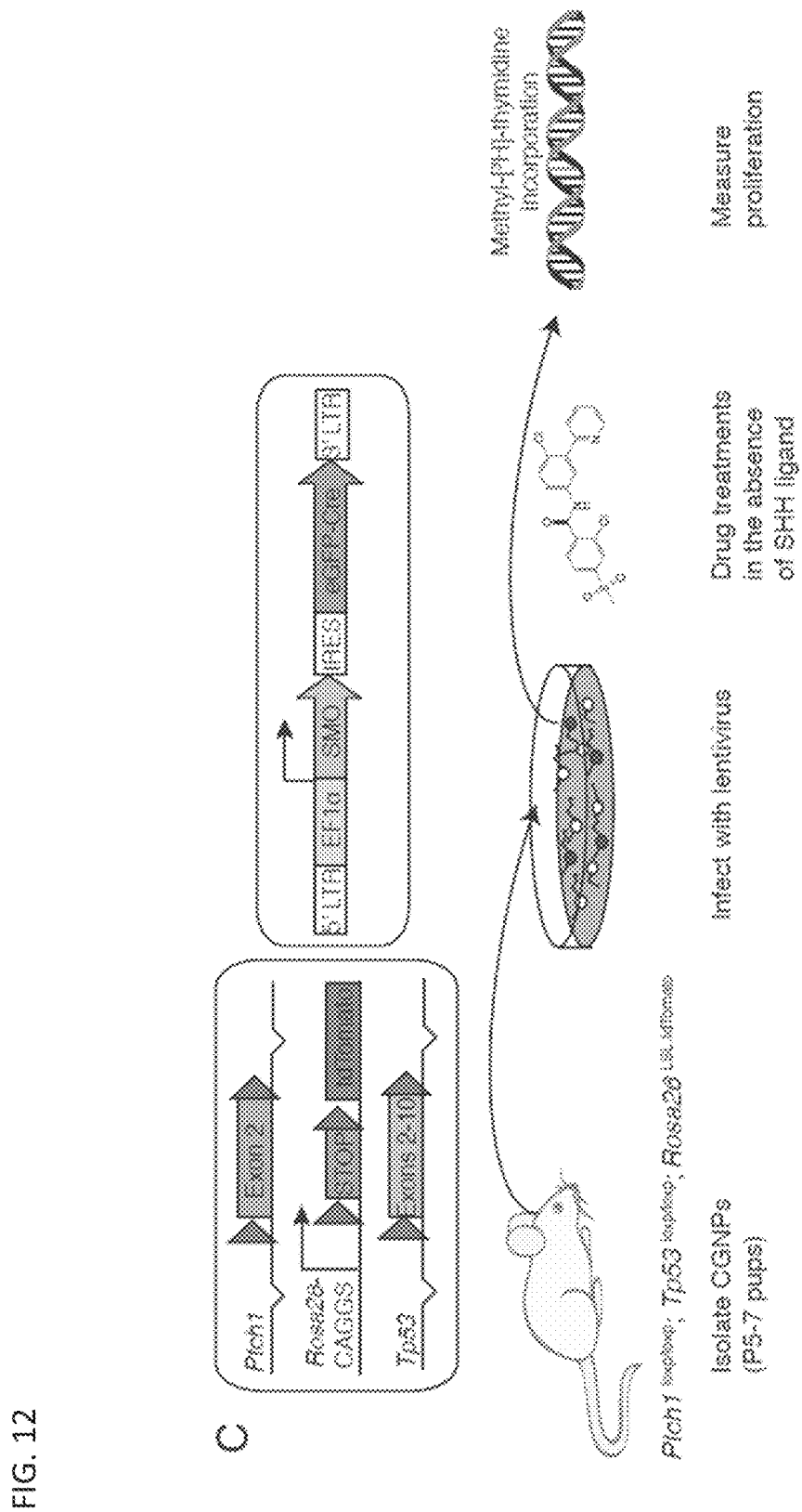
Figure 12:
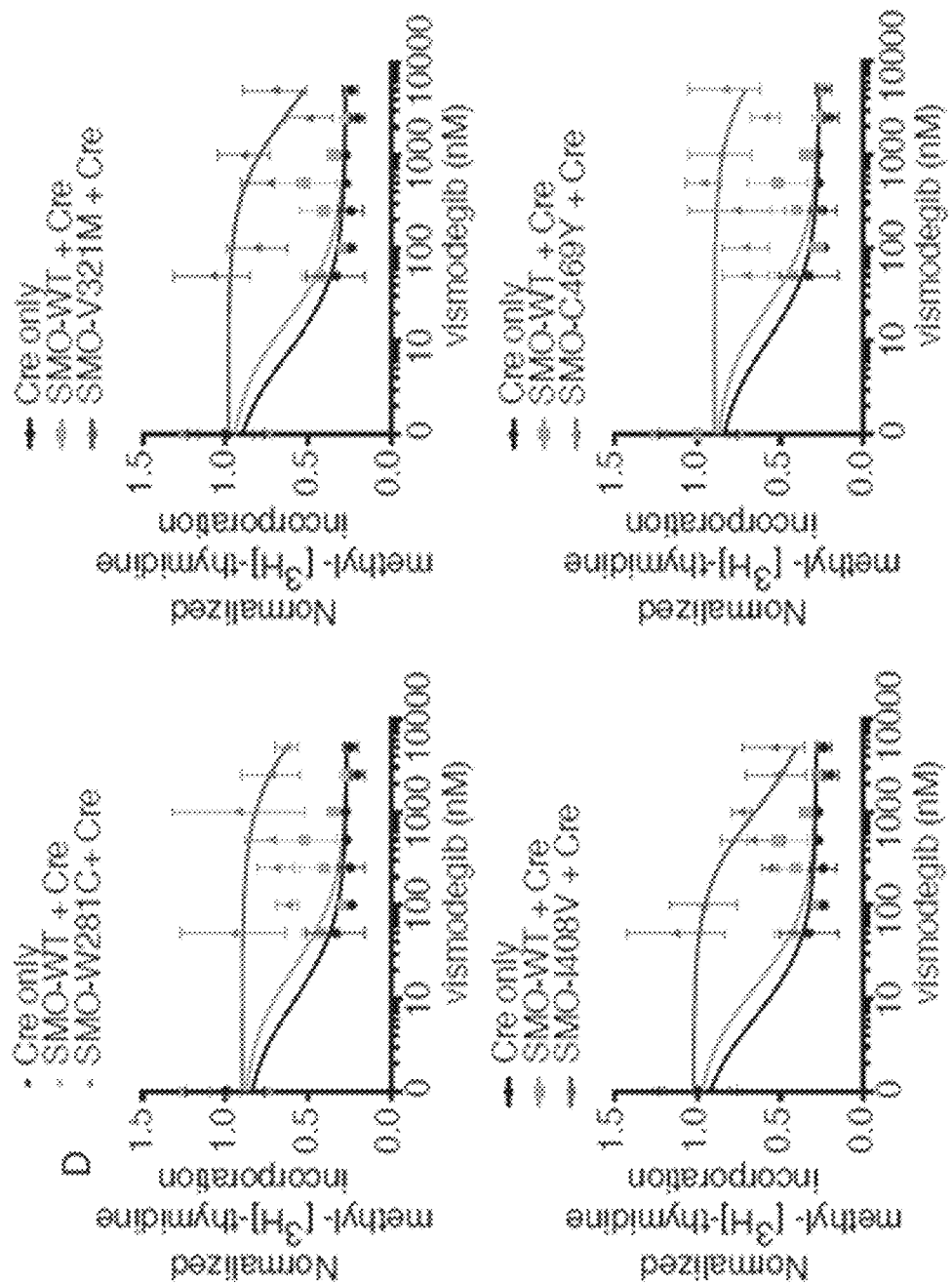

To test the functional impact of mutations in the DBP, a Gli-luciferase based Hh reporter assay was used. The DBP mutations increased the IC50 of vismodegib 12 to 49-fold over that of SMO-WT, which had an IC50 of 80 nM (FIG. 12A). It should be noted that these IC50 values are overestimates due to overexpression of SMO in this assay (Dijkgraaf et al., 2011). Although each DBP mutant displayed a small (<1.5 fold) increase in basal activity compared to SMO-WT (FIG. 11A), all but SMO-I408V were readily inhibited by PTCH1 overexpression (FIG. 11B). The binding of [3H]-labeled vismodegib to SMO-I408V and SMO-W281C was next tested, which respectively exhibited the smallest and largest increases in IC50 (FIG. 12A). Both mutants were expressed at cell surface levels similar to SMO-WT, but displayed impaired vismodegib binding (FIGS. 12B and 11C).

It has been demonstrated in preclinical tumor models that the Hh pathway must be inhibited >90% at the transcriptional level to induce tumor regression (Wong et al., 2011). To better understand the impact of these SMO mutations on cell proliferation in the presence of vismodegib, an assay for viral transduction of cerebellar granule neuron precursor (CGNP) cells was developed. It has previously been noted that Hh-driven tumor cells rapidly lose their Hh pathway dependence during culturing (Sasai et al., 2006). However, CGNPs proliferate in vivo in a Hh dependent manner and maintain their Hh pathway dependence in culture for a finite period (Wechsler-Reya and Scott, 1999). CGNPs isolated from Ptch1loxp/loxp Tp53loxp/loxp Rosa26LSL-tdTomato (PPT) pups were infected with lentiviral constructs expressing a SMO variant together with an enhanced green fluorescent protein (eGFP)-Cre fusion protein (FIG. 12C). The Cre recombinase induces loss of Ptch1 and thus ensures that only transduced CGNPs can proliferate in the absence of exogenous Sonic hedgehog ligand (SHH; FIG. 11D). This allowed us to test the ability of the various SMO mutants to promote proliferation in the presence of vismodegib and other inhibitors, after removal of SHH ligand. Proliferation by methyl-[3H]-thymidine incorporation was monitored, while Cre-dependent tandem dimer (td) Tomato expression enabled visualization and quantification of infected cells. This system also enabled better model patient genetics because most of the SMO mutations were identified in tumors that harbored TP53 mutations and were driven by loss of PTCH1. PPT CGNPs infected with SMO-WT and Cre had an IC50 of ~22 nM and proliferation was maximally inhibited at 100 nM vismodegib. In contrast, all DBP mutations had a dramatic effect on vismodegib sensitivity, with infected cells continuing to proliferate at high levels of vismodegib (>1 µM; FIG. 12D). Surprisingly, cells infected with either SMO-W281C or SMO-C469Y continued to proliferate at near untreated levels even in the presence of 5 µM vismodegib possibly reflecting the direct role of these residues in drug binding. It was confirmed that CGNPs were infected at similar frequencies by fluorescence-activated cell sorting (FACS) analysis for Cre-dependent tdTomato reporter expression, and that the SMO variants were expressed at equivalent levels by quantitative reverse transcription (qRT) PCR.

Figure 13:
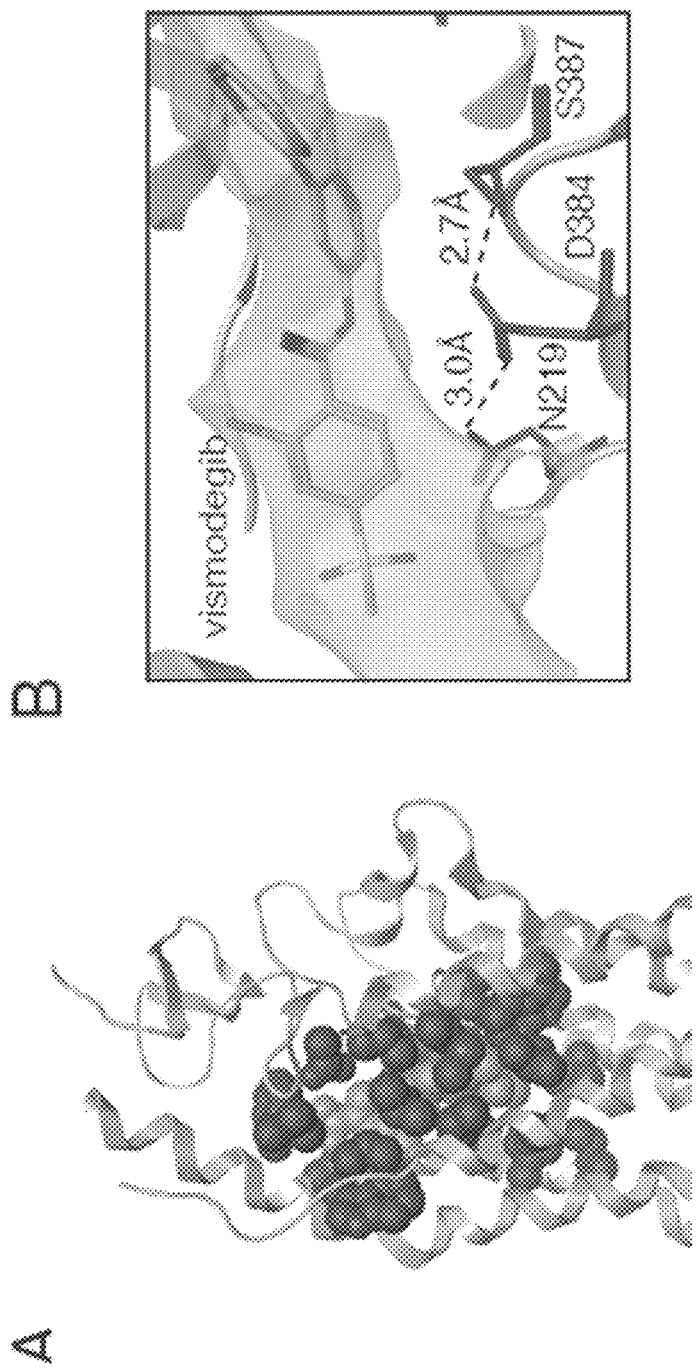
FIG. 13A is a model showing that a total of 21 residues (dark gray balls) are predicted to have atoms within 4.5 Å of vismodegib (light gray balls) bound to the SMO TM structure (gray helices).
FIG. 13B is a model showing that N219, D384 and S387 form a hydrogen-bonding network (dashed lines). Mutation of any of these residues is likely to change the shape of the vismodegib-binding pocket.
FIG. 13C shows a Gli-luciferase reporter activity in C3H10T½ cells transfected with indicated SMO constructs and treated with 1 μM vismodegib. Values were normalized to untreated activity levels for each construct and data plotted are mean+/−SD of triplicates.
Figure 13:
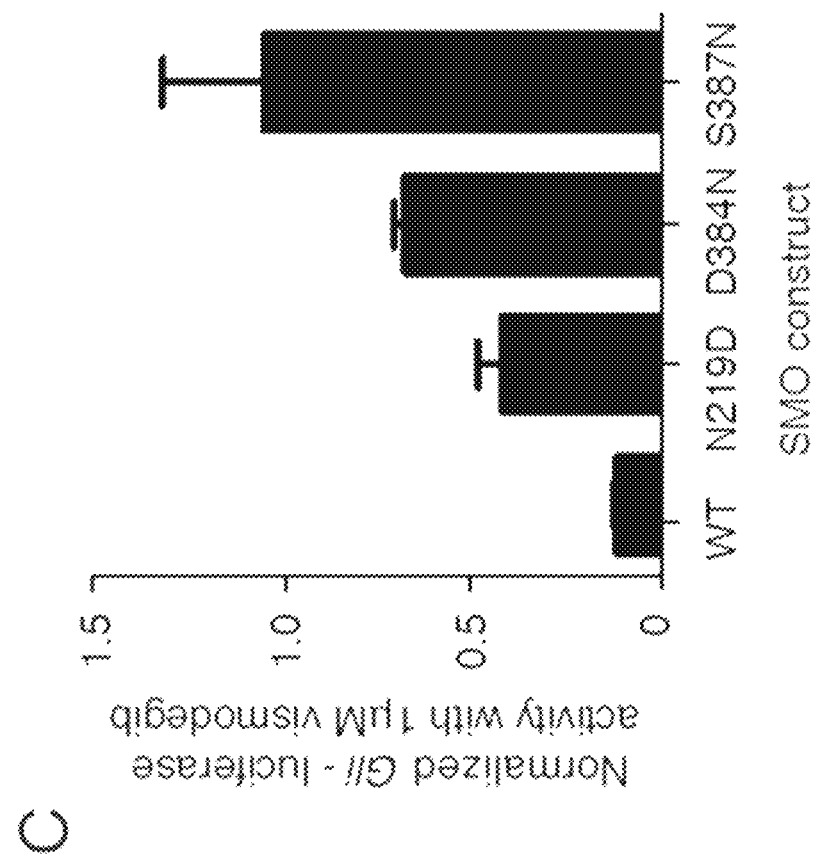

Example 6: Predicting Resistance to Vismodegib Through Mutation of the SMO Drug Binding Pocket To investigate whether other DBP mutations could promote drug resistance, a computational model was used to identify the 21 SMO residues with atoms located within 4.5 Å of vismodegib (FIG. 13A). An algorithm was used to identify 160 different single nucleotide variants that resulted in non-synonymous changes to these DBP residues, including SMO-W281C and SMO-I408V from this study (Table 4).

TABLE 4

Identification of SMO residues with atoms within 4.5 Angstroms of both vismodegib and LY2940680

| AA Position | AA | Codon | Non-synonymous single nucleotide changes | AA changes | C/G > T/A changes | Mutation comments |
|---|---|---|---|---|---|---|
| 219 | N | AAC | TAC, GAC, CAC, ATC, AGC, ACC, AAA, AAG | Y, D, H, I, S, T, K, K | None | N219D reduced sensitivity to vismodegib and LDE-225 (This study and Buonamici et al. 2010) |
| 221 | L | CTC | ATC, TTC, GTC, CAC, CGC, CCC | I, F, V, H, R, P | F | L221R reduced sensitivity to LDE-225 (Buonamici et al. 2010) |
| 230 | M | ATG | TTG, GTG, CTG, AAG, AGG, ACG, ATA, ATT, ATC | L, V, L, K, R, T, I, I, I | | |
| 281 | W | TGG | AGG, GGG, CGG, TAG, TTG, TCG, TGA, TGT, TGC | R, G, R, *, L, S, *, C, C | * | W281C, this study and Brinkhuizen et al. 2014 |
| 325 | L | CTG | ATG, GTG, CAG, CGG, CCG | M, V, Q, R, P | None | |
| 384 | D | GAC | AAC, TAC, CAC, GTC, GGC, GCC, GAA, GAG | N, Y, H, V, G, A, E, E | N | D384N reduced sensitivity to vismodegib and LDE-225 (This study and Buonamici et al. 2010) |

TABLE 4-continued

Identification of SMO residues with atoms within
4.5 Angstroms of both vismodegib and LY2940680

| AA Position | AA | Codon | Non-synonymous single nucleotide changes | AA changes | C/G > T/A changes | Mutation comments |
|---|---|---|---|---|---|---|
| 389 | I | ATT | TTT, GTT, CTT, AAT, AGT, ACT, ATG | F, V, L, N, S, T, M | None | |
| 391 | F | TTT | ATT, GTT, CTT, TAT, TGT, TCT, TTA, TTG | I, V, L, Y, C, S, L, L | None | |
| 394 | Y | TAC | AAC, GAC, CAC, TTC, TGC, TCC, TAA, TAG | N, D, H, F, C, S, *, * | None | |
| 400 | R | CGT | AGT, TGT, GGT, CAT, CTT, CCT | S, C, G, H, L, P | C | R400A, partially functional (Dijkgraaf et al. 2011) |
| 408 | I | ATC | TTC, GTC, CTC, AAC, AGC, ACC, ATG | F, V, L, N, S, T, M | None | I408V, this study |
| 470 | H | CAC | AAC, TAC, GAC, CTC, CGC, CCC, CAA, CAG | N, Y, D, L, R, P, Q, Q | Y | H470A not expressed (Dijkgraaf et al. 2011) |
| 477 | Q | CAG | AAG, TAG, GAG, CTG, CGG, CCG, CAT, CAC | K, *, E, L, R, P, H, H | E | |
| 480 | W | TGG | AGG, GGG, CGG, TAG, TTG, TCG, TGA, TGT, TGC | R, G, R, *, L, S, *, C, C | * | W480A not expressed, (Dijkgraaf et al. 2011) |
| 481 | E | GAG | AAG, TAG, CAG, GTG, GGG, GCG, GAT, GAC | K, *, Q, V, G, A, D, D | K | |
| 484 | F | TTC | ATC, GTC, CTC, TAC, TGC, TCC, TTA, TTG | I, V, L, Y, C, S, L, L | None | |
| 515 | L | CTT | ATT, TTT, GTT, CAT, CGT, CCT | I, F, V, H, R, P | F | L515A expressed, activating, sensitive to 1 mM inhibition by vismodegib (Dijkgraaf et al. 2011) |
| 518 | E | GAG | AAG, TAG, CAG, GTG, GGG, GCG, GAT, GAC | K, *, Q, V, G, A, D, D | K | E518K and E518A reduced sensitivity to vismodegib (Dijkgraaf et al. 2011) |
| 521 | N | AAC | TAC, GAC, CAC, ATC, AGC, ACC, AAA, AAG | Y, D, H, I, S, T, K, K | None | N521A not expreessed (Dijkgraaf et al. 2011) |
| 522 | L | CTG | ATG, GTG, CAG, CGG, CCG | M, V, Q, R, P | None | |
| 525 | M | ATG | TTG, GTG, CTG, AAG, AGG, ACG, ATA, ATT, ATC | L, V, L, K, R, T, I, I, I | I | |
| 241 | T | ACG | TCG, GCG, CCG, AAG, ATG, AGG | S, A, P, K, M, R | M | T241M, this study |
| 321 | V | GTG | ATG, TTG, CTG, GAG, GGG, GCG | M, L, L, E, G, A | M | V321M, this study and Brinkhuizen et al. 2014 |
| 387 | S | AGT | TGT, GGT, CGT, AAT, ATT, ACT, AGA, AGG | C, G, R, N, I, T, R, R | N | S387N reduced sensitivity to vismodegib and LDE-225 (This study and Buonamici et al. 2010) |
| 459 | A | GCC | ACC, TCC, CCC, GAC, GTC, GGC | T, S, P, D, V, G | V | A459V, this study |
| 469 | C | TGC | AGC, GGC, CGC, TAC, TTC, TCC, TGA, TGG | S, G, R, Y, F, S, *, W | Y | C469Y, this study |
| 473 | D | GAC | AAC, TAC, CAC, GTC, GGC, GCC, GAA, GAG | N, Y, H, V, G, A, E, E | N | D473H (Yauch et al. 2009) All aa except P reduce sensitivity to vismodegib (Dijkgraaf et al. 2011) |

The amino acids corresponding to positions 219, 221, 281, 384, 408 and 518 of SEQ ID NO: 1 are in the vismodegib binding pocket. The amino acids corresponding to positions 241, 321, 387, 459, 469 and 473 of SEQ ID NO: 1 are associated with clinical mutations but are not found within 4.5 Angstroms of vismodegib when bound to SMO. SMO-D473 was not identified with this method, but the SMO crystal structure revealed that D473 forms a hydrogen-bonding network with several residues that do directly contact vismodegib including R400, H470, E518 and N521 (Wang et al., 2013; Yauch et al., 2009). SMOE518 was previously identified by alanine scan mutagenesis as a residue that affects vismodegib sensitivity when mutated (Dijkgraaf et al., 2011). This approach also identified residues that were previously implicated in preclinical models of resistance to the SMO inhibitor sonidegib (LDE225) including N219 and D384 (Table 4; Buonamici et al., 2010), which are predicted to stabilize the SMO conformation through a hydrogen bonding network (FIG. 13B). Surprisingly, SMO-N219D, SMO-D384N and SMO-S387N all displayed reduced sensitivity to vismodegib compared to SMO-WT in the Gli luciferase based Hh reporter assay (FIG. 13C). Moreover, it was found that the SMO inhibitor LY2940680 and vismodegib share 14 contact residues (Table 4). Without wishing to be bound by theory, this suggests that chemically distinct inhibitors interact with overlapping SMO residues and that cross resistance between inhibitors might occur in the clinic.

Figure 14:
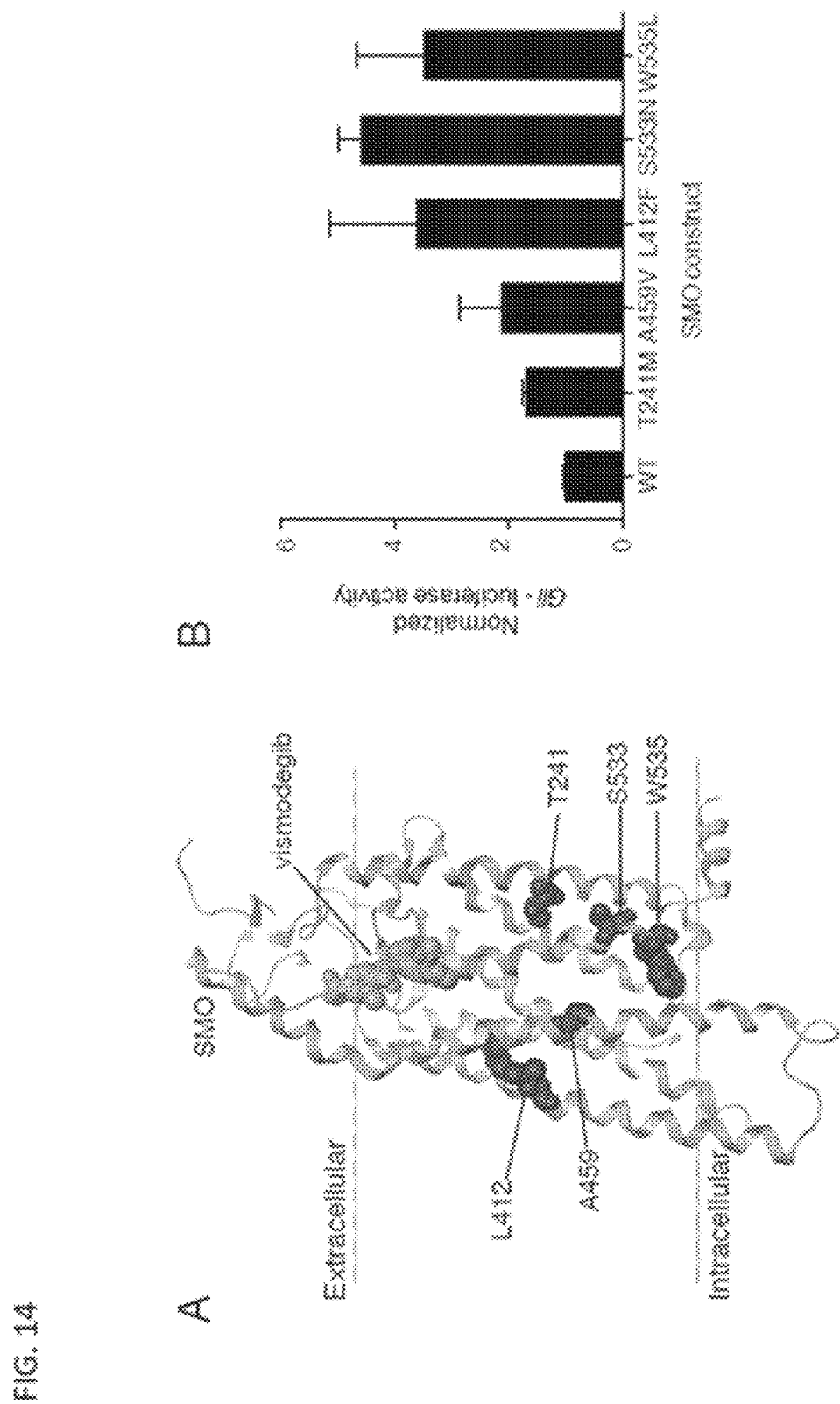
FIG. 14A shows a computational model of vismodegib (light gray balls) docked onto the crystal structure of the SMO TM region (grey helices; Wang et al., 2013). Mutant residues distal to the drugbinding pocket are highlighted in dark gray.
FIG. 14B is a bar graph showing results from a Gli-luciferase reporter activity in C3H10T½ cells transfected with indicated SMO constructs. Values were normalized to activity levels of SMO-WT and data plotted are mean+/−SD of triplicates.
FIG. 14C is a graph showing normalized Gli-luciferase reporter activity in C3H10T½ cells transfected with indicated SMO constructs, following a dose response with vismodegib. Data plotted are mean+/−SD of triplicates.
FIG. 14D is a graph showing normalized methyl-[3H]-thymidine incorporation of PPT CGNPs transduced with indicated viruses, following a dose response with vismodegib after removal of SHH ligand. Data plotted are mean+/−SD of triplicates.
Figure 14:
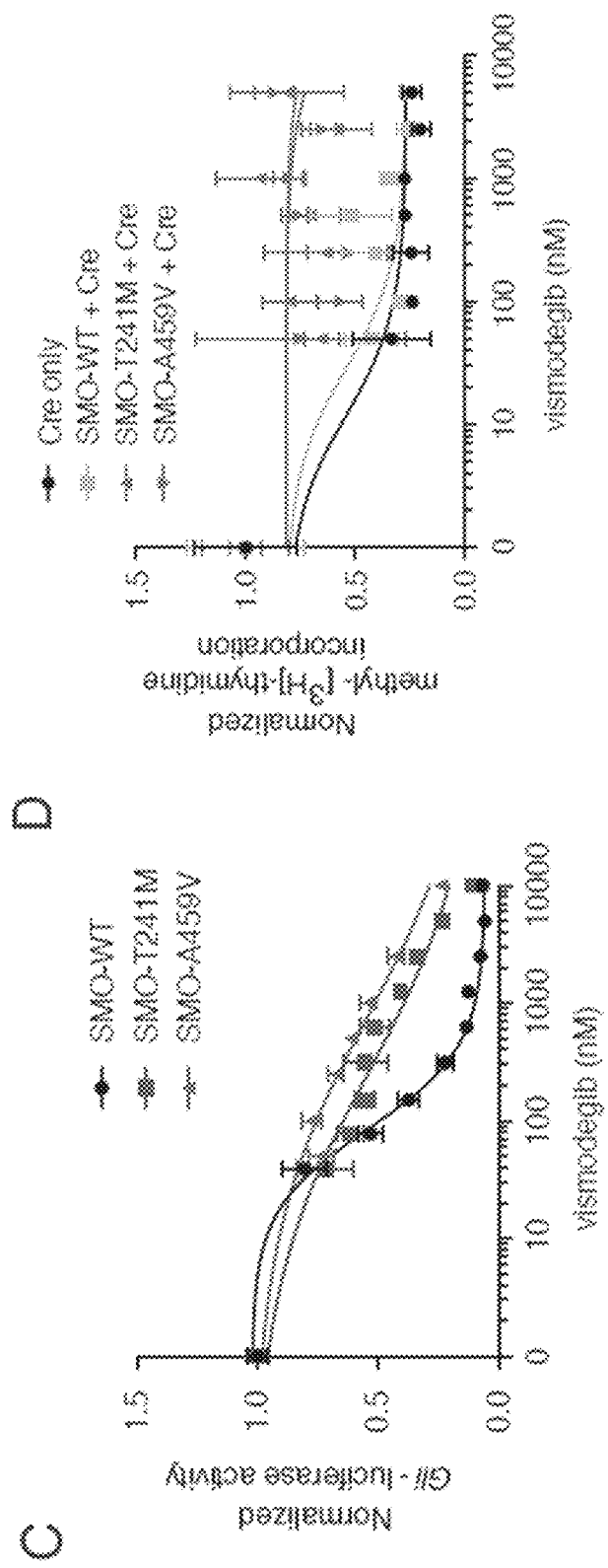
Figure 15:
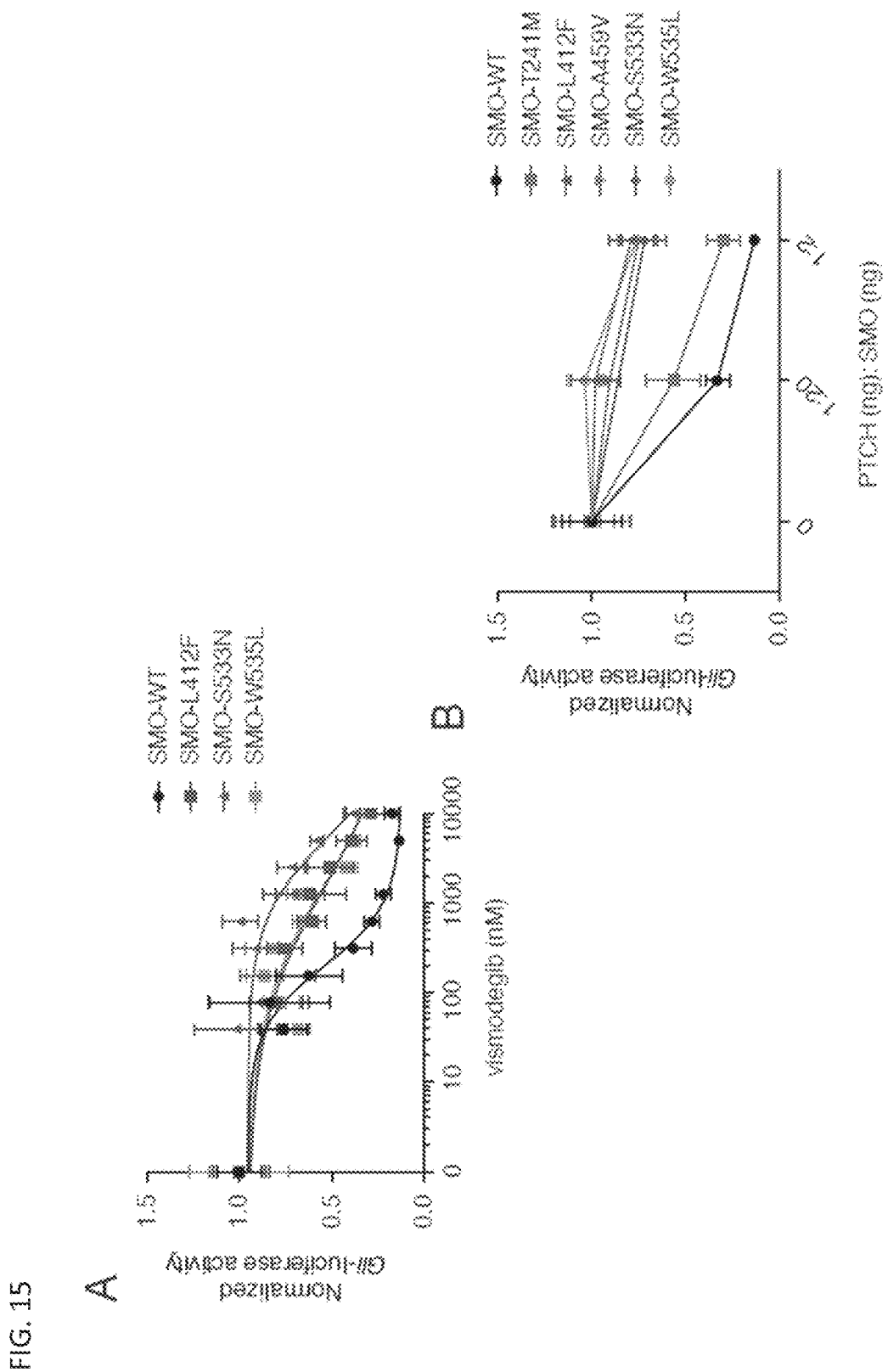
FIG. 15A is a graph showing normalized Gli-luciferase reporter activity in C3H10T½ cells transfected with indicated SMO constructs, following a dose response with vismodegib. Data plotted are mean+/−SD of triplicates.
FIG. 15B is a graph showing results from a Gli-luciferase reporter assay in C3H10T½ cells transfected with indicated ratios of PTCH1 to SMO expression constructs. Values were normalized to activity without PTCH1 co-transfection and data plotted are mean+/−SD of triplicates.
FIG. 15C is a bar graph illustrating binding of [3H]-vismodegib to HEK-293 cells transfected with indicated SMO construct. Untransfected cells (Un) and cells transfected with an empty vector (EV) were included as controls. Drug binding was measured in counts per minute (cpm) and specific binding was calculated after competition with an excess of unlabeled vismodegib by subtracting non-specific binding from total binding.
FIG. 15D is a table showing cell surface expression of activating SMO mutants in HEK-293 cells. Values shown are the percentage of viable cells with cell surface expression of SMO, as determined by FACS for 10,000 cell events and gating on empty vector transfected cells and PI.
FIG. 15E is a graph showing normalized methyl-[$^3$H]-thymidine incorporation of PPT CGNPs transduced with indicated viruses, following a dose response with vismodegib after removal of SHH ligand. Data plotted are mean+/−SD of triplicates. Two independent experiments are shown.
Figure 15:
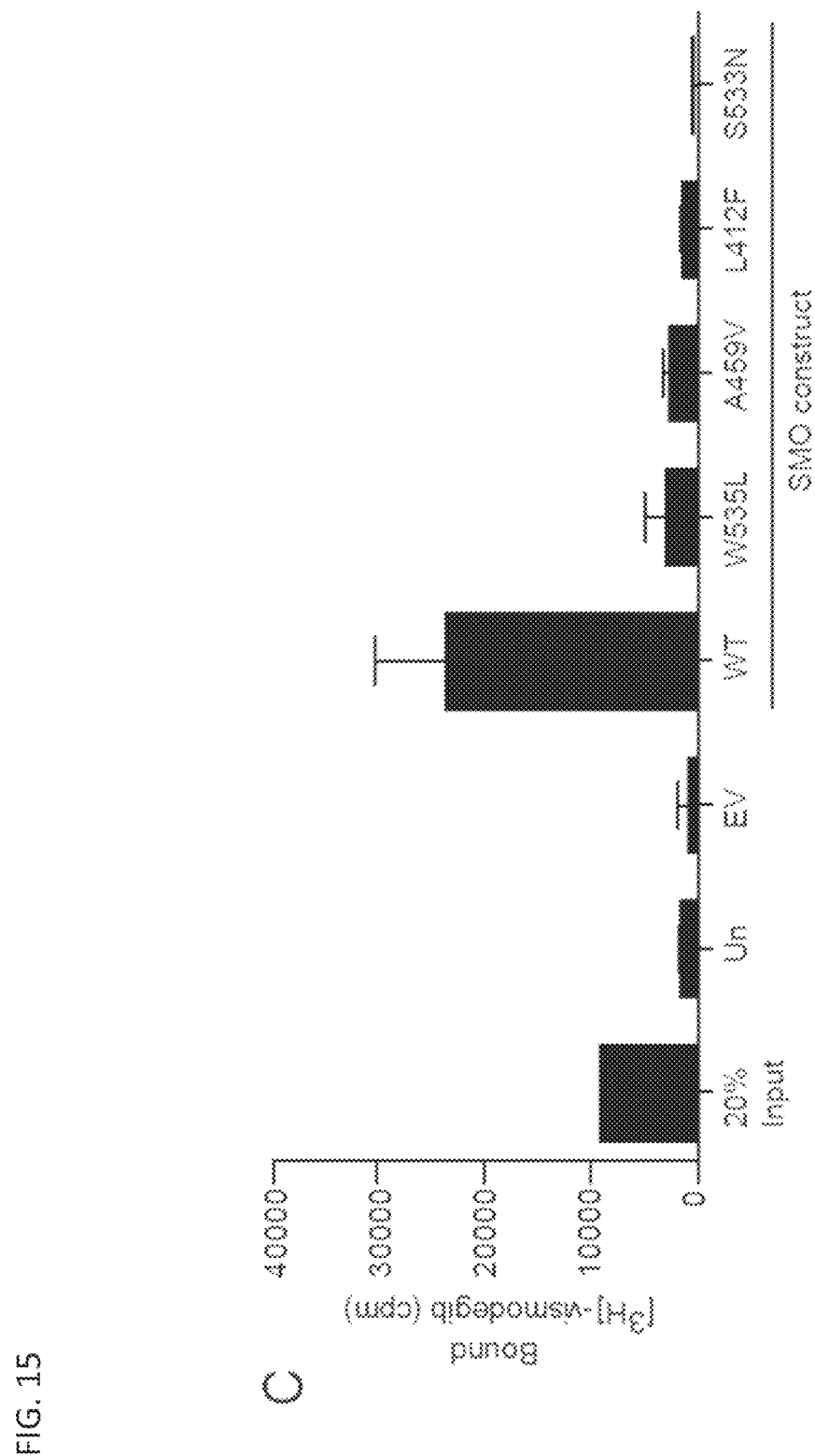
Figure 15:
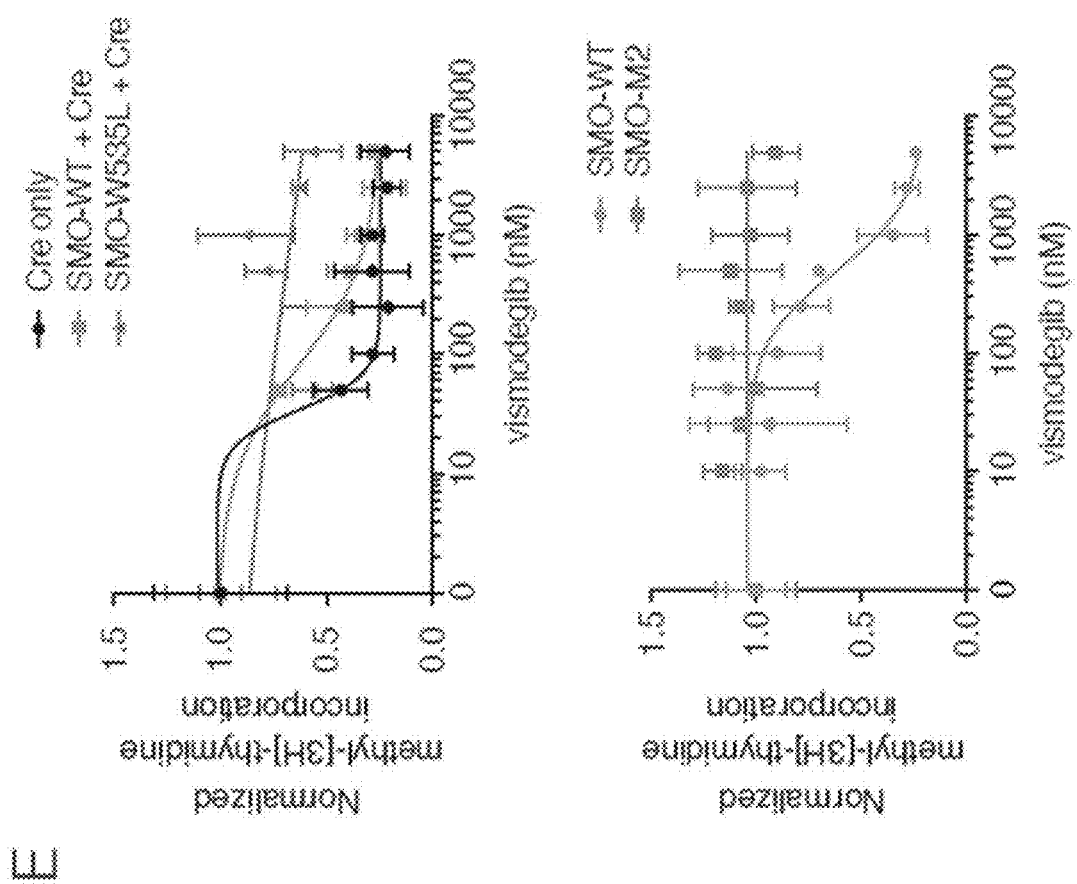

Example 7: SMO Mutations Beyond the Drug-Binding Pocket Confer Vismodegib Resistance SMO mutations located distally with respect to the vismodegib-binding pocket were also associated with vismodegib resistance (FIG. 14A). Interestingly, both SMO-T241M and SMO-A459V display increased basal activity over SMO-WT, albeit to a lesser extent than the established oncogenic mutations (FIG. 14B). This elevated activity correlated with reduced sensitivity to inhibition by both vismodegib (FIGS. 14C and 15A) and PTCH1 overexpression (FIG. 15B), with SMO-T241M and SMO-A459V shifting the IC50 of vismodegib approximately 3- and 9-fold, respectively. Additionally, all activating mutants tested displayed impaired vismodegib binding despite comparable levels of cell surface expression to SMO-WT (FIGS. 15C and 15D).

A PPT CGNP assay was used to investigate the impact of non-DBP SMO mutations on proliferation in the presence of vismodegib. SMO-T241M, SMO-A459V and SMOW535L expressing CGNPs continued to proliferate at high concentrations of vismodegib (FIGS. 14D and 15E). These data are consistent with mutations outside the DBP destabilizing the SMO architecture to promote activation and reduce affinity for antagonists, as has been observed for GPCRs (Gether et al., 1997). However, it cannot be ruled out potential allosteric effects on the DBP by these mutations, for example, in the case of SMO-T241M, which only slightly increased basal activity (FIG. 8B). Several BCCs (from PT01, PT07 and PT11) that were PTCH1 wild-type and harbored oncogenic SMO mutations initially responded to treatment despite the fact that these SMO mutations reduce sensitivity to vismodegib inhibition (FIG. 15A). This could suggest a role for PTCH1 loss-of-function in the sensitivity of SMO mutants to vismodegib.

Example 8: Therapeutic Options to Overcome Vismodegib Resistance

Figure 16:
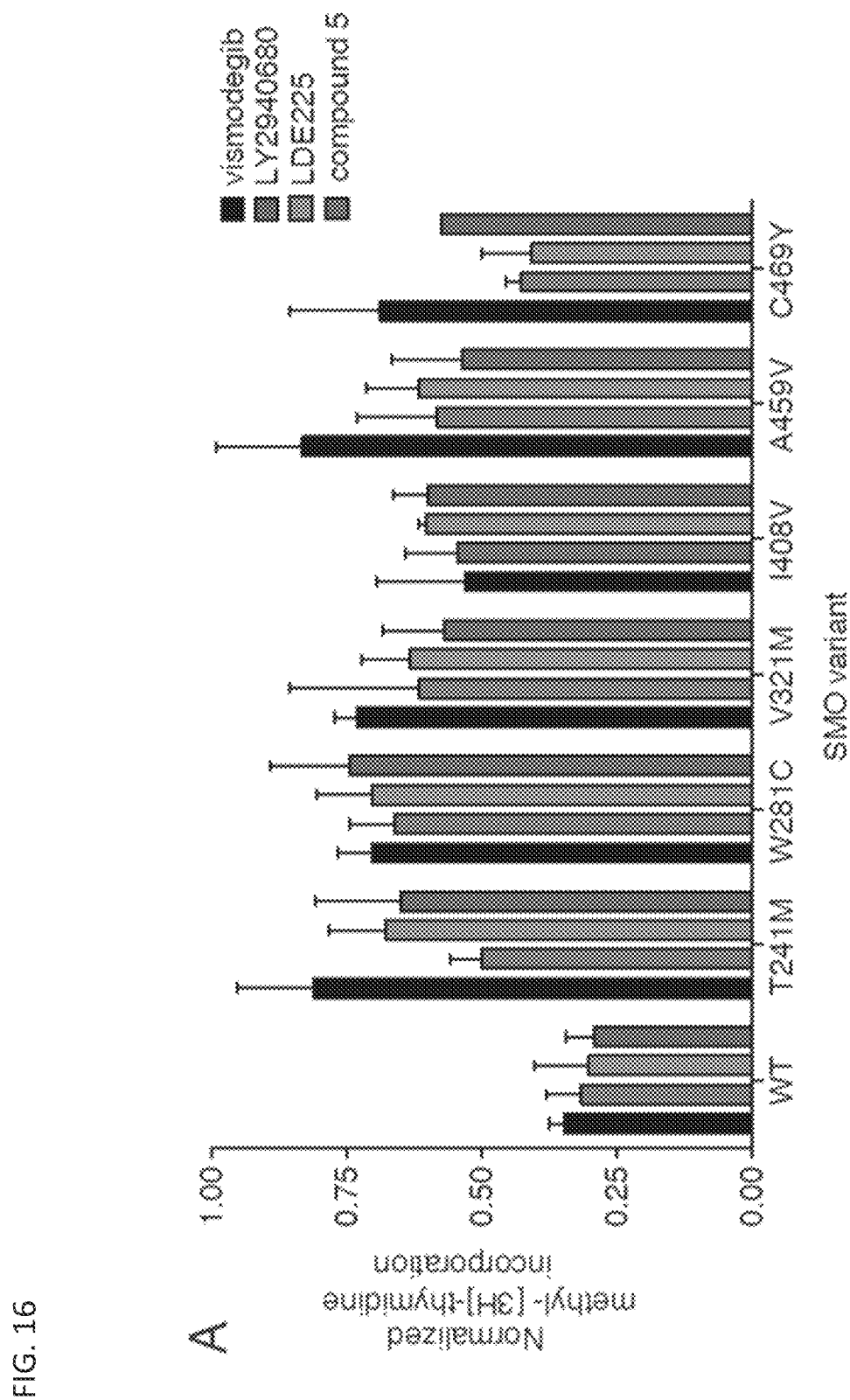
FIG. 16A shows normalized methyl-[$^3$H]-thymidine incorporation of PPT CGNPs transduced with various SMO variants and treated with 500 nM of indicated compounds. For each set of data for wildtype (WT) or SMO mutant evaluated, data for each of the following treatment conditions is presented as bars in the following order from left to right: vismodegib, LY2940680, LDE225, and compound 5. Values were normalized to proliferation levels without drug and data plotted are mean+/−SD of triplicates. Note that the residual proliferation of SMO-WT in the presence of drug is due to fibroblast and glial contamination of these primary CGNP cultures.
FIG. 16B shows the same data as in 16A, but transduced CGNPs were treated with 1 µM of either vismodegib or JQ1. Note that there is less residual proliferation in SMO-WT with JQ1, suggesting that this compound also inhibits Hh-independent cell proliferation.
Figure 16:
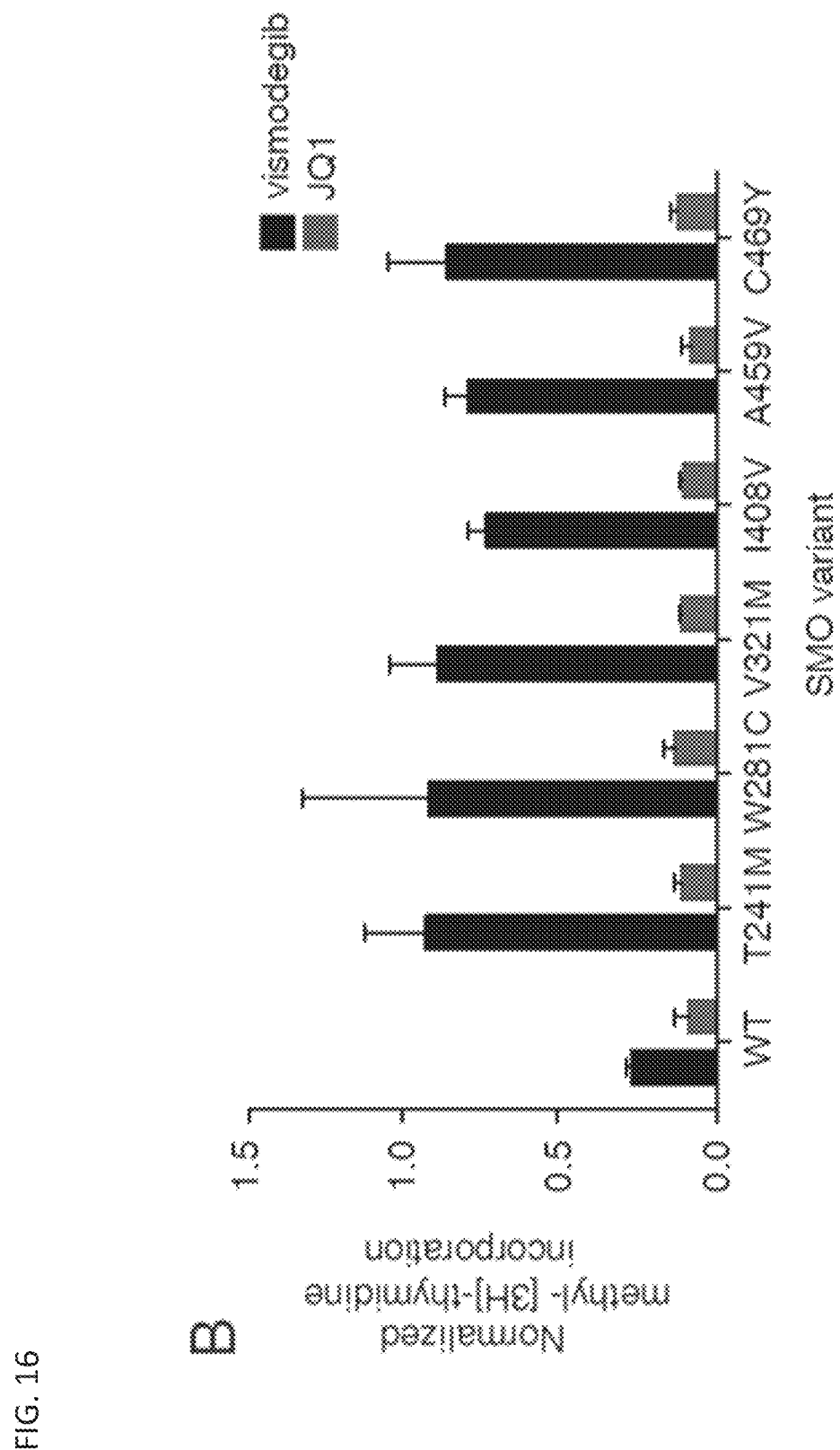

Having established that multiple SMO mutations can confer resistance to vismodegib, whether chemically distinct SMO inhibitors could overcome vismodegib resistance was next addressed. LY2940680 and LDE225 are currently in clinical trials for various cancers (Clinicaltrials.gov) and compound 5 is a SMO inhibitor that showed preclinical efficacy against SMO-D473H (Dijkgraaf et al., 2011). While all compounds similarly inhibited the proliferation of SMO-WT expressing PPT CGNPs, SMO-mutant expressing cells continued to proliferate, albeit to differing extents (FIG. 16A). This observed cross resistance between the various SMO inhibitors is consistent with the structural predictions, and suggests that combining SMO antagonists is not a suitable therapeutic option to overcome acquired resistance. Moreover, the identification of recurrent SUFU and GLI2 variants in relapsed tumors could additionally argue for targeting Hh pathway components downstream of SMO. While GLI inhibitors developed so far lack potency and bioavailability, recent studies found that the bromodomain-containing protein BRD4 occupies GLI promoters and is required for transcriptional output of the Hh pathway (Long et al., 2014; Tang et al., 2014). PPT CGNPs expressing vismodegib-resistant SMO mutants showed reduced proliferation the presence of the bromodomain inhibitor JQ1 (FIG. 16B).

Materials and Methods for Examples 2-9

Patient and Tissue Specimens

Specimens from vismodegib-treated patients were collected after receiving written informed consent according to federal guidelines and as approved by institutional review boards (IRB) of contributing centers participating in the clinical studies SI-IHH3925g, SHH4476g and STEVIE. For analysis of vismodegib resistance mechanisms, biopsies were obtained at time of disease progression from 12 patients with locally-advanced or metastatic BCC, who experienced a prior, investigator-assessed, clinical benefit on therapy, as described previously (LoRusso et al., 2011; Sekulic et al., 2012). Biopsies from 43 untreated patients were collected and sequenced for comparison according to protocols approved by University of Michigan and Stanford University IRBs.

Genomic Analyses

DNA from 15 vismodegib-resistant BCC samples, 48 untreated BCCs and 52 matched blood samples were subjected to WES. WES of tumor biopsies was achieved with a minimum average coverage of more than 67-fold. Copy number changes were assessed for vismodegib-resistant BCCs by SNP or CGH arrays. RNA from 11 resistant BCC samples was subjected to RNA-seq. DNA from 7 FFPE samples was analyzed by pyrosequencing. RNA-seq data from five normal skin samples (procured from ProteoGenex) were used as baseline gene expression for comparisons with BCC patient samples.

Animals

All mice were housed and maintained according to protocols approved by the Genentech Inc. institutional animal care and use committee, which conformed to the animal-use guidelines of Genentech Inc. and to California State legal and ethical practices.

Functional Analyses

SMO mutants were generated in pRK5-SMO vectors as described (Dijkgraaf et al., 2011; Yauch et al., 2009) and were either utilized in Gli-luciferase reporter assays as described (Dijkgraaf et al., 2011) or cloned into lentiviral vectors for transduction of primary CGNP cultures. Proliferation was assayed using methyl-[3H]-thymidine incorporation (Kool et al., 2014). Binding of [3H]-vismodegib to SMO mutants was carried out in HEK-293 cells as described (Dijkgraaf et al., 2011).

Patient Samples

Relapsed tumor samples were collected after receiving written informed consent according to federal and institutional review board (IRB) guidelines on contributing centers. Untreated sporadic BCC samples were obtained according to University of Michigan IRB-approved protocols HUM00069052 and HUM00050085. Untreated Gorlin patient samples were obtained according to the Stanford University IRB approved protocol 2012-029.

Histology

FFPE and O.C.T. compound (Tissue-Tek) embedded samples were sectioned and H&E stained according to standard procedures. Images were acquired using a Zeiss Axioskop 2 microscope (Zeiss).

DNA and RNA Isolation

Frozen BCC tumors were homogenized in RLT plus lysis buffer (Qiagen) using either a Bullet Blender (Next Advance) or Tissue Lyzer (Qiagen). Nucleic acids were isolated with the Allprep DNA/RNA Mini Kit (Qiagen) following the manufacturer's protocol. FFPE tumor sections were macrodissected, deparaffinized and extracted using the Allprep DNA/RNA FFPE Kit (Qiagen).

Exome Capture and Sequencing

Exome capture was performed using Agilent SureSelect (Santa Clara, Calif.) Human All Exome kit (50 Mb). Exome capture libraries were sequenced on HiSeq 2000 (Illumina, CA) to generate 2×75 bp paired-end data.

Variant Calling

Exome-Seq reads were aligned to the UCSC human genome (GRCh37/hg19) using gsnap (Wu and Nacu, 2010) version 2013-10-10 with the parameters "-M 2 -n 10 -B 2 -i 1 --pairmax-dna=1000 --terminal-threshold=1000 --gmap-mode=none --clip-overlap". Local realignment was performed using the GATK Indel Realigner (DePristo et al., 2011). Duplicated reads were removed using Picard. Somatic variant calling on tumor and matched normal samples file was performed using VariantTools2 with default parameters (http://www.bioconductor.org/packages/release/bioc/html/VariantTools.html). Known germline variations represented in dbSNP Build 131 (Sherry et al., 2001) but absent in COSMIC v62 (Forbes et al., 2010) were filtered out for all samples. The effect of all nonsynonymous somatic mutations on gene function was predicted using Condel (Gonzalez-Perez and Lopez-Bigas, 2011). All variants were annotated using Ensembl Release 63.

RNA Sequencing and Data Analysis

RNA-seq libraries were prepared using TruSeq RNA Sample Preparation kit (Illumina, CA). The libraries were multiplexed three per lane and sequenced on HiSeq 2000 to obtain at least ~30 million paired-end (2×75 bp) reads per sample. RNA-seq reads were aligned to the UCSC human genome (GRCh37/hg19) using gsnap (Wu and Nacu, 2010) version 2013-10-10 with the parameters "-M 2 -n 10 -B 2 -i 1 -N 1 -w 200000 -E 1 -- pairmax-rna=200000 --clip-overlap". Expression counts per gene were obtained by counting the number of reads aligning concordantly within a pair and uniquely to each gene locus as defined by NCBI and Ensembl gene annotations, and RefSeq mRNA sequences. Differential gene expression analysis was performed using the Bioconductor DESeq2 package (Anders and Huber, 2010).

Sequence Data Processing

All sequencing reads were evaluated for quality using the Bioconductor ShortRead package (Morgan et al., 2009). To confirm that all samples were identified correctly, all exome and RNA-seq data variants were cross-compared and checked for genetic consistency using the Bioconductor VariantTools2 package. All patient paired samples matched correctly and did not match with any other patient using a cutoff of 90%.

Comparative Genomic Hybridization (CGH)

Tumor samples were assayed on Agilent Human Genome CGH 1M microarrays. Human male genomic DNA (Promega P/N G1471) was used as reference. Individual log 2 ratios of background subtracted signal intensities were obtained from the Agilent Feature Extraction software version 10.7. The log 2 ratios were corrected for the GC content wave effect (Diskin et al., 2008) using 1 Mb windows for genome GC content. The resulting log 2 ratio values for each probe were segmented using the cghFLasso algorithm (Tibshirani and Wang, 2008) one sample and chromosome at a time. Segmentation was performed using the parameters lambda1=0 and lambda2=1000*the fraction of probes on the current chromosome. All probes within the genomic bounds of a given segment were given the mean copy number value of probes within that segment.

SNP Array

Illumina HumanOmni 2.5-8 arrays were processed using a previously used, modified version of a method developed by (Rudin et al., 2012). As before, a large panel of normal samples was used to learn the behavior of the two probes for each SNP. For the current analysis, 450 HapMap normal samples were used. As before, the raw signal for each probe in each sample was transformed onto a scale where 0, 1, or 2 true underlying copies of a given allele mapped to 1, 2, or 3, as required by PICNIC's hidden Markov model. These values for the probes A and B for each allele were used to calculate the Copy Number Ratio (CNR, Formula 1) and Theta (Formula 2). CNR can be interpreted as the ratio of the total copy number at a given locus to the overall sample ploidy, i.e., average copy number across the genome. The CNR values were corrected for the GC content wave effect (Diskin et al., 2008) using 1 Mb windows for genome GC content.

$$CNR=(A+B)/4 \quad \text{Formula 1:}$$

$$\text{Theta}=2/\pi*\arctan(B/A) \quad \text{Formula 2:}$$

CNR and Theta were then input to PICNIC's pre-processing step, which estimates $\alpha$, the background value for CNR when zero copies are present; $\pi$, the fraction of signal coming from normal cell contamination; and $\phi$, global ploidy or the mean copy number across all interrogated SNP positions. This estimation requires an initial segmentation of CNR along the genome. In the present work, cghFLasso (L2L1VitPath with lambda1=0 and lambda2=1000, (Tibshirani and Wang, 2008)) was used, which has been found to provide a more accurate segmentation than either CBS (Venkatraman and Olshen, 2007) or PICNIC's internal algorithm. Further, PICNIC's procedure for estimating $\alpha$, $\pi$, and $\phi$ was corrected to use a sex-specific expected copy number (pi) for chromosomes X and Y. Finally PICNIC's original prior distributions for these three parameters were found to be inappropriate for this array platform. Instead, $\alpha$ was modeled as a Gaussian with a mean of 0.7 and a standard deviation of 0.05; $\pi$ was modeled as a beta distribution with alpha parameter of 0.05 and a beta parameter of 100; and $\phi$ was modeled as a gamma distribution with shape parameter of 6.7143, and a scale parameter of 0.35.

Once α, π, and φ were estimated for each sample, PICNIC's HMM was applied to segment the data and generate integer allele-specific copy number. Genome segments where the lesser of the allele-specific copy number was equal to zero are regions of LOH.

Although the HMM fit was generally quite accurate for most chromosomes in most samples, it was observed that CNR occasionally fell between the values expected for two adjacent integers. This produced jittering between two adjacent HMM states that is believed not to be a reflection of the biological reality. To address this, the integer estimate of total copy number produced by PICNIC's HMM was replaced with the unconstrained value produced by cghFLasso (CNR). To produce reported total copy number and adjust for normal contamination, estimates of α, π, and φ, and were applied to the cghFLasso results as per PICNIC:

$$\delta = (1-\alpha)/((2\pi) + \phi(1-\pi)) \qquad \text{Formula 3.}$$

$$CN_i((\overline{CNR}_i - \alpha)/\delta - p_i\pi)/1-\pi \qquad \text{Formula 4.}$$

Tumor Cell Fractions

Tumor cell fractions were calculated as described (Nik-Zainal et al., 2012). Briefly, tumor cells carrying a given mutation were determined using the following formula:

$$f = \min\left(1, \frac{r}{R}\frac{\rho\eta_T + (1-\rho)\eta_N}{\rho}\right),$$

where r is the fraction of cells in a biopsy that are tumor cells, as determined by SNP array; r is the number of reads reporting the variant allele out of R total reads across the base of interest; and $h_T$ and $h_N$ are the copy number of the genome at that base in the tumor and normal genomes respectively. All frequencies were converted to percentages. Some tumor cell frequencies were greater than 100% because this model does not account for germline mutations or copy neutral LOH. For verified germline mutations, the formula was adjusted to account for mutant reads at a different ratio in the contaminating tissue:

$$f = \min\left(1, \frac{r}{R}\rho\eta_T + (1-\rho)\eta_N\right).$$

Vismodegib Binding Model

The crystal structure of SMO with LY2940680 bound (PDB ID: 4JKV) served as a starting point for docking. The Schrodinger suite of programs available in Maestro version 9.5 (Schrodinger, Inc.) was used to carry out protein preparation with PrepWiz, ligand preparation of vismodegib with Ligprep, and docking with Glide Standard Precision, retaining default parameters for all steps except for the following modifications in the Glide docking step. Fifty poses were included for performing post-docking minimization, with strain correction terms turned on. The top ten poses were written out for analysis, all of which gave similar binding modes. The pyridine and the adjacent ortho-chlorophenyl rings stayed in approximately the same positions, with variations in the amide torsion angles causing slight variations in the positions of the methylsulfone and its attached ring. The top pose was selected for figures in this study, but the variations described above would not have changed any interpretations regarding mutational effects. FIGS. 2B, 3A-C, 5A-B and 6A were prepared using MOE 2013.0801 (Chemical Computing Group, Inc.). The surface areas shown for the binding pocket and the Ile-408 interaction are solvent-accessible.

Pyrosequencing

Mutation-specific PCR (BSP) primers were designed using PyroMark Assay Design software v2.0 (Qiagen). PCR primers were synthesized with a 5' biotin label on either the forward or reverse primer to facilitate binding of the PCR product to Streptavidin Sepharose beads. Sequencing primers were designed in the reverse direction of the 5'-biotin-labeled PCR primer using PyroMark Assay Design software v2.0 (Qiagen). Genomic DNA (20 ng) was amplified in a 25 µl reaction using Platinum PCR Supermix (Invitrogen) and 20 µl of PCR product was used for sequencing on the Pyromark Q24 (Qiagen). PCR products were incubated with Streptavidin Sepharose beads for 10 minutes followed by washes with 70% ethanol, Pyromark denaturation solution, and Pyromark wash buffer. Denatured PCR products were then sequenced using 0.3 µM sequencing primer. Pyrograms were visualized and evaluated for sequence quality, and percent mutant at SMO positions T241, L412, A549 and C469 was determined using PyroMark software version 2.0.4 (Qiagen).

Copy Number Assay

Genomic DNA was isolated from blood, pre- and post-treatment tumor samples, and 10 ng per reaction was used as template in quadruplicate Taqman assays (Applied Biosystems/Life Technologies) to determine PTCH1 and RNASE P (reference) copy number with CopyCaller software (Applied Biosystems/Life Technologies).

Real-Time RT-PCR

One to four µg of total RNA was reverse transcribed using the high capacity cDNA kit (Applied Biosystems/Life Technologies). Quantitative PCR reactions were performed using the TaqMan Universal PCR Master Mix (Applied Biosystems/Life Technologies). Gene-specific Taqman primer/probe sequences are available upon request.

Plasmids

SMO point mutants were generated in pRK5-SMO with the QuikChange II Site-Directed Mutagenesis Kit (Stratagene). SMO point mutants were cloned into pRK5-SMO-Flag and pRK7-gD-SMO-myc. pRK5-PTCH1 and pRK5-eGFP were previously described by (Yauch et al., 2009). The Hh luciferase reporter Gli-BS construct was previously described by (Murone et al., 1999) and the *Renilla* transfection control plasmid pRL-TKis from Promega. pGEIGC is a HIV-based self-inactivating lentiviral vector that was created by replacing the $Zeo^R$-$CMV_{ic}$-tGFP-IRES-$Puro^R$-shRNA-WRE content of pGIPZ (Open Biosystems) with a fragment containing the EF1α promoter, a multiple cloning site (MCS), an internal ribosome entry site (IRES) and Cre-recombinase fused to the C terminus of enhanced green fluorescent protein (eGFP-Cre; Harfe et al., 2004). All constructs were confirmed by sequencing; cloning details, vector maps and sequence files are available upon request.

Luciferase Reporter Assay

C3H10T½ cells (ATCC) were seeded into six-well plates at 1.75×10E5 cells/well in DMEM High Glucose with 4 mM glutamine, 10 mM Hepes pH 7.2 and 10% FBS. After 16 h cells were transfected with 400 ng of expression construct, 400 ng of 9x-Gli-BS and 200 ng of pRL-TK per well using GeneJuice Transfection Reagent (Novagen). For the PTCH1 inhibition experiments, cells were transfected with 200 ng SMO expression construct and an additional 200 ng of DNA containing varying ratios of PTCH1 to empty vector. Six hours later, cells from one well were trypsinized and redistributed over four wells of a 12-well plate. After 16 hours the FBS content of the culture medium was reduced to 0.5% to induce formation of primary cilia, and small molecule Hh inhibitors were added at indicated concentrations. Firefly luciferase activity was determined 24 hours later with the Dual-Glo Luciferase Assay System (Promega) and read using a Wallac EnVision plate reader (Perkin Elmer). Values were divided by *renilla* luciferase activities to normalize for transfection efficiency. Individual experiments were carried out in duplicate or triplicate and repeated at least once. Dose response data were fit to a 4-parameter equation in GraphPad Prism:

$$Y = 1 + \frac{1-B}{(1+10^{((\log IC_{50}-X)H)})},$$

where 'Y' is normalized Gli-luciferase signal or normalized thymidine incorporation calculated as a fraction of control that did not include inhibitor, and 'X' is the inhibitor concentration. The top and bottom (B) values were constrained to be equal for each sample. 'H' is the Hill Slope.

[$^3$H]-Vismodegib Binding Assay

2×10E6 HEK-293 cells were seeded into 10-cm plates and transfected 16 hours later with 3 µg of either empty vector or SMO expression construct using GeneJuice (Novagen). Cells were harvested 40 hours later in PBS with 1 mM EDTA and fixed in PBS with 4% PFA for 10 minutes at room temperature (RT), after which they were washed 3× in PBS with 1 mM EDTA and plated into 96-well plates at 100,000 cells per well. Cells were incubated for 1 hour at RT with 5 nM [$^3$H]-vismodegib (Selcia) in the absence or presence of 50 µM unlabeled vismodegib, and were subsequently transferred to a filter plate (Perkin Elmer) using a Filtermate Cell harvester (Perkin Elmer). Forty m of MicroScint fluid (Perkin Elmer) was added per well and counts per minute were assessed using a PerkinElmer TopCount NXT. All samples were analyzed in triplicate. Specific binding was calculated after competition with an excess of unlabeled vismodegib by subtracting non-specific binding from total binding.

FACS Analysis of gD-SMO Cell Surface Expression

1×10E6 HEK-293 cells were seeded into 10-cm plates and transfected 6 hours later with 3 µg of gD-SMO expression construct using GeneJuice (Novagen). Cells were dislodged 48 hours later in PBS with 1 mM EDTA and sequentially incubated for 30 min with anti-gD antibody (5B6, at 1 µg/ml), followed by two 20 min incubations with 1:100 biotin-SP conjugated Affinipure goat anti-mouse IgG and 1:50 R-Phycoerythrin-conjugated Streptavidin (both Jackson Immunoresearch Labs). Cells were resuspended in propidium iodide (500 ng/ml) and analyzed on a HTS FacsCalibur (BD Biosciences).

Virus Production and Titering

HEK-293T cells were plated on 15-cm dishes at 1.5×10E6 cells/plate in DMEM High Glucose with 10% heat inactivated FBS 24 hours prior to transfection. Lentiviral supernatants were prepared by co-transfection using 6 µg of pGEIGC-SMO, 12 µg of the packaging vector Δ8.9 (Zufferey et al., 1997), 3 µg of the envelope vector pVSV-G (Clontech) and the transfection reagent GeneJuice (Novagen). The culture medium was replaced 12 hours after transfection and viral supernatant was collected 24 hours later, filtered through a 0.45 µm PES filter (Nalgene) and stored at 4° C. until further processing. Viral supernatants were concentrated 200-fold by ultracentrifugation at 100,000×g for 1 hours 30 min (Zufferey and Trono, 2000). Viral pellets were resuspended in CGNP media and stored at −80° C. Viral titers were determined on HEK-293T cells that were plated at 2×10$^5$ cells/well in six-well plates. Cells were allowed to adhere for 12 hr, after which the medium was replaced with 2 ml of either 1:400 or 1:4000 diluted viral concentrate. The number of cells per well was counted at the time of virus addition and the average of six wells was used to calculate the viral titer. Viral supernatants remained on the cells for 60 hr, after which the cells were harvested and analyzed for fluorescent protein expression by FACS. Viral titers were calculated in transducing units (TU)/ml according to the equation [cell number/100×% fluorescent cells]× 1000 per al of viral concentrate (Zufferey and Trono, 2000). Only transductions that resulted in fewer than 15% fluorescent cells were used for titer calculations.

Mice

The Ptch1 loxp strain was a kind gift from R. Thftgard and S. Teglund (Karolinska Institutet, Stockholm, Sweden; Kasper et al., 2011). The Tp53$^{loxp}$ strain was a kind gift from A. Berns (Netherlands Cancer institute, Amsterdam. The Netherlands; Jonkers et al., 2001). The Rosa26$^{LsLtdTomato}$ strain was purchased from Jackson Labs (Stock number: 007909; Madisen et al., 2010). All mice were housed and maintained according to the animal-use guidelines of Genentech Inc., conforming to California State legal and ethical practices.

Isolation and Transduction of CGNPs

Cerebella from post-natal day 5-7 Ptch1$^{loxp/loxp}$ Rosa26$^{LSLtdTomato}$ Tp53$^{loxp/loxp}$ mice were dissociated in 0.05% Trypsin for 10 min at 37° C. Cells were collected by centrifugation at 514×g for 10 min at 4° C., resuspended in CGNP media (Neurobasal medium (Life Technologies) containing 1×B27 (without vitamin A; Life Technologies), 0.45% glucose (Sigma Aldrich), 25 mM KCl, 0.4% bovine serum albumin (Sigma Aldrich), 2 mM glutamine, 100 U/ml Penicillin (Life Technologies), 100 µg/ml Streptomycin (Life Technologies), 200 ng/ml octylated recombinant SHH) and filtered through a 0.45 µm filter (Falcon). Cells were plated in poly-D-lysine coated 6-well plates (Corning) at 5×10E5 cells/well and infected with lentivirus at a multiplicity of infection (MOI) of 1. After 24 hr, cells were harvested by trypsinization, collected in CGNP media and replated for downstream applications.

Methyl-[3H]-Thymidine Incorporation

To examine the effects of HPIs on proliferation, virally transduced CGNPs were plated in poly-D-lysine-coated 96-well plates (Corning) at 25,000 cells/well in CGNP media without SHH. Inhibitor concentrations were tested in triplicate wells and were 25, 50, 100, 250, 500, 1000 and 5000 nM for vismodegib, 500 nM for LDE225, 500 nM for LY2940680, 500 nM for compound 5, 1 µM for JQ1 and 0.1% for DMSO (highest concentration vehicle control). After 24 hr, cells were pulsed with 1 µCi/ml methyl-[$^3$H]-thymidine (Amersham/GE Healthcare) and cultured for an additional 16-24 hr. Cells were harvested onto 96-well filter plates (Perkin Elmer) using a Filtermate Cell Harvester (Perkin Elmer), and incorporated radioactivity was quantified by liquid scintillation spectrophotometry on a TopCount NXT (PerkinElmer).

Compounds

GDC-0449, compound 5 and JQ-1 were prepared as described in in WO2006028956, WO2007059157 and Filippakopoulos et al., 2010. LDE225 (HY-16582) and LY2940680 (HY-13242) were from MedchemExpress.

CITED REFERENCES

Amakye, D., Jagani, Z., and Dorsch, M. (2013). Unraveling the therapeutic potential of the Hedgehog pathway in cancer. Nature medicine 19, 1410-1422.

Atwood, S. X., Li, M., Lee, A., Tang, J. Y., and Oro, A. E. (2013). GLI activation by atypical protein kinase C iota/lambda regulates the growth of basal cell carcinomas. Nature 494, 484-488.

Brastianos, P. K., Horowitz, P. M., Santagata, S., Jones, R. T., McKenna, A., Getz, G., Ligon, K. L., Palescandolo, E., Van Hummelen, P., Ducar, M. D., et al. (2013). Genomic sequencing of meningiomas identifies oncogenic SMO and AKT1 mutations. Nature genetics 45, 285-289.

Brinkhuizen, T., Reinders, M. G., van Geel, M., Hendriksen, A. J., Paulussen, A. D., Winnepenninckx, V. J., Keymeulen, K. B., Soetekouw, P. M., van Steensel, M. A., and Mosterd, K. (2014). Acquired resistance to the Hedgehog pathway inhibitor vismodegib due to smoothened mutations in treatment of locally advanced basal cell carcinoma. Journal of the American Academy of Dermatology.

Buonamici, S., Williams, J., Morrissey, M., Wang, A., Guo, R., Vattay, A., Hsiao, K., Yuan, J., Green, J., Ospina, B., et al. (2010). Interfering with resistance to smoothened antagonists by inhibition of the PI3K pathway in medulloblastoma. Sci Transl Med 2, 51ra70.

Chang, A. L., and Oro, A. E. (2012). Initial assessment of tumor regrowth after vismodegib in advanced Basal cell carcinoma. Archives of dermatology 148, 1324-1325.

Clark, V. E., Erson-Omay, E. Z., Serin, A., Yin, J., Cotney, J., Ozduman, K., Avsar, T., Li, J., Murray, P. B., Henegariu, O., et al. (2013). Genomic analysis of non-NF2 meningiomas reveals mutations in TRAF7, KLF4, AKT1, and SMO. Science 339, 1077-1080.

Das Thakur, M., and Stuart, D. D. (2013). The evolution of melanoma resistance reveals therapeutic opportunities. Cancer research 73, 6106-6110.

Dijkgraaf, G. J., Alicke, B., Weinmann, L., Januario, T., West, K., Modrusan, Z., Burdick, D., Goldsmith, R., Robarge, K., Sutherlin, D., et al. (2011). Small molecule inhibition of GDC-0449 refractory smoothened mutants and downstream mechanisms of drug resistance. Cancer research 71, 435-444.

Gether, U., Ballesteros, J. A., Seifert, R., Sanders-Bush, E., Weinstein, H., and Kobilka, B. K. (1997). Structural instability of a constitutively active G protein-coupled receptor. Agonist-independent activation due to conformational flexibility. The Journal of biological chemistry 272, 2587-2590.

Gonzalez-Perez, A., and Lopez-Bigas, N. (2011). Improving the assessment of the outcome of nonsynonymous SNVs with a consensus deleteriousness score, Condel. American journal of human genetics 88, 440-449.

Greenman, C. D., Bignell, G., Butler, A., Edkins, S., Hinton, J., Beare, D., Swamy, S., Santarius, T., Chen, L., Widaa, S., et al. (2010). PICNIC: an algorithm to predict absolute allelic copy number variation with microarray cancer data. Biostatistics 11, 164-175.

Hahn, H., Wicking, C., Zaphiropoulous, P. G., Gailani, M. R., Shanley, S., Chidambaram, A., Vorechovsky, I., Holmberg, E., Unden, A. B., Gillies, S., et al. (1996). Mutations of the human homolog of Drosophila patched in the nevoid basal cell carcinoma syndrome. Cell 85, 841-851.

Inukai, M., Toyooka, S., Ito, S., Asano, H., Ichihara, S., Soh, J., Suehisa, H., Ouchida, M., Aoe, K., Aoe, M., et al. (2006). Presence of epidermal growth factor receptor gene T790M mutation as a minor clone in non-small cell lung cancer. Cancer research 66, 7854-7858.

Jayaraman, S. S., Rayhan, D. J., Hazany, S., and Kolodney, M. S. (2014). Mutational landscape of basal cell carcinomas by whole-exome sequencing. The Journal of investigative dermatology 134, 213-220.

Johnson, R. L., Rothman, A. L., Xie, J., Goodrich, L. V., Bare, J. W., Bonifas, J. M., Quinn, A. G., Myers, R. M., Cox, D. R., Epstein, E. H., Jr., and Scott, M. P. (1996). Human homolog of patched, a candidate gene for the basal cell nevus syndrome. Science 272, 1668-1671.

Kandoth, C., McLellan, M. D., Vandin, F., Ye, K., Niu, B., Lu, C., Xie, M., Zhang, Q., McMichael, J. F., Wyczalkowski, M. A., et al. (2013). Mutational landscape and significance across 12 major cancer types. Nature 502, 333-339.

Katritch, V., Cherezov, V., and Stevens, R. C. (2013). Structure-function of the G protein-coupled receptor superfamily. Annual review of pharmacology and toxicology 53, 531-556.

Kijima, C., Miyashita, T., Suzuki, M., Oka, H., and Fujii, K. (2012). Two cases of nevoid basal cell carcinoma syndrome associated with meningioma caused by a PTCH1 or SUFU germline mutation. Fam Cancer 11, 565-570.

Kool, M., Jones, D. T., Jager, N., Northcott, P. A., Pugh, T J., Hovestadt, V., Piro, R. M., Esparza, L. A., Markant, S. L., Remke, M., et al. (2014). Genome Sequencing of SHH Medulloblastoma Predicts Genotype-Related Response to Smoothened Inhibition. Cancer cell 25, 393-405.

Lackner, M. R., Wilson, T. R., and Settleman, J. (2012). Mechanisms of acquired resistance to targeted cancer therapies. Future Oncol 8, 999-1014.

Lee, Y., Kawagoe, R., Sasai, K., Li, Y., Russell, H. R., Curran, T., and McKinnon, P. J. (2007). Loss of suppressor-of-fused function promotes tumorigenesis. Oncogene 26, 6442-6447.

Long, J., Li, B., Rodriguez-Blanco, J., Pastori, C., Volmar, C. H., Wahlestedt, C., Capobianco, A., Bai, F., Pei, X. H., Ayad, N. G., and Robbins, D. J. (2014). The BET bromodomain inhibitor I-BET151 acts downstream of Smoothened to abrogate the growth of Hedgehog driven cancers. The Journal of biological chemistry.

LoRusso, P. M., Rudin, C. M., Reddy, J. C., Tibes, R., Weiss, G. J., Borad, M. J., Hann, C. L., Brahmer, J. R., Chang, I., Darbonne, W. C., et al. (2011). Phase I trial of hedgehog pathway inhibitor vismodegib (GDC-0449) in patients with refractory, locally advanced or metastatic solid tumors. Clinical cancer research: an official journal of the American Association for Cancer Research 17, 2502-2511.

Metcalfe, C., Alicke, B., Crow, A., Lamoureux, M., Dijkgraaf, G. J., Peale, F., Gould, S. E., and de Sauvage, F. J. (2013). PTEN loss mitigates the response of medulloblastoma to Hedgehog pathway inhibition. Cancer research 73, 7034-7042.

Miller, J. H. (1985). Mutagenic specificity of ultraviolet light. J Mol Biol 182, 45-65.

Nedelcu, D., Liu, J., Xu, Y., Jao, C., and Salic, A. (2013). Oxysterol binding to the extracellular domain of Smoothened in Hedgehog signaling. Nature chemical biology 9, 557-564.

Negrini, S., Gorgoulis, V. G., and Halazonetis, T. D. (2010). Genomic instability—an evolving hallmark of cancer. Nature reviews Molecular cell biology 11, 220-228.

Nik-Zainal, S., Van Loo, P., Wedge, D. C., Alexandrov, L. B., Greenman, C. D., Lau, K. W., Raine, K., Jones, D., Marshall, J., Ramakrishna, M., et al. (2012). The life history of 21 breast cancers. Cell 149, 994-1007.

Oro, A. E., Higgins, K. M., Hu, Z., Bonifas, J. M., Epstein, E. H., Jr., and Scott, M. P. (1997). Basal cell carcinomas in mice overexpressing sonic hedgehog. Science 276, 817-821.

Pastorino, L., Ghiorzo, P., Nasti, S., Battistuzzi, L., Cusano, R., Marzocchi, C., Garre, M. L., Clementi, M., and Scarra, G. B. (2009). Identification of a SUFU germline mutation in a family with Gorlin syndrome. Am J Med Genet A 149A, 1539-1543.

Pesz, K. A., Bieniek, A., Makowska, I., and Sasiadek, M. M. (2013). Basal cell carcinoma of the skin: whole genome screening by comparative genome hybridization revisited. Journal of cutaneous pathology 40, 25-29.

Pricl, S., Cortelazzi, B., Dal Col, V., Marson, D., Laurini, E., Fermeglia, M., Licitra, L., Pilotti, S., Bossi, P., and Perrone, F. (2014). Smoothened (SMO) receptor mutations dictate resistance to vismodegib in basal cell carcinoma. Molecular oncology.

Reifenberger, J., Wolter, M., Knobbe, C. B., Kohler, B., Schonicke, A., Scharwachter, C., Kumar, K., Blaschke, B., Ruzicka, T., and Reifenberger, G. (2005). Somatic mutations in the PTCH, SMOH, SUFUH and TP53 genes in sporadic basal cell carcinomas. Br J Dermatol 152, 43-51.

Reifenberger, J., Wolter, M., Weber, R. G., Megahed, M., Ruzicka, T., Lichter, P., and Reifenberger, G. (1998). Missense mutations in SMOH in sporadic basal cell carcinomas of the skin and primitive neuroectodermal tumors of the central nervous system. Cancer research 58, 1798-1803.

Sasai, K., Romer, J. T., Lee, Y., Finkelstein, D., Fuller, C., McKinnon, P. J., and Curran, T. (2006). Shh pathway activity is down-regulated in cultured medulloblastoma cells: implications for preclinical studies. Cancer research 66, 4215-4222.

Sekulic, A., Migden, M. R., Oro, A. E., Dirix, L., Lewis, K. D., Hainsworth, J. D., Solomon, J. A., Yoo, S., Arron, S. T., Friedlander, P. A., et al. (2012). Efficacy and safety of vismodegib in advanced basal-cell carcinoma. The New England journal of medicine 366, 2171-2179.

Smith, M. J., Beetz, C., Williams, S. G., Bhaskar, S. S., O'Sullivan, J., Anderson, B., Daly, S. B., Urquhart, J. E., Bholah, Z., Oudit, D., et al. (2014). Germline Mutations in SUFU Cause Gorlin Syndrome-Associated Childhood Medulloblastoma and Redefine the Risk Associated With PTCH1 Mutations. Journal of clinical oncology: official journal of the American Society of Clinical Oncology.

Stjernqvist, S., Ryden, T., and Greenman, C. D. (2011). Model-integrated estimation of normal tissue contamination for cancer SNP allelic copy number data. Cancer informatics 10, 159-173.

Stone, D. M., Murone, M., Luoh, S., Ye, W., Armanini, M. P., Gurney, A., Phillips, H., Brush, J., Goddard, A., de Sauvage, F. J., and Rosenthal, A. (1999). Characterization of the human suppressor of fused, a negative regulator of the zinc-finger transcription factor Gli. Journal of cell science 112 (Pt 23), 4437-4448.

Svard, J., Heby-Henricson, K., Persson-Lek, M., Rozell, B., Lauth, M., Bergstrom, A., Ericson, J., Toftgard, R., and Teglund, S. (2006). Genetic elimination of Suppressor of fused reveals an essential repressor function in the mammalian Hedgehog signaling pathway. Developmental cell 10, 187-197.

Sweeney, R. T., McClary, A. C., Myers, B. R., Biscocho, J., Neahring, L., Kwei, K. A., Qu, K., Gong, X., Ng, T., Jones, C. D., et al. (2014). Identification of recurrent SMO and BRAF mutations in ameloblastomas. Nature genetics 46, 722-725.

Tang, Y., Gholamin, S., Schubert, S., Willardson, M. I., Lee, A., Bandopadhayay, P., Bergthold, G., Masoud, S., Nguyen, B., Vue, N., et al. (2014). Epigenetic targeting of Hedgehog pathway transcriptional output through BET bromodomain inhibition. Nature medicine 20, 732-740.

Taylor, M. D., Liu, L., Raffel, C., Hui, C. C., Mainprize, T. G., Zhang, X., Agatep, R., Chiappa, S., Gao, L., Lowrance, A., et al. (2002). Mutations in SUFU predispose to medulloblastoma. Nature genetics 31, 306-310.

Wang, C., Wu, H., Katritch, V., Han, G. W., Huang, X. P., Liu, W., Siu, F. Y., Roth, B. L., Cherezov, V., and Stevens, R. C. (2013). Structure of the human smoothened receptor bound to an antitumour agent. Nature 497, 338-343.

Wang, G. Y., So, P. L., Wang, L., Libove, E., Wang, J., and Epstein, E. H., Jr. (2011). Establishment of murine basal cell carcinoma allografts: a potential model for preclinical drug testing and for molecular analysis. The Journal of investigative dermatology 131, 2298-2305.

Wechsler-Reya, R. J., and Scott, M. P. (1999). Control of neuronal precursor proliferation in the cerebellum by Sonic Hedgehog. Neuron 22, 103-114.

Wong, H., Alicke, B., West, K. A., Pacheco, P., La, H., Januario, T., Yauch, R. L., de Sauvage, F. J., and Gould, S. E. (2011). Pharmacokinetic-pharmacodynamic analysis of vismodegib in preclinical models of mutational and ligand-dependent Hedgehog pathway activation. Clinical cancer research: an official journal of the American Association for Cancer Research 17, 4682-4692.

Xie, J., Murone, M., Luoh, S. M., Ryan, A., Gu, Q., Zhang, C., Bonifas, J. M., Lam, C. W., Hynes, M., Goddard, A., et al. (1998). Activating Smoothened mutations in sporadic basal-cell carcinoma. Nature 391, 90-92.

Yauch, R. L., Dijkgraaf, G. J., Alicke, B., Januario, T., Ahn, C. P., Holcomb, T., Pujara, K., Stinson, J., Callahan, C. A., Tang, T., et al. (2009). Smoothened mutation confers resistance to a Hedgehog pathway inhibitor in medulloblastoma. Science 326, 572-574.

Anders, S., and Huber, W. (2010). Differential expression analysis for sequence count data. Genome biology 11, R106.

DePristo, M. A., Banks, E., Poplin, R., Garimella, K. V., Maguire, J. R., Hartl, C., Philippakis, A. A., del Angel, G., Rivas, M. A., Hanna, M., et al. (2011). A framework for variation discovery and genotyping using next-generation DNA sequencing data. Nature genetics 43, 491-498.

Diskin, S. J., Li, M., Hou, C., Yang, S., Glessner, J., Hakonarson, H., Bucan, M., Maris, J. M., and Wang, K. (2008). Adjustment of genomic waves in signal intensities from whole-genome SNP genotyping platforms. Nucleic acids research 36, e126.

Filippakopoulos, P., Qi, J., Picaud, S., Shen, Y., Smith, W. B., Fedorov, O., Morse, E. M., Keates, T., Hickman, T. T., Felletar, et. al. (2010). Selective Inhibition. of BET bromodomains. Nature 468, 1067-1073.

Forbes, S. A., Bindal, N., Bamford, S., Cole, C., Kok, C. Y., Beare, D., Jia, M., Shepherd, R., Leung, K., Menzies, A., et al. (2011). COSMIC: mining complete cancer genomes in the Catalogue of Somatic Mutations in Cancer. Nucleic acids research 39, D945-950.

Forbes, S. A., Tang, G., Bindal, N., Bamford, S., Dawson, E., Cole, C., Kok, Y., Jia, M., Ewing, R., Menzies, A., et al. (2010). COSMIC (the Catalogue of Somatic Mutations in Cancer): a resource to investigate acquired mutations in human cancer. Nucleic acids research 38, D652-657.

Gonzalez-Perez, A., and Lopez-Bigas, N. (2011). Improving the assessment of the outcome of nonsynonymous SNVs with a consensus deleteriousness score, Condel. American journal of human genetics 88, 440-449.

Harfe, B. D., Scherz, P. J., Nissim, S., Tian, H., McMahon, A. P., and Tabin, C. J. (2004). Evidence for an expansionbased temporal Shh gradient in specifying vertebrate digit identities. Cell 118, 517-528.

Jonkers, J., Meuwissen, R., van der Gulden, H., Peterse, H., van der Valk, M., and Berns, A. (2001). Synergistic tumor suppressor activity of BRCA2 and p53 in a conditional mouse model for breast cancer. Nature genetics 29, 418-425

Kasper, M., Jaks, V., Are, A., Bergstrom, A., Schwager, A., Svard, J., Teglund S., Barker, N. and Toftgard, R. (2011). Wounding enhances epidermal tumorigenesis by recruiting hair follicle keratinocytes. Proceedings of the National Academy of Sciences of the United States of America 108, 4099-4104.

Madisen, L., Zwingman, T. A., Sunkin, S. M., Oh, S. W., Zariwala, H. A., Gu, H., Ng, L. L., Palmiter, R. D., Hawrylycz, M. J., Jones, A. R., et al. (2010). Nature neuroscience 13, 133-140.

Morgan, M., et al. (2009). Bioinformatics 25, 2607-2608.

Murone, M. et al., (1999). Current biology: CB 9, 76-84.

Rudin, C et al., (2012). Nature genetics 44, 1111-1116.

Sherry, S et al., (2001). Nucleic acids research 29, 308-311.

Tibshirani, R., and Wang, P. (2008). Biostatistics 9, 18-29.

Venkatraman, E. et al., (2007). Bioinformatics 23, 657-663.

Wu, T. et al., (2010). Bioinformatics 26, 873-881.

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations. The foregoing Examples are for illustrative purposes only and should not be construed to limit the scope of the disclosure which is defined by the appended claims.

```
SEQUENCE LISTING
Human wildtype smoothened amino acid sequence (GenBank
Accesion No. NP_005622.1)
                                                              SEQ ID NO: 1
Met Ala Ala Ala Arg Pro Ala Arg Gly Pro Glu Leu Pro Leu Leu Gly Leu Leu Leu Leu Leu Leu Leu Gly Asp Pro Gly Arg Gly Ala Ala Ser Ser Gly Asn Ala Thr Gly Pro Gly Pro Arg Ser Ala Gly Gly Ser Ala Arg Arg Ser Ala Ala Val Thr Gly Pro Pro Pro Pro Leu Ser His Cys Gly Arg Ala Ala Pro Cys Glu Pro Leu Arg Tyr Asn Val Cys Leu Gly Ser Val Leu Pro Tyr Gly Ala Thr Ser Thr Leu Leu Ala Gly Asp Ser Asp Ser Gln Glu Glu Ala His Gly Lys Leu Val Leu Trp Ser Gly Leu Arg Asn Ala Pro Arg Cys Trp Ala Val Ile Gln Pro Leu Leu Cys Ala Val Tyr Met Pro Lys Cys Glu Asn Asp Arg Val Glu Leu Pro Ser Arg Thr Leu Cys Gln Ala Thr Arg Gly Pro Cys Ala Ile Val Glu Arg Glu Arg Gly Trp Pro Asp Phe Leu Arg Cys Thr Pro Asp Arg Phe Pro Glu Gly Cys Thr Asn Glu Val Gln Asn Ile Lys Phe Asn Ser Ser Gly Gln Cys Glu Val Pro Leu Val Arg Thr Asp Asn Pro Lys Ser Trp Tyr Glu Asp Val Glu Gly Cys Gly Ile Gln Cys Gln Asn Pro Leu Phe Thr Glu Ala Glu His Gln Asp Met His Ser Tyr Ile Ala Ala Phe Gly Ala Val Thr Gly Leu Cys Thr Leu Phe Thr Leu Ala Thr Phe Val Ala Asp Trp Arg Asn Ser Asn Arg Tyr Pro Ala Val Ile Leu Phe Tyr Val Asn Ala Cys Phe Phe Val Gly Ser Ile Gly Trp Leu Ala Gln Phe Met Asp Gly Ala Arg Arg Glu Ile Val Cys Arg Ala Asp Gly Thr Met Arg Leu Gly Glu Pro Thr Ser Asn Glu Thr Leu Ser Cys Val Ile Ile Phe Val Ile Val Tyr Tyr Ala Leu Met Ala Gly Val Val Trp Phe Val Val Leu Thr Tyr Ala Trp His Thr Ser Phe Lys Ala Leu Gly Thr Thr Tyr Gln Pro Leu Ser Gly Lys Thr Ser Tyr Phe His Leu Leu Thr Trp Ser Leu Pro Phe Val Leu Thr Val Ala Ile Leu Ala Val Ala Gln Val Asp Gly Asp Ser Val Ser Gly Ile Cys Phe Val Gly Tyr Lys Asn Tyr Arg Tyr Arg Ala Gly Phe Val Leu Ala Pro Ile Gly Leu Val Leu Ile Val Gly Gly Tyr Phe Leu Ile Arg Gly Val Met Thr Leu Phe Ser Ile Lys Ser Asn His Pro Gly Leu Leu Ser Glu Lys Ala Ala Ser Lys Ile Asn Glu Thr Met Leu Arg Leu Gly Ile Phe Gly Phe Leu Ala Phe Gly Phe Val Leu Ile Thr Phe Ser Cys His Phe Tyr Asp Phe Phe Asn Gln Ala Glu Trp Glu Arg Ser Phe Arg Asp Tyr Val Leu Cys Gln Ala Asn Val Thr Ile Gly
```

-continued

```
Leu Pro Thr Lys Gln Pro Ile Pro Asp Cys Glu Ile Lys Asn Arg Pro Ser Leu Leu Val

Glu Lys Ile Asn Leu Phe Ala Met Phe Gly Thr Gly Ile Ala Met Ser Thr Trp Val Trp

Thr Lys Ala Thr Leu Leu Ile Trp Arg Arg Thr Trp Cys Arg Leu Thr Gly Gln Ser Asp

Asp Glu Pro Lys Arg Ile Lys Lys Ser Lys Met Ile Ala Lys Ala Phe Ser Lys Arg His

Glu Leu Leu Gln Asn Pro Gly Gln Glu Leu Ser Phe Ser Met His Thr Val Ser His Asp

Gly Pro Val Ala Gly Leu Ala Phe Asp Leu Asn Glu Pro Ser Ala Asp Val Ser Ser Ala

Trp Ala Gln His Val Thr Lys Met Val Ala Arg Arg Gly Ala Ile Leu Pro Gln Asp Ile

Ser Val Thr Pro Val Ala Thr Pro Val Pro Pro Glu Glu Gln Ala Asn Leu Trp Leu Val

Glu Ala Glu Ile Ser Pro Glu Leu Gln Lys Arg Leu Gly Arg Lys Lys Lys Arg Arg Lys

Arg Lys Lys Glu Val Cys Pro Leu Ala Pro Pro Pro Glu Leu His Pro Pro Ala Pro Ala

Pro Ser Thr Ile Pro Arg Leu Pro Gln Leu Pro Arg Gln Lys Cys Leu Val Ala Ala Gly

Ala Trp Gly Ala Gly Asp Ser Cys Arg Gln Gly Ala Trp Thr Leu Val Ser Asn Pro Phe

Cys Pro Glu Pro Ser Pro Pro Gln Asp Pro Phe Leu Pro Ser Ala Pro Ala Pro Val Ala

Trp Ala His Gly Arg Arg Gln Gly Leu Gly Pro Ile His Ser Arg Thr Asn Leu Met Asp

Thr Glu Leu Met Asp Ala Asp Ser Asp Phe
```

Human smoothened amino acid sequence having mutation at amino acid position 281 of SMO

SEQ ID NO: 2

```
Met Ala Ala Ala Arg Pro Ala Arg Gly Pro Glu Leu Pro Leu Leu Gly Leu Leu Leu

Leu Leu Leu Leu Gly Asp Pro Gly Arg Gly Ala Ala Ser Ser Gly Asn Ala Thr Gly Pro

Gly Pro Arg Ser Ala Gly Gly Ser Ala Arg Arg Ser Ala Ala Val Thr Gly Pro Pro Pro

Pro Leu Ser His Cys Gly Arg Ala Ala Pro Cys Glu Pro Leu Arg Tyr Asn Val Cys Leu

Gly Ser Val Leu Pro Tyr Gly Ala Thr Ser Thr Leu Leu Ala Gly Asp Ser Asp Ser Gln

Glu Glu Ala His Gly Lys Leu Val Leu Trp Ser Gly Leu Arg Asn Ala Pro Arg Cys Trp

Ala Val Ile Gln Pro Leu Leu Cys Ala Val Tyr Met Pro Lys Cys Glu Asn Asp Arg Val

Glu Leu Pro Ser Arg Thr Leu Cys Gln Ala Thr Arg Gly Pro Cys Ala Ile Val Glu Arg

Glu Arg Gly Trp Pro Asp Phe Leu Arg Cys Thr Pro Asp Arg Phe Pro Glu Gly Cys

Thr Asn Glu Val Gln Asn Ile Lys Phe Asn Ser Ser Gly Gln Cys Glu Val Pro Leu Val

Arg Thr Asp Asn Pro Lys Ser Trp Tyr Glu Asp Val Glu Gly Cys Gly Ile Gln Cys Gln

Asn Pro Leu Phe Thr Glu Ala Glu His Gln Asp Met His Ser Tyr Ile Ala Ala Phe Gly

Ala Val Thr Gly Leu Cys Thr Leu Phe Thr Leu Ala Thr Phe Val Ala Asp Trp Arg

Asn Ser Asn Arg Tyr Pro Ala Val Ile Leu Phe Tyr Val Asn Ala Cys Phe Phe Val Gly

Ser Ile Gly Xaa Leu Ala Gln Phe Met Asp Gly Ala Arg Arg Glu Ile Val Cys Arg Ala

Asp Gly Thr Met Arg Leu Gly Glu Pro Thr Ser Asn Glu Thr Leu Ser Cys Val Ile Ile

Phe Val Ile Val Tyr Tyr Ala Leu Met Ala Gly Val Val Trp Phe Val Val Leu Thr Tyr

Ala Trp His Thr Ser Phe Lys Ala Leu Gly Thr Thr Tyr Gln Pro Leu Ser Gly Lys Thr

Ser Tyr Phe His Leu Leu Thr Trp Ser Leu Pro Phe Val Leu Thr Val Ala Ile Leu Ala

Val Ala Gln Val Asp Gly Asp Ser Val Ser Gly Ile Cys Phe Val Gly Tyr Lys Asn Tyr

Arg Tyr Arg Ala Gly Phe Val Leu Ala Pro Ile Gly Leu Val Leu Ile Val Gly Gly Tyr

Phe Leu Ile Arg Gly Val Met Thr Leu Phe Ser Ile Lys Ser Asn His Pro Gly Leu Leu

Ser Glu Lys Ala Ala Ser Lys Ile Asn Glu Thr Met Leu Arg Leu Gly Ile Phe Gly Phe

Leu Ala Phe Gly Phe Val Leu Ile Thr Phe Ser Cys His Phe Tyr Asp Phe Phe Asn Gln
```

-continued

Ala Glu Trp Glu Arg Ser Phe Arg Asp Tyr Val Leu Cys Gln Ala Asn Val Thr Ile Gly
Leu Pro Thr Lys Gln Pro Ile Pro Asp Cys Glu Ile Lys Asn Arg Pro Ser Leu Leu Val
Glu Lys Ile Asn Leu Phe Ala Met Phe Gly Thr Gly Ile Ala Met Ser Thr Trp Val Trp
Thr Lys Ala Thr Leu Leu Ile Trp Arg Arg Thr Trp Cys Arg Leu Thr Gly Gln Ser Asp
Asp Glu Pro Lys Arg Ile Lys Lys Ser Lys Met Ile Ala Lys Ala Phe Ser Lys Arg His
Glu Leu Leu Gln Asn Pro Gly Gln Glu Leu Ser Phe Ser Met His Thr Val Ser His Asp
Gly Pro Val Ala Gly Leu Ala Phe Asp Leu Asn Glu Pro Ser Ala Asp Val Ser Ser Ala
Trp Ala Gln His Val Thr Lys Met Val Ala Arg Arg Gly Ala Ile Leu Pro Gln Asp Ile
Ser Val Thr Pro Val Ala Thr Pro Val Pro Glu Glu Gln Ala Asn Leu Trp Leu Val
Glu Ala Glu Ile Ser Pro Glu Leu Gln Lys Arg Leu Gly Arg Lys Lys Lys Arg Arg Lys
Arg Lys Lys Glu Val Cys Pro Leu Ala Pro Pro Pro Glu Leu His Pro Pro Ala Pro Ala
Pro Ser Thr Ile Pro Arg Leu Pro Gln Leu Pro Arg Gln Lys Cys Leu Val Ala Ala Gly
Ala Trp Gly Ala Gly Asp Ser Cys Arg Gln Gly Ala Trp Thr Leu Val Ser Asn Pro Phe
Cys Pro Glu Pro Ser Pro Pro Gln Asp Pro Phe Leu Pro Ser Ala Pro Ala Pro Val Ala
Trp Ala His Gly Arg Arg Gln Gly Leu Gly Pro Ile His Ser Arg Thr Asn Leu Met Asp
Thr Glu Leu Met Asp Ala Asp Ser Asp Phe

Human smoothened amino acid sequence having mutation at amino
acid position 459 of SMO
SEQ ID NO: 3
Met Ala Ala Ala Arg Pro Ala Arg Gly Pro Glu Leu Pro Leu Leu Gly Leu Leu Leu
Leu Leu Leu Leu Gly Asp Pro Gly Arg Gly Ala Ala Ser Ser Gly Asn Ala Thr Gly Pro
Gly Pro Arg Ser Ala Gly Gly Ser Ala Arg Arg Ser Ala Ala Val Thr Gly Pro Pro Pro
Pro Leu Ser His Cys Gly Arg Ala Ala Pro Cys Glu Pro Leu Arg Tyr Asn Val Cys Leu
Gly Ser Val Leu Pro Tyr Gly Ala Thr Ser Thr Leu Leu Ala Gly Asp Ser Asp Ser Gln
Glu Glu Ala His Gly Lys Leu Val Leu Trp Ser Gly Leu Arg Asn Ala Pro Arg Cys Trp
Ala Val Ile Gln Pro Leu Leu Cys Ala Val Tyr Met Pro Lys Cys Glu Asn Asp Arg Val
Glu Leu Pro Ser Arg Thr Leu Cys Gln Ala Thr Arg Gly Pro Cys Ala Ile Val Glu Arg
Glu Arg Gly Trp Pro Asp Phe Leu Arg Cys Thr Pro Asp Arg Phe Pro Glu Gly Cys
Thr Asn Glu Val Gln Asn Ile Lys Phe Asn Ser Ser Gly Gln Cys Glu Val Pro Leu Val
Arg Thr Asp Asn Pro Lys Ser Trp Tyr Glu Asp Val Glu Gly Cys Gly Ile Gln Cys Gln
Asn Pro Leu Phe Thr Glu Ala Glu His Gln Asp Met His Ser Tyr Ile Ala Ala Phe Gly
Ala Val Thr Gly Leu Cys Thr Leu Phe Thr Leu Ala Thr Phe Val Ala Asp Trp Arg
Asn Ser Asn Arg Tyr Pro Ala Val Ile Leu Phe Tyr Val Asn Ala Cys Phe Phe Val Gly
Ser Ile Gly Trp Leu Ala Gln Phe Met Asp Gly Ala Arg Arg Glu Ile Val Cys Arg Ala
Asp Gly Thr Met Arg Leu Gly Glu Pro Thr Ser Asn Glu Thr Leu Ser Cys Val Ile Ile
Phe Val Ile Val Tyr Tyr Ala Leu Met Ala Gly Val Val Trp Phe Val Val Leu Thr Tyr
Ala Trp His Thr Ser Phe Lys Ala Leu Gly Thr Thr Tyr Gln Pro Leu Ser Gly Lys Thr
Ser Tyr Phe His Leu Leu Thr Trp Ser Leu Pro Phe Val Leu Thr Val Ala Ile Leu Ala
Val Ala Gln Val Asp Gly Asp Ser Val Ser Gly Ile Cys Phe Val Gly Tyr Lys Asn Tyr
Arg Tyr Arg Ala Gly Phe Val Leu Ala Pro Ile Gly Leu Val Leu Ile Val Gly Gly Tyr
Phe Leu Ile Arg Gly Val Met Thr Leu Phe Ser Ile Lys Ser Asn His Pro Gly Leu Leu
Ser Glu Lys Ala Ala Ser Lys Ile Asn Glu Thr Met Leu Arg Leu Gly Ile Phe Gly Phe -continued Leu Xaa Phe Gly Phe Val Leu Ile Thr Phe Ser Cys His Phe Tyr Asp Phe Phe Asn Gln Ala Glu Trp Glu Arg Ser Phe Arg Asp Tyr Val Leu Cys Gln Ala Asn Val Thr Ile Gly Leu Pro Thr Lys Gln Pro Ile Pro Asp Cys Glu Ile Lys Asn Arg Pro Ser Leu Leu Val Glu Lys Ile Asn Leu Phe Ala Met Phe Gly Thr Gly Ile Ala Met Ser Thr Trp Val Trp Thr Lys Ala Thr Leu Leu Ile Trp Arg Arg Thr Trp Cys Arg Leu Thr Gly Gln Ser Asp Asp Glu Pro Lys Arg Ile Lys Lys Ser Lys Met Ile Ala Lys Ala Phe Ser Lys Arg His Glu Leu Leu Gln Asn Pro Gly Gln Glu Leu Ser Phe Ser Met His Thr Val Ser His Asp Gly Pro Val Ala Gly Leu Ala Phe Asp Leu Asn Glu Pro Ser Ala Asp Val Ser Ser Ala Trp Ala Gln His Val Thr Lys Met Val Ala Arg Arg Gly Ala Ile Leu Pro Gln Asp Ile Ser Val Thr Pro Val Ala Thr Pro Val Pro Pro Glu Glu Gln Ala Asn Leu Trp Leu Val Glu Ala Glu Ile Ser Pro Glu Leu Gln Lys Arg Leu Gly Arg Lys Lys Lys Arg Arg Lys Arg Lys Lys Glu Val Cys Pro Leu Ala Pro Pro Glu Leu His Pro Pro Ala Pro Ala Pro Ser Thr Ile Pro Arg Leu Pro Gln Leu Pro Arg Gln Lys Cys Leu Val Ala Ala Gly Ala Trp Gly Ala Gly Asp Ser Cys Arg Gln Gly Ala Trp Thr Leu Val Ser Asn Pro Phe Cys Pro Glu Pro Ser Pro Pro Gln Asp Pro Phe Leu Pro Ser Ala Pro Ala Pro Val Ala Trp Ala His Gly Arg Arg Gln Gly Leu Gly Pro Ile His Ser Arg Thr Asn Leu Met Asp Thr Glu Leu Met Asp Ala Asp Ser Asp Phe Human smoothened amino acid sequence having mutation at amino
acid position 535 of SMO

SEQ ID NO: 4

Met Ala Ala Ala Arg Pro Ala Arg Gly Pro Glu Leu Pro Leu Leu Gly Leu Leu Leu

Leu Leu Leu Leu Gly Asp Pro Gly Arg Gly Ala Ala Ser Ser Gly Asn Ala Thr Gly Pro

Gly Pro Arg Ser Ala Gly Gly Ser Ala Arg Arg Ser Ala Ala Val Thr Gly Pro Pro Pro

Pro Leu Ser His Cys Gly Arg Ala Ala Pro Cys Glu Pro Leu Arg Tyr Asn Val Cys Leu

Gly Ser Val Leu Pro Tyr Gly Ala Thr Ser Thr Leu Leu Ala Gly Asp Ser Asp Ser Gln

Glu Glu Ala His Gly Lys Leu Val Leu Trp Ser Gly Leu Arg Asn Ala Pro Arg Cys Trp

Ala Val Ile Gln Pro Leu Leu Cys Ala Val Tyr Met Pro Lys Cys Glu Asn Asp Arg Val

Glu Leu Pro Ser Arg Thr Leu Cys Gln Ala Thr Arg Gly Pro Cys Ala Ile Val Glu Arg

Glu Arg Gly Trp Pro Asp Phe Leu Arg Cys Thr Pro Asp Arg Phe Pro Glu Gly Cys

Thr Asn Glu Val Gln Asn Ile Lys Phe Asn Ser Ser Gly Gln Cys Glu Val Pro Leu Val

Arg Thr Asp Asn Pro Lys Ser Trp Tyr Glu Asp Val Glu Gly Cys Gly Ile Gln Cys Gln

Asn Pro Leu Phe Thr Glu Ala Glu His Gln Asp Met His Ser Tyr Ile Ala Ala Phe Gly

Ala Val Thr Gly Leu Cys Thr Leu Phe Thr Leu Ala Thr Phe Val Ala Asp Trp Arg

Asn Ser Asn Arg Tyr Pro Ala Val Ile Leu Phe Tyr Val Asn Ala Cys Phe Phe Val Gly

Ser Ile Gly Trp Leu Ala Gln Phe Met Asp Gly Ala Arg Arg Glu Ile Val Cys Arg Ala

Asp Gly Thr Met Arg Leu Gly Glu Pro Thr Ser Asn Glu Thr Leu Ser Cys Val Ile Ile

Phe Val Ile Val Tyr Tyr Ala Leu Met Ala Gly Val Val Trp Phe Val Val Leu Thr Tyr

Ala Trp His Thr Ser Phe Lys Ala Leu Gly Thr Thr Tyr Gln Pro Leu Ser Gly Lys Thr

Ser Tyr Phe His Leu Leu Thr Trp Ser Leu Pro Phe Val Leu Thr Val Ala Ile Leu Ala

Val Ala Gln Val Asp Gly Asp Ser Val Ser Gly Ile Cys Phe Val Gly Tyr Lys Asn Tyr

Arg Tyr Arg Ala Gly Phe Val Leu Ala Pro Ile Gly Leu Val Leu Ile Val Gly Gly Tyr

Phe Leu Ile Arg Gly Val Met Thr Leu Phe Ser Ile Lys Ser Asn His Pro Gly Leu Leu

-continued

Ser Glu Lys Ala Ala Ser Lys Ile Asn Glu Thr Met Leu Arg Leu Gly Ile Phe Gly Phe
Leu Ala Phe Gly Phe Val Leu Ile Thr Phe Ser Cys His Phe Tyr Asp Phe Asn Gln
Ala Glu Trp Glu Arg Ser Phe Arg Asp Tyr Val Leu Cys Gln Ala Asn Val Thr Ile Gly
Leu Pro Thr Lys Gln Pro Ile Pro Asp Cys Glu Ile Lys Asn Arg Pro Ser Leu Leu Val
Glu Lys Ile Asn Leu Phe Ala Met Phe Gly Thr Gly Ile Ala Met Ser Thr Xaa Val Trp
Thr Lys Ala Thr Leu Leu Ile Trp Arg Arg Thr Trp Cys Arg Leu Thr Gly Gln Ser Asp
Asp Glu Pro Lys Arg Ile Lys Lys Ser Lys Met Ile Ala Lys Ala Phe Ser Lys Arg His
Glu Leu Leu Gln Asn Pro Gly Gln Glu Leu Ser Phe Ser Met His Thr Val Ser His Asp
Gly Pro Val Ala Gly Leu Ala Phe Asp Leu Asn Glu Pro Ser Ala Asp Val Ser Ser Ala
Trp Ala Gln His Val Thr Lys Met Val Ala Arg Arg Gly Ala Ile Leu Pro Gln Asp Ile
Ser Val Thr Pro Val Ala Thr Pro Val Pro Pro Glu Glu Gln Ala Asn Leu Trp Leu Val
Glu Ala Glu Ile Ser Pro Glu Leu Gln Lys Arg Leu Gly Arg Lys Lys Lys Arg Arg Lys
Arg Lys Lys Glu Val Cys Pro Leu Ala Pro Pro Pro Glu Leu His Pro Pro Ala Pro Ala
Pro Ser Thr Ile Pro Arg Leu Pro Gln Leu Pro Arg Gln Lys Cys Leu Val Ala Ala Gly
Ala Trp Gly Ala Gly Asp Ser Cys Arg Gln Gly Ala Trp Thr Leu Val Ser Asn Pro Phe
Cys Pro Glu Pro Ser Pro Pro Gln Asp Pro Phe Leu Pro Ser Ala Pro Ala Pro Val Ala
Trp Ala His Gly Arg Arg Gln Gly Leu Gly Pro Ile His Ser Arg Thr Asn Leu Met Asp
Thr Glu Leu Met Asp Ala Asp Ser Asp Phe (WT SMO)

SEQ ID NO: 5 atggccgctg cccgcccagc gcggggggccg gagctcccgc tcctggggct gctgctgctg ctgctgctgg ggacccgggg ccgggggggcg gcctcgagcg ggaacgcgac cgggcctggg cctcggagcg cgggcgggag cgcgaggagg agcgcggcgg tgactggccc tccgccgccg ctgagccact gcggccgggc tgcccctgc gagccgctgc gctacaacgt gtgcctggc tcggtgctgc cctacgggc cacctccaca ctgctggccg gagactcgga ctcccaggag gaagcgcacg gcaagctcgt gctctggtcg ggcctccgga atgccccccg ctgctgggca gtgatccagc ccctgctgtg tgccgtatac atgcccaagt gtgagaatga ccgggtggag ctgcccagcc gtaccctctg ccaggccacc cgaggcccct gtgccatcgt ggagagggag cggggctggc ctgacttcct gcgctgcact cctgaccgct tccctgaagg ctgcacgaat gaggtgcaga acatcaagtt caacagttca ggccagtgcg aagtgccctt ggttcggaca gacaacccca agagctggta cgaggacgtg gagggctgcg gcatccagtg ccagaacccg ctcttcacag aggctgagca ccaggacatg cacagctaca tcgcggcctt cggggccgtc acgggcctct gcacgctctt caccctggcc acattcgtgg ctgactggcg gaactcgaat cgctaccctg ctgttattct cttctacgtc aatgcgtgct ctttgtggg cagcattggc tggctggccc agttcatgga tggtgcccgc cgagagatcg tctgccgtgc agatggcacc atgaggcttg gggagcccac ctccaatgag actctgtcct gcgtcatcat ctttgtcatc gtgtactacg ccctgatggc tggtgtggtt tggtttgtgg tcctcaccta tgcctggcac acttccttca agccctggg caccacctac cagcctctct cgggcaagac ctcctacttc cacctgctca cctggtcact ccccctttgtc ctcactgtgg caatccttgc tgtggcgcag gtgatgggg actctgtgag tggcatttgt tttgtgggct acaagaacta ccgataccgt gcgggcttcg tgctggcccc aatcggcctg tgctcatcg tgggaggcta cttcctcatc cgaggagtca tgactctgtt ctccatcaag agcaaccacc ccggggctgct gagtgagaag gctgccagca gatcaacga gaccatgctg cgcctgggca ttttttggctt cctggccttt ggctttgtgc tcattaccctt cagctgccac ttctacgact tcttcaacca ggctgagtgg gagcgcagct tccgggacta tgtgctatgt caggccaatg tgaccatcgg gctgcccacc aagcagccca tccctgactg tgagatcaag aatcgcccga gccttctggt ggagaagatc -continued

```
aacctgtttg ccatgtttgg aactggcatc gccatgagca cctgggtctg gaccaaggcc acgctgctca
tctggaggcg tacctggtgc aggttgactg ggcagagtga cgatgagcca agcggatca agaagagcaa
gatgattgcc aaggccttct ctaagcggca cgagctcctg cagaacccag gccaggagct gtccttcagc
atgcacactg tgtcccacga cgggcccgtg gcgggcttgg cctttgacct caatgagccc tcagctgatg
tctcctctgc ctgggcccag catgtcacca agatggtggc tcggagagga gccatactgc cccaggatat
ttctgtcacc cctgtggcaa ctccagtgcc cccagaggaa caagccaacc tgtggctggt tgaggcagag
atctccccag agctgcagaa gcgcctgggc cggaagaaga gaggaggaa gaggaagaag gaggtgtgcc
cgctggcgcc gccccctgag cttcaccccc ctgcccctgc cccagtacc attcctcgac tgcctcagct
gccccggcag aaatgcctgg tggctgcagg tgcctgggga gctgggact cttgccgaca gggagcgtgg
accctggtct ccaacccatt ctgcccagag cccagtcccc ctcaggatcc atttctgccc agtgcaccgg
ccccgtggc atgggctcat ggccgccgac agggcctggg gcctattcac tcccgcacca acctgatgga
cacagaactc atggatgcag actcggactt ctga
```

Human smoothened amino acid sequence having mutation at amino acid position 241 of SMO

SEQ ID NO: 6

Met Ala Ala Ala Arg Pro Ala Arg Gly Pro Glu Leu Pro Leu Leu Gly Leu Leu Leu
Leu Leu Leu Leu Gly Asp Pro Gly Arg Gly Ala Ala Ser Ser Gly Asn Ala Thr Gly Pro
Gly Pro Arg Ser Ala Gly Gly Ser Ala Arg Arg Ser Ala Ala Val Thr Gly Pro Pro Pro
Pro Leu Ser His Cys Gly Arg Ala Ala Pro Cys Glu Pro Leu Arg Tyr Asn Val Cys Leu
Gly Ser Val Leu Pro Tyr Gly Ala Thr Ser Thr Leu Leu Ala Gly Asp Ser Asp Ser Gln
Glu Glu Ala His Gly Lys Leu Val Leu Trp Ser Gly Leu Arg Asn Ala Pro Arg Cys Trp
Ala Val Ile Gln Pro Leu Leu Cys Ala Val Tyr Met Pro Lys Cys Glu Asn Asp Arg Val
Glu Leu Pro Ser Arg Thr Leu Cys Gln Ala Thr Arg Gly Pro Cys Ala Ile Val Glu Arg
Glu Arg Gly Trp Pro Asp Phe Leu Arg Cys Thr Pro Asp Arg Phe Pro Glu Gly Cys
Thr Asn Glu Val Gln Asn Ile Lys Phe Asn Ser Ser Gly Gln Cys Glu Val Pro Leu Val
Arg Thr Asp Asn Pro Lys Ser Trp Tyr Glu Asp Val Glu Gly Cys Gly Ile Gln Cys Gln
Asn Pro Leu Phe Thr Glu Ala Glu His Gln Asp Met His Ser Tyr Ile Ala Ala Phe Gly
Ala Val Xaa Gly Leu Cys Thr Leu Phe Thr Leu Ala Thr Phe Val Ala Asp Trp Arg
Asn Ser Asn Arg Tyr Pro Ala Val Ile Leu Phe Tyr Val Asn Ala Cys Phe Phe Val Gly
Ser Ile Gly Trp Leu Ala Gln Phe Met Asp Gly Ala Arg Arg Glu Ile Val Cys Arg Ala
Asp Gly Thr Met Arg Leu Gly Glu Pro Thr Ser Asn Glu Thr Leu Ser Cys Val Ile Ile
Phe Val Ile Val Tyr Tyr Ala Leu Met Ala Gly Val Val Trp Phe Val Val Leu Thr Tyr
Ala Trp His Thr Ser Phe Lys Ala Leu Gly Thr Thr Tyr Gln Pro Leu Ser Gly Lys Thr
Ser Tyr Phe His Leu Leu Thr Trp Ser Leu Pro Phe Val Leu Thr Val Ala Ile Leu Ala
Val Ala Gln Val Asp Gly Asp Ser Val Ser Gly Ile Cys Phe Val Gly Tyr Lys Asn Tyr
Arg Tyr Arg Ala Gly Phe Val Leu Ala Pro Ile Gly Leu Val Leu Ile Val Gly Gly Tyr
Phe Leu Ile Arg Gly Val Met Thr Leu Phe Ser Ile Lys Ser Asn His Pro Gly Leu Leu
Ser Glu Lys Ala Ala Ser Lys Ile Asn Glu Thr Met Leu Arg Leu Gly Ile Phe Gly Phe
Leu Ala Phe Gly Phe Val Leu Ile Thr Phe Ser Cys His Phe Tyr Asp Phe Phe Asn Gln
Ala Glu Trp Glu Arg Ser Phe Arg Asp Tyr Val Leu Cys Gln Ala Asn Val Thr Ile Gly
Leu Pro Thr Lys Gln Pro Ile Pro Asp Cys Glu Ile Lys Asn Arg Pro Ser Leu Leu Val
Glu Lys Ile Asn Leu Phe Ala Met Phe Gly Thr Gly Ile Ala Met Ser Thr Trp Val Trp

```
Thr Lys Ala Thr Leu Leu Ile Trp Arg Arg Thr Trp Cys Arg Leu Thr Gly Gln Ser Asp
Asp Glu Pro Lys Arg Ile Lys Lys Ser Lys Met Ile Ala Lys Ala Phe Ser Lys Arg His
Glu Leu Leu Gln Asn Pro Gly Gln Glu Leu Ser Phe Ser Met His Thr Val Ser His Asp
Gly Pro Val Ala Gly Leu Ala Phe Asp Leu Asn Glu Pro Ser Ala Asp Val Ser Ser Ala
Trp Ala Gln His Val Thr Lys Met Val Ala Arg Arg Gly Ala Ile Leu Pro Gln Asp Ile
Ser Val Thr Pro Val Ala Thr Pro Val Pro Glu Glu Gln Ala Asn Leu Trp Leu Val
Glu Ala Glu Ile Ser Pro Glu Leu Gln Lys Arg Leu Gly Arg Lys Lys Lys Arg Arg Lys
Arg Lys Lys Glu Val Cys Pro Leu Ala Pro Pro Glu Leu His Pro Ala Pro Ala
Pro Ser Thr Ile Pro Arg Leu Pro Gln Leu Pro Arg Gln Lys Cys Leu Val Ala Ala Gly
Ala Trp Gly Ala Gly Asp Ser Cys Arg Gln Gly Ala Trp Thr Leu Val Ser Asn Pro Phe
Cys Pro Glu Pro Ser Pro Pro Gln Asp Pro Phe Leu Pro Ser Ala Pro Ala Pro Val Ala
Trp Ala His Gly Arg Arg Gln Gly Leu Gly Pro Ile His Ser Arg Thr Asn Leu Met Asp
Thr Glu Leu Met Asp Ala Asp Ser Asp Phe
```

Human smoothened amino acid sequence having mutation at amino acid position 408 of SMO

SEQ ID NO: 7

```
Met Ala Ala Ala Arg Pro Ala Arg Gly Pro Glu Leu Pro Leu Leu Gly Leu Leu Leu
Leu Leu Leu Leu Gly Asp Pro Gly Arg Gly Ala Ala Ser Ser Gly Asn Ala Thr Gly Pro
Gly Pro Arg Ser Ala Gly Gly Ser Ala Arg Arg Ser Ala Ala Val Thr Gly Pro Pro Pro
Pro Leu Ser His Cys Gly Arg Ala Ala Pro Cys Glu Pro Leu Arg Tyr Asn Val Cys Leu
Gly Ser Val Leu Pro Tyr Gly Ala Thr Ser Thr Leu Leu Ala Gly Asp Ser Asp Ser Gln
Glu Glu Ala His Gly Lys Leu Val Leu Trp Ser Gly Leu Arg Asn Ala Pro Arg Cys Trp
Ala Val Ile Gln Pro Leu Leu Cys Ala Val Tyr Met Pro Lys Cys Glu Asn Asp Arg Val
Glu Leu Pro Ser Arg Thr Leu Cys Gln Ala Thr Arg Gly Pro Cys Ala Ile Val Glu Arg
Glu Arg Gly Trp Pro Asp Phe Leu Arg Cys Thr Pro Asp Arg Phe Pro Glu Gly Cys
Thr Asn Glu Val Gln Asn Ile Lys Phe Asn Ser Ser Gly Gln Cys Glu Val Pro Leu Val
Arg Thr Asp Asn Pro Lys Ser Trp Tyr Glu Asp Val Glu Gly Cys Gly Ile Gln Cys Gln
Asn Pro Leu Phe Thr Glu Ala Glu His Gln Asp Met His Ser Tyr Ile Ala Ala Phe Gly
Ala Val Thr Gly Leu Cys Thr Leu Phe Thr Leu Ala Thr Phe Val Ala Asp Trp Arg
Asn Ser Asn Arg Tyr Pro Ala Val Ile Leu Phe Tyr Val Asn Ala Cys Phe Phe Val Gly
Ser Ile Gly Trp Leu Ala Gln Phe Met Asp Gly Ala Arg Arg Glu Ile Val Cys Arg Ala
Asp Gly Thr Met Arg Leu Gly Glu Pro Thr Ser Asn Glu Thr Leu Ser Cys Val Ile Ile
Phe Val Ile Val Tyr Tyr Ala Leu Met Ala Gly Val Val Trp Phe Val Val Leu Thr Tyr
Ala Trp His Thr Ser Phe Lys Ala Leu Gly Thr Thr Tyr Gln Pro Leu Ser Gly Lys Thr
Ser Tyr Phe His Leu Leu Thr Trp Ser Leu Pro Phe Val Leu Thr Val Ala Ile Leu Ala
Val Ala Gln Val Asp Gly Asp Ser Val Ser Gly Ile Cys Phe Val Gly Tyr Lys Asn Tyr
Arg Tyr Arg Ala Gly Phe Val Leu Ala Pro Xaa Gly Leu Val Leu Ile Val Gly Gly Tyr
Phe Leu Ile Arg Gly Val Met Thr Leu Phe Ser Ile Lys Ser Asn His Pro Gly Leu Leu
Ser Glu Lys Ala Ala Ser Lys Ile Asn Glu Thr Met Leu Arg Leu Gly Ile Phe Gly Phe
Leu Ala Phe Gly Phe Val Leu Ile Thr Phe Ser Cys His Phe Tyr Asp Phe Phe Asn Gln
Ala Glu Trp Glu Arg Ser Phe Arg Asp Tyr Val Leu Cys Gln Ala Asn Val Thr Ile Gly
Leu Pro Thr Lys Gln Pro Ile Pro Asp Cys Glu Ile Lys Asn Arg Pro Ser Leu Leu Val
```

-continued

```
Glu Lys Ile Asn Leu Phe Ala Met Phe Gly Thr Gly Ile Ala Met Ser Thr Trp Val Trp
Thr Lys Ala Thr Leu Leu Ile Trp Arg Arg Thr Trp Cys Arg Leu Thr Gly Gln Ser Asp
Asp Glu Pro Lys Arg Ile Lys Lys Ser Lys Met Ile Ala Lys Ala Phe Ser Lys Arg His
Glu Leu Leu Gln Asn Pro Gly Gln Glu Leu Ser Phe Ser Met His Thr Val Ser His Asp
Gly Pro Val Ala Gly Leu Ala Phe Asp Leu Asn Glu Pro Ser Ala Asp Val Ser Ser Ala
Trp Ala Gln His Val Thr Lys Met Val Ala Arg Arg Gly Ala Ile Leu Pro Gln Asp Ile
Ser Val Thr Pro Val Ala Thr Pro Val Pro Pro Glu Gln Ala Asn Leu Trp Leu Val
Glu Ala Glu Ile Ser Pro Glu Leu Gln Lys Arg Leu Gly Arg Lys Lys Arg Arg Lys
Arg Lys Lys Glu Val Cys Pro Leu Ala Pro Pro Glu Leu His Pro Ala Pro Ala
Pro Ser Thr Ile Pro Arg Leu Pro Gln Leu Pro Arg Gln Lys Cys Leu Val Ala Ala Gly
Ala Trp Gly Ala Gly Asp Ser Cys Arg Gln Gly Ala Trp Thr Leu Val Ser Asn Pro Phe
Cys Pro Glu Pro Ser Pro Pro Gln Asp Pro Phe Leu Pro Ser Ala Pro Ala Pro Val Ala
Trp Ala His Gly Arg Arg Gln Gly Leu Gly Pro Ile His Ser Arg Thr Asn Leu Met Asp
Thr Glu Leu Met Asp Ala Asp Ser Asp Phe
```

Human smoothened amino acid sequence having mutation at amino acid position 469 of SMO

SEQ ID NO: 8

```
Met Ala Ala Ala Arg Pro Ala Arg Gly Pro Glu Leu Pro Leu Leu Gly Leu Leu Leu
Leu Leu Leu Leu Gly Asp Pro Gly Arg Gly Ala Ala Ser Ser Gly Asn Ala Thr Gly Pro
Gly Pro Arg Ser Ala Gly Gly Ser Ala Arg Arg Ser Ala Ala Val Thr Gly Pro Pro Pro
Pro Leu Ser His Cys Gly Arg Ala Ala Pro Cys Glu Pro Leu Arg Tyr Asn Val Cys Leu
Gly Ser Val Leu Pro Tyr Gly Ala Thr Ser Thr Leu Leu Ala Gly Asp Ser Asp Ser Gln
Glu Glu Ala His Gly Lys Leu Val Leu Trp Ser Gly Leu Arg Asn Ala Pro Arg Cys Trp
Ala Val Ile Gln Pro Leu Leu Cys Ala Val Tyr Met Pro Lys Cys Glu Asn Asp Arg Val
Glu Leu Pro Ser Arg Thr Leu Cys Gln Ala Thr Arg Gly Pro Cys Ala Ile Val Glu Arg
Glu Arg Gly Trp Pro Asp Phe Leu Arg Cys Thr Pro Asp Arg Phe Pro Glu Gly Cys
Thr Asn Glu Val Gln Asn Ile Lys Phe Asn Ser Ser Gly Gln Cys Glu Val Pro Leu Val
Arg Thr Asp Asn Pro Lys Ser Trp Tyr Glu Asp Val Glu Gly Cys Gly Ile Gln Cys Gln
Asn Pro Leu Phe Thr Glu Ala Glu His Gln Asp Met His Ser Tyr Ile Ala Ala Phe Gly
Ala Val Thr Gly Leu Cys Thr Leu Phe Thr Leu Ala Thr Phe Val Ala Asp Trp Arg
Asn Ser Asn Arg Tyr Pro Ala Val Ile Leu Phe Tyr Val Asn Ala Cys Phe Phe Val Gly
Ser Ile Gly Trp Leu Ala Gln Phe Met Asp Gly Ala Arg Arg Glu Ile Val Cys Arg Ala
Asp Gly Thr Met Arg Leu Gly Glu Pro Thr Ser Asn Glu Thr Leu Ser Cys Val Ile Ile
Phe Val Ile Val Tyr Ala Leu Met Ala Gly Val Val Trp Phe Val Val Leu Thr Tyr
Ala Trp His Thr Ser Phe Lys Ala Leu Gly Thr Thr Tyr Gln Pro Leu Ser Gly Lys Thr
Ser Tyr Phe His Leu Leu Thr Trp Ser Leu Pro Phe Val Leu Thr Val Ala Ile Leu Ala
Val Ala Gln Val Asp Gly Asp Ser Val Ser Gly Ile Cys Phe Val Gly Tyr Lys Asn Tyr
Arg Tyr Arg Ala Gly Phe Val Leu Ala Pro Ile Gly Leu Val Leu Ile Val Gly Gly Tyr
Phe Leu Ile Arg Gly Val Met Thr Leu Phe Ser Ile Lys Ser Asn His Pro Gly Leu Leu
Ser Glu Lys Ala Ala Ser Lys Ile Asn Glu Thr Met Leu Arg Leu Gly Ile Phe Gly Phe
Leu Ala Phe Gly Phe Val Leu Ile Thr Phe Ser Xaa His Phe Tyr Asp Phe Phe Asn Gln
Ala Glu Trp Glu Arg Ser Phe Arg Asp Tyr Val Leu Cys Gln Ala Asn Val Thr Ile Gly
```

```
Leu Pro Thr Lys Gln Pro Ile Pro Asp Cys Glu Ile Lys Asn Arg Pro Ser Leu Leu Val

Glu Lys Ile Asn Leu Phe Ala Met Phe Gly Thr Gly Ile Ala Met Ser Thr Trp Val Trp

Thr Lys Ala Thr Leu Leu Ile Trp Arg Arg Thr Trp Cys Arg Leu Thr Gly Gln Ser Asp

Asp Glu Pro Lys Arg Ile Lys Lys Ser Lys Met Ile Ala Lys Ala Phe Ser Lys Arg His

Glu Leu Leu Gln Asn Pro Gly Gln Glu Leu Ser Phe Ser Met His Thr Val Ser His Asp

Gly Pro Val Ala Gly Leu Ala Phe Asp Leu Asn Glu Pro Ser Ala Asp Val Ser Ser Ala

Trp Ala Gln His Val Thr Lys Met Val Ala Arg Arg Gly Ala Ile Leu Pro Gln Asp Ile

Ser Val Thr Pro Val Ala Thr Pro Val Pro Pro Glu Glu Gln Ala Asn Leu Trp Leu Val

Glu Ala Glu Ile Ser Pro Glu Leu Gln Lys Arg Leu Gly Arg Lys Lys Lys Arg Arg Lys

Arg Lys Lys Glu Val Cys Pro Leu Ala Pro Pro Glu Leu His Pro Ala Pro Ala

Pro Ser Thr Ile Pro Arg Leu Pro Gln Leu Pro Arg Gln Lys Cys Leu Val Ala Ala Gly

Ala Trp Gly Ala Gly Asp Ser Cys Arg Gln Gly Ala Trp Thr Leu Val Ser Asn Pro Phe

Cys Pro Glu Pro Ser Pro Pro Gln Asp Pro Phe Leu Pro Ser Ala Pro Ala Pro Val Ala

Trp Ala His Gly Arg Arg Gln Gly Leu Gly Pro Ile His Ser Arg Thr Asn Leu Met Asp

Thr Glu Leu Met Asp Ala Asp Ser Asp Phe
```

Human smoothened amino acid sequence having mutation at amino acid position 533 of SMO

SEQ ID NO: 9

```
Met Ala Ala Ala Arg Pro Ala Arg Gly Pro Glu Leu Pro Leu Leu Gly Leu Leu Leu

Leu Leu Leu Leu Gly Asp Pro Gly Arg Gly Ala Ala Ser Ser Gly Asn Ala Thr Gly Pro

Gly Pro Arg Ser Ala Gly Gly Ser Ala Arg Arg Ser Ala Ala Val Thr Gly Pro Pro Pro

Pro Leu Ser His Cys Gly Arg Ala Ala Pro Cys Glu Pro Leu Arg Tyr Asn Val Cys Leu

Gly Ser Val Leu Pro Tyr Gly Ala Thr Ser Thr Leu Leu Ala Gly Asp Ser Asp Ser Gln

Glu Glu Ala His Gly Lys Leu Val Leu Trp Ser Gly Leu Arg Asn Ala Pro Arg Cys Trp

Ala Val Ile Gln Pro Leu Leu Cys Ala Val Tyr Met Pro Lys Cys Glu Asn Asp Arg Val

Glu Leu Pro Ser Arg Thr Leu Cys Gln Ala Thr Arg Gly Pro Cys Ala Ile Val Glu Arg

Glu Arg Gly Trp Pro Asp Phe Leu Arg Cys Thr Pro Asp Arg Phe Pro Glu Gly Cys

Thr Asn Glu Val Gln Asn Ile Lys Phe Asn Ser Ser Gly Gln Cys Glu Val Pro Leu Val

Arg Thr Asp Asn Pro Lys Ser Trp Tyr Glu Asp Val Glu Gly Cys Gly Ile Gln Cys Gln

Asn Pro Leu Phe Thr Glu Ala Glu His Gln Asp Met His Ser Tyr Ile Ala Ala Phe Gly

Ala Val Thr Gly Leu Cys Thr Leu Phe Thr Leu Ala Thr Phe Val Ala Asp Trp Arg

Asn Ser Asn Arg Tyr Pro Ala Val Ile Leu Phe Tyr Val Asn Ala Cys Phe Phe Val Gly

Ser Ile Gly Trp Leu Ala Gln Phe Met Asp Gly Ala Arg Arg Glu Ile Val Cys Arg Ala

Asp Gly Thr Met Arg Leu Gly Glu Pro Thr Ser Asn Glu Thr Leu Ser Cys Val Ile Ile

Phe Val Ile Val Tyr Tyr Ala Leu Met Ala Gly Val Val Trp Phe Val Val Leu Thr Tyr

Ala Trp His Thr Ser Phe Lys Ala Leu Gly Thr Thr Tyr Gln Pro Leu Ser Gly Lys Thr

Ser Tyr Phe His Leu Leu Thr Trp Ser Leu Pro Phe Val Leu Thr Val Ala Ile Leu Ala

Val Ala Gln Val Asp Gly Asp Ser Val Ser Gly Ile Cys Phe Val Gly Tyr Lys Asn Tyr

Arg Tyr Arg Ala Gly Phe Val Leu Ala Pro Ile Gly Leu Val Leu Ile Val Gly Gly Tyr

Phe Leu Ile Arg Gly Val Met Thr Leu Phe Ser Ile Lys Ser Asn His Pro Gly Leu Leu

Ser Glu Lys Ala Ala Ser Lys Ile Asn Glu Thr Met Leu Arg Leu Gly Ile Phe Gly Phe

Leu Ala Phe Gly Phe Val Leu Ile Thr Phe Ser Cys His Phe Tyr Asp Phe Phe Asn Gln
```

Ala Glu Trp Glu Arg Ser Phe Arg Asp Tyr Val Leu Cys Gln Ala Asn Val Thr Ile Gly

Leu Pro Thr Lys Gln Pro Ile Pro Asp Cys Glu Ile Lys Asn Arg Pro Ser Leu Leu Val

Glu Lys Ile Asn Leu Phe Ala Met Phe Gly Thr Gly Ile Ala Met Xaa Thr Trp Val Trp

Thr Lys Ala Thr Leu Leu Ile Trp Arg Arg Thr Trp Cys Arg Leu Thr Gly Gln Ser Asp

Asp Glu Pro Lys Arg Ile Lys Lys Ser Lys Met Ile Ala Lys Ala Phe Ser Lys Arg His

Glu Leu Leu Gln Asn Pro Gly Gln Glu Leu Ser Phe Ser Met His Thr Val Ser His Asp

Gly Pro Val Ala Gly Leu Ala Phe Asp Leu Asn Glu Pro Ser Ala Asp Val Ser Ser Ala

Trp Ala Gln His Val Thr Lys Met Val Ala Arg Arg Gly Ala Ile Leu Pro Gln Asp Ile

Ser Val Thr Pro Val Ala Thr Pro Val Pro Pro Glu Glu Gln Ala Asn Leu Trp Leu Val

Glu Ala Glu Ile Ser Pro Glu Leu Gln Lys Arg Leu Gly Arg Lys Lys Arg Arg Lys

Arg Lys Lys Glu Val Cys Pro Leu Ala Pro Pro Pro Glu Leu His Pro Ala Pro Ala

Pro Ser Thr Ile Pro Arg Leu Pro Gln Leu Pro Arg Gln Lys Cys Leu Val Ala Ala Gly

Ala Trp Gly Ala Gly Asp Ser Cys Arg Gln Gly Ala Trp Thr Leu Val Ser Asn Pro Phe

Cys Pro Glu Pro Ser Pro Pro Gln Asp Pro Phe Leu Pro Ser Ala Pro Ala Pro Val Ala

Trp Ala His Gly Arg Arg Gln Gly Leu Gly Pro Ile His Ser Arg Thr Asn Leu Met Asp

Thr Glu Leu Met Asp Ala Asp Ser Asp Phe human Suppressor of Fused (SuFu) amino acid sequence
(GenBank Accesion No. NM_016169.2)

SEQ ID NO: 10

MAELRPSGAPGPTAPPAPGPTAPPAFASLFPPGLHAIYGECRRLYPDQP

NPLQVTAIVKYWLGGPDPLDYVSMYRNVGSPSANIPEHWHYISFGLSDLYGD

NRVHEFTGTDGPSGFGFELTFRLKRETGESAPPTWPAELMQGLARYVFQSEN

TFCSGDHVSWHSPLDNSESRIQHMLLTEDPQMQPVQTPFGVVTFLQIVGVCTE

ELHSAQQWNGQGILELLRTVPIAGGPWLITDMRRGETIFEIDPHLQERVDKGIE

TDGSNLSGVSAKCAWDDLSRPPEDDEDSRSICIGTQPRRLSGKDTEQIRETLRR

GLEINSKPVLPPINPQRQNGLAHDRAPSRKDSLESDSSTAIIPHELIRTRQLESV

HLKFNQESGALIPLCLRGRLLHGRHFTYKSITGDMAITFVSTGVEGAFATEEHP

YAAHGPWLQILLTEEFVEKMLEDLEDLTSPEEFKLPKEYSWPEKKLKVSILPD

VVFDSPLH human Suppressor of Fused (SuFu) cDNA sequence
(GenBank Accesion No. NM_016169.2)

SEQ ID NO: 11

CGCCGTGCGCAGGCGCGGAGCTAGACCTCGCTGCAGCCCCCATCGC

CTCGGGGAGTCTCACCCACCGAGTCCGCCCGCTGGCCCGTCAGTGCTCTCC

CCGTCGTTTGCCCTCTCCAGTTCCCCCAGTGCCTGCCCTACGCACCCCGAT

GGCGGAGCTGCGGCCTAGCGGCGCCCCCGGCCCCACCGCGCCCCCGGCCC

CTGGCCCGACTGCCCCCCCGGCCTTCGCTTCGCTCTTTCCCCCGGGACTGC

ACGCCATCTACGGAGAGTGCCGCCGCCTTTACCCTGACCAGCCGAACCCG

CTCCAGGTTACCGCTATCGTCAAGTACTGGTTGGGTGGCCCAGACCCCTTG

GACTATGTTAGCATGTACAGGAATGTGGGAGCCCTTCTGCTAACATCCC

CGAGCACTGGCACTACATCAGCTTCGGCCTGAGTGATCTCTATGGTGACA

ACAGAGTCCATGAGTTTACAGGAACAGATGGACCTAGTGGTTTTGGCTTT

GAGTTGACCTTTCGTCTGAAGAGAGAAACTGGGGAGTCTGCCCCACCAAC

-continued

```
ATGGCCCGCAGAGTTAATGCAGGGCTTGGCACGATACGTGTTCCAGTCAG

AGAACACCTTCTGCAGTGGGGACCATGTGTCCTGGCACAGCCCTTTGGAT

AACAGTGAGTCAAGAATTCAGCACATGCTGCTGACAGAGGACCCACAGAT

GCAGCCCGTGCAGACACCCTTTGGGGTAGTTACCTTCCTCCAGATCGTTGG

TGTCTGCACTGAAGAGCTACACTCAGCCCAGCAGTGGAACGGGCAGGGCA

TCCTGGAGCTGCTGCGGACAGTGCCTATTGCTGGCGGCCCCTGGCTGATA

ACTGACATGCGGAGGGGAGAGACCATATTTGAGATCGATCCACACCTGCA

AGAGAGAGTTGACAAAGGCATCGAGACAGATGGCTCCAACCTGAGTGGT

GTCAGTGCCAAGTGTGCCTGGGATGACCTGAGCCGGCCCCCCGAGGATGA

CGAGGACAGCCGGAGCATCTGCATCGGCACACAGCCCCGGCGACTCTCTG

GCAAAGACACAGAGCAGATCCGGGAGACCCTGAGGAGAGGACTCGAGAT

CAACAGCAAACCTGTCCTTCCACCAATCAACCCTCAGCGGCAGAATGGCC

TCGCCCACGACCGGGCCCCGAGCCGCAAAGACAGCCTGGAAAGTGACAG

CTCCACGGCCATCATTCCCCATGAGCTGATTCGCACGCGGCAGCTTGAGA

GCGTACATCTGAAATTCAACCAGGAGTCCGGAGCCCTCATTCCTCTCTGCC

TAAGGGGCAGGCTCCTGCATGGACGGCACTTTACATATAAAAGTATCACA

GGTGACATGGCCATCACGTTTGTCTCCACGGGAGTGGAAGGCGCCTTTGC

CACTGAGGAGCATCCTTACGCGGCTCATGGACCCTGGTTACAAATTCTGTT

GACCGAAGAGTTTGTAGAGAAAATGTTGGAGGATTTAGAAGATTTGACTT

CTCCAGAGGAATTCAAACTTCCCAAAGAGTACAGCTGGCCTGAAAAGAAG

CTGAAGGTCTCCATCCTGCCTGACGTGGTGTTCGACAGTCCGCTACACTAG

CCTGGGCTGGGCCCTGCAGGGGCCAGCAGGGAGCCCAGCTGCTCCCCAGT

GACTTCCAGTGTAACAGTTGTGTCAACGAGATCTCCACAAATAAAAGGAC

AAGTGTGAGGAAGACTGCGCAGTGCCACCCCGCAGCCCAGTGGGGTGCCA

TGCACAGGCCACAGGCCCTCCACCTCACCTCCAGCTCAGGGGCCGCACCC

CGCCGCTGGCTAAGCCTTGTGACCCATCAGGCCAGTGAGTGGGCAAATGC

GGACCCTCCCTGCCTGCAGCCTGCACAGATTCTGGTTTGAGGTTTGACTCT

GGACCCTGGCTGTGCCCCTAGGTGGAGACAGCCCTCTTTCTCACCTACCCC

CTGCCGCACAGCCCAGCAGGAGGGAGGCGGACAGCCAGATGCAGAGCGA

GTGGATGCACTTCCCAGCTCATCTCTGGAAGCCTTTGCTACTCAAGCTCCT

CTGGCCGCGGAACAATTCCTCTGATCATGTTTGGTTTTCTTCTTCCTTATTT

TATTTTGTAGAAACCGGGTGGTATTTTATTGCTCTGCAAAGATGTCCAGAA

GCCATGTATATAATGTTTTTTAAACAGAACTTCATTCCCCGTTGAACTTTC

GCATTCTCTGACAGAGGCCTAGGGCTGTATCTCTCCCTGGGCTGCCACCAG

AGAAGGTGCTTGGTGTTCGCCTGCCAGCCCAGAGCCCTGGAGGAGCCGGC

TGCACAGAGAGGCTTTTCTTCCCAGCTGGGCCTGATGGAGCCCGGGGCAG

GGGGAGAGTAGAGACACTCCCTTGTGCAGCTTTGAGCCTAGTTTAGCTGG

GGCCAGGGAGGGGTGCTACTGTTTTCCAAGTGAATGGGTCTCAAAGACTT

GGTGACCCCAGCCTCATCTTCTAGGCCTTTTCCATCCAACCAGGCCTACCT

GGGAGAGGGTGAGGTTCAGCACATCACACACCATCCCCACTGTCATTCAG

GGCCTGGGTCTCCAGCTCTGTAACCAGTCCTGTCCCATTTCCTCAGTCCCT
```

-continued

```
GGGCCTCCCAGCCTTCAGGCTGTAGGGCTGCCTTACTAAAATTGAAAAAT
CCACCTCTTAACATCTCTTTCACTTTGGTTTTGCTAACACTGCTCTCTGCTG
CCCTCCCATCCTCCCTGTATCCATTCATGCCCTATCTTTCATTCTCCACTCC
TAATCCCTCTCCTTTCTGGCATCCTGGCCTCTCGTGGTCCTCAGCCCCTCAC
CCCCAGTACTGCAGATCTCACAGTTTGCCTTCCAGAAGCCAGCCTATCTCT
AGCCCATGGTTTTGGAGTTCCTCTCGGGTTATCTCCCACGCCTGACCTGGA
ACCAGCAAGCCCCTTTCCTGCCTTCTTACCCCCAACTCTAGGGATGGGACT
GTTACAATACTTCAAGATCACTCTTTACACCTCTTCAAAGCAAAGTCATGA
CAATGCAGGGCTCCTCATTGCTCCCATCTGCCTCTGCTGCACACACAGGCA
CCAGCAGGGATGCCACAGGAGTGCCCACAGGGTGCAGGACTCCACTGATG
AGAGATCCAGCCAAAGAGCTGCCCCCAGGGGTATGAGGGCACCAGCTGG
GTTCTCCAGGGAGCAGGAGTTGGACCTCCATGGAGCCACTAGGCCTGGCC
TCCTCTACACATCCCCAGGGCTATCTGGTTAATTCCATCAAGCTCAGAGTT
AAAAGGCATATCAGCCTGGAGTATTTGGGAGAGACTGGCTGCAGATCCCC
GCCAGCCAAGATGCAAGCCACTCGGGACCTGATGTCGGCAGCTGTGCCTC
TACTGCCCTGAGGACTTACCAGAGGGAGCCCTACTGGCCTTCCCCCACCA
CAGCAGCCCTGCCTGTGAAGCTCTTGTTTCTGACATTTCACAGGCAGAGAG
GTGCCATCAGTTCGCCTCCATTCCTTGCCACCATGACCAGCCTCTCCCTGA
ACTCTCTCTTGCTCGGGACCTGCCTGAGGGCTCCCTGCTGCAGTTCGCCGT
ACTTCCATCTGCTGGGTGCCTCCATCGTTGGTTGGGTGGGGATGGGGCATT
TTCTGAGCTAAGCTTTGTCATTAGTTTGTGAAGCACCTGGTCAGCAACCTG
CCCCAGACCTGGAGGGTCTTTGTGGACTGAAGGTAGACACCAGCCAGCAT
GGTGGCCCTGTTCTGGGGGAGCAGGGTAAGGCAGGAGGAAGTGGGTGAG
CTCCGAGATGATGAGCACATGAAGCCTGTGGCCCCTTCGTACCTGCAATA
TGTCAGGAGCCTCACGCTCACCCAAGATCCTGCAGGGGCCAGGCTCCATC
TCACTGGCTCTGAGGGCAGGACAGGGTATCACACATTTCTCACCAGGCCT
CCTTTCCTATGGGCATTGGTGCCTCCCAGAGGTTTCTTGGGCTGCTGGCTG
GTGAGAGAGGACCCTTAAAGAAGATCAAGCCAAGCTGACCTTGGACCCTG
TCCAGCACAGCTTCTGGCACAGGATGCTTGGTGAATGTACCCTTTCTTTCC
CTCCCTGCAGCTCTGAGGGAGCCCCTGACCTTGTAGTGGGTGGAGGAGGT
AAGGGGCCTCCCTCCCTAAATCTGCCTCTTCTGCAAGCTACTTGGAGACTT
GCCTAGTTGTACCCACCCCTCCAGGTCCCTGGTGCTAGAGCTTCTGAGAAG
GGCCTTTCCCTTTCCTCTTTGCCTGCTATATAAGGCAGGCTCCTGTGGCTCT
GCTGGCTCAGTGTGGGCTGCAGGAGGACTGCAGACTCAGCTGCAATTCTG
AGGGGGGTTTGGGAGGCTTGTGCGAGGTCTCAGGCCTGTGTGGGGAGCTG
GTGCCTCTTCCTGCCCGTATCTTTCTCTTCCAAGGGCAGTGCTCCAAGGCA
GGGACTGGAGAAGCCAAGGGGAGAGTCTAAAAGGGCTAGAGCATTTTTA
AAAATAGACACAGGGTCTTGGGACTGGGGTTTCGGATTGAGTTGCAAGCA
GGGAGAAAACCTGAAGGTCGGTGCCCCTATGGGGCTGACCAGTAGAGAA
TTTCCTTTACTGTATTTTTGTGTCTGGTCTTCCCTTTCTGGCTTCTAGGACAT
```

-continued
CCATGCCAGGTGAGGTGCCTGGGTCCCTGTTACAAGTCAGGAGCCCTGTA

GGGAGACCCCTCCTTTTGTACAAGTACCTGAATGCTGCGACAAGCAGATT

TTTGTAAAATTTTATATTAGTTTTTAATGTCAGTGGCGACTCGGTTCCTGG

GGCTGCAGCCAGCCTGGGACTTTTGTAAGAATTTTTGGGTGACTCACTTAG

ATGTCGTTTCCTTCTTGCCCCCTCTTCCTCTCTGTAATCTAAGTGCATTAAA

CATCTTTGCAG

---

What is claimed is:

1. A method of screening for compounds that inhibit signaling of a mutant SMO (Smoothened) protein having an amino acid sequence of SEQ ID NO: 6, wherein said amino acid sequence has an amino acid other than threonine at amino acid 241, comprising contacting said mutant SMO with a test compound, and detecting binding of said compound to said mutant SMO, whereby binding of said test compound to mutant SMO indicates that said test compound is an inhibitor of mutant SMO.

2. A method of screening for compounds that inhibit signaling of a mutant SMO (Smoothened) protein having an amino acid sequence of SEQ ID NO: 6, wherein said amino acid sequence has an amino acid other than threonine at amino acid 241, comprising contacting a cell that expresses said mutant SMO with a test compound and detecting activity of Gli (glioma-associated oncogene) in said cell whereby the presence of Gli activity indicates that said test compound is not an inhibitor of mutant SMO.

3. A method of screening for compounds that inhibit signaling of a mutant SMO (Smoothened) protein having an amino acid sequence of SEQ ID NO: 8, wherein said amino acid sequence has an amino acid other than cysteine at amino acid 469, comprising contacting said mutant SMO with a test compound and detecting binding of said compound to mutant SMO indicates that said test compound is an inhibitor of mutant SMO.

4. A method of screening for compounds that inhibit signaling of a mutant SMO (Smoothened) protein having an amino acid sequence of SEQ ID NO: 8, wherein said amino acid sequence has an amino acid other than cysteine at amino acid 469, comprising contacting a cell that expresses said mutant SMO with a test compound and detecting activity of Gli (glioma-associated oncogene) in said cell whereby the presence of Gli activity indicates that said test compound is not an inhibitor of mutant SMO.

5. An isolated mutant SMO (Smoothened) protein having the amino acid sequence of
   (a) SEQ ID NO: 6 wherein said amino acid sequence has an amino acid other than threonine at amino acid 241, or
   (b) SEQ ID NO: 8 wherein said amino acid sequence has an amino acid other than cysteine at amino acid 469.

6. The isolated mutant SMO protein of claim 5, wherein said amino acid sequence has
   (a) methionine (M) at amino acid 241, or
   (b) tyrosine (Y) at amino acid 469.

7. A method of identifying a hedgehog pathway inhibitor, wherein the method comprises:
   (a) contacting a cell with an amount of a test agent, wherein the cell is responsive to hedgehog protein or has increased hedgehog signaling and/or activation of the hedgehog signaling pathway, and wherein the cell expresses a mutant SMO (Smoothened) protein of claim 5, and
   (b) determining, as compared to a control, whether the test agent inhibits hedgehog signaling in the cell,
   wherein if the test agent inhibits hedgehog signaling in the cell relative to the control, then the test agent is identified as a hedgehog pathway inhibitor.

8. The method of claim 7, wherein the ability of the test agent to inhibit hedgehog signaling in the cell is determined using a Gli1 (glioma-associated oncogene) expression assay.

9. The method of claim 7, wherein the control is a cell expressing a wildtype SMO protein.

10. The method of claim 7, wherein the control is a cell expressing the same mutant SMO proteins as the cell contacted with the test agent, wherein the control is treated with a control agent to which the mutant SMO protein is partially or completely resistant.

11. The method of claim 10, wherein the control agent is vismodegib.

12. The method of claim 10, wherein the control agent is LY2940680.

13. The method of claim 10, wherein the control agent is LDE225.

14. The method of claim 10, wherein the control agent is compound 5.

15. The method of claim 7, wherein the test agent binds to mutant SMO protein but not wildtype SMO protein.

16. The method of claim 7, wherein the test agent binds to both the mutant SMO protein and wildtype SMO protein.

17. The method of claim 7, wherein the test agent is more effective in inhibiting the hedgehog signaling pathway in a cell expressing mutant SMO protein than in a cell expressing wildtype SMO protein.

18. A method of identifying a hedgehog pathway inhibitor, wherein the method comprises:
   (a) contacting a cell with an amount of a test agent, wherein the cell is responsive to hedgehog protein or has increased hedgehog signaling and/or activation of the hedgehog signaling pathway, and wherein the cell expresses a mutant SMO (Smoothened) protein of claim 5, and
   (b) determining, as compared to a control, whether the test agent inhibits growth and/or proliferation of the cell,
   wherein if the test agent inhibits growth and/or proliferation of the cell relative to the control, then the test agent is identified as a hedgehog pathway inhibitor.

19. The method of claim 18, wherein the test agent is more effective in inhibiting growth and/or proliferation of a cell expressing mutant SMO protein than of a cell expressing wildtype SMO protein.

20. The method of claim 18, wherein the control is a cell expressing a wildtype SMO protein.

21. The method of claim 18, wherein the control is a cell expressing the same mutant SMO proteins as the cell contacted with the test agent, wherein the control is treated with a control agent to which the mutant SMO protein is partially or completely resistant.

22. The method of claim 21, wherein the control agent is vismodegib.

23. The method of claim 21, wherein the control agent is LY2940680.

24. The method of claim 21, wherein the control agent is LDE225.

25. The method of claim 21, wherein the control agent is compound 5.

26. The method of claim 18, wherein the test agent binds to mutant SMO protein but not wildtype SMO protein.

27. The method of claim 18, wherein the test agent binds to both the mutant SMO protein and wildtype SMO protein.

28. A method of identifying a hedgehog pathway inhibitor, wherein the method comprises:
  (a) contacting a cell with an amount of a test agent, wherein the cell is responsive to hedgehog protein or has increased hedgehog signaling and/or activation of the hedgehog signaling pathway, and wherein the cell expresses a vector comprising a nucleic acid molecule encoding a mutant SMO (Smoothened) protein of claim 5, and
  (b) determining, as compared to a control, whether the test agent inhibits hedgehog signaling in the cell,
wherein if the test agent inhibits hedgehog signaling in the cell relative to the control, then the test agent is identified as a hedgehog pathway inhibitor.

29. The method of claim 28, wherein the ability of the test agent to inhibit hedgehog signaling in the cell is determined using a Gli1 (glioma-associated oncogene) expression assay.

30. The method of claim 28, wherein the control is a cell expressing a wildtype SMO protein.

31. The method of claim 28, wherein the control is a cell expressing the same mutant SMO protein as the cell contacted with the test agent, wherein the control is treated with a control agent to which the mutant SMO protein is partially or completely resistant.

32. The method of claim 31, wherein the control agent is vismodegib.

33. The method of claim 31, wherein the control agent is LY2940680.

34. The method of claim 31, wherein the control agent is LDE225.

35. The method of claim 31, wherein the control agent is compound 5.

36. The method of claim 28, wherein the test agent binds to mutant SMO protein but not wildtype SMO protein.

37. The method of claim 28, wherein the test agent binds to both the mutant SMO protein and wildtype SMO protein.

38. The method of claim 28, wherein the test agent is more effective in inhibiting the hedgehog signaling pathway in a cell expressing mutant SMO protein than in a cell expressing wildtype SMO protein.

39. A method of identifying a hedgehog pathway inhibitor, wherein the method comprises:
  (a) contacting a cell with an amount of a test agent, wherein the cell is responsive to hedgehog protein or has increased hedgehog signaling and/or activation of the hedgehog signaling pathway, and wherein the cell expresses a vector comprising a nucleic acid molecule encoding a mutant SMO (Smoothened) protein of claim 5, and
  (b) determining, as compared to a control, whether the test agent inhibits growth and/or proliferation of the cell,
wherein if the test agent inhibits growth and/or proliferation of the cell relative to the control, then the test agent is identified as a hedgehog pathway inhibitor.

40. The method of claim 39, wherein the control is a cell expressing a wildtype SMO protein.

41. The method of claim 39, wherein the control is a cell expressing the same mutant SMO protein as the cell contacted with the test agent, wherein the control is treated with a control agent to which the mutant SMO protein is partially or completely resistant.

42. The method of claim 41, wherein the control agent is vismodegib.

43. The method of claim 41, wherein the control agent is LY2940680.

44. The method of claim 41, wherein the control agent is LDE225.

45. The method of claim 41, wherein the control agent is compound 5.

46. The method of claim 39, wherein the test agent binds to mutant SMO protein but not wildtype SMO protein.

47. The method of claim 39, wherein the test agent binds to both the mutant SMO protein and wildtype SMO protein.

48. The method of claim 39, wherein the test agent is more effective in inhibiting growth and/or proliferation of a cell expressing mutant SMO protein than of a cell expressing wildtype SMO protein.

49. An isolated nucleic acid molecule encoding a mutant SMO (Smoothened) protein, having a parental nucleic acid sequence of SEQ ID NO: 5, wherein said sequence has a mutation that alters the sequence encoding
  (a) amino acid 241 to encode amino acid other than threonine, or
  (b) amino acid 469 to encode amino acid other than cysteine.

50. The isolated nucleic acid molecule of claim 49, wherein the mutant SMO protein has the amino acid sequence of
  (a) SEQ ID NO: 6 wherein said amino acid sequence has a methionine (M) at amino acid 241, or
  (b) SEQ ID NO: 8 wherein said amino acid sequence has a tyrosine (Y) at amino acid 469.

51. A vector comprising the nucleic acid of claim 49.

52. A host cell comprising the vector of claim 51.

53. A nucleic acid probe capable of specifically hybridizing under high stringency conditions to a nucleic acid encoding a mutated SMO (Smoothened) protein of claim 5 or encoding a fragment thereof incorporating said mutation at amino acid 241 or 469.

54. The probe of claim 53 wherein said probe is complementary to said nucleic acid encoding the mutated SMO or said fragment thereof.

55. The probe of claim 53 having a length of about 10 to about 50 nucleotides.

56. The probe of claim 53 further comprising a detectable label.

* * * * *

SEQUENCE LISTING

<160> NUMBER OF SEQ ID NOS: 11

<210> SEQ ID NO 1
<211> LENGTH: 787
<212> TYPE: PRT
<213> ORGANISM: Homo sapiens

<400> SEQUENCE: 1

```
Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
            20                  25                  30

Ser Gly Asn Ala Thr Gly Pro Gly Pro Arg Ser Ala Gly Gly Ser Ala
        35                  40                  45

Arg Arg Ser Ala Ala Val Thr Gly Pro Pro Pro Leu Ser His Cys
50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95

Asp Ser Gln Glu Glu Ala His Gly Lys Leu Val Leu Trp Ser Gly Leu
            100                 105                 110

Arg Asn Ala Pro Arg Cys Trp Ala Val Ile Gln Pro Leu Leu Cys Ala
        115                 120                 125

Val Tyr Met Pro Lys Cys Glu Asn Asp Arg Val Glu Leu Pro Ser Arg
130                 135                 140

Thr Leu Cys Gln Ala Thr Arg Gly Pro Cys Ala Ile Val Glu Arg Glu
145                 150                 155                 160

Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
            180                 185                 190

Cys Glu Val Pro Leu Val Arg Thr Asp Asn Pro Lys Ser Trp Tyr Glu
        195                 200                 205

Asp Val Glu Gly Cys Gly Ile Gln Cys Gln Asn Pro Leu Phe Thr Glu
210                 215                 220

Ala Glu His Gln Asp Met His Ser Tyr Ile Ala Ala Phe Gly Ala Val
225                 230                 235                 240

Thr Gly Leu Cys Thr Leu Phe Thr Leu Ala Thr Phe Val Ala Asp Trp
                245                 250                 255

Arg Asn Ser Asn Arg Tyr Pro Ala Val Ile Leu Phe Tyr Val Asn Ala
            260                 265                 270

Cys Phe Phe Val Gly Ser Ile Gly Trp Leu Ala Gln Phe Met Asp Gly
        275                 280                 285
```

```
Ala Arg Arg Glu Ile Val Cys Arg Ala Asp Gly Thr Met Arg Leu Gly
    290                 295                 300

Glu Pro Thr Ser Asn Glu Thr Leu Ser Cys Val Ile Ile Phe Val Ile
305                 310                 315                 320

Val Tyr Tyr Ala Leu Met Ala Gly Val Val Trp Phe Val Val Leu Thr
                    325                 330                 335

Tyr Ala Trp His Thr Ser Phe Lys Ala Leu Gly Thr Thr Tyr Gln Pro
                340                 345                 350

Leu Ser Gly Lys Thr Ser Tyr Phe His Leu Leu Thr Trp Ser Leu Pro
            355                 360                 365

Phe Val Leu Thr Val Ala Ile Leu Ala Val Ala Gln Val Asp Gly Asp
370                 375                 380

Ser Val Ser Gly Ile Cys Phe Val Gly Tyr Lys Asn Tyr Arg Tyr Arg
385                 390                 395                 400

Ala Gly Phe Val Leu Ala Pro Ile Gly Leu Val Leu Ile Val Gly Gly
                    405                 410                 415

Tyr Phe Leu Ile Arg Gly Val Met Thr Leu Phe Ser Ile Lys Ser Asn
                420                 425                 430

His Pro Gly Leu Leu Ser Glu Lys Ala Ala Ser Lys Ile Asn Glu Thr
            435                 440                 445

Met Leu Arg Leu Gly Ile Phe Gly Phe Leu Ala Phe Gly Phe Val Leu
450                 455                 460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
                    485                 490                 495

Gly Leu Pro Thr Lys Gln Pro Ile Pro Asp Cys Glu Ile Lys Asn Arg
                500                 505                 510

Pro Ser Leu Leu Val Glu Lys Ile Asn Leu Phe Ala Met Phe Gly Thr
            515                 520                 525

Gly Ile Ala Met Ser Thr Trp Val Trp Thr Lys Ala Thr Leu Leu Ile
530                 535                 540

Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                    565                 570                 575

His Glu Leu Leu Gln Asn Pro Gly Gln Glu Leu Ser Phe Ser Met His
                580                 585                 590

Thr Val Ser His Asp Gly Pro Val Ala Gly Leu Ala Phe Asp Leu Asn
            595                 600                 605

Glu Pro Ser Ala Asp Val Ser Ser Ala Trp Ala Gln His Val Thr Lys
610                 615                 620

Met Val Ala Arg Arg Gly Ala Ile Leu Pro Gln Asp Ile Ser Val Thr
625                 630                 635                 640

Pro Val Ala Thr Pro Val Pro Pro Glu Glu Gln Ala Asn Leu Trp Leu
                    645                 650                 655

Val Glu Ala Glu Ile Ser Pro Glu Leu Gln Lys Arg Leu Gly Arg Lys
                660                 665                 670

Lys Lys Arg Arg Lys Arg Lys Lys Glu Val Cys Pro Leu Ala Pro Pro
            675                 680                 685

Pro Glu Leu His Pro Ala Pro Ala Pro Ser Thr Ile Pro Arg Leu
690                 695                 700

Pro Gln Leu Pro Arg Gln Lys Cys Leu Val Ala Ala Gly Ala Trp Gly
```

```
                    705                 710                 715                 720
Ala Gly Asp Ser Cys Arg Gln Gly Ala Trp Thr Leu Val Ser Asn Pro
                725                 730                 735

Phe Cys Pro Glu Pro Ser Pro Pro Gln Asp Pro Phe Leu Pro Ser Ala
                740                 745                 750

Pro Ala Pro Val Ala Trp Ala His Gly Arg Arg Gln Gly Leu Gly Pro
                755                 760                 765

Ile His Ser Arg Thr Asn Leu Met Asp Thr Glu Leu Met Asp Ala Asp
                770                 775                 780

Ser Asp Phe
785

<210> SEQ ID NO 2
<211> LENGTH: 787
<212> TYPE: PRT
<213> ORGANISM: Homo sapiens
<220> FEATURE:
<221> NAME/KEY: MOD_RES
<222> LOCATION: (281)..(281)
<223> OTHER INFORMATION: Any amino acid

<400> SEQUENCE: 2

Met Ala Ala Ala Arg Pro Ala Arg Gly Pro Glu Leu Pro Leu Leu Gly
 1               5                  10                  15

Leu Leu Leu Leu Leu Leu Leu Gly Asp Pro Gly Arg Gly Ala Ala Ser
                20                  25                  30

Ser Gly Asn Ala Thr Gly Pro Gly Pro Arg Ser Ala Gly Gly Ser Ala
                35                  40                  45

Arg Arg Ser Ala Ala Val Thr Gly Pro Pro Pro Leu Ser His Cys
 50                  55                  60

Gly Arg Ala Ala Pro Cys Glu Pro Leu Arg Tyr Asn Val Cys Leu Gly
 65                  70                  75                  80

Ser Val Leu Pro Tyr Gly Ala Thr Ser Thr Leu Leu Ala Gly Asp Ser
                85                  90                  95

Asp Ser Gln Glu Glu Ala His Gly Lys Leu Val Leu Trp Ser Gly Leu
                100                 105                 110

Arg Asn Ala Pro Arg Cys Trp Ala Val Ile Gln Pro Leu Leu Cys Ala
                115                 120                 125

Val Tyr Met Pro Lys Cys Glu Asn Asp Arg Val Glu Leu Pro Ser Arg
                130                 135                 140

Thr Leu Cys Gln Ala Thr Arg Gly Pro Cys Ala Ile Val Glu Arg Glu
145                 150                 155                 160

Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
                180                 185                 190

Cys Glu Val Pro Leu Val Arg Thr Asp Asn Pro Lys Ser Trp Tyr Glu
                195                 200                 205

Asp Val Glu Gly Cys Gly Ile Gln Cys Gln Asn Pro Leu Phe Thr Glu
                210                 215                 220

Ala Glu His Gln Asp Met His Ser Tyr Ile Ala Ala Phe Gly Ala Val
225                 230                 235                 240

Thr Gly Leu Cys Thr Leu Phe Thr Leu Ala Thr Phe Val Ala Asp Trp
                245                 250                 255

Arg Asn Ser Asn Arg Tyr Pro Ala Val Ile Leu Phe Tyr Val Asn Ala
                260                 265                 270
```

```
Cys Phe Phe Val Gly Ser Ile Gly Xaa Leu Ala Gln Phe Met Asp Gly
            275                 280                 285

Ala Arg Arg Glu Ile Val Cys Arg Ala Asp Gly Thr Met Arg Leu Gly
    290                 295                 300

Glu Pro Thr Ser Asn Glu Thr Leu Ser Cys Val Ile Ile Phe Val Ile
305                 310                 315                 320

Val Tyr Tyr Ala Leu Met Ala Gly Val Val Trp Phe Val Val Leu Thr
                325                 330                 335

Tyr Ala Trp His Thr Ser Phe Lys Ala Leu Gly Thr Thr Tyr Gln Pro
                340                 345                 350

Leu Ser Gly Lys Thr Ser Tyr Phe His Leu Leu Thr Trp Ser Leu Pro
            355                 360                 365

Phe Val Leu Thr Val Ala Ile Leu Ala Val Ala Gln Val Asp Gly Asp
370                 375                 380

Ser Val Ser Gly Ile Cys Phe Val Gly Tyr Lys Asn Tyr Arg Tyr Arg
385                 390                 395                 400

Ala Gly Phe Val Leu Ala Pro Ile Gly Leu Val Leu Ile Val Gly Gly
                405                 410                 415

Tyr Phe Leu Ile Arg Gly Val Met Thr Leu Phe Ser Ile Lys Ser Asn
                420                 425                 430

His Pro Gly Leu Leu Ser Glu Lys Ala Ala Ser Lys Ile Asn Glu Thr
            435                 440                 445

Met Leu Arg Leu Gly Ile Phe Gly Phe Leu Ala Phe Gly Phe Val Leu
    450                 455                 460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
                485                 490                 495

Gly Leu Pro Thr Lys Gln Pro Ile Pro Asp Cys Glu Ile Lys Asn Arg
                500                 505                 510

Pro Ser Leu Leu Val Glu Lys Ile Asn Leu Phe Ala Met Phe Gly Thr
            515                 520                 525

Gly Ile Ala Met Ser Thr Trp Val Trp Thr Lys Ala Thr Leu Leu Ile
    530                 535                 540

Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                565                 570                 575

His Glu Leu Leu Gln Asn Pro Gly Gln Glu Leu Ser Phe Ser Met His
            580                 585                 590

Thr Val Ser His Asp Gly Pro Val Ala Gly Leu Ala Phe Asp Leu Asn
            595                 600                 605

Glu Pro Ser Ala Asp Val Ser Ser Ala Trp Ala Gln His Val Thr Lys
    610                 615                 620

Met Val Ala Arg Arg Gly Ala Ile Leu Pro Gln Asp Ile Ser Val Thr
625                 630                 635                 640

Pro Val Ala Thr Pro Val Pro Glu Glu Gln Ala Asn Leu Trp Leu
                645                 650                 655

Val Glu Ala Glu Ile Ser Pro Glu Leu Gln Lys Arg Leu Gly Arg Lys
                660                 665                 670

Lys Lys Arg Arg Lys Arg Lys Glu Val Cys Pro Leu Ala Pro Pro
                675                 680                 685
```

```
Pro Glu Leu His Pro Pro Ala Pro Ala Pro Ser Thr Ile Pro Arg Leu
        690             695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
            725                 730                 735

Phe Cys Pro Glu Pro Ser Pro Gln Asp Pro Phe Leu Pro Ser Ala
            740             745             750

Pro Ala Pro Val Ala Trp Ala His Gly Arg Arg Gln Gly Leu Gly Pro
            755             760                 765

Ile His Ser Arg Thr Asn Leu Met Asp Thr Glu Leu Met Asp Ala Asp
770                 775                 780

Ser Asp Phe
785

<210> SEQ ID NO 3
<211> LENGTH: 787
<212> TYPE: PRT
<213> ORGANISM: Homo sapiens
<220> FEATURE:
<221> NAME/KEY: MOD_RES
<222> LOCATION: (459)..(459)
<223> OTHER INFORMATION: Any amino acid

<400> SEQUENCE: 3

Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
                20                  25                  30

Ser Gly Asn Ala Thr Gly Pro Gly Pro Arg Ser Ala Gly Gly Ser Ala
            35                  40                  45

Arg Arg Ser Ala Ala Val Thr Gly Pro Pro Pro Leu Ser His Cys
50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95

Asp Ser Gln Glu Glu Ala His Gly Lys Leu Val Leu Trp Ser Gly Leu
            100                 105                 110

Arg Asn Ala Pro Arg Cys Trp Ala Val Ile Gln Pro Leu Leu Cys Ala
        115                 120                 125

Val Tyr Met Pro Lys Cys Glu Asn Asp Arg Val Glu Leu Pro Ser Arg
        130                 135                 140

Thr Leu Cys Gln Ala Thr Arg Gly Pro Cys Ala Ile Val Glu Arg Glu
145                 150                 155                 160

Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
            180                 185                 190

Cys Glu Val Pro Leu Val Arg Thr Asp Asn Pro Lys Ser Trp Tyr Glu
        195                 200                 205

Asp Val Glu Gly Cys Gly Ile Gln Cys Gln Asn Pro Leu Phe Thr Glu
    210                 215                 220

Ala Glu His Gln Asp Met His Ser Tyr Ile Ala Ala Phe Gly Ala Val
225                 230                 235                 240

Thr Gly Leu Cys Thr Leu Phe Thr Leu Ala Thr Phe Val Ala Asp Trp
```

-continued

```
                245                 250                 255
Arg Asn Ser Asn Arg Tyr Pro Ala Val Ile Leu Phe Tyr Val Asn Ala
            260                 265                 270

Cys Phe Phe Val Gly Ser Ile Gly Trp Leu Ala Gln Phe Met Asp Gly
            275                 280                 285

Ala Arg Arg Glu Ile Val Cys Arg Ala Asp Gly Thr Met Arg Leu Gly
            290                 295                 300

Glu Pro Thr Ser Asn Glu Thr Leu Ser Cys Val Ile Ile Phe Val Ile
305                 310                 315                 320

Val Tyr Tyr Ala Leu Met Ala Gly Val Val Trp Phe Val Val Leu Thr
                325                 330                 335

Tyr Ala Trp His Thr Ser Phe Lys Ala Leu Gly Thr Thr Tyr Gln Pro
                340                 345                 350

Leu Ser Gly Lys Thr Ser Tyr Phe His Leu Leu Thr Trp Ser Leu Pro
                355                 360                 365

Phe Val Leu Thr Val Ala Ile Leu Ala Val Ala Gln Val Asp Gly Asp
            370                 375                 380

Ser Val Ser Gly Ile Cys Phe Val Gly Tyr Lys Asn Tyr Arg Tyr Arg
385                 390                 395                 400

Ala Gly Phe Val Leu Ala Pro Ile Gly Leu Val Leu Ile Val Gly Gly
                405                 410                 415

Tyr Phe Leu Ile Arg Gly Val Met Thr Leu Phe Ser Ile Lys Ser Asn
                420                 425                 430

His Pro Gly Leu Leu Ser Glu Lys Ala Ala Ser Lys Ile Asn Glu Thr
            435                 440                 445

Met Leu Arg Leu Gly Ile Phe Gly Phe Leu Xaa Phe Gly Phe Val Leu
450                 455                 460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
                485                 490                 495

Gly Leu Pro Thr Lys Gln Pro Ile Pro Asp Cys Glu Ile Lys Asn Arg
            500                 505                 510

Pro Ser Leu Leu Val Glu Lys Ile Asn Leu Phe Ala Met Phe Gly Thr
            515                 520                 525

Gly Ile Ala Met Ser Thr Trp Val Trp Thr Lys Ala Thr Leu Leu Ile
            530                 535                 540

Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                565                 570                 575

His Glu Leu Leu Gln Asn Pro Gly Gln Glu Leu Ser Phe Ser Met His
            580                 585                 590

Thr Val Ser His Asp Gly Pro Val Ala Gly Leu Ala Phe Asp Leu Asn
            595                 600                 605

Glu Pro Ser Ala Asp Val Ser Ser Ala Trp Ala Gln His Val Thr Lys
            610                 615                 620

Met Val Ala Arg Arg Gly Ala Ile Leu Pro Gln Asp Ile Ser Val Thr
625                 630                 635                 640

Pro Val Ala Thr Pro Val Pro Glu Glu Gln Ala Asn Leu Trp Leu
                645                 650                 655

Val Glu Ala Glu Ile Ser Pro Glu Leu Gln Lys Arg Leu Gly Arg Lys
            660                 665                 670
```

```
Lys Lys Arg Arg Lys Arg Lys Lys Glu Val Cys Pro Leu Ala Pro Pro
            675                 680                 685

Pro Glu Leu His Pro Pro Ala Pro Ala Pro Ser Thr Ile Pro Arg Leu
            690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Pro Gln Asp Pro Phe Leu Pro Ser Ala
                    740                 745                 750

Pro Ala Pro Val Ala Trp Ala His Gly Arg Arg Gln Gly Leu Gly Pro
                        755                 760                 765

Ile His Ser Arg Thr Asn Leu Met Asp Thr Glu Leu Met Asp Ala Asp
                            770                 775                 780

Ser Asp Phe
785

<210> SEQ ID NO 4
<211> LENGTH: 787
<212> TYPE: PRT
<213> ORGANISM: Homo sapiens
<220> FEATURE:
<221> NAME/KEY: MOD_RES
<222> LOCATION: (535)..(535)
<223> OTHER INFORMATION: Any amino acid

<400> SEQUENCE: 4

Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
                20                  25                  30

Ser Gly Asn Ala Thr Gly Pro Gly Pro Arg Ser Ala Gly Gly Ser Ala
            35                  40                  45

Arg Arg Ser Ala Ala Val Thr Gly Pro Pro Pro Leu Ser His Cys
50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95

Asp Ser Gln Glu Glu Ala His Gly Lys Leu Val Leu Trp Ser Gly Leu
            100                 105                 110

Arg Asn Ala Pro Arg Cys Trp Ala Val Ile Gln Pro Leu Leu Cys Ala
            115                 120                 125

Val Tyr Met Pro Lys Cys Glu Asn Asp Arg Val Glu Leu Pro Ser Arg
        130                 135                 140

Thr Leu Cys Gln Ala Thr Arg Gly Pro Cys Ala Ile Val Glu Arg Glu
145                 150                 155                 160

Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
            180                 185                 190

Cys Glu Val Pro Leu Val Arg Thr Asp Asn Pro Lys Ser Trp Tyr Glu
        195                 200                 205

Asp Val Glu Gly Cys Gly Ile Gln Cys Gln Asn Pro Leu Phe Thr Glu
    210                 215                 220
```

-continued

```
Ala Glu His Gln Asp Met His Ser Tyr Ile Ala Phe Gly Ala Val
225                 230                 235                 240

Thr Gly Leu Cys Thr Leu Phe Thr Leu Ala Thr Phe Val Ala Asp Trp
                245                 250                 255

Arg Asn Ser Asn Arg Tyr Pro Ala Val Ile Leu Phe Tyr Val Asn Ala
            260                 265                 270

Cys Phe Phe Val Gly Ser Ile Gly Trp Leu Ala Gln Phe Met Asp Gly
        275                 280                 285

Ala Arg Arg Glu Ile Val Cys Arg Ala Asp Gly Thr Met Arg Leu Gly
    290                 295                 300

Glu Pro Thr Ser Asn Glu Thr Leu Ser Cys Val Ile Ile Phe Val Ile
305                 310                 315                 320

Val Tyr Tyr Ala Leu Met Ala Gly Val Val Trp Phe Val Val Leu Thr
                325                 330                 335

Tyr Ala Trp His Thr Ser Phe Lys Ala Leu Gly Thr Thr Tyr Gln Pro
            340                 345                 350

Leu Ser Gly Lys Thr Ser Tyr Phe His Leu Leu Thr Trp Ser Leu Pro
        355                 360                 365

Phe Val Leu Thr Val Ala Ile Leu Ala Val Ala Gln Val Asp Gly Asp
    370                 375                 380

Ser Val Ser Gly Ile Cys Phe Val Gly Tyr Lys Asn Tyr Arg Tyr Arg
385                 390                 395                 400

Ala Gly Phe Val Leu Ala Pro Ile Gly Leu Val Leu Ile Val Gly Gly
                405                 410                 415

Tyr Phe Leu Ile Arg Gly Val Met Thr Leu Phe Ser Ile Lys Ser Asn
            420                 425                 430

His Pro Gly Leu Leu Ser Glu Lys Ala Ala Ser Lys Ile Asn Glu Thr
        435                 440                 445

Met Leu Arg Leu Gly Ile Phe Gly Phe Leu Ala Phe Gly Phe Val Leu
    450                 455                 460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
                485                 490                 495

Gly Leu Pro Thr Lys Gln Pro Ile Pro Asp Cys Glu Ile Lys Asn Arg
            500                 505                 510

Pro Ser Leu Leu Val Glu Lys Ile Asn Leu Phe Ala Met Phe Gly Thr
        515                 520                 525

Gly Ile Ala Met Ser Thr Xaa Val Trp Thr Lys Ala Thr Leu Leu Ile
    530                 535                 540

Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                565                 570                 575

His Glu Leu Leu Gln Asn Pro Gly Gln Glu Leu Ser Phe Ser Met His
            580                 585                 590

Thr Val Ser His Asp Gly Pro Val Ala Gly Leu Ala Phe Asp Leu Asn
        595                 600                 605

Glu Pro Ser Ala Asp Val Ser Ser Ala Trp Ala Gln His Val Thr Lys
    610                 615                 620

Met Val Ala Arg Arg Gly Ala Ile Leu Pro Gln Asp Ile Ser Val Thr
625                 630                 635                 640

Pro Val Ala Thr Pro Val Pro Pro Glu Glu Gln Ala Asn Leu Trp Leu
```

```
            645                 650                 655
Val Glu Ala Glu Ile Ser Pro Glu Leu Gln Lys Arg Leu Gly Arg Lys
            660                 665                 670

Lys Lys Arg Arg Lys Arg Lys Lys Glu Val Cys Pro Leu Ala Pro Pro
        675                 680                 685

Pro Glu Leu His Pro Pro Ala Pro Ala Pro Ser Thr Ile Pro Arg Leu
        690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Pro Gln Asp Pro Phe Leu Pro Ser Ala
                740                 745                 750

Pro Ala Pro Val Ala Trp Ala His Gly Arg Arg Gln Gly Leu Gly Pro
            755                 760                 765

Ile His Ser Arg Thr Asn Leu Met Asp Thr Glu Leu Met Asp Ala Asp
        770                 775                 780

Ser Asp Phe
785

<210> SEQ ID NO 5
<211> LENGTH: 2364
<212> TYPE: DNA
<213> ORGANISM: Homo sapiens

<400> SEQUENCE: 5
atggccgctg cccgcccagc gcgggggccg gagctcccgc tcctggggct gctgctgctg      60
ctgctgctgg ggacccgggg ccgggggccg gcctcgagcg ggaacgcgac cgggcctggg     120
cctcggagcg cgggcgggag cgcgaggagg agcgcggcg tgactggccc tccgccgccg     180
ctgagccact gcggccgggc tgccccctgc gagccgctgc gctacaacgt gtgcctgggc     240
tcggtgctgc cctacggggc cacctccaca ctgctggccg agactcggga ctcccaggag     300
gaagcgcacg gcaagctcgt gctctggtcg ggcctccgga tgccccccg ctgctgggca     360 gtgatccagc ccctgctgtg tgccgtatac atgcccaagt gtgagaatga ccgggtggag     420
ctgcccagcc gtaccctctg ccaggccacc cgaggcccct gtgccatcgt ggagagggag     480
cggggctggc ctgacttcct cgctgcact cctgaccgct tccctgaagg ctgcacgaat     540
gaggtgcaga acatcaagtt caacagttca ggccagtgcg aagtgccctt ggttcggaca     600 gacaaccca agagctggta cgaggacgtg gagggctgcg gcatccagtg ccagaacccg     660
ctcttcacag aggctgagca ccaggacatg cacagctaca tcgcggcctt cggggccgtc     720
acgggcctct gcacgctctt caccctggcc acattcgtgg ctgactggcg gaactcgaat     780
cgctaccctg ctgttattct cttctacgtc aatgcgtgct ctttgtggg cagcattggc     840 tggctggccc agttcatgga tggtgcccgc cgagagatcg tctgccgtgc agatggcacc     900
atgaggcttg gggagcccac tccaatgag actctgtcct gcgtcatcat ctttgtcatc     960
gtgtactacg ccctgatggc tggtgtggtt tggtttgtgg tcctcaccta tgcctggcac    1020
acttccttca aagccctggg caccacctac cagcctctct cgggcaagac ctcctacttc    1080
cacctgctca cctggtcact ccctttgtc ctcactgtgg caatccttgc tgtggcgcag    1140
gtggatgggg actctgtgag tggcatttgt tttgtgggct acaagaacta ccgataccgt    1200
gcgggcttcg tgctggcccc aatcggcctg gtgctcatcg tgggaggcta cttcctcatc    1260
```

```
cgaggagtca tgactctgtt ctccatcaag agcaaccacc ccgggctgct gagtgagaag    1320
gctgccagca agatcaacga gaccatgctg cgcctgggca ttttggctt cctggccttt     1380 ggctttgtgc tcattacctt cagctgccac ttctacgact tcttcaacca ggctgagtgg    1440
gagcgcagct tccgggacta tgtgctatgt caggccaatg tgaccatcgg gctgcccacc    1500
aagcagccca tccctgactg tgagatcaag aatcgcccga gccttctggt ggagaagatc    1560
aacctgtttg ccatgtttgg aactggcatc gccatgagca cctgggtctg gaccaaggcc    1620
acgctgctca tctggaggcg tacctggtgc aggttgactg ggcagagtga cgatgagcca    1680
aagcggatca agaagagcaa gatgattgcc aaggccttct ctaagcggca cgagctcctg    1740
cagaacccag gccaggagct gtccttcagc atgcacactg tgtcccacga cgggcccgtg    1800
gcgggcttgg cctttgacct caatgagccc tcagctgatg tctcctctgc ctgggcccag    1860
catgtcacca agatggtggc tcggagagga gccatactgc cccaggatat ttctgtcacc    1920
cctgtggcaa ctccagtgcc cccagaggaa caagccaacc tgtggctggt tgaggcagag    1980
atctccccag agctgcagaa cgcctgggc cggaagaaga agaggaggaa gaggaagaag     2040
gaggtgtgcc cgctggcgcc gccccctgag cttcaccccc ctgcccctgc ccccagtacc    2100
attcctcgac tgcctcagct gccccggcag aaatgcctgg tggctgcagg tgcctgggga    2160 gctgggact cttgccgaca gggagcgtgg accctggtct ccaacccatt ctgcccagag     2220
cccagtcccc ctcaggatcc atttctgccc agtgcaccgg ccccgtggc atgggctcat    2280 ggccgccgac agggcctggg gccattcac tcccgcacca acctgatgga cacagaactc     2340
atggatgcag actcggactt ctga                                            2364
```

<210> SEQ ID NO 6
<211> LENGTH: 787
<212> TYPE: PRT
<213> ORGANISM: Homo sapiens
<220> FEATURE:
<221> NAME/KEY: MOD_RES
<222> LOCATION: (241)..(241)
<223> OTHER INFORMATION: Any amino acid

<400> SEQUENCE: 6

```
Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
            20                  25                  30

Ser Gly Asn Ala Thr Gly Pro Gly Pro Arg Ser Ala Gly Gly Ser Ala
        35                  40                  45

Arg Arg Ser Ala Ala Val Thr Gly Pro Pro Pro Leu Ser His Cys
    50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95

Asp Ser Gln Glu Glu Ala His Gly Lys Leu Val Leu Trp Ser Gly Leu
            100                 105                 110

Arg Asn Ala Pro Arg Cys Trp Ala Val Ile Gln Pro Leu Leu Cys Ala
        115                 120                 125

Val Tyr Met Pro Lys Cys Glu Asn Asp Arg Val Glu Leu Pro Ser Arg
    130                 135                 140

Thr Leu Cys Gln Ala Thr Arg Gly Pro Cys Ala Ile Val Glu Arg Glu
145                 150                 155                 160
```

```
Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
            180                 185                 190

Cys Glu Val Pro Leu Val Arg Thr Asp Asn Pro Lys Ser Trp Tyr Glu
        195                 200                 205

Asp Val Glu Gly Cys Gly Ile Gln Cys Gln Asn Pro Leu Phe Thr Glu
    210                 215                 220

Ala Glu His Gln Asp Met His Ser Tyr Ile Ala Ala Phe Gly Ala Val
225                 230                 235                 240

Xaa Gly Leu Cys Thr Leu Phe Thr Leu Ala Thr Phe Val Ala Asp Trp
                245                 250                 255

Arg Asn Ser Asn Arg Tyr Pro Ala Val Ile Leu Phe Tyr Val Asn Ala
            260                 265                 270

Cys Phe Phe Val Gly Ser Ile Gly Trp Leu Ala Gln Phe Met Asp Gly
        275                 280                 285

Ala Arg Arg Glu Ile Val Cys Arg Ala Asp Gly Thr Met Arg Leu Gly
    290                 295                 300

Glu Pro Thr Ser Asn Glu Thr Leu Ser Cys Val Ile Ile Phe Val Ile
305                 310                 315                 320

Val Tyr Tyr Ala Leu Met Ala Gly Val Val Trp Phe Val Val Leu Thr
                325                 330                 335

Tyr Ala Trp His Thr Ser Phe Lys Ala Leu Gly Thr Thr Tyr Gln Pro
            340                 345                 350

Leu Ser Gly Lys Thr Ser Tyr Phe His Leu Leu Thr Trp Ser Leu Pro
        355                 360                 365

Phe Val Leu Thr Val Ala Ile Leu Ala Val Ala Gln Val Asp Gly Asp
    370                 375                 380

Ser Val Ser Gly Ile Cys Phe Val Gly Tyr Lys Asn Tyr Arg Tyr Arg
385                 390                 395                 400

Ala Gly Phe Val Leu Ala Pro Ile Gly Leu Val Leu Ile Val Gly Gly
                405                 410                 415

Tyr Phe Leu Ile Arg Gly Val Met Thr Leu Phe Ser Ile Lys Ser Asn
            420                 425                 430

His Pro Gly Leu Leu Ser Glu Lys Ala Ala Ser Lys Ile Asn Glu Thr
        435                 440                 445

Met Leu Arg Leu Gly Ile Phe Gly Phe Leu Ala Phe Gly Phe Val Leu
    450                 455                 460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
                485                 490                 495

Gly Leu Pro Thr Lys Gln Pro Ile Pro Asp Cys Glu Ile Lys Asn Arg
            500                 505                 510

Pro Ser Leu Leu Val Glu Lys Ile Asn Leu Phe Ala Met Phe Gly Thr
        515                 520                 525

Gly Ile Ala Met Ser Thr Trp Val Trp Thr Lys Ala Thr Leu Leu Ile
    530                 535                 540

Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                565                 570                 575
```

His Glu Leu Leu Gln Asn Pro Gly Gln Glu Leu Ser Phe Ser Met His
                580                 585                 590

Thr Val Ser His Asp Gly Pro Val Ala Gly Leu Ala Phe Asp Leu Asn
            595                 600                 605

Glu Pro Ser Ala Asp Val Ser Ser Ala Trp Ala Gln His Val Thr Lys
        610                 615                 620

Met Val Ala Arg Arg Gly Ala Ile Leu Pro Gln Asp Ile Ser Val Thr
625                 630                 635                 640

Pro Val Ala Thr Pro Val Pro Pro Glu Glu Gln Ala Asn Leu Trp Leu
                645                 650                 655

Val Glu Ala Glu Ile Ser Pro Glu Leu Gln Lys Arg Leu Gly Arg Lys
            660                 665                 670

Lys Lys Arg Arg Lys Arg Lys Lys Glu Val Cys Pro Leu Ala Pro Pro
        675                 680                 685

Pro Glu Leu His Pro Pro Ala Pro Ala Pro Ser Thr Ile Pro Arg Leu
690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Gln Asp Pro Phe Leu Pro Ser Ala
            740                 745                 750

Pro Ala Pro Val Ala Trp Ala His Gly Arg Arg Gln Gly Leu Gly Pro
        755                 760                 765

Ile His Ser Arg Thr Asn Leu Met Asp Thr Glu Leu Met Asp Ala Asp
770                 775                 780

Ser Asp Phe
785

<210> SEQ ID NO 7
<211> LENGTH: 787
<212> TYPE: PRT
<213> ORGANISM: Homo sapiens
<220> FEATURE:
<221> NAME/KEY: MOD_RES
<222> LOCATION: (408)..(408)
<223> OTHER INFORMATION: Any amino acid

<400> SEQUENCE: 7

Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
                20                  25                  30

Ser Gly Asn Ala Thr Gly Pro Gly Pro Arg Ser Ala Gly Gly Ser Ala
            35                  40                  45

Arg Arg Ser Ala Ala Val Thr Gly Pro Pro Pro Leu Ser His Cys
    50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95

Asp Ser Gln Glu Glu Ala His Gly Lys Leu Val Leu Trp Ser Gly Leu
            100                 105                 110

Arg Asn Ala Pro Arg Cys Trp Ala Val Ile Gln Pro Leu Leu Cys Ala
        115                 120                 125

Val Tyr Met Pro Lys Cys Glu Asn Asp Arg Val Glu Leu Pro Ser Arg

```
            130                 135                 140
Thr Leu Cys Gln Ala Thr Arg Gly Pro Cys Ala Ile Val Glu Arg Glu
145                 150                 155                 160

Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
                180                 185                 190

Cys Glu Val Pro Leu Val Arg Thr Asp Asn Pro Lys Ser Trp Tyr Glu
                195                 200                 205

Asp Val Glu Gly Cys Gly Ile Gln Cys Gln Asn Pro Leu Phe Thr Glu
            210                 215                 220

Ala Glu His Gln Asp Met His Ser Tyr Ile Ala Ala Phe Gly Ala Val
225                 230                 235                 240

Thr Gly Leu Cys Thr Leu Phe Thr Leu Ala Thr Phe Val Ala Asp Trp
                245                 250                 255

Arg Asn Ser Asn Arg Tyr Pro Ala Val Ile Leu Phe Tyr Val Asn Ala
                260                 265                 270

Cys Phe Phe Val Gly Ser Ile Gly Trp Leu Ala Gln Phe Met Asp Gly
            275                 280                 285

Ala Arg Arg Glu Ile Val Cys Arg Ala Asp Gly Thr Met Arg Leu Gly
290                 295                 300

Glu Pro Thr Ser Asn Glu Thr Leu Ser Cys Val Ile Ile Phe Val Ile
305                 310                 315                 320

Val Tyr Tyr Ala Leu Met Ala Gly Val Val Trp Phe Val Val Leu Thr
                325                 330                 335

Tyr Ala Trp His Thr Ser Phe Lys Ala Leu Gly Thr Thr Tyr Gln Pro
                340                 345                 350

Leu Ser Gly Lys Thr Ser Tyr Phe His Leu Leu Thr Trp Ser Leu Pro
                355                 360                 365

Phe Val Leu Thr Val Ala Ile Leu Ala Val Ala Gln Val Asp Gly Asp
            370                 375                 380

Ser Val Ser Gly Ile Cys Phe Val Gly Tyr Lys Asn Tyr Arg Tyr Arg
385                 390                 395                 400

Ala Gly Phe Val Leu Ala Pro Xaa Gly Leu Val Leu Ile Val Gly Gly
                405                 410                 415

Tyr Phe Leu Ile Arg Gly Val Met Thr Leu Phe Ser Ile Lys Ser Asn
                420                 425                 430

His Pro Gly Leu Leu Ser Glu Lys Ala Ala Ser Lys Ile Asn Glu Thr
            435                 440                 445

Met Leu Arg Leu Gly Ile Phe Gly Phe Leu Ala Phe Gly Phe Val Leu
450                 455                 460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
                485                 490                 495

Gly Leu Pro Thr Lys Gln Pro Ile Pro Asp Cys Glu Ile Lys Asn Arg
                500                 505                 510

Pro Ser Leu Leu Val Glu Lys Ile Asn Leu Phe Ala Met Phe Gly Thr
            515                 520                 525

Gly Ile Ala Met Ser Thr Trp Val Trp Thr Lys Ala Thr Leu Leu Ile
530                 535                 540

Trp Arg Arg Thr Trp Cys Arg Leu Thr Gly Gln Ser Asp Asp Glu Pro
545                 550                 555                 560
```

```
Lys Arg Ile Lys Lys Ser Lys Met Ile Ala Lys Ala Phe Ser Lys Arg
                565                 570                 575

His Glu Leu Leu Gln Asn Pro Gly Gln Glu Leu Ser Phe Ser Met His
            580                 585                 590

Thr Val Ser His Asp Gly Pro Val Ala Gly Leu Ala Phe Asp Leu Asn
        595                 600                 605

Glu Pro Ser Ala Asp Val Ser Ser Ala Trp Ala Gln His Val Thr Lys
    610                 615                 620

Met Val Ala Arg Arg Gly Ala Ile Leu Pro Gln Asp Ile Ser Val Thr
625                 630                 635                 640

Pro Val Ala Thr Pro Val Pro Glu Glu Gln Ala Asn Leu Trp Leu
                645                 650                 655

Val Glu Ala Glu Ile Ser Pro Glu Leu Gln Lys Arg Leu Gly Arg Lys
                660                 665                 670

Lys Lys Arg Arg Lys Arg Lys Lys Glu Val Cys Pro Leu Ala Pro Pro
            675                 680                 685

Pro Glu Leu His Pro Pro Ala Pro Ala Pro Ser Thr Ile Pro Arg Leu
    690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Gln Asp Pro Phe Leu Pro Ser Ala
                740                 745                 750

Pro Ala Pro Val Ala Trp Ala His Gly Arg Arg Gln Gly Leu Gly Pro
            755                 760                 765

Ile His Ser Arg Thr Asn Leu Met Asp Thr Glu Leu Met Asp Ala Asp
    770                 775                 780

Ser Asp Phe
785

<210> SEQ ID NO 8
<211> LENGTH: 787
<212> TYPE: PRT
<213> ORGANISM: Homo sapiens
<220> FEATURE:
<221> NAME/KEY: MOD_RES
<222> LOCATION: (469)..(469)
<223> OTHER INFORMATION: Any amino acid

<400> SEQUENCE: 8

Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
            20                  25                  30

Ser Gly Asn Ala Thr Gly Pro Gly Pro Arg Ser Ala Gly Gly Ser Ala
        35                  40                  45

Arg Arg Ser Ala Ala Val Thr Gly Pro Pro Pro Leu Ser His Cys
    50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95

Asp Ser Gln Glu Glu Ala His Gly Lys Leu Val Leu Trp Ser Gly Leu
            100                 105                 110
```

-continued

```
Arg Asn Ala Pro Arg Cys Trp Ala Val Ile Gln Pro Leu Leu Cys Ala
            115                 120                 125
Val Tyr Met Pro Lys Cys Glu Asn Asp Arg Val Glu Leu Pro Ser Arg
130                 135                 140
Thr Leu Cys Gln Ala Thr Arg Gly Pro Cys Ala Ile Val Glu Arg Glu
145                 150                 155                 160
Arg Gly Trp Pro Asp Phe Leu Arg Cys Thr Pro Asp Arg Phe Pro Glu
                165                 170                 175
Gly Cys Thr Asn Glu Val Gln Asn Ile Lys Phe Asn Ser Ser Gly Gln
            180                 185                 190
Cys Glu Val Pro Leu Val Arg Thr Asp Asn Pro Lys Ser Trp Tyr Glu
        195                 200                 205
Asp Val Glu Gly Cys Gly Ile Gln Cys Gln Asn Pro Leu Phe Thr Glu
210                 215                 220
Ala Glu His Gln Asp Met His Ser Tyr Ile Ala Ala Phe Gly Ala Val
225                 230                 235                 240
Thr Gly Leu Cys Thr Leu Phe Thr Leu Ala Thr Phe Val Ala Asp Trp
                245                 250                 255
Arg Asn Ser Asn Arg Tyr Pro Ala Val Ile Leu Phe Tyr Val Asn Ala
            260                 265                 270
Cys Phe Phe Val Gly Ser Ile Gly Trp Leu Ala Gln Phe Met Asp Gly
        275                 280                 285
Ala Arg Arg Glu Ile Val Cys Arg Ala Asp Gly Thr Met Arg Leu Gly
290                 295                 300
Glu Pro Thr Ser Asn Glu Thr Leu Ser Cys Val Ile Ile Phe Val Ile
305                 310                 315                 320
Val Tyr Tyr Ala Leu Met Ala Gly Val Val Trp Phe Val Val Leu Thr
                325                 330                 335
Tyr Ala Trp His Thr Ser Phe Lys Ala Leu Gly Thr Thr Tyr Gln Pro
            340                 345                 350
Leu Ser Gly Lys Thr Ser Tyr Phe His Leu Leu Thr Trp Ser Leu Pro
        355                 360                 365
Phe Val Leu Thr Val Ala Ile Leu Ala Val Ala Gln Val Asp Gly Asp
370                 375                 380
Ser Val Ser Gly Ile Cys Phe Val Gly Tyr Lys Asn Tyr Arg Tyr Arg
385                 390                 395                 400
Ala Gly Phe Val Leu Ala Pro Ile Gly Leu Val Leu Ile Val Gly Gly
                405                 410                 415
Tyr Phe Leu Ile Arg Gly Val Met Thr Leu Phe Ser Ile Lys Ser Asn
            420                 425                 430
His Pro Gly Leu Leu Ser Glu Lys Ala Ala Ser Lys Ile Asn Glu Thr
        435                 440                 445
Met Leu Arg Leu Gly Ile Phe Gly Phe Leu Ala Phe Gly Phe Val Leu
450                 455                 460
Ile Thr Phe Ser Xaa His Phe Tyr Asp Phe Phe Asn Gln Ala Glu Trp
465                 470                 475                 480
Glu Arg Ser Phe Arg Asp Tyr Val Leu Cys Gln Ala Asn Val Thr Ile
                485                 490                 495
Gly Leu Pro Thr Lys Gln Pro Ile Pro Asp Cys Glu Ile Lys Asn Arg
            500                 505                 510
Pro Ser Leu Leu Val Glu Lys Ile Asn Leu Phe Ala Met Phe Gly Thr
        515                 520                 525
Gly Ile Ala Met Ser Thr Trp Val Trp Thr Lys Ala Thr Leu Leu Ile
```

```
                530             535             540
Trp Arg Arg Thr Trp Cys Arg Leu Thr Gly Gln Ser Asp Asp Glu Pro
545                 550             555             560

Lys Arg Ile Lys Lys Ser Lys Met Ile Ala Lys Ala Phe Ser Lys Arg
                565             570             575

His Glu Leu Leu Gln Asn Pro Gly Gln Glu Leu Ser Phe Ser Met His
            580             585             590

Thr Val Ser His Asp Gly Pro Val Ala Gly Leu Ala Phe Asp Leu Asn
        595             600             605

Glu Pro Ser Ala Asp Val Ser Ser Ala Trp Ala Gln His Val Thr Lys
610             615             620

Met Val Ala Arg Arg Gly Ala Ile Leu Pro Gln Asp Ile Ser Val Thr
625             630             635             640

Pro Val Ala Thr Pro Val Pro Glu Gln Ala Asn Leu Trp Leu
                645             650             655

Val Glu Ala Glu Ile Ser Pro Glu Leu Gln Lys Arg Leu Gly Arg Lys
                660             665             670

Lys Lys Arg Arg Lys Arg Lys Lys Glu Val Cys Pro Leu Ala Pro Pro
            675             680             685

Pro Glu Leu His Pro Pro Ala Pro Ala Pro Ser Thr Ile Pro Arg Leu
            690             695             700

Pro Gln Leu Pro Arg Gln Lys Cys Leu Val Ala Ala Gly Ala Trp Gly
705             710             715             720

Ala Gly Asp Ser Cys Arg Gln Gly Ala Trp Thr Leu Val Ser Asn Pro
                725             730             735

Phe Cys Pro Glu Pro Ser Pro Pro Gln Asp Pro Phe Leu Pro Ser Ala
                740             745             750

Pro Ala Pro Val Ala Trp Ala His Gly Arg Arg Gln Gly Leu Gly Pro
            755             760             765

Ile His Ser Arg Thr Asn Leu Met Asp Thr Glu Leu Met Asp Ala Asp
        770             775             780

Ser Asp Phe
785

<210> SEQ ID NO 9
<211> LENGTH: 787
<212> TYPE: PRT
<213> ORGANISM: Homo sapiens
<220> FEATURE:
<221> NAME/KEY: MOD_RES
<222> LOCATION: (533)..(533)
<223> OTHER INFORMATION: Any amino acid

<400> SEQUENCE: 9

Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
                20                  25                  30

Ser Gly Asn Ala Thr Gly Pro Gly Pro Arg Ser Ala Gly Gly Ser Ala
            35                  40                  45

Arg Arg Ser Ala Ala Val Thr Gly Pro Pro Pro Leu Ser His Cys
        50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95
```

-continued

```
Asp Ser Gln Glu Glu Ala His Gly Lys Leu Val Leu Trp Ser Gly Leu
            100                 105                 110

Arg Asn Ala Pro Arg Cys Trp Ala Val Ile Gln Pro Leu Leu Cys Ala
        115                 120                 125

Val Tyr Met Pro Lys Cys Glu Asn Asp Arg Val Glu Leu Pro Ser Arg
130                 135                 140

Thr Leu Cys Gln Ala Thr Arg Gly Pro Cys Ala Ile Val Glu Arg Glu
145                 150                 155                 160

Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
            180                 185                 190

Cys Glu Val Pro Leu Val Arg Thr Asp Asn Pro Lys Ser Trp Tyr Glu
        195                 200                 205

Asp Val Glu Gly Cys Gly Ile Gln Cys Gln Asn Pro Leu Phe Thr Glu
210                 215                 220

Ala Glu His Gln Asp Met His Ser Tyr Ile Ala Ala Phe Gly Ala Val
225                 230                 235                 240

Thr Gly Leu Cys Thr Leu Phe Thr Leu Ala Thr Phe Val Ala Asp Trp
                245                 250                 255

Arg Asn Ser Asn Arg Tyr Pro Ala Val Ile Leu Phe Tyr Val Asn Ala
            260                 265                 270

Cys Phe Phe Val Gly Ser Ile Gly Trp Leu Ala Gln Phe Met Asp Gly
        275                 280                 285

Ala Arg Arg Glu Ile Val Cys Arg Ala Asp Gly Thr Met Arg Leu Gly
290                 295                 300

Glu Pro Thr Ser Asn Glu Thr Leu Ser Cys Val Ile Ile Phe Val Ile
305                 310                 315                 320

Val Tyr Tyr Ala Leu Met Ala Gly Val Val Trp Phe Val Val Leu Thr
                325                 330                 335

Tyr Ala Trp His Thr Ser Phe Lys Ala Leu Gly Thr Thr Tyr Gln Pro
            340                 345                 350

Leu Ser Gly Lys Thr Ser Tyr Phe His Leu Leu Thr Trp Ser Leu Pro
        355                 360                 365

Phe Val Leu Thr Val Ala Ile Leu Ala Val Ala Gln Val Asp Gly Asp
370                 375                 380

Ser Val Ser Gly Ile Cys Phe Val Gly Tyr Lys Asn Tyr Arg Tyr Arg
385                 390                 395                 400

Ala Gly Phe Val Leu Ala Pro Ile Gly Leu Val Leu Ile Val Gly Gly
                405                 410                 415

Tyr Phe Leu Ile Arg Gly Val Met Thr Leu Phe Ser Ile Lys Ser Asn
            420                 425                 430

His Pro Gly Leu Leu Ser Glu Lys Ala Ala Ser Lys Ile Asn Glu Thr
        435                 440                 445

Met Leu Arg Leu Gly Ile Phe Gly Phe Leu Ala Phe Gly Phe Val Leu
450                 455                 460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
                485                 490                 495

Gly Leu Pro Thr Lys Gln Pro Ile Pro Asp Cys Glu Ile Lys Asn Arg
            500                 505                 510
```

-continued

```
Pro Ser Leu Leu Val Glu Lys Ile Asn Leu Phe Ala Met Phe Gly Thr
        515                 520                 525

Gly Ile Ala Met Xaa Thr Trp Val Trp Thr Lys Ala Thr Leu Leu Ile
    530                 535                 540

Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                565                 570                 575

His Glu Leu Leu Gln Asn Pro Gly Gln Glu Leu Ser Phe Ser Met His
            580                 585                 590

Thr Val Ser His Asp Gly Pro Val Ala Gly Leu Ala Phe Asp Leu Asn
        595                 600                 605

Glu Pro Ser Ala Asp Val Ser Ser Ala Trp Ala Gln His Val Thr Lys
    610                 615                 620

Met Val Ala Arg Arg Gly Ala Ile Leu Pro Gln Asp Ile Ser Val Thr
625                 630                 635                 640

Pro Val Ala Thr Pro Val Pro Pro Glu Glu Gln Ala Asn Leu Trp Leu
                645                 650                 655

Val Glu Ala Glu Ile Ser Pro Glu Leu Gln Lys Arg Leu Gly Arg Lys
            660                 665                 670

Lys Lys Arg Arg Lys Arg Lys Lys Glu Val Cys Pro Leu Ala Pro Pro
        675                 680                 685

Pro Glu Leu His Pro Pro Ala Pro Ala Pro Ser Thr Ile Pro Arg Leu
    690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Gln Asp Pro Phe Leu Pro Ser Ala
            740                 745                 750

Pro Ala Pro Val Ala Trp Ala His Gly Arg Arg Gln Gly Leu Gly Pro
        755                 760                 765

Ile His Ser Arg Thr Asn Leu Met Asp Thr Glu Leu Met Asp Ala Asp
    770                 775                 780

Ser Asp Phe
785

<210> SEQ ID NO 10
<211> LENGTH: 484
<212> TYPE: PRT
<213> ORGANISM: Homo sapiens

<400> SEQUENCE: 10

Met Ala Glu Leu Arg Pro Ser Gly Ala Pro Gly Pro Thr Ala Pro Pro
1               5                   10                  15

Ala Pro Gly Pro Thr Ala Pro Ala Phe Ala Ser Leu Phe Pro Pro
            20                  25                  30

Gly Leu His Ala Ile Tyr Gly Glu Cys Arg Arg Leu Tyr Pro Asp Gln
        35                  40                  45

Pro Asn Pro Leu Gln Val Thr Ala Ile Val Lys Tyr Trp Leu Gly Gly
    50                  55                  60

Pro Asp Pro Leu Asp Tyr Val Ser Met Tyr Arg Asn Val Gly Ser Pro
65                  70                  75                  80

Ser Ala Asn Ile Pro Glu His Trp His Tyr Ile Ser Phe Gly Leu Ser
                85                  90                  95
```

Asp Leu Tyr Gly Asp Asn Arg Val His Glu Phe Thr Gly Thr Asp Gly
            100                 105                 110

Pro Ser Gly Phe Gly Phe Glu Leu Thr Phe Arg Leu Lys Arg Glu Thr
        115                 120                 125

Gly Glu Ser Ala Pro Pro Thr Trp Pro Ala Glu Leu Met Gln Gly Leu
130                 135                 140

Ala Arg Tyr Val Phe Gln Ser Glu Asn Thr Phe Cys Ser Gly Asp His
145                 150                 155                 160

Val Ser Trp His Ser Pro Leu Asp Asn Ser Glu Ser Arg Ile Gln His
                165                 170                 175

Met Leu Leu Thr Glu Asp Pro Gln Met Gln Pro Val Gln Thr Pro Phe
            180                 185                 190

Gly Val Val Thr Phe Leu Gln Ile Val Gly Val Cys Thr Glu Glu Leu
        195                 200                 205

His Ser Ala Gln Gln Trp Asn Gly Gln Gly Ile Leu Glu Leu Leu Arg
210                 215                 220

Thr Val Pro Ile Ala Gly Gly Pro Trp Leu Ile Thr Asp Met Arg Arg
225                 230                 235                 240

Gly Glu Thr Ile Phe Glu Ile Asp Pro His Leu Gln Glu Arg Val Asp
                245                 250                 255

Lys Gly Ile Glu Thr Asp Gly Ser Asn Leu Ser Gly Val Ser Ala Lys
            260                 265                 270

Cys Ala Trp Asp Asp Leu Ser Arg Pro Pro Glu Asp Asp Glu Asp Ser
        275                 280                 285

Arg Ser Ile Cys Ile Gly Thr Gln Pro Arg Arg Leu Ser Gly Lys Asp
290                 295                 300

Thr Glu Gln Ile Arg Glu Thr Leu Arg Arg Gly Leu Glu Ile Asn Ser
305                 310                 315                 320

Lys Pro Val Leu Pro Pro Ile Asn Pro Gln Arg Gln Asn Gly Leu Ala
                325                 330                 335

His Asp Arg Ala Pro Ser Arg Lys Asp Ser Leu Glu Ser Asp Ser Ser
            340                 345                 350

Thr Ala Ile Ile Pro His Glu Leu Ile Arg Thr Arg Gln Leu Glu Ser
        355                 360                 365

Val His Leu Lys Phe Asn Gln Glu Ser Gly Ala Leu Ile Pro Leu Cys
370                 375                 380

Leu Arg Gly Arg Leu Leu His Gly Arg His Phe Thr Tyr Lys Ser Ile
385                 390                 395                 400

Thr Gly Asp Met Ala Ile Thr Phe Val Ser Thr Gly Val Glu Gly Ala
                405                 410                 415

Phe Ala Thr Glu Glu His Pro Tyr Ala Ala His Gly Pro Trp Leu Gln
            420                 425                 430

Ile Leu Leu Thr Glu Glu Phe Val Lys Met Leu Glu Asp Leu Glu
        435                 440                 445

Asp Leu Thr Ser Pro Glu Glu Phe Lys Leu Pro Lys Glu Tyr Ser Trp
        450                 455                 460

Pro Glu Lys Lys Leu Lys Val Ser Ile Leu Pro Asp Val Val Phe Asp
465                 470                 475                 480

Ser Pro Leu His

<210> SEQ ID NO 11
<211> LENGTH: 4898
<212> TYPE: DNA

<213> ORGANISM: Homo sapiens

<400> SEQUENCE: 11

```
cgccgtgcgc aggcgcggag ctagacctcg ctgcagcccc catcgcctcg gggagtctca      60
cccaccgagt ccgcccgctg gcccgtcagt gctctcccg tcgtttgccc tctccagttc     120
ccccagtgcc tgccctacgc accccgatgg cggagctgcg gcctagcggc gccccggcc     180
ccaccgcgcc cccggcccct ggcccgactg ccccccccggc cttcgcttcg ctcttttcccc   240
cgggactgca cgccatctac ggagagtgcc gccgccttta ccctgaccag ccgaacccgc    300
tccaggttac cgctatcgtc aagtactggt tgggtggccc agacccttg gactatgtta     360
gcatgtacag gaatgtgggg agcccttctg ctaacatccc cgagcactgg cactacatca    420
gcttcggcct gagtgatctc tatggtgaca acagagtcca tgagtttaca ggaacagatg    480
gacctagtgg ttttggcttt gagttgacct ttcgtctgaa gagagaaact ggggagtctg    540
ccccaccaac atggcccgca gagttaatgc agggcttggc acgatacgtg ttccagtcag    600
agaacaccttt ctgcagtggg gaccatgtgt cctggcacag ccctttggat aacagtgagt   660
caagaattca gcacatgctg ctgacagagg acccacagat gcagcccgtg cagacaccct    720
ttggggtagt taccttcctc cagatcgttg gtgtctgcac tgaagagcta cactcagccc    780
agcagtggaa cgggcagggc atcctggagc tgctgcggac agtgccatt gctggcggcc     840
cctggctgat aactgacatg cggaggggag agaccatatt tgagatcgat ccacacctgc    900
aagagagagt tgacaaaggc atcgagacag atggctccaa cctgagtggt gtcagtgcca    960
agtgtgcctg ggatgacctg agccggcccc ccgaggatga cgaggacagc cggagcatct   1020
gcatcggcac acagcccgg cgactctctg gcaaagacac agagcagatc cgggagaccc   1080
tgaggagagg actcgagatc aacagcaaac ctgtccttcc accaatcaac cctcagcggc   1140
agaatggcct cgcccacgac cgggccccga ccgcaaaga cagcctggaa agtgacagct   1200
ccacggccat cattccccat gagctgattc gcacgcggca gcttgagagc gtacatctga    1260
aattcaacca ggagtccgga gccctcattc ctctctgcct aaggggcagg ctcctgcatg   1320
gacggcactt tacatataaa agtatcacag gtgacatggc catcacgttt gtctccacgg   1380
gagtggaagg cgcctttgcc actgaggagc atccttacgc ggctcatgga ccctggttac   1440
aaattctgtt gaccgaagag tttgtagaga aaatgtttga ggatttaga gatttgactt    1500
ctccagagga attcaaactt cccaaagagt acagctggcc tgaaaagaag ctgaaggtct   1560
ccatcctgcc tgacgtggtg ttcgacagtc cgctacacta gcctgggctg ggccctgcag   1620
gggccagcag ggagcccagc tgctccccag tgacttccag tgtaacagtt gtgtcaacga    1680
gatctccaca aataaaagga caagtgtgag gaagactgcg cagtgccacc ccgcagccca    1740
gtggggtgcc atgcacaggc cacaggccct ccacctcacc tccagctcag ggccgcacc    1800
ccgccgctgg ctaagccttg tgacccatca ggccagtgag tgggcaaatg cggaccctcc   1860
ctgcctgcag cctgcacaga ttctggtttg aggtttgact ctggaccctg ctgtgcccc    1920
taggtggaga cagccctctt tctcacctac ccctgccgc acagcccagc aggagggagg    1980
cggacagcca gatgcagagc gagtggatgc acttcccagc tcatctctgg aagcctttgc    2040
tactcaagct cctctggccg cggaacaatt cctctgatca tgtttggttt tcttcttcct   2100
tattttattt tgtagaaacc gggtggtatt ttattgctct gcaaagatgt ccagaagcca   2160
tgtatataat gttttttaaa cagaacttca ttccccgttg aactttcgca ttctctgaca   2220
gaggcctagg gctgtatctc tccctgggct gccaccagag aaggtgcttg gtgttcgcct   2280
```

```
gccagcccag agccctggag gagccggctg cacagagagg cttttcttcc cagctgggcc    2340
tgatggagcc cggggcaggg ggagagtaga gacactccct tgtgcagctt tgagcctagt    2400
ttagctgggg ccagggaggg gtgctactgt tttccaagtg aatgggtctc aaagacttgg    2460
tgaccccagc ctcatcttct aggccttttc catccaacca ggcctacctg ggagagggtg    2520
aggttcagca catcacacac catccccact gtcattcagg gcctgggtct ccagctctgt    2580
aaccagtcct gtcccatttc ctcagtccct gggcctccca gccttcaggc tgtagggctg    2640
ccttactaaa attgaaaaat ccacctctta acatctcttt cactttggtt ttgctaacac    2700
tgctctctgc tgccctccca tcctccctgt atccattcat gccctatctt tcattctcca    2760
ctcctaatcc ctctcctttc tggcatcctg gcctctcgtg gtcctcagcc cctcaccccc    2820
agtactgcag atctcacagt ttgccttcca gaagccagcc tatctctagc ccatggtttt    2880
ggagttcctc tcgggttatc tcccacgcct gacctggaac cagcaagccc ctttcctgcc    2940
ttcttacccc caactctagg gatgggactg ttacaatact tcaagatcac tctttacacc    3000
tcttcaaagc aaagtcatga caatgcaggg ctcctcattg ctcccatctg cctctgctgc    3060
acacacaggc accagcaggg atgccacagg agtgcccaca gggtgcagga ctccactgat    3120
gagagatcca gccaaagagc tgcccccagg ggtatgaggg caccagctgg gttctccagg    3180
gagcaggagt tggacctcca tggagccact aggcctggcc tcctctacac atccccaggg    3240
ctatctggtt aattccatca agctcagagt taaaaggcat atcagcctgg agtatttggg    3300
agagactggc tgcagatccc cgccagccaa gatgcaagcc actcgggacc tgatgtcggc    3360
agctgtgcct ctactgccct gaggacttac cagagggagc cctactggcc ttcccccacc    3420
acagcagccc tgcctgtgaa gctcttgttt ctgacatttc acaggcagag aggtgccatc    3480
agttcgcctc cattccttgc caccatgacc agcctctccc tgaactctct cttgctcggg    3540
acctgcctga gggctccctg ctgcagttcg ccgtacttcc atctgctggg tgcctccatc    3600
gttggttggg tggggatggg gcattttctg agctaagctt tgtcattagt ttgtgaagca    3660
cctggtcagc aacctgcccc agacctggag ggtctttgtg gactgaaggt agacaccagc    3720
cagcatggtg gccctgttct gggggagcag ggtaaggcag gaggaagtgg gtgagctccg    3780
agatgatgag cacatgaagc ctgtggcccc ttcgtacctg caatatgtca ggagcctcac    3840
gctcacccaa gatcctgcag gggccaggct ccatctcact ggctctgagg gcaggacagg    3900
gtatcacaca tttctcacca ggcctccttt cctatgggca ttggtgcctc ccagaggttt    3960
cttgggctgc tggctggtga gagaggaccc ttaaagaaga tcaagccaag ctgaccttgg    4020
accctgtcca gcacagcttc tggcacagga tgcttggtga atgtacccct tctttccctc    4080
cctgcagctc tgagggagcc cctgaccttg tagtgggtgg aggaggtaag gggcctccct    4140
ccctaaatct gcctcttctg caagctactt ggagacttgc ctagttgtac ccaccccctcc    4200 aggtccctgg tgctagagct tctgagaagg gcctttccct ttcctctttg cctgctatat    4260
aaggcaggct cctgtggctc tgctggctca gtgtgggctg caggaggact gcagactcag    4320
ctgcaattct gagggggggtt tgggaggctt gtgcgaggtc tcaggcctgt gtggggagct    4380
ggtgcctctt cctgcccgta tctttctctt ccaagggcag tgctccaagg cagggactgg    4440
agaagccaag gggagagtct aaaagggcta gagcattttt aaaaatagac acagggtctt    4500
gggactgggg tttcggattg agttgcaagc agggagaaaa cctgaaggtc ggtgcccta    4560 tggggctgac cagtagagaa tttcctttac tgtattttg tgtctggtct tccctttctg    4620
```

```
gcttctagga  catccatgcc  aggtgaggtg  cctgggtccc  tgttacaagt  caggagccct    4680
gtagggagac  ccctcctttt  gtacaagtac  ctgaatgctg  cgacaagcag  atttttgtaa    4740
aattttatat  tagtttttaa  tgtcagtggc  gactcggttc  ctggggctgc  agccagcctg    4800
ggacttttgt  aagaattttt  gggtgactca  cttagatgtc  gtttccttct  tgccccctct    4860
tcctctctgt  aatctaagtg  cattaaacat  ctttgcag                              4898
```